US012655122B2

(12) United States Patent
Watanabe et al.

(10) Patent No.: US 12,655,122 B2
(45) **Date of Patent: *Jun. 16, 2026**

(54) HETEROARYL CARBOXAMIDE COMPOUND

(71) Applicants: Astellas Pharma Inc., Tokyo (JP); Kotobuki Pharmaceutical Co., Ltd., Nagano (JP)

(72) Inventors: Hideyuki Watanabe, Tokyo (JP); Takashi Kamikubo, Tokyo (JP); Akio Kamikawa, Tokyo (JP); Takuya Washio, Tokyo (JP); Yohei Seki, Tokyo (JP); Keiichiro Okuyama, Tokyo (JP); Osamu Ikeda, Tokyo (JP); Hiroshi Tomiyama, Nagano (JP); Yoshinori Iwai, Nagano (JP); Akihiko Nakamura, Nagano (JP); Kozo Miyasaka, Nagano (JP)

(73) Assignees: Astellas Pharma Inc., Tokyo (JP); Kotobuki Pharmaceutical Co., Ltd., Nagano (JP)

( * ) Notice: Subject to any disclaimer, the term of this patent is extended or adjusted under 35 U.S.C. 154(b) by 291 days.

This patent is subject to a terminal disclaimer.

(21) Appl. No.: 18/254,829

(22) PCT Filed: Nov. 29, 2021

(86) PCT No.: PCT/JP2021/043540

§ 371 (c)(1),
(2) Date: May 26, 2023

(87) PCT Pub. No.: WO2022/114164

PCT Pub. Date: Jun. 2, 2022

(65) Prior Publication Data

US 2024/0043403 A1 Feb. 8, 2024

(30) Foreign Application Priority Data

Nov. 30, 2020 (JP) ................................ 2020-197899

(51) Int. Cl.

| | |
|---|---|
| ***C07D 401/12*** | (2006.01) |
| ***A61K 31/454*** | (2006.01) |
| ***A61K 31/4545*** | (2006.01) |
| ***A61K 31/496*** | (2006.01) |
| ***A61K 31/501*** | (2006.01) |
| ***A61K 31/519*** | (2006.01) |
| ***A61P 35/00*** | (2006.01) |
| ***C07D 401/14*** | (2006.01) |
| ***C07D 403/12*** | (2006.01) |
| ***C07D 403/14*** | (2006.01) |
| ***C07D 405/14*** | (2006.01) |
| ***C07D 413/04*** | (2006.01) |
| ***C07D 413/14*** | (2006.01) |
| ***C07D 487/04*** | (2006.01) |

(52) U.S. Cl.

CPC .......... *C07D 401/12* (2013.01); *A61K 31/454* (2013.01); *A61K 31/4545* (2013.01); *A61K 31/496* (2013.01); *A61K 31/501* (2013.01); *A61K 31/519* (2013.01); *A61P 35/00* (2018.01); *C07D 401/14* (2013.01); *C07D 403/12* (2013.01); *C07D 403/14* (2013.01); *C07D 405/14* (2013.01); *C07D 413/04* (2013.01); *C07D 413/14* (2013.01); *C07D 487/04* (2013.01)

(58) Field of Classification Search

None

See application file for complete search history.

(56) References Cited

U.S. PATENT DOCUMENTS

| | | | | |
|---|---|---|---|---|
| 7,381,401 | B2 | 6/2008 | Gajewski | |
| 8,163,746 | B2 * | 4/2012 | Sugasawa | A61P 29/00 548/200 |
| 12,077,519 | B2 | 9/2024 | Watanabe et al. | |
| 2005/0266510 | A1 | 12/2005 | Gajewski | |
| 2009/0286766 | A1 | 11/2009 | Sugasawa et al. | |
| 2022/0315603 | A1 | 10/2022 | Watanabe et al. | |

FOREIGN PATENT DOCUMENTS

| | | | |
|---|---|---|---|
| EP | 4253373 | A1 | 10/2023 |
| JP | 2008-528520 | A | 7/2008 |
| JP | 2009-524677 | A | 7/2009 |
| JP | 2014-221840 | A | 11/2014 |
| JP | 2020-532561 | A | 11/2020 |
| WO | 2006/081391 | A2 | 8/2006 |
| WO | 2007/087427 | A2 | 8/2007 |
| WO | 2007/123269 | A1 | 11/2007 |

(Continued)

OTHER PUBLICATIONS

U.S. Appl. No. 17/427,426, filed Jul. 30, 2021, 2022-0315603, Published.
U.S. Appl. No. 18/521,400, filed Nov. 28, 2023, Pending.
Velnati et al., Identification of a novel DGKalpha inhibitor for XLP-1 therapy by virtual screening. Eur J Med Chem. Feb. 15, 2019;164:378-390.
European Office Action for Application No. 21898136.3, dated Oct. 16, 2024, 8 pages.
European Office Action for Application No. 20906466.6, dated Nov. 22, 2023, 5 pages.
Bardhan et al., The PD1:PD-L1/2 Pathway from Discovery to Clinical Implementation. Front Immunol. Dec. 12, 2016;7:550, 7 pages.

(Continued)

*Primary Examiner* — Noble E Jarrell
(74) *Attorney, Agent, or Firm* — McCarter & English, LLP; Wei Song; James M. Alburger

(57) ABSTRACT

Provided herein are heteroaryl carboxamide compounds which have a DGK ξ (DGKzeta) inhibitory effect. The compounds described herein are useful as an active ingredient of a pharmaceutical composition for the treatment of cancer related to activation of immune cells or cancers resistant to anti-PD-1 antibody/anti-PD-L1 antibody therapy.

9 Claims, No Drawings

(56) References Cited

FOREIGN PATENT DOCUMENTS

| | | | |
|---|---|---|---|
| WO | 2008/054702 | A1 | 5/2008 |
| WO | 2019/046944 | A1 | 3/2019 |
| WO | 2020/006018 | A1 | 1/2020 |
| WO | 2021/132422 | A1 | 7/2021 |
| WO | 2021/214019 | A1 | 10/2021 |
| WO | 2021/214020 | A1 | 10/2021 |

OTHER PUBLICATIONS

Gharbi et al., Transient PKCalpha shuttling to the immunological synapse is governed by DGKzeta and regulates L-selectin shedding. J Cell Sci. May 15, 2013;126(Pt 10):2176-86.

Jing et al., T Cells Deficient in Diacylglycerol Kinase zeta Are Resistant to PD-1 Inhibition and Help Create Persistent Host Immunity to Leukemia. Cancer Res. Oct. 15, 2017;77(20):5676-5686.

Joshi et al., Diacylglycerol kinases: regulated controllers of T cell activation, function, and development. Int J Mol Sci. Mar. 26, 2013;14(4):6649-73.

Krishna et al., Role of diacylglycerol kinases in T cell development and function. Crit Rev Immunol. 2013;33(2):97-118.

O'Donnell et al., Resistance to PD1/PDL1 checkpoint inhibition. Cancer Treat Rev. Jan. 2017;52:71-81.

Riese et al., Diacylglycerol Kinases (DGKs): Novel Targets for Improving T Cell Activity in Cancer. Front Cell Dev Biol. Oct. 17, 2016;4:108, 7 pages.

Yang et al., Diacylglycerol Kinase zeta Is a Target to Enhance NK Cell Function. J Immunol. Aug. 1, 2016;197(3):934-41.

Zhong et al., Diacylglycerol kinases in immune cell function and self-tolerance. Immunol Rev. Aug. 2008;224:249-64.

International Search Report and Written Opinion for Application No. PCT/JP2020/048337, dated Feb. 22, 2021, 14 pages.

International Preliminary Report on Patentability for Application No. PCT/JP2020/048337, dated Jul. 7, 2022, 6 pages.

International Search Report and Written Opinion for Application No. PCT/JP2021/043540, dated Jan. 11, 2022, 12 pages.

Ruger et al., Synthesis of tetra-substituted pyrazoles. Tetrahedron. 2012;68:8823-8829.

* cited by examiner

HETEROARYL CARBOXAMIDE COMPOUND

RELATED APPLICATIONS

This application is a 35 U.S.C. § 371 national stage filing of International Application No. PCT/JP2021/043540, filed on Nov. 29, 2021, which in turn claims priority to Japanese Patent Application No. 2020-197899, filed on Nov. 30, 2020.

TECHNICAL FIELD

The present invention relates to a heteroaryl carboxamide compound which is useful as a pharmaceutical composition, for example, a diacylglycerol kinase ξ (DGKzeta) inhibitor, and is expected to be useful as an active ingredient of, for example, a pharmaceutical composition for treatment of cancer related to activation of immune cells or cancer resistant to anti-PD-1 antibody/anti-PD-L1 antibody therapy, particularly a pharmaceutical composition for treatment of cancer related to activation of immune cells, which has resistance to anti-PD-1 antibody/anti-PD-L1 antibody therapy.

BACKGROUND ART

Cancer immunotherapy has drawn attention as the fourth mainstay cancer treatment method following conventional surgical treatment, radiation therapy and cancer drug therapy (chemotherapy and molecular targeted drugs). It is an anti-cytotoxic T-lymphocyte antigen (CTLA)-4 antibody (ipilimumab) and an anti-PD-1 antibody (nivolumab or pembrolizumab) that have paved the way for the cancer immunotherapy. CTLA-4 and PD-1 are called immune checkpoint molecules, and function as "costimulatory molecules capable of transducing inhibitory signals". Currently, the anti-PD-1 antibody is proven to be effective in clinical practice against many cancers including melanoma and non-small cell lung cancer, and application of the anti-PD-1 antibody is expanding. In recent years, development of antibodies targeting checkpoint molecules other than CTLA-4 and PD-1 has become active throughout the world.

DGK is an enzyme which converts diacyl glycerol (DAG) into phosphatidic acid (PA) by phosphorylation. In mammals, DGK has ten isoforms, which are classified broadly into five types according to structural characteristics. These five types of isoforms are type I (α, β, γ), type II (δ, η, κ), type III (ε), type IV (ξ, τ) and type V (θ). All the isoforms have a catalytic domain, which is highly homologous among them, in the C-terminal portion, and a C1 domain, which has a homology with protein kinase C (PKC), in the molecule. The C1 domain is considered to be a domain to which phorbol ester/DAG binds (Int. J. Mol. Sci. 2013, 14: 6649-6673).

In T-cells, phospholipase Cγ1 (PLCγ1) activated by antigenic stimulation produces DAG and inositol triphosphate (IP3) from phosphatidylinositol 4,5-bisphosphate (PIP2). The produced DAG activates a plurality of downstream signals including RAS, NF-κB and AKT pathways, leading to activation of T-cells. On the other hand, IP3 activates nuclear factor of activated T-cells (NFAT) signals via discharge of $Ca^{2+}$ from the endoplasmic reticulum, and is involved in not only activation of T-cells but also induction of anergy. The anergy of T-cells is an incomplete activated state caused by depression of costimulatory (CD28 signal)

or inhibition of costimulatory during antigen recognition, and in this state, no response is produced even by restimulation.

DGK α and DGK ξ are two main isoforms in T-cells, and each of these isoforms adjusts the intensity of the DAG signal down stream of antigenic stimulation to prevent excessive activation of T-cells. Further, DGK α and DGK ξ promote anergy of T-cells, and play an important role in immune tolerance of T-cells (J Cell Sci. 2013, 126:2176-2186, Crit Rev Immunol. 2013, 33: 97-118., Immunol rev. 2008, 224: 249-264).

Further, activation of T-cells lacking DGK ξ has been reported to produce resistance to inhibitory signals from PD-1, and resistance to a transforming growth factor (TGF)-β and PD-1 independent immunosuppressive factors such as Adenosine and PGE2 (Cancer Res. 2017, 77: 5676-5686., Front Cell Dev Biol. 2016, 4: 108.). It has been reported that T-cells having overexpressed PD-1 molecules are extremely exhausted, and that in this state, the anti-PD-1 antibody has no effect. Immunosuppressive factors such as TGF-β are considered to be one of resistance mechanisms of anti-PD-1 therapy (Cancer treatment Reviews 2017, 52: 71-81). It has been reported that in NK cells, DGK ξ negatively controls activation of NK cells by activated receptor stimulation, and that in DGK ξ KO mice, growth of a major histocompatibility complex (MHC) class I-deficient tumor is suppressed (J Immunol. 2016, 197: 934-941).

Therefore, a DGK ξ inhibitor to be produced is expected to have antitumor action through activation of immune cells, particularly activation of T-cells. Further, it has been reported that the response rate of anti-PD-1 antibody therapy varies depending on a type of cancer, but is approximately 30% in general, (Front Immunol. 2016, 7: 550), and the DGK ξ inhibitor is also expected to be useful for patients with resistance to anti-PD-1 antibody therapy.

Patent Literature 1 discloses that R59022 and R59499 have DGK ξ inhibitory effect, alleviate anergy of T-cells, and upregulate the immune response.

[Chemical Formula 1]

(R59022)

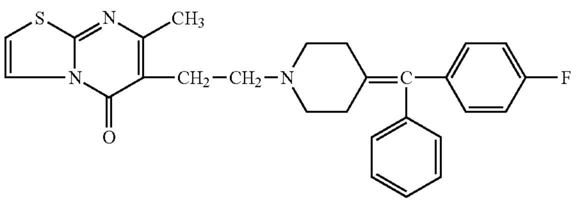

(R59499)

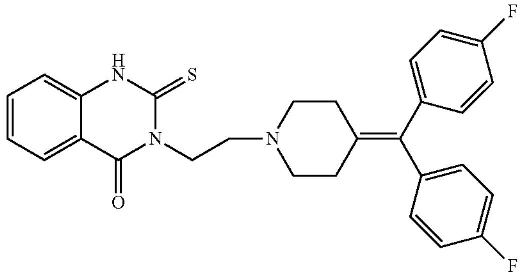

Patent Literature 2 discloses that the compound of the following formula has trkA receptor inhibitory effect, and is useful for treatment or prevention of frequent urination and urge to urinate associated with the hyperactive bladder, etc.

[Chemical Formula 2]

(A)

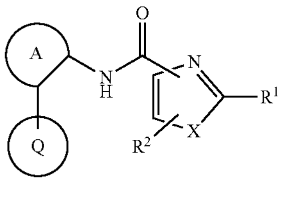

(See the publication for the meanings of the symbols in the formula) In Patent Literature 2, however, there is no specific disclosure of cancer treatment applications and the compound of the present invention comprising a phenyl group having a series of four adjacent substituents as imperative constituent elements.

Patent Literature 3 discloses that the compound of the following general formula is useful for treatment or prevention of proliferative diseases, etc. as a protein kinase inhibitor against a cyclin dependent kinase (CDK) etc.

[Chemical Formula 3]

(B)

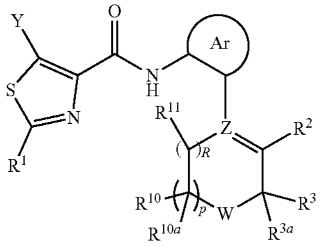

(See the publication for the meanings of the symbols in the formula)

In Patent Literature 3, however, there is no specific disclosure of DGK and the compound of the present invention comprising a phenyl group having a series of four adjacent substituents as imperative constituent elements.

In Patent Literature 4, it is disclosed by the applicator of the present application that a compound of the following formula can be used as a drug for treatment of cancer related to activation of immune cells or cancer resistant to anti-PD-1 antibody/anti-PD-L1 antibody therapy as a DGK ξ inhibitor.

[Chemical Formula 4]

(C)

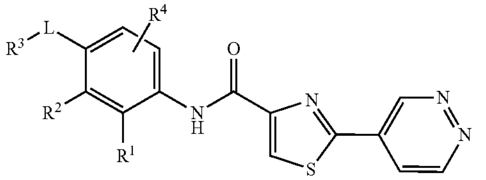

(See the publication for the meanings of the symbols in the formula)

In Patent Literature 4, however, there is no specific disclosure of the present inventive compound, and Patent Literature 4 is a document published after the priority date of the present application.

CITATION LIST

Patent Literature

PTL 1: U.S. Pat. No. 7,381,401
PTL 2: International Publication No. WO 2007/123269
PTL 3: International Publication No. WO 2008/054702
PTL 4: International Publication No. WO 2021/132422

SUMMARY OF INVENTION

Technical Problem

A compound which is useful as a pharmaceutical composition, for example, a DGK ξ inhibitor, and is expected to be useful as an active ingredient of a pharmaceutical composition for treatment of cancer related to activation of immune cells or cancer resistant to anti-PD-1 antibody/anti-PD-L1 antibody therapy, particularly a pharmaceutical composition for treatment of cancer related to activation of immune cells, which has resistance to anti-PD-1 antibody/anti-PD-L1 antibody therapy is provided.

Solution to Problem

The present inventors have extensively conducted studies on a compound useful as an active ingredient of a pharmaceutical composition for treatment of cancer related to activation of immune cells or cancer resistant to anti-PD-1 antibody/anti-PD-L1 antibody therapy, particularly a pharmaceutical composition for treatment of cancer related to activation of immune cells, which has resistance to anti-PD-1 antibody/anti-PD-L1 antibody therapy. As a result, the present inventors have found that a heteroaryl carboxamide compound of formula (I) comprising a phenyl group having a series of four adjacent substituents as imperative constituent elements, which is generally considered difficult to be synthesized, has excellent DGK ξ inhibitory activity, leading to completion of the present invention.

Thus, the present invention relates to a compound of formula (I) or a salt thereof, and a pharmaceutical composition containing a compound of formula (I) or a salt thereof, and one or more pharmaceutically acceptable excipients:

[Chemical Formula 5]

(I)

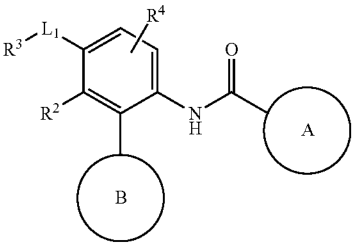

wherein

A is a group of formula (A-i), (A-ii), (A-iii), (A-iv) or (A-v):

[Chemical Formula 6]

(A-i)

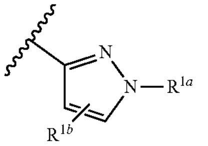

(A-ii)

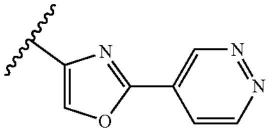

(A-iii)

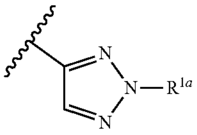

(A-iv)

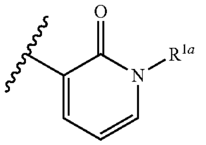

(A-v)

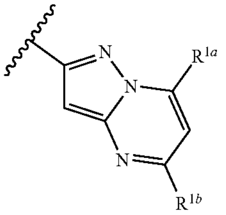

B is a group of formula (B-i), (B-ii), (B-iii) or (B-iv):

[Chemical Formula 7]

(B-i)

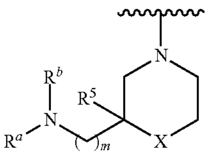

(B-ii)

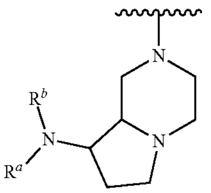

(B-iii)

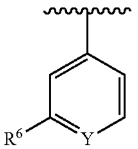

-continued (B-iv)

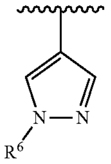

where B is a group of formula (B-i) when $R^{1a}$ is a halogeno-$C_{1-6}$ alkyl, $R^{1a}$ is pyridazinyl or a halogeno-$C_{1-6}$ alkyl, $R^{1b}$ is H or a $C_{1-6}$ alkyl, $R^2$ is a $C_{3-5}$ cycloalkyl, an —O—($C_{1-6}$ alkyl), a halogeno-$C_{1-6}$ alkyl, a halogen or a phenyl, $R^3$ is i) a phenyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulfonyl and a halogen, ii) a $C_{3-8}$ cycloalkyl optionally substituted with a group selected from the group consisting of a $C_{1-6}$ alkyl and a halogen, iii) a pyridyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulfonyl and a halogen, or iv) five- or six-membered partially unsaturated heterocyclic ring containing one to four hetero atoms selected from oxygen, sulfur and nitrogen, $R^4$ is H or F, $R^5$ is H or F, $R^6$ is -$L_2$-$(CH_2)_2NR^aR^b$ or piperidinyl, $L_1$ is a bond, O or NH, $L_2$ is a bond, O or $CH_2$, X is $CH_2$ or N-methyl, Y is CH or N, $R^a$ is H or methyl, $R^b$ is H, methyl, ethyl, cyclopropyl or —$(CH_2)_2O$—$CH_3$, and m is 1, 2 or 3.

When symbols in a chemical formula are used in other chemical formulae in the present description, the same symbols have the same meanings unless otherwise specified.

The present invention relates to a pharmaceutical composition for treatment of cancer related to activation of immune cells or cancer resistant to anti-PD-1 antibody/anti-PD-L1 antibody therapy, containing a compound of formula (I) or a salt thereof and one or more pharmaceutically acceptable excipients, particularly a pharmaceutical composition for treatment of cancer related to activation of immune cells, which has resistance to anti-PD-1 antibody/anti-PD-L1 antibody therapy. Note that, the pharmaceutical composition includes a therapeutic agent for treatment of cancer related to activation of immune cells or cancer resistant to anti-PD-1 antibody/anti-PD-L1 antibody therapy, containing a compound of formula (I) or a salt thereof, particularly a therapeutic agent for treatment of cancer related to activation of immune cells, which has resistance to anti-PD-1 antibody/anti-PD-L1 antibody therapy.

The present invention relates to a compound of formula (I) or a salt thereof which is a DGK ξ inhibitor; a compound of formula (I) or a salt thereof which is used as a DGK ξ inhibitor; a DGK ξ inhibitor containing a compound of formula (I) or a salt thereof; use of a compound of formula (I) or a salt thereof for the manufacture of a pharmaceutical composition for treatment of cancer related to activation of immune cells or cancer resistant to anti-PD-1 antibody/anti-PD-L1 antibody therapy, particularly use of a compound of formula (I) or a salt thereof for the manufacture of a pharmaceutical composition for treatment of cancer related to activation of immune cells, which has resistance to anti-PD-1 antibody/anti-PD-L1 antibody therapy; use of a compound of formula (I) or a salt thereof for treatment of cancer related to activation of immune cells or cancer resistant to anti-PD-1 antibody/anti-PD-L1 antibody therapy, particularly use of a compound of formula (I) or a salt thereof for treatment of cancer related to activation of immune cells, which has resistance to anti-PD-1 antibody/anti-PD-L1 antibody therapy; a compound of formula (I) or a salt thereof which is used for treatment of cancer related to activation of immune cells or cancer resistant to anti-PD-1 antibody/anti-PD-L1 antibody therapy, particularly a compound of formula (I) or a salt thereof which is used for treatment of cancer related to activation of immune cells, which has resistance to anti-PD-1 antibody/anti-PD-L1 antibody therapy; and a method for treatment of cancer related to activation of immune cells or cancer resistant to anti-PD-1 antibody/anti-PD-L1 antibody therapy, particularly a method for treatment of cancer related to activation of immune cells, which has resistance to anti-PD-1 antibody/anti-PD-L1 antibody therapy, the method comprising administering an effective amount of a compound of formula (I) or a salt thereof to a subject. The "subject" is a human or another animal in need of prevention or treatment of the cancer. In an embodiment, the "subject" is a human in need of prevention or treatment of the cancer.

Advantageous Effects of Invention

A compound of formula (I) or a salt thereof has DGK ξ inhibitory effect, and can be used as a therapeutic agent for treatment of cancer related to activation of immune cells or cancer resistant to anti-PD-1 antibody/anti-PD-L1 antibody therapy, particularly a therapeutic agent for treatment of cancer related to activation of immune cells, which has resistance to anti-PD-1 antibody/anti-PD-L1 antibody therapy.

DESCRIPTION OF EMBODIMENTS

Hereinafter, the present invention will be described in detail.

In the present description, the following terms have the following meanings unless otherwise specified. The following definitions are intended to clarify the defined terms rather than limiting the terms. If a term used herein is not specifically defined, such a term is used with a meaning which is commonly accepted by those skilled in the art.

In the present description, the "$C_{1-6}$ alkyl" is a linear or branched alkyl having 1 to 6 carbon atoms (hereinafter, abbreviated as $C_{1-6}$). Examples thereof include methyl, ethyl, n-propyl, isopropyl, n-butyl, isobutyl, sec-butyl, tert-butyl, n-pentyl and n-hexyl. In an embodiment, the "$C_{1-6}$ alkyl" is a $C_{1-3}$ alkyl. In an embodiment, the "$C_{1-6}$ alkyl" is methyl or ethyl. In an embodiment, the "$C_{1-6}$ alkyl" is methyl. In an embodiment, the "$C_{1-6}$ alkyl" is ethyl.

The "halogeno-$C_{1-6}$ alkyl" is a $C_{1-6}$ alkyl substituted with one or more halogens. In an embodiment, the "halogeno-$C_{1-6}$ alkyl" is a $C_{1-6}$ alkyl substituted with one to five halogens. In an embodiment, the "halogeno-$C_{1-6}$ alkyl" is a $C_{1-3}$ alkyl substituted with one to five halogens. In an embodiment, the "halogeno-$C_{1-6}$ alkyl" is trifluoromethyl, difluoromethyl, difluoroethyl or trifluoroethyl. In an embodiment, the "halogeno-$C_{1-6}$ alkyl" is difluoroethyl or trifluoromethyl. In an embodiment, the "halogeno-$C_{1-6}$ alkyl" is difluoroethyl. In an embodiment, the "halogeno-$C_{1-6}$ alkyl" is trifluoromethyl. In an embodiment, the "halogeno-$C_{1-6}$ alkyl" is 2,2-difluoroethyl.

The "$C_{3-8}$ cycloalkyl" is a saturated hydrocarbon ring group of $C_{3-8}$, and may be crosslinked, or may form a spiro-ring. Examples thereof include cyclopropyl, cyclobutyl, cyclopentyl, cyclohexyl, cycloheptyl, cyclooctyl, bicyclo[2,2,1]heptyl, bicyclo[3,10]hexyl, bicyclo[3,1,1]heptyl and spiro[2,5]octyl. In an embodiment, the "$C_{3-8}$ cycloalkyl" is a $C_{3-5}$ cycloalkyl. In an embodiment, the $C_{3-5}$ cycloalkyl is cyclopropyl, cyclobutyl or cyclopentyl. In an embodiment, the $C_{3-5}$ cycloalkyl is cyclopropyl. In an embodiment, the $C_{3-5}$ cycloalkyl is cyclobutyl. In an embodiment, the $C_{3-5}$ cycloalkyl is cyclopentyl.

The "halogen" is F, Cl, Br or I. In an embodiment, the "halogen" is F or Cl. In an embodiment, the "halogen" is F. In an embodiment, the "halogen" is Cl.

The "five- or six-membered partially unsaturated heterocyclic ring" is a monocyclic heterocyclic ring having an unsaturated bond in a part of the five- or six-membered ring containing one to four hetero atoms selected from oxygen, sulfur and nitrogen. Sulfur or nitrogen which is a ring atom may be oxidized to form an oxide or a dioxide. The "five- or six-membered partially unsaturated heterocyclic ring" is, for example, dihydropyridyl, tetrahydropyridyl, dihydrofuranyl, dihydrothienyl, dihydropyranyl, thiopyranyl, dihydrothiopyranyl or the like. In an embodiment, the "five- or six-membered partially unsaturated heterocyclic ring" is tetrahydropyridyl. In an embodiment, the "five- or six-membered partially unsaturated heterocyclic ring" is dihydrofuranyl. In an embodiment, the "five- or six-membered partially unsaturated heterocyclic ring" is dihydropyranyl.

The term "optionally substituted" means being unsubstituted, or being "substituted with one or more substituents (e.g. substituents as defined below)". The substituent may occur at any position as long as hydrogen is normally present at the position. In an embodiment, the term "optionally substituted" means being "optionally substituted with one to five substituents". In another embodiment, the term "optionally substituted" means being "optionally substituted with one to three substituents". When there is a plurality of substituents, these substituents may be the same or different.

One or more embodiments can be combined with another embodiment even though a specific combination is not described. That is, all embodiments can be freely combined.

The "activation of immune cells" means that immune cells having the capability of suppressing growth of cancer cells or shrinking or eliminating cancer cells (hereinafter, referred to as antitumor activity), particularly T-cells are reactivated, and/or that the number of immune cells, particularly activated T-cells is increased. In an embodiment, the "activation of immune cells" means activation of immune cells based on DGK ξ inhibitory effect.

The "cancer related to activation of immune cells" is a cancer having immune responsiveness. In an embodiment, the "cancer related to activation of immune cells" is a cancer in which growth of cancer cells is suppressed or cancer cells are shrunk or eliminated by activation of immune cells. In an embodiment, the "cancer related to activation of immune cells" is a cancer in which growth of cancer cells is suppressed by activation of immune cells. In an embodiment, the "cancer related to activation of immune cells" is a cancer in which cancer cells are shrunk or eliminated by activation of immune cells. In an embodiment, the "cancer related to activation of immune cells” is a cancer in which growth of cancer cells is suppressed or cancer cells are shrunk or eliminated by activation of immune cells based on DGK ξ inhibitory effect. In an embodiment, the “cancer related to activation of immune cells” is a cancer in which growth of cancer cells is suppressed by activation of immune cells based on DGK ξ inhibitory effect. In an embodiment, the “cancer related to activation of immune cells” is a cancer in which cancer cells are shrunk or eliminated by activation of immune cells based on DGK ξ inhibitory effect.

The cancer to which the present invention can be applied is not particularly limited, and examples thereof include small cell lung cancer, head and neck cancer, kidney cancer, ovarian cancer, non-small cell lung cancer, mismatch repair-deficient colon cancer, urothelial cancer, melanoma, hepatocellular carcinoma, gastric cancer and bladder cancer.

The term “resistant to anti-PD-1 antibody/anti-PD-L1 antibody therapy” means being resistant to an anti-PD-1 antibody and/or an anti-PD-L1 antibody therapy. In an embodiment, the term “resistant to anti-PD-1 antibody/anti-PD-L1 antibody therapy” means being resistant to an anti-PD-1 antibody and an anti-PD-L1 antibody therapy. In an embodiment, the term “resistant to anti-PD-1 antibody/anti-PD-L1 antibody therapy” means being resistant to an anti-PD-1 antibody therapy. In an embodiment, the term “resistant to anti-PD-1 antibody/anti-PD-L1 antibody therapy” means being resistant to an anti-PD-L1 antibody therapy. The “resistance” includes a primary resistance in which the anti-PD-1 antibody/anti-PD-L1 antibody has no effect from the beginning, or an acquired resistance in which the anti-PD-1 antibody/anti-PD-L1 antibody becomes less effective as the treatment is continued. In an embodiment, the term “resistant to anti-PD-1 antibody/anti-PD-L1 antibody therapy” means having a primary resistance to anti-PD-1 antibody and the anti-PD-L1 antibody therapy. In an embodiment, the term “resistant to anti-PD-1 antibody/anti-PD-L1 antibody therapy” means having an acquired resistance to anti-PD-1 antibody and the anti-PD-L1 antibody therapy. In an embodiment, the term “resistant to anti-PD-1 antibody/anti-PD-L1 antibody therapy” means having a primary resistance to anti-PD-1 antibody therapy. In an embodiment, the term “resistant to anti-PD-1 antibody/anti-PD-L1 antibody therapy” means having an acquired resistance to anti-PD-1 antibody therapy. In an embodiment, the term “resistant to anti-PD-1 antibody/anti-PD-L1 antibody therapy” means having a primary resistance to anti-PD-L1 antibody therapy. In an embodiment, the term “resistant to anti-PD-1 antibody/anti-PD-L1 antibody therapy” means having an acquired resistance to anti-PD-L1 antibody therapy.

The “cancer resistant to anti-PD-1 antibody/anti-PD-L1 antibody therapy” means a cancer resistant to an anti-PD-1 antibody and/or an anti-PD-L1 antibody therapy. In an embodiment, the “cancer resistant to anti-PD-1 antibody/anti-PD-L1 antibody therapy” is a cancer resistant to an anti-PD-1 antibody and an anti-PD-L1 antibody therapy. In an embodiment, the “cancer resistant to anti-PD-1 antibody/anti-PD-L1 antibody therapy” is a cancer resistant to an anti-PD-1 antibody therapy. In an embodiment, the “cancer resistant to anti-PD-L1 antibody/anti-PD-L1 antibody therapy” is a cancer resistant to an anti-PD-L1 antibody therapy. In an embodiment, the “cancer resistant to anti-PD-L1 antibody/anti-PD-L1 antibody therapy” is a cancer resistant to anti-PD-1 antibody and anti-PD-L1 antibody therapy. In an embodiment, the “cancer resistant to anti-PD-1 antibody/anti-PD-L1 antibody therapy” is a cancer resistant to anti-PD-1 antibody therapy. In an embodiment, the “cancer resistant to anti-PD-1 antibody/anti-PD-L1 antibody therapy” is a cancer resistant to anti-PD-L1 antibody therapy. In an embodiment, the “cancer resistant to anti-PD-1 antibody/anti-PD-L1 antibody therapy” is a cancer having a primary resistance to anti-PD-1 antibody and anti-PD-L1 antibody therapy. In an embodiment, the “cancer resistant to anti-PD-1 antibody/anti-PD-L1 antibody therapy” is a cancer having an acquired resistance to anti-PD-1 antibody and anti-PD-L1 antibody therapy. In an embodiment, the “cancer resistant to anti-PD-1 antibody/anti-PD-L1 antibody therapy” is a cancer having a primary resistance to anti-PD-1 antibody therapy. In an embodiment, the “cancer resistant to anti-PD-1 antibody/anti-PD-L1 antibody therapy” is a cancer having an acquired resistance to anti-PD-1 antibody therapy. In an embodiment, the “cancer resistant to anti-PD-1 antibody/anti-PD-L1 antibody therapy” is a cancer having a primary resistance to anti-PD-L1 antibody therapy. In an embodiment, the “cancer resistant to anti-PD-1 antibody/anti-PD-L1 antibody therapy” is a cancer having an acquired resistance to anti-PD-L1 antibody therapy.

The cancer to which the present invention can be applied is not particularly limited, and examples thereof include cancers resistant to anti-PD-1 antibody and/or anti-PD-L1 antibody therapy against small cell lung cancer, head and neck cancer, kidney cancer, ovarian cancer, non-small cell lung cancer, mismatch repair-deficient colon cancer, urothelial cancer, melanoma, hepatocellular carcinoma, gastric cancer, bladder cancer and the like.

The “anti-PD-1 antibody/anti-PD-L1 antibody” is not particularly limited, and examples thereof include antibodies selected from Nivolumab, Pembrolizumab, Atezolizumab, Pidilizumab, Avelumab and Durvalumab.

An embodiment of the compound of formula (I) or a salt thereof of the present invention will be shown below:

(1-1) a compound or a salt thereof in which A is a group of the following formula (A-i), (A-ii), (A-iii), (A-iv) or (A-v):

[Chemical Formula 8]

(A-i)

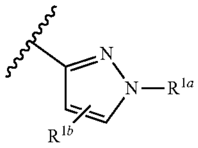

(A-ii)

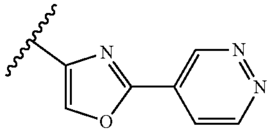

(A-iii)

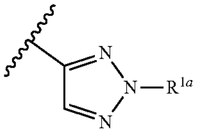

(A-iv)

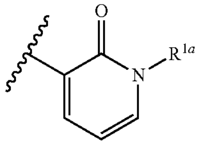

-continued (A-v)

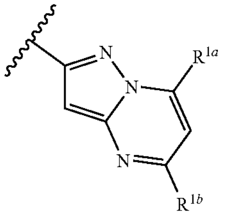

(1-2) a compound or a salt thereof in which A is a group of the following formula (A-i) or (A-ii):

[Chemical Formula 9]

(A-i)

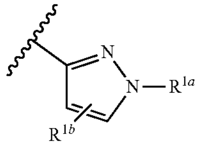

(A-ii)

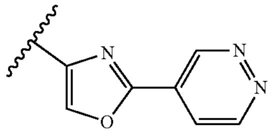

(2-1) a compound or a salt thereof in which B is a group of the following formula (B-i), (B-ii), (B-iii) or (B-iv), where B is (B-i) when $R^{1a}$ is a halogeno-$C_{1-6}$ alkyl:

[Chemical Formula 10]

(B-i)

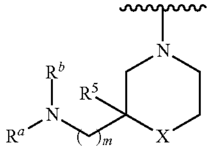

(B-ii)

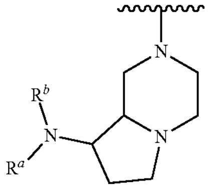

(B-iii)

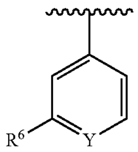

(B-iv)

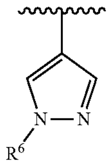

(2-2) a compound or a salt thereof in which B is a group of the following formula (B-i-a) or (B-ii), where B is (B-i-a) when $R^{1a}$ is a halogeno-$C_{1-6}$ alkyl:

[Chemical Formula 11]

(B-i-a)

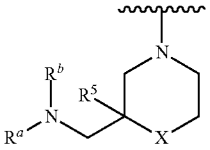

(B-ii)

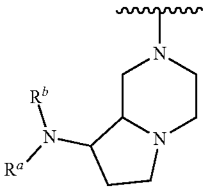

(3-1) a compound or a salt thereof in which B is a group of (B-i) when $R^{1a}$ is a halogeno-$C_{1-6}$ alkyl;

(3-2) a compound or a salt thereof in which B is a group of (B-i-a) when $R^{1a}$ is a halogeno-$C_{1-6}$ alkyl;

(3-3) a compound or a salt thereof in which B is a group of (B-i-a) when $R^{1a}$ is a halogeno-$C_{1-3}$ alkyl;

(4) a compound or a salt thereof in which $R^{1a}$ is pyridazinyl or a halogeno-$C_{1-6}$ alkyl; in an embodiment, a compound or a salt thereof in which $R^{1a}$ is pyridazinyl or a halogeno-$C_{1-3}$ alkyl; in an embodiment, a compound or a salt thereof in which $R^{1a}$ is pyridazinyl, trifluoromethyl, difluoromethyl, difluoroethyl or trifluoroethyl, in an embodiment, a compound or a salt thereof in which $R^{1a}$ is pyridazinyl or 2,2-difluoroethyl; a compound or a salt thereof in which $R^{1a}$ is pyridazinyl; or in an embodiment, a compound or a salt thereof in which $R^{1a}$ is 2,2-difluoroethyl;

(5) a compound or a salt thereof in which $R^{1b}$ is H or a $C_{1-6}$ alkyl; in an embodiment, a compound or a salt thereof in which $R^{1b}$ is H or a $C_{1-3}$ alkyl; in an embodiment, a compound or a salt thereof in which $R^{1b}$ is H or methyl; in an embodiment, a compound or a salt thereof in which $R^{1b}$ is H; or in an embodiment, a compound or a salt thereof in which $R^{1b}$ is methyl;

(6) a compound or a salt thereof in which $R^2$ is a $C_{3-5}$ cycloalkyl, an —O—($C_{1-6}$ alkyl), a halogeno-$C_{1-6}$ alkyl, a halogen or a phenyl; in an embodiment, a compound or a salt thereof in which $R^2$ is a halogeno-$C_{1-6}$ alkyl or a halogen; in an embodiment, a compound or a salt thereof in which $R^2$ is a halogeno-$C_{1-3}$ alkyl, F, Cl or Br; in an embodiment, a compound or a salt thereof in which $R^2$ is $CF_3$, F or Cl; in an embodiment, a compound or a salt thereof in which $R^2$ is $CF_3$; in an embodiment, a compound or a salt thereof in which $R^2$ is F; or in an embodiment, a compound or a salt thereof in which $R^2$ is Cl;

(7-1) a compound or a salt thereof in which $R^3$ is i) a phenyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulfonyl and a halogen, ii) a $C_{3-8}$ cycloalkyl optionally substituted with a group selected from the group consisting of a $C_{1-6}$ alkyl and a halogen, iii) a pyridyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulfonyl and a halogen, or iv) five- or six-membered partially unsaturated heterocyclic ring containing one to four hetero atoms selected from oxygen, sulfur and nitrogen;

(7-2) a compound or a salt thereof in which $R^3$ is i) a phenyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulfonyl and a halogen, or ii) a $C_{3-8}$ cycloalkyl optionally substituted with a group selected from the group consisting of a $C_{1-6}$ alkyl and a halogen;

(7-3) a compound or a salt thereof in which $R^3$ is a phenyl optionally substituted with a group selected from the group consisting of a $C_{1-6}$ alkyl and a halogen, or a $C_{3-5}$ cycloalkyl;

(8) a compound or a salt thereof in which $R^4$ is H or F; in an embodiment, a compound or a salt thereof in which $R^4$ is H; or in an embodiment, a compound or a salt thereof in which $R^4$ is F;

(9) a compound or a salt thereof in which $R^5$ is H or F; in an embodiment, a compound or a salt thereof in which $R^5$ is H; or in an embodiment, a compound or a salt thereof in which $R^5$ is F;

(10) a compound or a salt thereof in which $R^6$ is $-L_2-(CH_2)_2NR^aR^b$ or piperidinyl; in an embodiment, a compound or a salt thereof in which $R^6$ is $-L_2-(CH_2)_2NR^aR^b$; or in an embodiment, a compound or a salt thereof in which $R^6$ is piperidinyl;

(11) a compound or a salt thereof in which $L_1$ is a bond, O or NH; in an embodiment, a compound or a salt thereof in which $L_1$ is a bond or O; in an embodiment, a compound or a salt thereof in which $L_1$ is a bond; or in an embodiment, a compound or a salt thereof in which $L_1$ is O;

(12) a compound or a salt thereof in which $L_2$ is a bond, O or $CH_2$; in an embodiment, a compound or a salt thereof in which $L_2$ is O or $CH_2$; in an embodiment, a compound or a salt thereof in which $L_2$ is O; or in an embodiment, a compound or a salt thereof in which $L_2$ is $CH_2$;

(13) a compound or a salt thereof in which X is $CH_2$ or N-methyl; in an embodiment, a compound or a salt thereof in which X is $CH_2$; or in an embodiment, a compound or a salt thereof in which X is N-methyl;

(14) a compound or a salt thereof in which Y is CH or N; in an embodiment, a compound or a salt thereof in which Y is CH; or in an embodiment, a compound or a salt thereof in which Y is N;

(15) a compound or a salt thereof in which $R^a$ is H or methyl; in an embodiment, a compound or a salt thereof in which $R^a$ is H; or in an embodiment, a compound or a salt thereof in which $R^a$ is methyl;

(16) a compound or a salt thereof in which $R^b$ is H, methyl, ethyl, cyclopropyl or $—(CH_2)_2O—CH_3$; in an embodiment, a compound or a salt thereof in which $R^b$ is H or methyl; in an embodiment, a compound or a salt thereof in which $R^b$ is H; or in an embodiment, a compound or a salt thereof in which $R^b$ is methyl;

(17) a compound or a salt thereof in which m is 1, 2 or 3; in an embodiment, a compound or a salt thereof in which m is 1 or 2; or in an embodiment, a compound or a salt thereof in which m is 1; or

(18) a compound or a salt thereof that is a combination of any two or more of embodiments (1-1) to (17), which does not cause a contradiction.

Specific examples of the combination described in (18) include the following embodiments:

(19) a compound or a salt thereof in which A is a group of formula (A-i), (A-ii), (A-iii), (A-iv) or (A-v):

[Chemical Formula 12]

(A-i)

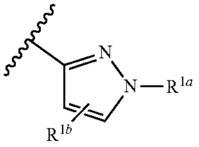

(A-ii)

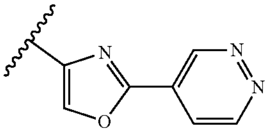

(A-iii)

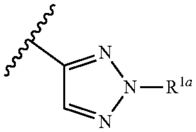

(A-iv)

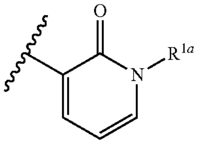

(A-v)

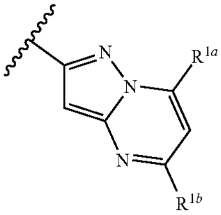

B is a group of the following formula (B-i), (B-ii), (B-iii) or (B-iv):

[Chemical Formula 13]

(B-i)

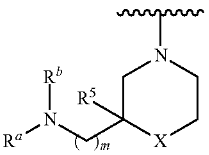

(B-ii)

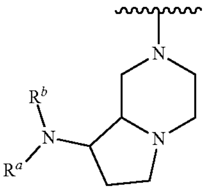

-continued (B-iii)

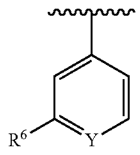

(B-iv)

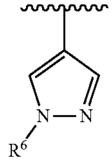

where B is a group of (B-i) when $R^{1a}$ is a halogeno-$C_{1-6}$ alkyl; $R^{1a}$ is pyridazinyl or a halogeno-$C_{1-6}$ alkyl; $R^{1b}$ is H or a $C_{1-6}$ alkyl; $R^2$ is a $C_{3-5}$ cycloalkyl, an —O—($C_{1-6}$ alkyl), a halogeno-$C_{1-6}$ alkyl, a halogen or a phenyl; $R^3$ is i) a phenyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulfonyl and a halogen, ii) a $C_{3-8}$ cycloalkyl optionally substituted with a group selected from the group consisting of a $C_{1-6}$ alkyl and a halogen, iii) a pyridyl optionally substituted with a group selected from the group consisting of a $C_{1-6}$ alkyl, a halogeno-$C_{16}$ alkyl, a $C_{3-5}$ cycloalkyl, an —O—($C_{1-6}$ alkyl), an —O-(halogeno-$C_{1-6}$ alkyl), cyano, nitro, methanesulfonyl and a halogen, or iv) five- or six-membered partially unsaturated heterocyclic ring containing one to four hetero atoms selected from oxygen, sulfur and nitrogen; $R^4$ is H or F; $R^5$ is H or F; $R^6$ is -$L_2$($CH_2$)$_2$N$R^aR^b$ or piperidinyl; $L_1$ is a bond, O or NH; $L_2$ is a bond, O or $CH_2$; X is $CH_2$ or N-methyl; Y is CH or N; $R^a$ is H or methyl; $R^b$ is H, methyl, ethyl, cyclopropyl or —$(CH_2)_2$O—$CH_3$, and m is 1, 2 or 3;

(20) the compound or a salt thereof described in (19) in which $R^2$ is a halogeno-$C_{1-6}$ alkyl or a halogen; $R^3$ is i) a phenyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulfonyl and a halogen, or ii) a $C_{3-8}$ cycloalkyl optionally substituted with a group selected from the group consisting of a $C_{1-6}$ alkyl and a halogen; and $L_1$ is a bond or O;

(21) the compound or a salt thereof described in (20) in which B is a group of the following formula (B-i-a) or (B-ii):

[Chemical Formula 14]

(B-i-a)

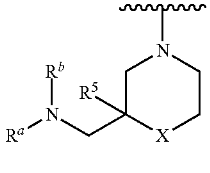

-continued (B-ii)

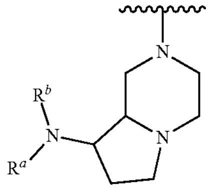

where B is a group of (B-i-a) when $R^{1a}$ is a halogeno-$C_{1-6}$ alkyl;

(22) the compound or a salt thereof described in (21) in which A is a group of the following formula (A-i) or (A-ii):

[Chemical Formula 15]

(A-i)

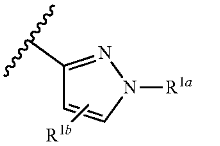

(A-ii)

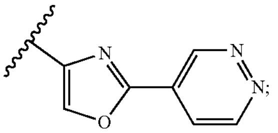

or

(23) the compound or a salt thereof described in (22) in which $R^3$ is a phenyl optionally substituted with a group selected from the group consisting of a $C_{1-6}$ alkyl and a halogen, or a $C_{3-5}$ cycloalkyl, and $R^b$ is H or methyl.

Examples of specific compounds encompassed by the present invention include the following compounds or salts thereof:

N-{2-[(3S)-3-(aminomethyl)piperidin-1-yl]-4-(2-fluorophenoxy)-3-(trifluoromethyl)phenyl}-1-(2,2-difluoroethyl)-1H-pyrazole-3-carboxamide;

N-{2-[(3S)-3-(aminomethyl)-4-methylpiperazin-1-yl]-4-(2-chlorophenoxy)-3-(trifluoromethyl)phenyl}-1-(2,2-difluoroethyl)-1H-pyrazole-3-carboxamide;

N-{2-[(3S)-3-(aminomethyl)-4-methylpiperazin-1-yl]-3-chloro-4-(2-chlorophenoxy)phenyl}-1-(2,2-difluoroethyl)-1H-pyrazole-3-carboxamide;

N-[4-(2-fluorophenoxy)-2-{(3S)-4-methyl-3-[(methylamino)methyl]piperazin-1-yl}-3-(trifluoromethyl)phenyl]-1-(pyridazin-4-yl)-1H-pyrazole-3-carboxamide;

N-{2-[(3R)-3-(aminomethyl)-3-fluoropiperidin-1-yl]-4-(2-fluorophenoxy)-3-(trifluoromethyl)phenyl}-1-(pyridazin-4-yl)-1H-pyrazole-3-carboxamide;

N-[4-(2-fluorophenoxy)-2-{(3R)-4-methyl-3-[(methylamino)methyl]piperazin-1-yl}-3-(trifluoromethyl)phenyl]-1-(pyridazin-4-yl)-1H-pyrazole-3-carboxamide;

N-[4-cyclopentyl-2-{(3S)-4-methyl-3-[(methylamino)methyl]piperazin-1-yl}-3-(trifluoromethyl)phenyl]-1-(pyridazin-4-yl)-1H-pyrazole-3-carboxamide;

N-{2-[(8R,8aS)-8-aminohexahydropyrrolo[1,2-a]pyrazin-2(1H)-yl]-4-(2-fluorophenoxy)-3-(trifluoromethyl)phenyl}-2-(pyridazin-4-yl)-1,3-oxazole-4-carboxamide; and N-[3-chloro-4-(2-fluorophenoxy)-2-{(3S)-4-methyl-3-[(methylamino)methyl]piperazin-1-yl}phenyl]-1-(pyridazin-4-yl)-1H-pyrazole-3-carboxamide.

Examples of specific compounds encompassed by the present invention or salts thereof include the following compounds or salts thereof:

N-[4-(2-fluorophenoxy)-2-{(3S)-4-methyl-3-[(methylamino)methyl]piperazin-1-yl}-3-(trifluoromethyl)phenyl]-1-(pyridazin-4-yl)-1H-pyrazole-3-carboxamide monobutanedioate;

N-[4-(2-fluorophenoxy)-2-{(3R)-4-methyl-3-[(methylamino)methyl]piperazin-1-yl}-3-(trifluoromethyl)phenyl]-1-(pyridazin-4-yl)-1H-pyrazole-3-carboxamide monobutanedioate;

N-[4-cyclopentyl-2-{(3S)-4-methyl-3-[(methylamino)methyl]piperazin-1-yl}-3-(trifluoromethyl)phenyl]-1-(pyridazin-4-yl)-1H-pyrazole-3-carboxamide monobutanedioate;

N-[3-chloro-4-(2-fluorophenoxy)-2-{(3S)-4-methyl-3-[(methylamino)methyl]piperazin-1-yl}phenyl]-1-(pyridazin-4-yl)-1H-pyrazole-3-carboxamide monobutanedioate; and N-{2-[(3R)-3-(aminomethyl)-3-fluoropiperidin-1-yl]-4-(2-fluorophenoxy)-3-(trifluoromethyl)phenyl}-1-(pyridazin-4-yl)-1H-pyrazole-3-carboxamide monobutanedioate.

The compound of formula (I) can have tautomers and geometric isomers depending on the type of a substituent. In the present description, the compound of formula (I) or a salt thereof may be described in only one isomer form, but the present invention encompasses other isomers, isolated forms of isomers, or mixtures thereof. The compound of formula (I) or a salt thereof may have an asymmetric center or axial asymmetry, based on which enantiomers (optical isomers) can be present. The compound of formula (I) or a salt thereof encompass all of isolated individual enantiomers such as (R) and (S) configurations and mixtures thereof (including racemic mixtures or non-racemic mixtures). In an embodiment, the enantiomer is "stereochemically pure". The term "stereochemically pure" refers to a purity with which those skilled in the art can recognize the enantiomer as being substantially stereochemically pure. In another embodiment, the enantiomer is a compound having a stereochemical purity of, for example, 90% ee (enantiomeric excess) or more, 95% ee or more, 98% ee or more or 99% ee or more.

The salt of the compound of formula (I) is a pharmaceutically acceptable salt of the compound of formula (I), and an acid addition salt or a salt with a base may be formed depending on the type of a substituent. Specific examples thereof include acid addition salts with inorganic acids such as hydrochloric acid, hydrobromic acid, hydroiodic acid, sulfuric acid, nitric acid and phosphoric acid, and organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid and glutamic acid; and salts with inorganic bases such as sodium, potassium, magnesium, calcium and aluminum, various amino acids such as acetylleucine, and amino acid derivatives.

Further, the present invention encompasses various hydrates, solvates and substances of crystalline polymorphism of the compounds of formula (I) and salts thereof.

Further, the present invention encompasses pharmaceutically acceptable prodrugs of compounds of formula (I). The pharmaceutically acceptable prodrug is a compound having a group which can be converted into an amino group, a hydroxyl group, a carboxyl group or the like by solvolysis or under physiological conditions. Examples of the group that forms the prodrug include groups as described in Prog. Med., 5, 2157-2161 (1985) and "Pharmaceutical research and development" (Hirokawa Shoten Co., 1990), Vol. 7, Molecular Design, 163-198.

The present invention encompasses all of compounds of formula (I) which are labeled with one or more pharmaceutically acceptable radioactive or non-radioactive isotopes, or salts thereof. Examples of preferred isotopes used for isotope labels for the compound of the present invention include isotopes of hydrogen (e.g. $^{2}H$ and $^{3}H$), carbon (e.g. $^{11}C$, $^{13}C$ and $^{14}C$), nitrogen (e.g. $^{13}N$ and $^{15}N$), oxygen (e.g. $^{15}O$, $^{17}O$ and $^{18}O$), fluorine (e.g. $^{18}F$), chlorine (e.g. $^{36}Cl$), iodine (e.g. $^{123}I$ and $^{125}I$), phosphorus (e.g. $^{32}P$) and sulfur (e.g. $^{35}S$).

The isotopically labeled compound of the invention of the present application can be used for studies on histological distributions of drugs and/or substrates. For example, radioactive isotopes such as tritium ($^{3}H$) and carbon 14 ($^{14}C$) can be used for this purpose from the viewpoint of ease of labeling and convenience of detection.

Replacement by a heavier isotope, for example replacement of hydrogen by deuterium (2H) may be therapeutically advantageous because metabolic stability is improved (e.g. increased in vivo half-life, decreased necessary dose or declined drug interaction).

Replacement by positron-emitting isotopes (e.g. $^{11}C$, $^{18}F$, $^{15}O$ and $^{13}N$) can be applied in positron emission tomography (PET) tests for examining the substrate acceptor occupancy rate.

The isotopically labeled compound of the present invention can be generally prepared by a conventional method known to those skilled in the art, or by the same preparation method as in Examples or Preparation Examples using appropriate isotopically labeled reagents instead of non-labeled reagents.

In the powder X-ray diffraction patterns described herein, crystal lattice intervals and general patterns are important due to the nature of the data for identification of crystals. Diffraction angles and diffraction intensity should not be taken in a strict sense because there may be some errors depending on the direction of crystal growth, the size of particles and the measurement conditions. Herein, the diffraction angle (2θ (°)) in the powder X-ray diffraction pattern is interpreted while an error range normally allowable in such a measurement method is taken into account. In an embodiment, the diffraction angle may be within the error range of ±0.2°. For example, when the compound is measured in a state of a mixture with an excipient, a peak which exists near a peak derived from the excipient and lies on a slope of a base line may apparently shift within the range of ±0.3°.

(Preparation Method)

The compound of formula (I) and a salt thereof can be prepared by applying various known synthesis methods by making use of characteristics based on the basic structure or the type of a substituent of the compound. Here, depending on the type of a functional group, replacement of the functional group by an appropriate protective group (group easily convertible into the functional group) during formation of an intermediate from a raw material may be effective as a preparation technique. Examples of the protective group include protective groups as described in P. G. M. Wuts and T. W. Greene, "Greene's Protective Groups in Organic Synthesis (Fourth Edition, 2006)", and according to the reaction conditions, an appropriate protective group may be selected and used. In this method, such a protective group is introduced, and a reaction is carried out, followed by removing the protective group if necessary to obtain a desired compound.

The prodrug for the compound of formula (I) can be prepared by introducing a specific group during formation of an intermediate from a raw material as in the case of the above-described protective group, or by further carrying out a reaction using the resulting compound of formula (I). The reaction can be carried out by applying a method known to those skilled in the art, such as common esterification, amidation or dehydration.

Hereinafter, a typical method for preparing the compound of formula (I) will be described. Each preparation method can be carried out by referring to the references cited in the description. The preparation method according to the present invention is not limited to the example shown below.

In the present description, the following abbreviations may be used.

- DMF=N,N-dimethylformamide, DMSO=dimethyl sulfoxide, EtOAc=ethyl acetate, EtOH=ethanol, Hex=hexane, MeCN=acetonitrile, MeOH=methanol, THF=tetrahydrofuran, DMI=1,3-dimethylimidazolidin-2-one, NMP=N-methyl-2-pyrrolidone, $CH_2Cl_2$=dichloromethane.
- Boc=tert-butoxycarbonyl, Ph=phenyl, tBu=tert-butyl, Et=ethyl, Me=methyl, Ac=acetyl, Ns=2-nitrobenzenesulfonyl.
- CDI=1,1'-carbonylbis(1H-imidazole), DCC=N,N'-dicyclohexylcarbodiimide, TEA=triethylamine, DIPEA=N,N-diisopropylethylamine, DABCO=1,4-diazabicyclo[2.2.2]octane, DPPA=diphenylphosphoryl azide, HATU=O-(7-azabenzotriazol-1-yl)-N,N,N',N'-tetramethyluronium hexafluorophosphate, HOBt=1-hydroxybenzotriazole, KOtBu=potassium tert-butoxide, NaOtBu=sodium tert-butoxide, NMM=N-methylmorpholine, Pd/C=palladium-carrying carbon, TFA=trifluoroacetic acid, TFAA=trifluoroacetic anhydride, WSC·HCl=N-[3-(dimethylamino)propyl]-N'-ethylcarbodiimide hydrochloride.
- $Pd(PPh_3)_4$=tetrakis(triphenylphosphine)palladium, $PdCl_2(PPh_3)_2$=bis(triphenylphosphine)palladium (II) dichloride, $Pd(dppf)Cl_2 \cdot CH_2Cl_2$=[1,1'-bis(diphenylphosphino)ferrocene]palladium (II) dichloride dichloromethane adduct, $Pd_2(dba)_3$=(1E,4E)-1,5-diphenylpenta-1,4-dien-3-one/palladium (3:2).
- brine=saturated NaCl aqueous solution, $MgSO_4$=anhydrous magnesium sulfate, $Na_2SO_4$=anhydrous sodium sulfate, $NaHCO_3$=sodium hydrogencarbonate, $NH_4Cl$=ammonium chloride, $NaBH(OAc)_3$=sodium triacetoxyborohydride.

[Chemical Formula 16]

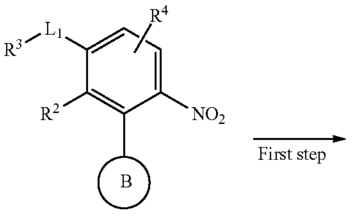

(1)

-continued

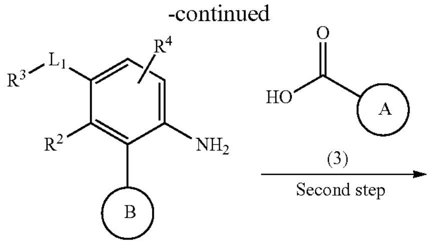

(2)

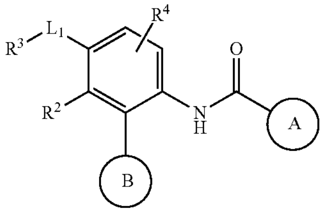

(I)

(First Step)

This step is a method in which compound (1) is subjected to a reduction reaction to obtain compound (2).

This reaction can be carried out by stirring compound (1) and a metal at room temperature or under reflux by heating under acidic conditions in a mixed solvent of MeOH, EtOH, 1,4-dioxane or the like and water for 1 hour to 5 days. As the acid, $NH_4Cl$, AcOH, HCl or the like is used. As the metal, Fe, Zn, Sn or the like is used.

In addition, this reaction can be carried out by stirring compound (1) in the presence of a metal catalyst under cooling or heating, preferably at room temperature, in a solvent inactive to the reaction, such as MeOH, EtOH or EtOAc, and a mixed solvent thereof, in a hydrogen atmosphere for 1 hour to 5 days. As the metal catalyst, palladium catalysts such as Pd/C, palladium black and palladium hydroxide-carrying carbon, platinum catalysts such as platinum-carrying carbon and platinum oxide, nickel catalysts such as reduced nickel and Raney nickel, and the like are used.

(Second Step)

This step is a method in which compound (2) and compound (3) are subjected to an amidation reaction, and substituents are then appropriately converted to obtain the compound of formula (I).

In the amidation reaction, compound (2) and compound (3) are used in such a manner that the amounts of the compounds are equal to each other, or the amount of one of the compounds is excessive, and a mixture of the compounds is stirred in the presence of a condensing agent under cooling or heating, preferably at −20° C. to 60° C., in a solvent inactive to the reaction, typically for 0.1 hours to 5 days. The solvent used here is not particularly limited, and examples thereof include aromatic hydrocarbons such as benzene, toluene and xylene, halogenated hydrocarbons such as $CH_2Cl_2$, 1,2-dichloroethane and chloroform, ethers such as diethyl ether, THF, 1,4-dioxane and 1,2-dimethoxyethane, DMF, DMSO, EtOAc, MeCN, water, and mixtures thereof. Examples of the condensing agent include, but are not limited to, WSC·HCl, DCC, CDI, DPPA and HATU. Use of an additive (e.g. HOBt) may be favorable to the reaction. It may be advantageous to carry out the reaction in the presence of an organic base such as TEA, DIPEA or NMM or an inorganic base such as $K_2CO_3$, $Na_2CO_3$ or KOH for causing the reaction to smoothly proceed.

In addition, an amidation reaction can be used in which compound (3) is converted into a reactive derivative, and then reacted with compound (2). Examples of the reactive derivative of compound (3) include acid halides obtained by reaction of the compound with a halogenating agent such as $POCl_3$ or $SOCl_2$, mixed acid anhydrides obtained by reaction of the compound with isobutyl chloroformate or the like, and active esters obtained by condensing the compound with HOBt or the like. This reaction can be carried out under cooling or under reflux by heating, preferably at −20° C. to 120° C., in a solvent inactive to the reaction, such as a halogenated hydrocarbon, an aromatic hydrocarbon or an ether.

After the amidation reaction, a protective group is introduced and/or removed if necessary, and substituents are appropriately converted to obtain the compound of formula (I).

(Synthesis of Raw Material 1)

(7) is prepared through a Buchwald-Hartwig reaction using compound (5) and an amine compound.

In this reaction, the compound is stirred at room temperature or under reflux by heating in the presence of a base and a palladium catalyst in a solvent inactive to the reaction typically for 0.1 hours to 5 days. The solvent used here is not particularly limited, and examples thereof include halogenated hydrocarbons such as $CH_2Cl_2$, 1,2-dichloroethane and chloroform, aromatic hydrocarbons such as benzene, toluene and xylene, ethers such as diethyl ether, THF, 1,4-dioxane and 1,2-dimethoxyethane, alcohols such as MeOH, EtOH, isopropyl alcohol and butanol, DMF, DMSO, MeCN, DMI, water, and mixtures thereof. Examples of the base include inorganic bases such as NaH, $K_2CO_3$, $Na_2CO_3$, $Cs_2CO_3$, $K_3PO_4$ and CsF. Examples of the palladium catalyst include $Pd(PPh_3)_4$, $PdCl_2(PPh_3)_2$, $Pd(dppf)Cl_2{\cdot}CH_2Cl_2$ and $Pd_2(dba)_3$. It may be advantageous to carry out the reaction in the presence of a ligand such as dicyclohexyl(2',

[Chemical Formula 17]

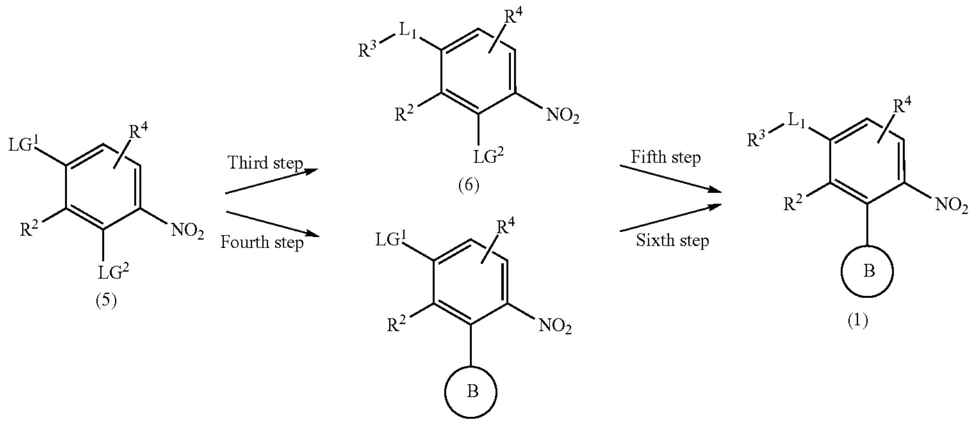

(5) (6) (7) (1)

wherein $LG^1$ and $LG^2$ each represent a leaving group; and $LG^1$ and $LG^2$ are halogens etc., and may be mutually different.

This preparation method is a method for preparing raw material compound (1).

(Third Step)

This step is a method in which compound (6) is prepared from compound (5) through an ipso-substitution reaction.

In this reaction, the compound is stirred under cooling or under reflux by heating, preferably at 0° C. to 120° C., in a solvent inactive to the reaction or under a solvent-free condition, typically for 0.1 hours to 5 days. The solvent used here is not particularly limited, and examples thereof include halogenated hydrocarbons such as $CH_2Cl_2$, 1,2-dichloroethane and chloroform, aromatic hydrocarbons such as benzene, toluene and xylene, ethers such as diethyl ether, THF, 1,4-dioxane and 1,2-dimethoxyethane, DMF, DMSO, NMP, EtOAc, MeCN, and mixtures thereof. It may be advantageous to carry out the reaction in the presence of an organic base such as TEA, DIPEA, NMM or DABCO or an inorganic base such as NaH, $K_2CO_3$, $Na_2CO_3$, $Cs_2CO_3$ or NaOtBu for causing the reaction to smoothly proceed.

(Fourth Step)

This step is a method in which compound (7) is prepared through a Suzuki coupling reaction using compound (5) and an organoboron compound, or a method in which compound 6'-dimethoxybiphenyl-2-yl)phosphine (SPhos) for causing the reaction to smoothly proceed. It may be advantageous to heat the reaction mixture by microwave irradiation for causing the reaction to smoothly proceed. As references for this reaction, for example, it is possible to refer to the following.

J. Am. Chem. Soc. 127, 4685-4696, 2005

Angew. Chem., Int. Ed. Engl. 34, 1384-1350, 1995

In addition, compound (7) can be prepared from compound (5) and an amine compound through an ipso-substitution reaction. Here, the reaction conditions are the same as in the third step.

(Fifth Step)

This step is a method in which compound (1) is prepared from compound (6) and an amine compound through an ipso-substitution reaction.

The reaction conditions are the same as in the third step.

(Sixth Step)

This step is a method in which compound (1) is prepared from compound (7) through an ipso-substitution reaction, or a method in which compound (1) is prepared through a Suzuki coupling reaction using compound (7) and an organoboron compound.

The reaction conditions in the ipso-substitution reaction are the same as in the third step. In addition, the reaction conditions in the Suzuki coupling reaction are the same as in the fourth step.

(Synthesis of Raw Material 2)

[Chemical Formula 18]

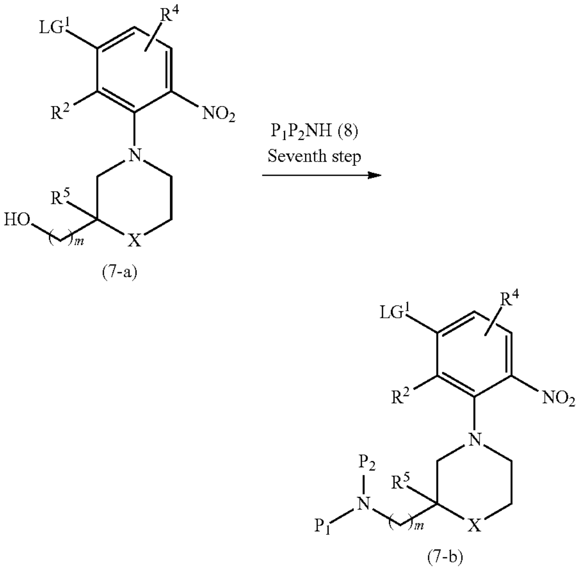

(7-a)

(7-b)

wherein $P^1$ represents H or a protective group, and $P^2$ represents a protective group.

This preparation method is a method for preparing raw material compound (7-b) which is an embodiment of compound (7) described above (in Synthesis of Raw Material 1).

(Seventh Step)

This step is a method in which compound (7-a) is oxidized, and then subjected to a reductive amination reaction with compound (8) to produce compound (7-b).

In the oxidation reaction of compound (7-a), compound (7-a) and a predetermined oxidizing agent are used in such a manner that the amounts of the compounds are equal to each other, or the amount of one of the compounds is excessive, and the mixture of the compounds is stirred under cooling with ice or under reflux by heating, in a solvent inactive to the reaction, typically for 0.1 hours to 5 days. The predetermined oxidizing agent is not particularly limited, and examples thereof include Dess-Martin periodinane. The solvent used here is not particularly limited, and examples thereof include halogenated hydrocarbons such as $CH_2Cl_2$, 1,2-dichloroethane, chloroform and carbon tetrachloride.

In the reductive amination reaction, an aldehyde obtained through the oxidation reaction and compound (8) are used in such a manner that the amounts of the compounds are equal to each other, or the amount of one of the compounds is excessive, and the mixture of the compounds is stirred in the presence of a reducing agent at −45° C. or higher or under reflux by heating, in a solvent inactive to the reaction, typically for 0.1 hours to 5 days. The solvent used here is not particularly limited, and examples thereof include alcohols such as MeOH and EtOH, ethers such as diethyl ether, THF, 1,4-dioxane and dimethoxyethane, and mixtures thereof. Examples of the reducing agent include sodium cyanoborohydride, sodium triacetoxyborohydride and sodium borohydride. It may be preferable to carry out the reaction in the presence of a dehydrating agent such as molecular sieves, or an acid such as acetic acid, hydrochloric acid or a titanium (IV) isopropoxide complex.

(Synthesis of Raw Material 3)

[Chemical Formula 19]

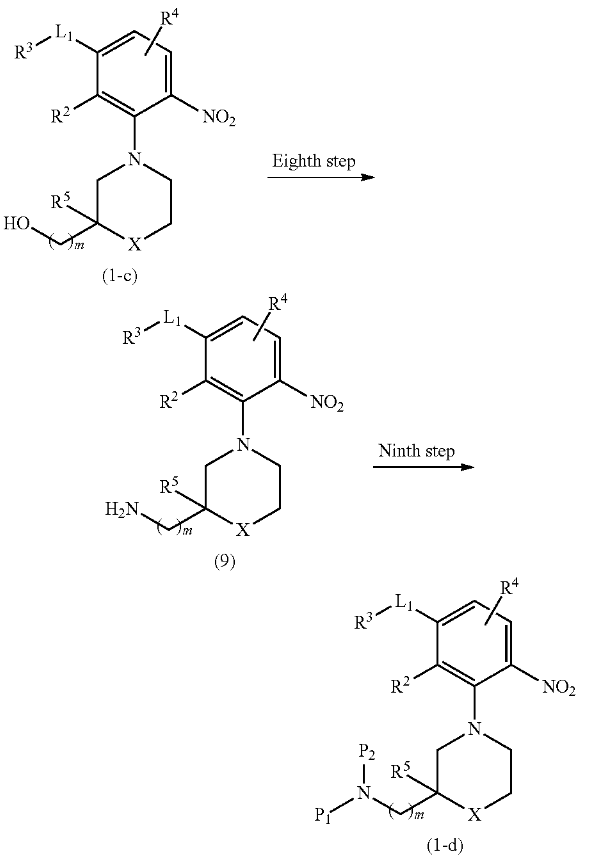

(1-c)

(9)

(1-d)

wherein $P^1$ represents H or a protective group, and $P^2$ represents a protective group.

This preparation method is a method for preparing compound (1-d) which is an embodiment of compound (1) described above (in Synthesis of Raw Material 1).

(Eighth Step)

This step is a method in which a leaving group is introduced into compound (1-c), and compound (1-c) is then subjected to a Gabriel amine reaction to produce compound (9). In this reaction, a compound obtained by reacting compound (1-c) with a halogenated sulfonyl compound such as MsCl or TsCl or an acid anhydride such as methanesulfonic anhydride or p-toluenesulfonic anhydride in the presence of a base in a solvent inactive to the reaction and potassium phthalimide are used in such a manner that the amounts of the compounds are equal to each other, or the amount of one of the compounds is excessive, and the mixture of the compounds is stirred in the presence of a base under cooling with ice or under reflux by heating, preferably at 0° C. to 120° C., in a solvent inactive to the reaction, typically for 0.1 hours to 5 days. The solvent is not particularly limited, and examples thereof include aromatic hydrocarbons such as toluene, ethers such as 1,4-dioxane, halogenated hydrocarbons such as $CH_2Cl_2$, DMF, DMSO, EtOAc, MeCN and mixtures thereof. Examples of the base include organic bases such as TEA, DIPEA and NMM, and inorganic bases such as K2CO3, Na2CO3 and KOH.

After the above reaction, compound (9) can be obtained through deprotection of phthalimide using hydrazine in a solvent inactive to the reaction.

As references for this reaction, for example, it is possible to refer to the following.

Angew. Chem., Int. Ed. Engl. 7, 919-930, 1968

(Ninth Step)

This step is a method in which a protective group is introduced from compound (9) to produce compound (1-d).

Examples of the protective group used in this reaction include protective groups as described in P. G. M. Wuts and T. W. Greene, “Greene's Protective Groups in Organic Synthesis (Fourth Edition, 2006)”, and according to the reaction conditions, an appropriate protective group may be selected and used.

(Synthesis of Raw Material 4)

[Chemical Formula 20]

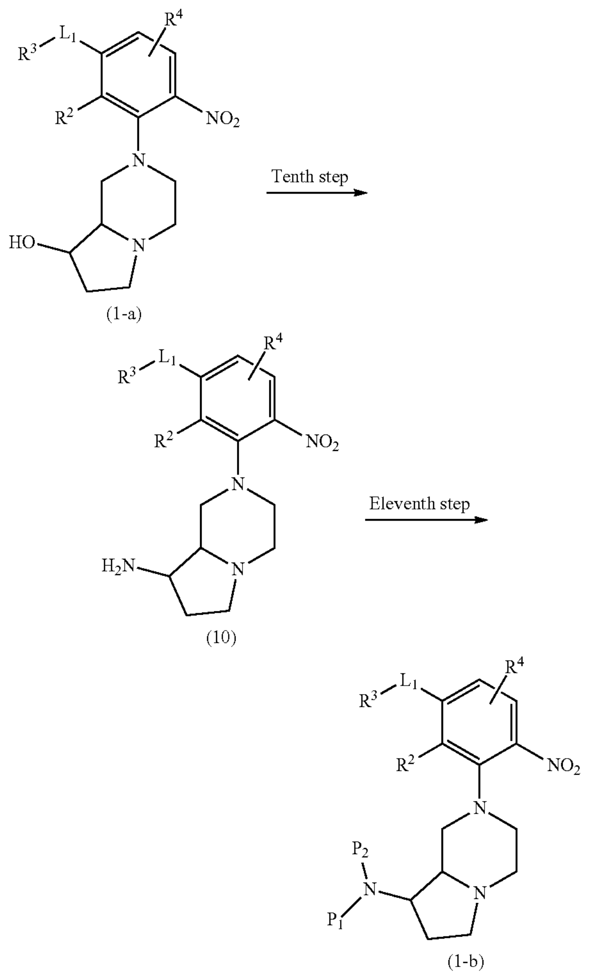

(1-a)

(10)

(1-b)

wherein $P_1$ represents H or a protective group, and $P_2$ represents a protective group.

This preparation method is a method for preparing compound (1-b) which is an embodiment of compound (1) described above (in Synthesis of Raw Material 1).

(Tenth Step)

This step is a method in which a Mitsunobu reaction of compound (1-a) with phthalimide is carried out, and the reaction product is then subjected to deprotection of phthalimide groups to produce compound (10).

In the Mitsunobu reaction of compound (1-a), compound (1-a) and phthalimide are used in such a manner that the amounts of the compounds are equal to each other, or the amount of one of the compounds is excessive, and the mixture of the compounds is stirred in the presence of a known diazo-carboxylic acid ester or diazo-carboxylic amide and a known phosphine under cooling or under reflux by heating, preferably at 0° C. to 150° C., in a solvent inactive to the reaction, typically for 0.1 hours to 5 days. The solvent used here is not particularly limited, and examples thereof include aromatic hydrocarbons, ethers, halogenated hydrocarbons, DMF, DMSO, EtOAc, MeCN and mixtures thereof.

After the above reaction, compound (10) can be obtained through deprotection of phthalimide using hydrazine in a solvent inactive to the reaction.

As references for the above Mitsunobu reaction, for example, it is possible to refer to the following.

Synthesis (1981), 1

(Eleventh Step)

This step is a method in which a protective group is introduced from compound (10) to produce compound (1-b).

The reaction conditions are the same as in the ninth step.

The compound of formula (I) is isolated as a free compound, or a salt, a hydrate, a solvate or a crystal-polymorphic substance thereof, and purified. The salt of the compound of formula (I) can be prepared by subjecting the compound to a conventional salt formation reaction.

The isolation and purification are performed by applying normal chemical operations such as extraction, fractional crystallization and various kinds of chromatography.

Various isomers can be prepared by selection of an appropriate raw material compound, or separated by making use of a difference in physicochemical properties between isomers. For example, optical isomers can be obtained by a general method for optically resolving racemates (e.g. fractional crystallization to derive a diastereomer salt with an optically active base or acid, or chromatography using a chiral column), or prepared from an appropriate optically active raw material compound.

The pharmacological activity of the compound of formula (I) can be confirmed through the following test, or a known improvement test. In the present description, the dose of a test compound is shown in terms of a weight in a free form. When a commercially available reagent, kit or the like is used, the test can be conducted in accordance with the instructions of the commercially available product.

Test Example 1: Evaluation of DGK Inhibitory Effect

The inhibitory effect of a test compound on human recombinant DGK ξ (Carna Biosciences, Inc., 12-410-20N) was examined by the following method in which detection is performed with ADP-Glo™ Kinase Assay (Promega Corporation).

To a 384-well plate (Greiner Bio-One Co., Ltd.), 3 μL of a DGK ξ enzyme dissolved in an assay buffer (40 mM Tris-HCl pH 7.5, 10 mM $MgCl_2$, 1 mM dithiothreitol (DTT) and 0.1 mg/mL bovine serum albumin (BSA)) (90 ng/mL) was added, and 3 μL of the test compound diluted with the same assay buffer was added so that an intended final concentration was obtained. The mixture was left standing at room temperature for 15 minutes, 3 μL of a substrate (150 μM 1-oleoyl-2-acetyl-sn-glycerol (Sigma-Aldrich Co. LLC), 480 μM phosphatidylserine (Avanti, Inc.) and 150 μM UltraPure-ATP (attached to ADP-Glo)) was then added, and the mixture was left standing at room temperature for 30 minutes to react. Thereafter, 3 μL of an ADP-Glo Reagent was added, and the mixture was left standing at room temperature for 40 minutes to stop the enzyme reaction. Further, 6 μL of a Kinase-Detection Reagent was added, the mixture was left standing at room temperature for 30 minutes, and the luminescence was then measured using ARVO X3 (PerkinElmer, Inc.). The half maximal inhibitory concentration ($IC_{50}$) was calculated by Sigmoid-Emax model non-linear regression analysis, where the signal value in solvent treatment was set to 0% inhibition and the signal value without addition of the DGK ξ enzyme was set to 100% inhibition. Table 1 shows the results for some test compounds of formula (I). In the table, Ex represents the number of each Example described below.

TABLE 1

| Ex | $IC_{50}$ (nM) |
|---|---|
| 1 | 16 |
| 2 | 28 |
| 3 | 150 |
| 4 | 170 |
| 5 | 330 |
| 6 | 57 |
| 7 | 190 |
| 8 | 88 |
| 9 | 9.3 |
| 10 | 93 |
| 11 | 35 |
| 12 | 30 |
| 13 | 18 |
| 14 | 150 |
| 15 | 99 |
| 16 | 73 |
| 17 | 190 |
| 18 | 130 |
| 19 | 960 |
| 20 | 20 |
| 21 | 1100 |
| 22 | 18 |
| 23 | 63 |
| 24 | 36 |
| 25 | 73 |
| 26 | 19 |
| 27 | 37 |
| 28 | 240 |
| 29 | 10 |
| 30 | 7.7 |
| 31 | 23 |
| 32 | 100 |
| 33 | 4.8 |
| 34 | 3.1 |
| 35 | 45 |
| 36 | 55 |
| 37 | 23 |
| 38 | 4.1 |
| 39 | 39 |
| 40 | 5.2 |
| 41 | 5.0 |
| 42 | 150 |
| 43 | 30 |
| 44 | 8.6 |
| 45 | 12 |
| 46 | 3.1 |
| 47 | 6.7 |
| 48 | 5.8 |
| 49 | 7.8 |
| 50 | 55 |
| 51 | 17 |
| 52 | 46 |
| 53 | 29 |
| 54 | 12 |
| 55 | 12 |
| 56 | 0.89 |
| 57 | 0.42 |
| 58 | 21 |
| 59 | 11 |

TABLE 1-continued

| Ex | $IC_{50}$ (nM) |
|---|---|
| 60 | 27 |
| 61 | 46 |
| 62 | 6.9 |
| 63 | 70 |
| 64 | 13 |
| 65 | 22 |
| 66 | 180 |
| 67 | 35 |
| 68 | 24 |
| 69 | 60 |
| 70 | 55 |
| 71 | 21 |
| 72 | 62 |
| 73 | 43 |
| 74 | 16 |
| 75 | 69 |
| 76 | 7.6 |
| 77 | 5.6 |
| 78 | 1.3 |
| 79 | 7.8 |
| 80 | 45 |
| 81 | 110 |
| 82 | 31 |
| 83 | 3.5 |
| 84 | 2.1 |
| 85 | 5.2 |
| 86 | 2.9 |
| 87 | 4.1 |
| 88 | 110 |
| 89 | 27 |
| 90 | 4.9 |
| 91 | 25 |
| 92 | 92 |
| 93 | 2.8 |
| 94 | 1.4 |
| 95 | 3.8 |
| 96 | 30 |
| 97 | 12 |
| 98 | 7.5 |
| 99 | 33 |
| 100 | 60 |
| 101 | 69 |
| 102 | 210 |
| 103 | 46 |
| 104 | 37 |
| 105 | 46 |
| 106 | 7.5 |
| 107 | 220 |
| 108 | 8.9 |
| 109 | 110 |
| 110 | 190 |
| 111 | 280 |
| 112 | 52 |
| 113 | 21 |
| 114 | 37 |
| 115 | 7.9 |
| 116 | 44 |
| 117 | 20 |
| 118 | 1.4 |
| 119 | 41 |
| 120 | 4.3 |
| 121 | 14 |
| 122 | 3.2 |
| 123 | 4.0 |
| 124 | 3.8 |
| 125 | 1.8 |
| 126 | 6.2 |

Test Example 2: Evaluation of IL-2 Production in Human T-Cell Leukemia Cell Line Jurkat E6.1

The effect of the test compound on the IL-2 production by T-cell receptor (TCR) stimulation (anti-CD3/anti-CD28) in Jurkat E6.1 cells (ECACC, 88042803) was evaluated.

A 5 μg/mL anti-CD3 antibody (eBioscience, Inc., OKT3 clone) diluted with phosphate buffer saline (PBS) was added to a 96-well plate (Iwaki & Co., Ltd.) at 50 μL/well, and left standing at 4° C. for 12 hours or more to provide an anti-CD3 antibody-coated plate in advance. When the plate was used for experiments, the plate was washed with 200 μL of PBS once, an anti-CD28 antibody (eBioscience, Inc., 28.2 clone) diluted to a concentration of 10 μg/mL with a culture medium (RPMI1640 (Sigma-Aldlich Co. LLC.) containing 10% fetal bovine serum (Hyclone Laboratories, Inc.)) was then added at 10 μL/well, and the plate was used for assay as a culture plate for TCR stimulation.

Subsequently, the test compound was mixed with Jurkat E6.1 cells in such a manner that an intended final concentration was obtained, and the mixture was plated at 90 μL/well so that the number of cells per well was $1\times10^5$ (that is, finally the culture was performed at $1\times10^5$ cells/100 μL/well). For culture cell conditions, the culture was performed at 37° C. in the presence of 5% $CO_2$ using RPMI1640 medium containing 10% fatal bovine serum.

After 24 hours, the culture supernatant was collected, and IL-2 was quantitatively determined using AlphaLISA human IL2 Immunoassay Research Kit (PerkinElmer, Inc.). The IL-2 measurement was performed under Alpha Screen standard setting conditions (the fluorescence intensity at 570 nm was measured with an excitation wavelength of 680 nm) using EnVision 2104-0010 and EnVision 2104-0020 (PerkinElmer, Inc.). The IL-2 quantitative value of the solvent treatment control was set to 1, and the test compound concentration at which the IL-2 quantitative value of the test compound treatment sample increased to 10 times the IL-2 quantitative value of the control ($EC_{10fold}$) was calculated by inverse estimation with the aid of Sigmoid-Emax model non-linear regression analysis. Table 2 shows the results for some test compounds of formula (I). In the table, Ex represents the number of each Example described below.

TABLE 2

| Ex | $EC_{10fold}$ (nM) |
|---|---|
| 1 | 110 |
| 13 | 340 |
| 20 | 36 |
| 29 | 40 |
| 45 | 8.1 |
| 47 | 72 |
| 48 | 35 |
| 80 | 460 |
| 86 | 24 |
| 122 | 110 |
| 123 | 26 |
| 124 | 410 |
| 125 | 56 |
| 126 | 31 |

Test Example 3: Evaluation of Antitumor Effect in Syngeneic Mouse Model Bearing Mouse Melanoma Cell Line B16-F1

A cell suspension liquid prepared by suspending B16-F1 cells (ATCC, CRL-6323) in PBS at $2.0\times10^6$ cells/mL was subcutaneously inoculated into 5-week-old female mice (C57BL/6J from Charles River Laboratories Japan, Inc.) in a volume of 50 μL. 5 days after the inoculation, the mice were grouped in such a manner that there was substantially no difference in tumor volume between groups, and administration of the test compound was started. The test was conducted with a solvent group and a test compound administration group each having 10 mice. 0.5% methylcellulose (Shin-Etsu Chemical Co., Ltd.) was orally administered to the solvent group, and 0.5% methylcellulose mixed with the test compound was orally administered to the test compound administration group. The administration was performed for 10 days once daily, and the tumor diameter and the body weight were measured twice a week. The following expression was used for calculation of the tumor volume.

$$[\text{tumor volume (mm}^3)]=[\text{tumor major diameter (mm)}]\times[\text{tumor minor diameter (mm)}]^2\times0.5$$

The relative tumor growth inhibition (%) of the test compound was calculated, where the tumor volume of the solvent group immediately before the start of administration was set to 100% inhibition, and the tumor volume of the solvent group on the day after the last administration was set to 0% inhibition. Table 3 shows the results for some test compounds of formula (I). In the table, Ex represents the number of each Example described below.

TABLE 3

| Ex | Dose (mg/kg) | Antitumor effect |
|---|---|---|
| 1 | 0.03 | 35% inhibition |
| 13 | 0.3 | 36% inhibition |
| 20 | 0.3 | 33% inhibition |
| 29 | 0.3 | 41% inhibition |
| 45 | 0.03 | 30% inhibition |
| 47 | 0.3 | 42% inhibition |
| 48 | 0.3 | 40% inhibition |
| 80 | 0.3 | 31% inhibition |
| 86 | 0.3 | 31% inhibition |

The results of the above test showed that some compounds of formula (I) had DGK ξ inhibitory effect (Test Example 1). In addition, some compounds of formula (I) were confirmed to cause IL-2 production in the human T-cell leukemia cell line (Test Example 2). Further, some compounds of formula (I) were confirmed to have antitumor effect in the mouse model (Test Example 3). In particular, B16-F1 cells used in Test Example 3 are cells on which an anti-PD-1 antibody/anti-PD-L1 antibody is generally known to have no pharmacological efficacy in B16-F1 cells. Even in the mouse model bearing the cells, some compounds of formula (I) were confirmed to have antitumor effect. Therefore, a compound of formula (I) can be used for treatment of, for example, cancer related to activation of immune cells or cancer resistant to anti-PD-1 antibody/anti-PD-L1 antibody therapy, particularly cancer related to activation of immune cells, which has resistance to anti-PD-1 antibody/anti-PD-L1 antibody therapy, etc.

A pharmaceutical composition containing one or more of the compounds of formula (I) or salts thereof as active ingredients can be prepared by a commonly used method with an excipient commonly used in the art, i.e. an excipient for pharmaceutical use, a carrier for pharmaceutical use, or the like.

The administration may be either oral administration with tablets, pills, capsules, granules, powders, solutions or the like, or parenteral administration with injection preparations for intraarticular injection, intravenous injection, intramuscular injection or the like, suppositories, eye-drops, eye ointments, transdermal solutions, ointments, transdermal patches, transmucosal solutions, transmucosal patches, inhalations or the like.

As a solid composition for oral administration, a tablet, a powder, a granule or the like is used. In such a solid composition, one or more active ingredients are mixed with at least one inactive excipient. The composition may conventionally contain inactive additives, for example a lubricant, a disintegrant, a stabilizer and a solubilizing agent. The tablet, powder, granule or pill may be coated with a wax, a sugarcoating or a stomach-soluble or enteric substance film.

Liquid compositions for oral administration include pharmaceutically acceptable emulsions, solutions, suspensions, syrups or elixirs, and contain a commonly used inactive diluents, for example purified water or ethanol. Such a liquid composition may contain adjuvants such as a solubilizer, a wetting agent and a suspension, a sweetening agent, a flavor, a fragrance and a preservative in addition to the inactive diluent.

The injection preparation for parenteral administration contains a sterile aqueous or nonaqueous solution, a suspension or an emulsion. Examples of the aqueous solvent include distilled water for injection of physiological saline solutions. Examples of the nonaqueous solvent include alcohols such as ethanol. Such a composition may further contain a tonicity agent, a preservative, a wetting agent, an emulsifier, a dispersant, a stabilizer or a solubilizing agent. The composition is sterilized by, for example, filtration involving passage through a bacteria retention filter, addition of a bactericide or irradiation. In addition, a sterile solid composition can be prepared, and dissolved or suspended in sterile water or a sterile solvent for injection before use.

The external preparation encompasses ointments, plasters, creams, gelatinous preparations, cataplasms, sprays, lotions, eye-drops, and eye ointments. The external preparation contains a commonly used ointment base, lotion base, aqueous or nonaqueous solution, suspension, emulsion or the like.

The transmucosal preparation such as an inhalation or a nasal preparation is solid, liquid or semisolid, and can be prepared in accordance with a known conventional method. For example, a known excipient, and a pH adjuster, a preservative, a surfactant, a lubricant, a stabilizer, a thickener and the like may be added to the transmucosal preparation, as appropriate. For administration, an appropriate device for inhalation or insufflation can be used. For example, using a known device such as a metered administration/inhalation device, or a sprayer, the compound can be administered alone, as powder of a prescribed mixture, or a solution or suspension liquid obtained by combining the compound with a pharmaceutically acceptable carrier. The dry powder inhaler or the like may be one for single-dose administration or multi-dose administration, and enables use of dry powder or a dry powder-containing capsule, or may be in the form of a press aerosol spray using an appropriate ejection agent, for example a suitable gas such as a chlorofluoroalkane or carbon dioxide.

Normally, in the case of oral administration, the appropriate daily dose per body weight is about 0.001 to 100 mg/kg, preferably 0.1 to 30 mg/kg, more preferably 0.1 to 10 mg/kg, in a single dose or 2 to 4 divided doses. In the case of intravenous administration, the appropriate daily dose per body weight is about 0.0001 to 10 mg/kg in a single dose or two or more divided doses. In the case of transmucosal administration, the daily dose per body weight is about 0.001 to 100 mg/kg in a single dose or two or more divided doses. The dose is appropriately determined with consideration given to a symptom, an age, a sex and the like.

Depending on an administration route, a dosage form, an administration site, and types of excipients and additives, the pharmaceutical composition according to the present invention contains one or more compounds of formula (I) or salts thereof as active ingredients in an amount of 0.01 to 100 wt %, or 0.01 to 50 wt % in an embodiment.

The compound of formula (I) can be used in combination with various therapeutic agents or prophylactic agents for diseases against which the compound of formula (I) may be effective. The combined use may be simultaneous administration, separate and sequential administration, or administration at a desired time interval. Preparations for simultaneous administration may be in the form of a combination preparation, or may be separately formulated preparations.

EXAMPLES

Hereinafter, the method for preparing the compound of formula (I) will be described in more detail by way of Examples. The present invention is not limited to the compounds described in Examples. Methods for preparing raw material compounds will be shown in preparation examples. The method for preparing the compound of formula (I) is not limited to the specific methods of Examples shown below, and the compound of formula (I) can be also prepared by a combination of these preparation methods, or methods obvious to those skilled in the art.

In the present description, naming software such as ACD/Name (registered trademark)(Advanced Chemistry Development, Inc.) may be used for naming a compound.

For convenience, mol/l as a unit of concentration is represented by M. For example, the 1 M sodium hydroxide aqueous solution means a sodium hydroxide aqueous solution at 1 mol/l.

The powder X-ray diffraction results described herein are obtained by measurement performed under the conditions of bulb: Cu, tube current: 40 mA, tube voltage: 45 kV, step width: 0.013°, wavelength: 1.5418 angstrom and measurement diffraction angle range (2θ): 2.5 to 40° using Empyrean.

Preparation Example 1

To a mixture of 2-bromo-1-chloro-3-fluoro-4-nitrobenzene (1.0 g), TEA (1.2 g) and THF (10 ml) was added tert-Butyl (2R)-2-(hydroxymethyl)piperazine-1-carboxylate (935 mg), and the resulting mixture was stirred at room temperature for 16 hours. Water was added, and the resulting mixture was extracted with EtOAc three times. The combined organic layers were dried over $Na_2SO_4$ and concentrated under reduced pressure. The residue was purified by silica gel column chromatography (Hex/EtOAc) to give tert-butyl (2R)-4-(2-bromo-3-chloro-6-nitrophenyl)-2-(hydroxymethyl)piperazine-1-carboxylate (1.8 g) as a solid substance.

Preparation Example 2

A mixture of 2-bromo-4-fluoro-1-nitro-3-(trifluoromethyl)benzene (3.00 g), 2-fluorophenol (1.00 mL), potassium carbonate (2.88 g) and NMP (30 mL) was stirred at 50° C. overnight. The mixture was allowed to cool to room temperature, water, EtOAc and brine were then added, and the aqueous layer was separated. The aqueous layer was extracted with EtOAc, and the combined organic layers were dried over $MgSO_4$, and concentrated under reduced pressure. The residue was purified by silica gel chromatography (Hex/EtOAc) to give 2-bromo-4-(2-fluorophenoxy)-1-nitro-3-(trifluoromethyl)benzene (3.43 g).

Preparation Example 16

To a mixture of 2-bromo-4-fluoro-1-nitro-3-(trifluoromethyl)benzene (0.758 g), tert-butyl {2-[3-(4,4,5,5-tetramethyl-1,3,2-dioxabororan-2-yl)phenoxy]ethyl}carbamate (2.844 g), potassium carbamate (0.910 g), 1,4-dioxane (20 mL) and water (4 mL) was added Pd(dppf)$Cl_2$·$CH_2Cl_2$ (0.215 g), and the resulting mixture was stirred at 110° C. for 5 hours under an argon atmosphere. The reaction was allowed to cool to room temperature, and then poured into water, and the resulting mixture was extracted with EtOAc. The organic layer was separated, the aqueous layer was extracted with EtOAc, and the combined organic layers were washed with brine, then dried over $Na_2SO_4$, and concentrated under reduced pressure. The residue was purified by silica gel column chromatography (Hex/EtOAc) to give tert-butyl (2-{[3'-fluoro-6'-nitro-2'-(trifluoromethyl)[1,1'-biphenyl]-3-yl]oxy}ethyl)carbamate (0.502 g).

Preparation Example 20

To a mixed solution of (8S)-8-hydroxyhexahydropyrrolo[1,2-a]pyrazine-1,4-dione (3.250 g), DMF (48 mL) and imidazole (3.972 g) was added tert-Butylchlorodiphenylsilane (10.0 mL), and the resulting mixture was stirred at room temperature for 23 hours. The reaction liquid was poured into water, and the resulting mixture was extracted with EtOAc. The organic layer was separated, the aqueous layer was extracted with EtOAc, and the combined organic layers were washed with water and brine. The organic layers were dried over $Na_2SO_4$ and concentrated under reduced pressure. The residue was purified by silica gel column chromatography (EtOAc/MeOH) to give (8S,8aS)-8-{[tert-butyldi(phenyl)silyl]oxy}hexahydropyrrolo[1,2-a]pyrazine-1,4-dione (1.786 g) as a low-polarity substance and (8S,8aR)-8-{[tert-butyldi(phenyl)silyl]oxy}hexahydropyrrolo[1,2-a]pyrazine-1,4-dione (1.164 g) as a high-polarity substance.

Preparation Example 21

To a mixed liquid of lithium aluminum hydride (0.594 g) and THF (40 mL) was added a solution of (8S,8aR)-8-{[tert-butyldi(phenyl)silyl]oxy}hexahydropyrrolo[1,2-a]pyrazine-1,4-dione (1.164 g) in THF (10 mL), and the resulting mixture was stirred at reflux for 17 hours. The reaction suspension liquid was allowed to cool to room temperature, a mixed liquid of water (0.7 mL) and THF (7.7 mL) and a 4 N sodium hydroxide aqueous solution (0.7 mL) was then added, $Na_2SO_4$ was then added, and the resulting mixture was stirred at room temperature for 3 hours, and filtered with celite. The filtrate was concentrated under reduced pressure to give (8S,8aS)-octahydropyrrolo[1,2-a]pyrazin-8-ol (0.972 g), which was used in the next step without further purification.

Preparation Example 23

To a mixture of 2-bromo-4-fluoro-1-nitro-3-(trifluoromethyl)benzene (1.00 g), cyclopentanol (380 μL) and THF (10 mL) was added sodium hydride (60% oil dispersion, 181 mg) under ice-bath cooling under an argon atmosphere, and the resulting mixture was stirred at room temperature for 3 hours. Under ice-bath cooling, water was added, the resulting mixture was extracted with EtOAc, and the extract was washed with brine, dried over $MgSO_4$, and concentrated under reduced pressure. The residue was purified by silica gel column chromatography (Hex/EtOAc) to give 2-bromo-4-(cyclopentyloxy)-1-nitro-3-(trifluoromethyl)benzene (935 mg).

Preparation Example 33

To a mixture of [(2S)-4-benzylpiperazin-2-yl]methanol dihydrochloride (5.76 g), a 37% formaldehyde aqueous solution (3.35 mL), sodium acetate (3.38 g) and THF (60 mL) was added $NaBH(OAc)_3$ (8.74 g) under ice-bath cooling, and the resulting mixture was stirred at room temperature for 6 hours. A saturated $NaHCO_3$ aqueous solution was added until bubbles were eliminated, and the resulting mixture was extracted with EtOAc. A 5 M sodium hydroxide aqueous solution was added to the aqueous layer, and the resulting mixture was extracted with diethyl ether twice. The combined organic layers were dried over $Na_2SO_4$, and concentrated under reduced pressure to give [(2S)-4-benzyl-1-methylpiperazin-2-yl]methanol (4.48 g).

Preparation Example 34

A solution of [(2R)-4-benzyl-1-methylpiperazin-2-yl]methanol (5.27 g), TEA (6.7 mL) and THF (100 mL) was cooled in an ice-MeOH bath, and methanesulfonyl chloride (1.96 mL) was then slowly added. The resulting mixture was stirred under ice-bath cooling for 1 hour, a 40% methylamine aqueous solution (40 mL) was added, and the resulting mixture was then stirred at 70° C. for 3 hours, and allowed to cool. The reaction liquid was then concentrated under reduced pressure, water and $CH_2Cl_2$ were added to the residue, and the aqueous layer was separated. The aqueous layer was extracted with $CH_2Cl_2$ twice, and the combined organic layers were dried over $Na_2SO_4$, and then concentrated under reduced pressure.

The resulting oily substance (4.95 g) was dissolved in $CH_2Cl_2$ (100 mL), and di-tert-butyl dicarbonate (11 g) was added under ice-bath cooling. The resulting mixture was stirred at room temperature for 2 hours. $CH_2Cl_2$ and water were added to the reaction mixture, and the aqueous layer was separated. The aqueous layer was extracted with $CH_2Cl_2$, and the combined organic layers were dried over $Na_2SO_4$, and then concentrated under reduced pressure. The residue was purified by silica gel column chromatography (aqueous ammonia/MeOH/chloroform) to give tert-butyl {[(2R)-4-benzyl-1-methylpiperazin-2-yl]methyl}(methyl)carbamate (5.92 g).

Preparation Example 36

To a solution of tert-butyl {[(2R)-4-benzyl-1-methylpiperazin-2-yl]methyl}(methyl)carbamate (4.92 g) and EtOH (100 mL) was added activated carbon (500 mg), and the resulting mixture was stirred at room temperature for 10 minutes. The mixture was filtered with celite, and the filtrate was then concentrated under reduced pressure. To the resulting solution of an oily substance and EtOH (100 mL) was added 10% Pd/C (hydrous, 510 mg) under a nitrogen atmosphere. The reaction mixture was stirred under a hydrogen atmosphere at room temperature for 24 hours. The reaction mixture was filtered with celite, and the filtrate was then concentrated under reduced pressure to give tert-butyl methyl{[(2R)-1-methylpiperazin-2-yl]methyl}carbamate (3.43 g).

Preparation Example 38

To a mixture of 1-bromo-3-fluoro-4-nitro-2-(trifluoromethyl)benzene (500 mg), 2-fluorophenylboronic acid (316 mg), cesium carbonate (1.13 g), 1,4-dioxane (6 mL) and water (1.7 mL) was added Pd(dppf)$Cl_2$·$CH_2Cl_2$ (142 mg). The resulting mixture was stirred at 120° C. for 30 minutes under microwave irradiation, allowed to cool, then diluted with EtOAc, filtered with celite, and concentrated under reduced pressure. The residue was purified by silica gel column chromatography (Hex/EtOAc) to give 2'3-difluoro-4-nitro-2-(trifluoromethyl)-1,1'-biphenyl (403 mg).

Preparation Example 39

A mixture of tert-butyl methyl{[(2R)-1-methylpiperazin-2-yl]methyl}carbamate (735 mg), 2-bromo-4-(2-fluorophenoxy)-1-nitro-3-(trifluoromethyl)benzene (1.15 g), potassium carbonate (627 mg) and 1,4-dioxane (5.75 mL) was stirred at 110° C. for 24 hours, and allowed to cool. The reaction mixture was then diluted with EtOAc. The mixture was filtered with celite, and the filtrate was then concentrated under reduced pressure. The residue was purified by silica gel column chromatography (Hex/EtOAc) to give tert-butyl ({(2R)-4-[3-(2-fluorophenoxy)-6-nitro-2-(trifluoromethyl)phenyl]-1-methylpiperazin-2-yl}methyl)(methyl) carbamate (1.31 g).

Preparation Example 60

To a solution of 1-bromo-3-fluoro-4-nitro-2-(trifluoromethyl)benzene (2.07 g) in THF (21 mL) were added tert-butyl (2R)-2-(hydroxymethyl)piperazine-1-carboxylate (1.55 g) and TEA (1.10 mL) sequentially under ice-bath cooling. The reaction mixture was stirred under ice-bath cooling for 1 hour, and then stirred at room temperature for 64 hours. EtOAc and water were added to the reaction mixture, and the aqueous layer was separated. The aqueous layer was extracted with EtOAc, and the combined organic layers were washed with water and brine, dried over $Na_2SO_4$, and then concentrated under reduced pressure. The residue was purified by silica gel column chromatography (Hex/EtOAc) to give tert-butyl (2R)-4-[3-bromo-6-nitro-2-(trifluoromethyl)phenyl]-2-(hydroxymethyl)piperazine-1-carboxylate (2.27 g) as a solid substance.

Preparation Example 75

To a solution of tert-butyl (2R)-4-[3-bromo-6-nitro-2-(trifluoromethyl)phenyl]-2-(hydroxymethyl)piperazine-1-carboxylate (2.27 g) in $CH_2Cl_2$ (15.6 mL) was added a Dess-Martin reagent (2.98 g) under ice-bath cooling, and the resulting mixture was stirred at room temperature for 3 hours. A 10% sodium sulfite aqueous solution and a saturated $NaHCO_3$ aqueous solution were added under ice-bath cooling, and the resulting mixture was stirred at room temperature for 30 minutes. The aqueous layer was separated, and the aqueous layer was extracted with $CH_2Cl_2$. The combined organic layers were washed with brine, dried over $Na_2SO_4$, and concentrated under reduced pressure to give tert-butyl (2R)-4-[3-bromo-6-nitro-2-(trifluoromethyl)phenyl]-2-formylpiperazine-1-carboxylate (2.20 g) as a solid substance.

Preparation Example 91

To a solution of (1S,2R,5S)-5-methyl-2-(propan-2-yl)cyclohexyl (3S)-3-fluoro-2-oxopiperizine-3-carboxylate (2.6 g) in THF (29 mL) was added a borane-THF complex (0.91 M THF solution, 29 mL) under an argon atmosphere, and the resulting mixture was stirred at 70° C. overnight, and allowed to cool to room temperature. MeOH (30 mL) and 2 M hydrochloric acid (30 mL) were then added, and the resulting mixture was stirred at 60° C. for 1 hour, and concentrated under reduced pressure by azeotropic distillation with toluene. To a solution of the resulting residue in NMP (52 mL) were added 2-bromo-4-(2-fluorophenoxy)-1-nitro-3-(trifluoromethyl)benzene (2.3 g) and potassium carbonate (3 g), and the resulting mixture was stirred at 120° C. overnight. 2-Bromo-4-(2-fluorophenoxy)-1-nitro-3-(trifluoromethyl)benzene (730 mg) was added, and the resulting mixture was stirred at 120° C. overnight. The resulting mixture was diluted with EtOAc, washed with water and brine, and then dried over $MgSO_4$. The solvent was concentrated under reduced pressure, and the resulting residue was purified by silica gel column chromatography (Hex/EtOAc) to give {(3S)-3-fluoro-1-[3-(2-fluorophenoxy)-6-nitro-2-(trifluoromethyl)phenyl]piperizin-3-yl}methanol (1.9 g).

Preparation Example 92

To a mixture of tert-butyl (2R)-4-[3-bromo-6-nitro-2-(trifluoromethyl)phenyl]-2-formylpiperazine-1-carboxylate (2.20 g), a 2 M methylamine/THF solution (4.56 mL), acetic acid (522 μL) and $CH_2Cl_2$ (22 mL) was added $NaBH(OAc)_3$ (1.93 g), and the resulting mixture was stirred at room temperature for 16 hours. A saturated $NaHCO_3$ aqueous solution was added, and the resulting mixture was stirred at room temperature for 1 hour. The aqueous layer was separated, and extracted with $CH_2Cl_2$, and the combined organic layers were washed with brine, dried over $Na_2SO_4$, and concentrated under reduced pressure. The residue was purified by silica gel column chromatography (Hex/EtOAc+chloroform/MeOH) to give tert-butyl (2S)-4-[3-bromo-6-nitro-2-(trifluoromethyl)phenyl]-2-[(methylamino)methyl]piperazine-1-carboxylate (1.91 g).

Preparation Example 108

To a mixture of tert-butyl (2S)-4-[3-bromo-6-nitro-2-(trifluoromethyl)phenyl]-2-[(methylamino)methyl]piperazine-1-carboxylate (1.91 g), DIPEA (1.97 mL) and $CH_2Cl_2$ (19.1 mL) was added TFAA (1.08 mL) slowly under ice-bath cooling, and the resulting mixture was stirred at room temperature for 2 hours. A saturated $NH_4Cl$ aqueous solution was added, the resulting mixture was extracted with $CH_2Cl_2$ using an ISOLUTE (registered trademark) phase separator, and the extract was concentrated under reduced pressure. The residue was purified by silica gel column chromatography (Hex/EtOAc) to give tert-butyl (2R)-4-[3-bromo-6-nitro-2-(trifluoromethyl)phenyl]-2-{[methyl(trifluoroacetyl)amino]methyl}piperazine-1-carboxylate (1.42 g) as a solid substance.

Preparation Example 123

To a mixture of tert-butyl (2R)-4-[2-chloro-3-(2-fluorophenoxy)-6-nitrophenyl]-2-formylpiperazine-1-carboxylate (859 mg), a 2 M methylamine/THF solution (1.8 mL), $CH_2Cl_2$ (9 mL) and acetic acid (206 μL) was added $NaBH(OAc)_3$ (760 mg), and the resulting mixture was stirred at room temperature for 2 hours. A saturated $NaHCO_3$ aqueous solution was added, the resulting mixture was extracted with $CH_2Cl_2$ using an ISOLUTE (registered trademark) phase separator, and the extract was concentrated under reduced pressure. $CH_2Cl_2$ (9 mL) and DIPEA (920 μL) were added to the residue, TFAA (506 μL) was added under ice-bath cooling, and the resulting mixture was stirred at room temperature for 1 hour. DIPEA (230 μL) and TFAA (126 μL) were added under ice-bath cooling, and the resulting mixture was stirred at room temperature for 30 minutes. A saturated $NH_4Cl$ aqueous solution was added, the resulting mixture was extracted with $CH_2Cl_2$ using an ISOLUTE (registered trademark) phase separator, and the extract was concentrated under reduced pressure. The residue was purified by silica gel column chromatography (Hex/EtOAc) and silica gel column chromatography (Hex/chloroform→Hex/EtOAc) to give tert-butyl (2R)-4-[2-chloro-3-(2-fluorophenoxy)-6-nitrophenyl]-2-{[methyl(trifluoroacetyl)amino] methyl}piperazine-1-carboxylate (606 mg) as a solid substance.

Preparation Example 125

To a mixture of tert-butyl (2R)-4-[2-bromo-3-(2-fluorophenoxy)-6-nitrophenyl]-2-{[methyl(trifluoroacetyl)amino] methyl}piperazine-1-carboxylate (0.70 g), tricyclohexylphosphine (96 mg), cyclopropylboronic acid (0.28 g) and toluene (20 mL) was added an aqueous solution obtained by dissolving potassium phosphate (0.7 g) in water (2 mL). After the reaction vessel was purged with argon, palladium acetate (49 mg) was added, and the resulting mixture was stirred at 110° C. for 8 hours, allowed to cool to room temperature, then diluted with EtOAc, and washed with water and brine. The organic layer was dried over $Na_2SO_4$, and concentrated under reduced pressure. The residue was purified by silica gel column chromatography (Hex/EtOAc) to give tert-butyl (2R)-4-[2-cyclopropyl-3-(2-fluorophenoxy)-6-nitrophenyl]-2-{[methyl(trifluoroacetyl)amino] methyl}piperazine-1-carboxylate (0.42 g).

Preparation Example 127

To a solution of tert-butyl (2R)-4-[3-(2-chlorophenoxy)-6-nitro-2-(trifluoromethyl)phenyl]-2-(hydroxymethyl)piperazine-1-carboxylate (3.33 g) in $CH_2Cl_2$ (15 mL) was added a 4 M HCl/1,4-dioxane solution (15 mL) under ice-bath cooling, and the resulting mixture was stirred at room temperature for 2 hours. The reaction mixture was concentrated under reduced pressure to give {(2R)-4-[3-(2-chlorophenoxy)-6-nitro-2-(trifluoromethyl)phenyl]piperazin-2-yl}methanol monohydrochloride (3.1 g).

Preparation Example 144

To a mixture of {(2R)-4-[3-(2-chlorophenoxy)-6-nitro-2-(trifluoromethyl)phenyl]piperazin-2-yl}methanol monohydrochloride (2.93 g) and THF (80 mL) was added sodium acetate (770 mg) under ice-bath cooling, and the resulting mixture was stirred at room temperature for 10 minutes. 1H-benzotriazole-1-methanol (1.4 g) was added, and the resulting mixture was stirred at room temperature for 10 minutes. $NaBH(OAc)_3$ (2 g) was added, and the resulting mixture was stirred at room temperature for 12 hours. The reaction mixture was cooled in an ice bath, a saturated $NaHCO_3$ aqueous solution was then added, the resulting mixture was diluted with water and EtOAc, and two layers were separated. The aqueous layer was extracted with EtOAc, and the combined organic layers were dried over $Na_2SO_4$, and concentrated under reduced pressure. The residue was purified by silica gel column chromatography (Hex/chloroform/EtOAc→chloroform/MeOH) to give {(2R)-4-[3-(2-chlorophenoxy)-6-nitro-2-(trifluoromethyl) phenyl]-1-methylpiperazin-2-yl}methanol (2.65 g).

Preparation Example 150

To a mixture of tert-butyl (2R)-4-[2-chloro-3(2-fluorophenoxy)-6-nitrophenyl]-2-{[methyl(trifluoroacetyl)amino] methyl}piperazine-1-carboxylate (603 mg) and $CH_2Cl_2$ (6 mL) was added a 4 M HCl/1,4-dioxane solution (4 mL) under ice-bath cooling, and the resulting mixture was stirred at room temperature for 2 hours. The solvent was concentrated under reduced pressure. THF (12 mL) was added to the residue, 1H-benzotriazole-1-methanol (230 mg), sodium acetate (130 mg) and $NaBH(OAc)_3$ (330 mg) were added thereto, and the resulting mixture was stirred at room temperature for 1 hour. A saturated $NaHCO_3$ aqueous solution was added, the resulting mixture was extracted with a mixed solvent (chloroform/MeOH), and the organic layer was dried over $MgSO_4$, and concentrated under reduced pressure. The residue was purified by silica gel column chromatography (chloroform/MeOH), and the resulting substance was purified by silica gel column chromatography (chloroform/EtOAc) to give N-({(2R)-4-[2-chloro-3-(2-fluorophenoxy)-6-nitrophenyl]-1-methylpiperazin-2-yl}methyl)-2,2,2-trifluoro-N-methylacetamide (415 mg) as a solid substance.

Preparation Example 158

To a solution of {(2R)-4-[3-(2-chlorophenoxy)-6-nitro-2-(trifluoromethyl)phenyl]-1-methylpiperazin-2-yl}methanol (2.65 g) and DIPEA (2.4 mL) in $CH_2Cl_2$ (60 mL) was added methanesulfonic anhydride (1.74 g) under ice-bath cooling, and the resulting mixture was stirred for 1 hour under the same condition. Methanesulfonic anhydride (440 mg) was added, and the resulting mixture was stirred under the same condition. The reaction mixture was diluted with chloroform and water, and the aqueous layer was separated. The aqueous layer was extracted with chloroform, and the combined organic layers were dried over $Na_2SO_4$, and concentrated under reduced pressure to give {(2R)-4-[3-(2-chlorophenoxy)-6-nitro-2-(trifluoromethyl)phenyl]-1-methylpiperazin-2-yl}methyl methanesulfonate (3.18 g).

Preparation Example 164

To a mixture of {(2R)-4-[3-(2-chlorophenoxy)-6-nitro-2-(trifluoromethyl)phenyl]-1-methylpiperazin-2-yl}methyl methanesulfonate (3.18 g) and NMR (60 mL) was added potassium phthalimide (1.7 g), and the resulting mixture was stirred at 50° C. for 12 hours. A saturated $NH_4Cl$ aqueous solution, EtOAc and water were added under ice-bath cooling, and the aqueous layer was separated. The aqueous layer was extracted with EtOAc, and the combined organic layers were dried over $Na_2SO_4$ and concentrated under reduced pressure. The residue was purified by silica gel column chromatography (Hex/EtOAc) to give 2-({(2R)-4-[3-(2-chlorophenoxy)-6-nitro-2-(trifluoromethyl)phenyl]-1-methylpiperazin-2-yl}methyl)-1H-isoindole-1,3-dione (1.8 g).

Preparation Example 171

To a solution of {(3S)-3-fluoro-1-[3-(2-fluorophenoxy)-6-nitro-2-(trifluoromethyl)phenyl]piperizin-3-yl}methanol (1.9 g) in $CH_2Cl_2$ (38 mL) were added methanesulfonic anhydride (920 mg) and DIPEA (1.1 mL) under ice-bath cooling, and the resulting mixture was stirred for 1 hour. Water was added, the resulting mixture was extracted with chloroform using an ISOLUTE (registered trademark) phase separator, and the extract was concentrated under reduced pressure. To a solution of the resulting residue in NMP (19 mL) was added potassium phthalimide (1.2 g), and the resulting mixture was stirred at 60° C. overnight, heated to 120° C., and then stirred for 2 hours. Potassium phthalimide (800 mg) was added, and the resulting mixture was stirred at 100° C. for 7 days. Water and brine were added, the resulting mixture was extracted with EtOAc, and the organic layer was dried over $Na_2SO_4$, and concentrated under reduced pressure. The residue was purified by silica gel column chromatography (Hex/EtOAc) to give 2-({(3S)-3-fluoro-1-[3-(2-fluorophenoxy)-6-nitro-2-(trifluoromethyl)phenyl]piperidin-3-yl}methyl)-1H-isoindole-1,3(2H)-dione (1.2 g) as a solid substance.

Preparation Example 173

To a mixed solution of (8S,8aR)-2-[3-(2-fluorophenoxy)-6-nitro-2-(trifluoromethyl)phenyl]octahydropyrrolo[1,2-a]pyrazin-8-ol (0.886 g), THF (13.5 mL), benzoic acid (0.245 g) and triphenylphosphine (0.792 g) was added diisopropyl azodicarboxylate (0.6 mL) under ice-bath cooling under an argon atmosphere, and the resulting mixture was stirred at room temperature for 6.5 hours. The reaction liquid was concentrated under reduced pressure, and the residue was purified by silica gel column chromatography (Hex/EtOAc) to give a mixture mainly containing (8R,8aR)-2-[3-(2-fluorophenoxy)-6-nitro-2-(trifluoromethyl)phenyl]octahydropyrrolo[1,2-a]pyrazin-8-yl benzoate (1.648 g).

Preparation Example 174

To a mixed solution of a mixture mainly containing (8R,8aR)-2-[3-(2-fluorophenoxy)-6-nitro-2-(trifluoromethyl)phenyl]octahydropyrrolo[1,2-a]pyrazin-8-yl benzoate (1.648 g) and MeOH (20 mL) was added potassium carbonate (1.396 g), and the resulting mixture was stirred at room temperature for 6 hours. The reaction mixture was filtered with celite, and the filtrate was concentrated under reduced pressure. Water was added to the residue, and the resulting mixture was extracted with EtOAc. The organic layer was washed with brine, dried over $Na_2SO_4$, and concentrated under reduced pressure. The residue was purified by silica gel column chromatography (Hex/EtOAc) to give (8R,8aR)-2-[3-(2-fluorophenoxy)-6-nitro-2-(trifluoromethyl)phenyl]octahydropyrrolo[1,2-a]pyrazin-8-ol (0.631 g) as a solid substance.

Preparation Example 175

To a mixed solution of (8S,8aS)-2-[3-(2-fluorophenoxy)-6-nitro-2-(trifluoromethyl)phenyl]octahydropyrrolo[1,2-a]pyrazin-8-ol (0.922 g), THF (15 mL), phthalimide (0.322 g) and triphenylphosphine (0.824 g) was added diisopropyl azodicarboxylate (0.62 mL) under ice-bath cooling under an argon atmosphere, and the resulting mixture was stirred at room temperature for 2.5 hours. The reaction liquid was poured into water, and the resulting mixture was extracted with EtOAc. The organic layer was separated, the aqueous layer was extracted with EtOAc, and the combined organic layers were washed with brine. The organic layers were dried over $Na_2SO_4$ and concentrated under reduced pressure. The residue was purified by silica gel column chromatography (Hex/EtOAc) to give a mixture mainly containing 2-{(8R,8aS)-2-[3-(2-fluorophenoxy)-6-nitro-2-(trifluoromethyl)phenyl]octahydropyrrolo[1,2-a]pyrazin-8-yl}-1H-isoindole-1,3(2H)-dione (1.480 g).

Preparation Example 179

To a mixture of 1-{(3S)-1-[3-(2-fluorophenoxy)-6-nitro-2-(trifluoromethyl)phenyl]piperidin-3-yl}methaneamine (0.70 g), methoxyacetic acid (0.18 g), DIPEA (0.62 mL) and DMF (10 mL) was added HATU (0.96 g), and the resulting mixture was stirred at room temperature for 16 hours. Water was added, and the resulting mixture was extracted with EtOAc three times. The combined organic layers were dried over $Na_2SO_4$ and concentrated under reduced pressure. The residue was purified by silica gel column chromatography (Hex/EtOAc) to give N-({(3S)-1-[3-(2-fluorophenoxy)-6-nitro-2-(trifluoromethyl)phenyl]piperidin-3-yl}methyl)-2-methoxyacetamide (0.70 g).

Preparation Example 180

To a mixture of N-({(3S)-1-[3-(2-fluorophenoxy)-6-nitro-2-(trifluoromethyl)phenyl]piperidin-3-yl}methyl)-2-methoxyacetamide (0.50 g) and THF (10 mL) was added a borane THF complex (1 M THF solution, 3 mL) slowly, and the resulting mixture was stirred for 2 hours under ice-bath cooling. The reaction was quenched with MeOH, and the reaction mixture was concentrated under reduced pressure to give N-({(3S)-1-[3-(2-fluorophenoxy)-6-nitro-2-(trifluoromethyl)phenyl]piperidin-3-yl}methyl)-2-methoxyethan-1-amine (0.30 g), which was used in the next reaction without further purification.

Preparation Example 181

To a mixture of 2-({(3S)-3-fluoro-1-[3-(2-fluorophenoxy)-6-nitro-2-(trifluoromethyl)phenyl]piperidin-3-yl}methyl)-1H-isoindole-1,3(2H)-dione (1.2 g) and MeOH (12 mL) was added hydrazine monohydrate (520 μL), and the resulting mixture was stirred at 60° C. for 1 hour. Water was added, and the resulting mixture was extracted with chloroform using an ISOLUTE (registered trademark) phase separator, and the extract was concentrated under reduced pressure. The residue was purified by silica gel column chromatography (chloroform/MeOH) to give 1-{(3R)-3-fluoro-1-[3-(2-fluorophenoxy)-6-nitro-2-(trifluoromethyl)phenyl]piperidin-3-yl}methaneamine (270 mg).

Preparation Example 186

To a solution of 1-{(3R)-3-fluoro-1-[3-(2-fluorophenoxy)-6-nitro-2-(trifluoromethyl)phenyl]piperidin-3-yl}methaneamine (270 mg) in DMF (2.7 mL) were added di-tert-butyl dicarbonate (270 mg) and DIPEA (210 μL), and the resulting mixture was stirred at room temperature for 1 hour. Water was added, the resulting mixture was extracted with EtOAc twice, and the combined organic layers were washed with brine, dried over $Na_2SO_4$, and concentrated under reduced pressure. The residue was purified by silica gel column chromatography (Hex/EtOAc) to give tert-butyl ({(3R)-3-fluoro-1-[3-(2-fluorophenoxy)-6-nitro-2-(trifluoromethyl)phenyl]piperidin-3-yl}methyl)carbamate (310 mg).

Preparation Example 193

To a mixture of 2-({(2R)-4-[3-(2-chlorophenoxy)-6-nitro-2-(trifluoromethyl)phenyl]-1-methylpiperazin-2-yl}methyl)-1H-isoindole-1,3-dione (1.8 g) and MeOH (20 mL) was added hydrazine monohydrate (0.8 mL), and the resulting mixture was stirred at 60° C. for 2 hours, and allowed to cool to room temperature. Insoluble substances were then separated by filtration, and the filtrate was concentrated under reduced pressure. To a mixture of the residue with DMF (40 mL) and DIPEA (1.6 mL) was added di-tert-butyl dicarbonate (2 g), and the resulting mixture was stirred at room temperature for 3 hours. Water and EtOAc were added, and the aqueous layer was separated. The aqueous layer was extracted with EtOAc, and the combined organic layers were dried over $Na_2SO_4$, and concentrated under reduced pressure. The residue was purified by silica gel column chromatography (Hex/EtOAc) to give tert-butyl ({(2S)-4-[3-(2-chlorophenoxy)-6-nitro-2-(trifluoromethyl) phenyl]-1-methylpiperazin-2-yl}methyl)carbamate (1.60 g).

Preparation Example 201

To a mixture of N-({(2R)-4-[3-bromo-6-nitro-2-(trifluoromethyl)phenyl]piperazin-2-yl}methyl)-2,2,2-trifluoro-N-methylacetamide monohydrochloride (1.27 g), sodium acetate (295 mg), 1H-benzotriazole-1-methanol (536 mg) and THF (25.4 mL) was added $NaBH(OAc)_3$ (762 mg), and the resulting mixture was stirred at room temperature for 16 hours. A saturated $NaHCO_3$ aqueous solution was added, and the resulting mixture was stirred at room temperature for 10 minutes. EtOAc and water were added, and the aqueous layer was separated. The aqueous layer was extracted with EtOAc, and the combined organic layers were washed with water and brine, dried over $Na_2SO_4$, and concentrated under reduced pressure. The residue was purified by silica gel column chromatography (Hex/EtOAc) to give N-({(2R)-4-[3-bromo-6-nitro-2-(trifluoromethyl)phenyl]-1-methylpiperazin-2-yl}methyl)-2,2,2-trifluoro-N-methylacetamide (1.40 g) as a solid substance.

Preparation Example 210

To a mixture of N-({(2R)-4-[3-bromo-6-nitro-2-(trifluoromethyl)phenyl]-1-methylpiperazin-2-yl}methyl)-2,2,2-trifluoro-N-methylacetamide (1.0 g), MeOH (10 mL) and water (3.4 mL) was added potassium carbonate (700 mg), and the resulting mixture was stirred at 50° C. for 2 hours, and allowed to cool to room temperature. A saturated $NH_4Cl$ aqueous solution was then added, and the resulting mixture was stirred for 5 minutes. Chloroform and water were added, and the resulting mixture was extracted using an ISOLUTE (registered trademark) phase separator. The extract was dried over $Na_2SO_4$ and concentrated under reduced pressure. The residue was dissolved in THF (10 mL), di-tert-butyl dicarbonate (530 mg) and TEA (420 μL) were added, and the resulting mixture was stirred at room temperature for 16 hours. EtOAc and water were added, and the aqueous layer was separated. The aqueous layer was extracted with EtOAc, and the combined organic layers were washed with brine, dried over $Na_2SO_4$, and then concentrated under reduced pressure. The residue was purified by silica gel column chromatography (Hex/EtOAc) to give tert-butyl ({(2R)-4-[3-bromo-6-nitro-2-(trifluoromethyl)phenyl]-1-methylpiperazin-2-yl}methyl)(methyl)carbamate (720 mg).

Preparation Example 211

To a mixture of tert-butyl ({(2R)-4-[3-bromo-6-nitro-2-(trifluoromethyl)phenyl]-1-methylpiperazin-2-yl}methyl) (methyl)carbamate (490 mg), 1-cyclopentenylboronic acid (130 mg), potassium carbonate (260 mg), 1,4-dioxane (10 mL) and water (1 mL) was added $Pd(PPh_3)_4$ (110 mg), and the resulting mixture was stirred at 120° C. for 2 hours under microwave irradiation, and allowed to cool to room temperature. EtOAc and water were then added, the resulting mixture was stirred for 5 minutes, and the aqueous layer was separated. The aqueous was extracted with EtOAc. The combined organic layers were washed with water and brine, dried over $Na_2SO_4$, and concentrated under reduced pressure. The residue was purified by silica gel column chromatography (Hex/EtOAc) to give tert-butyl ({(2R)-4-[3-(cyclopenta-1-en-1-yl)-6-nitro-2-(trifluoromethyl)phenyl]-1-methylpiperazin-2-yl}methyl)(methyl)carbamate (420 mg).

Preparation Example 214

To a mixed solution of 4-[3-(cyclobutyloxy)-6-nitro-2-(trifluoromethyl)phenyl]-1-(oxan-2-yl)-1H-pyrazole (2.594 g) and $CH_2Cl_2$ (30 mL) was added TFA (15 mL), and the resulting mixture was stirred at room temperature for 2.5 hours. The reaction liquid was concentrated under reduced pressure, a saturated $NaHCO_3$ aqueous solution was added to the residue, and the resulting mixture was extracted with $CH_2Cl_2$ twice. The combined organic layers were dried over $Na_2SO_4$, concentrated under reduced pressure, and purified by silica gel column chromatography (Hex/EtOAc) to give 4-[3-(cyclobutyloxy)-6-nitro-2-(trifluoromethyl)phenyl]-1H-pyrazole (1.907 g) as a solid substance.

Preparation Example 215

To a mixed solution of 4-[3-(cyclobutyloxy)-6-nitro-2-(trifluoromethyl)phenyl]-1H-pyrazole (0.840 g), tert-butyl (3-bromopropyl)carbamate (0.732 g) and DMF (14 mL) was added cesium carbonate (1.254 g), and the resulting mixture was stirred at room temperature for 3 hours. The reaction liquid was poured into water, and the resulting mixture was extracted with EtOAc twice. The combined organic layers were washed with water and brine, dried over $Na_2SO_4$, and concentrated under reduced pressure. The residue was purified by silica gel column chromatography (Hex/EtOAc) to give tert-butyl (3-{4-[3-(cyclobutyloxy]-6-nitro-2-(trifluoromethyl)phenyl)-1H-pyrazol-1-yl}propyl)carbamate (0.831 g) as a solid substance.

Preparation Example 216

To a mixed solution of tert-butyl {(8R,8aS)-2-[3-(2-fluorophenoxy)-6-nitro-2-(trifluoromethyl)phenyl]octahydropyrrolo[1,2-a]pyrazin-8-yl}carbamate (0.200 g) and DMF (2.5 mL) was added sodium hydride (55% oil dispersion, 0.019 g) under ice-bath cooling under an argon atmosphere, and the resulting mixture was stirred for 40 minutes under ice-bath cooling. Methyl iodide (35 μL) was added to the reaction mixture under ice-bath cooling, and the resulting mixture was stirred at room temperature for 17 hours. The reaction liquid was poured into water, the resulting mixture was extracted with EtOAc, and the organic layer was washed with water and brine, dried over $Na_2SO_4$, and concentrated under reduced pressure. The residue was purified by silica gel column chromatography (Hex/EtOAc) to give tert-butyl {(8R,8aS)-2-[3-(2-fluorophenoxy)-6-nitro-2-(trifluoromethyl)phenyl]octahydropyrrolo[1,2-a]pyrazin-8-yl}(methyl)carbamate (0.131 g).

Preparation Example 222

To a solution of ethyl 5-methyl-1H-pyrazole-3-carboxylate (841 mg) in MeCN (20 mL) was added cesium carbonate (1.78 g), and the resulting mixture was stirred at room temperature for 10 minutes. 3,4,6-Trichloropyridazine (1 g) was added, and the resulting mixture was stirred at room temperature for 8 hours. The reaction mixture was diluted with EtOAc and filtered with celite to remove insoluble substances. The filtrate was concentrated under reduced pressure, and the residue was purified by silica gel column chromatography (EtOAc/Hex/chloroform) to give ethyl 1-(3,6-dichloropyridazin-4-yl)-5-methyl-1H-pyrazole-3-carboxylate (1.37 g) as a solid substance.

Preparation Example 225

To a solution of ethyl 1-(3,6-dichloropyridazin-4-yl)-5-methyl-1H-pyrazole-3-carboxylate (1.37 g) in THF/EtOH (1/1, 30 mL) were added TEA (1.3 mL) and a palladium-activated carbon ethylenediamine complex (3.5-6.5% Pd, 137 mg), and the resulting mixture was stirred in a hydrogen atmosphere at room temperature for 3 hours. Insoluble substances were removed by filtration with celite, and the filtrate was concentrated under reduced pressure to give a solid substance. This solid substance was diluted with chloroform and water, and two layers were then separated. The aqueous layer was extracted with chloroform, and the combined organic layers were dried over $Na_2SO_4$, and then concentrated under reduced pressure. The residue was purified by silica gel column chromatography (EtOAc/chloroform) to give ethyl 5-methyl-1-(pyridazin-4-yl)-1H-pyrazole-3-carboxylate (521 mg) as a solid substance.

Preparation Example 228

To a mixture of ethyl 5-methyl-1-(pyridazin-4-yl)-1H-pyrazole-3-carboxylate (521 mg) and THF/EtOH (1/1, 30 mL) was added a 1 M sodium hydroxide aqueous solution (10 mL) under ice-bath cooling, and the reaction mixture was stirred at room temperature for 4 hours. 1 M hydrochloric acid (10 mL) was added under ice-bath cooling, and the resulting mixture was concentrated under reduced pressure. The resulting residue was diluted with water, and the precipitated solid substance was taken by filtration, and dried under reduced pressure to give 5-methyl-1-(pyridazin-4-yl)-1H-pyrazole-3-carboxylic acid (395 mg) as a solid substance.

Preparation Example 231

To a mixture of N-cyclopropyl-2,2,2-trifluoro-N-({(2R)-4-[3-(2-fluorophenoxy)-6-nitro-2-(trifluoromethyl)phenyl]piperazin-2-yl}methyl)acetamide monohydrochloride (390 mg), DIPEA (342 μL) and DMF (4 mL) was added methyl iodide (124 μL), and the resulting mixture was stirred at room temperature for 16 hours. EtOAc and water were added, and the aqueous layer was separated. The aqueous layer was extracted with EtOAc, and the combined organic layers were washed with water and brine, dried with $Na_2SO_4$, and concentrated under reduced pressure. The residue was purified by silica gel chromatography (Hex/EtOAc) to give N-cyclopropyl-2,2,2-trifluoro-N-({(2R)-4-[3-(2-fluorophenoxy)-6-nitro-2-(trifluoromethyl)phenyl]-1-methylpiperazin-2-yl}methyl)acetamide (143 mg).

Preparation Example 232

To a solution of tert-butyl ({(2R)-4-[3-(2-fluorophenoxy)-6-nitro-2-(trifluoromethyl)phenyl]-1-methylpiperazin-2-yl}methyl)(methyl)carbamate (3.41 g) in 1,4-dioxane (50 mL) was added a solution of $NH_4Cl$ (3.36 g) in water (25 mL), zinc powder (4.11 g) was then added under ice-bath cooling, and the resulting mixture was stirred at room temperature for 3 hours. The reaction mixture was diluted with EtOAc and water, and then filtered with celite. The aqueous layer of the filtrate was separated. The aqueous layer was extracted with EtOAc, and the combined organic layers were dried over $Na_2SO_4$, and concentrated under reduced pressure to give tert-butyl ({(2R)-4-[6-amino-3-(2-fluorophenoxy)-2-(trifluoromethyl)phenyl]-1-methylpiperazin-2-yl}methyl)(methyl)carbamate (3.32 g).

Preparation Example 293

To tert-butyl ({(2R)-4-[3-(cyclopenta-1-en-1-yl)-6-nitro-2-(trifluoromethyl)phenyl]-1-methylpiperazin-2-yl}methyl)(methyl)carbamate (420 mg), $NH_4Cl$ (450 mg), 1,4-dioxane (4.2 mL) and water (1.7 mL) was added zinc powder (550 mg), and the resulting mixture was stirred at room temperature for 1 hour, and diluted with chloroform. The aqueous layer was separated using an ISOLUTE (registered trademark) phase separator. The organic layer was dried over $Na_2SO_4$ and concentrated under reduced pressure. The residue was dissolved in MeOH (8.4 mL), 10% Pd/C (50% hydrous, 180 mg) was added, and the resulting mixture was stirred under a hydrogen atmosphere (3 atm) at room temperature for 8 hours. Insoluble substances were removed by filtration with celite, and the filtrate was then concentrated under reduced pressure. The residue was dissolved in MeOH (8.4 mL), 10% Pd/C (50% hydrous, 360 mg) was added, and the resulting mixture was stirred under a hydrogen atmosphere (3 atm) at room temperature for 48 hours. Insoluble substances were removed by filtration with celite, and the filtrate was then concentrated under reduced pressure. The residue was purified by silica gel column chromatography (chloroform/MeOH) to give tert-butyl ({(2R)-4-[6-amino-3-cyclopentyl-2-(trifluoromethyl)phenyl]-1-methylpiperazin-2-yl}methyl)(methyl)carbamate (320 mg) as a solid substance.

Preparation Example 294

To a mixture of tert-butyl ({(2R)-4-[6-amino-3-(2-fluorophenoxy)-2-(trifluoromethyl)phenyl]-1-methylpiperazin-2-yl}methyl)(methyl)carbamate (3.22 g), 1-(pyridazin-4-yl)-1H-pyrazole-3-carboxylic acid (1.43 g), DIPEA (3.3 mL) and DMF (50 mL) was added HATU (3.58 g). The reaction mixture was stirred at 50° C. for 12 hours and allowed to cool to room temperature. Chloroform and water were added to the reaction mixture, and the aqueous layer was separated. The aqueous layer was extracted with chloroform, and the combined organic layers were dried over $Na_2SO_4$, and concentrated under reduced pressure. The residue was purified by silica gel column chromatography (chloroform/MeOH) to give tert-butyl ({(2R)-4-[3-(2-fluorophenoxy)-6-{[1-(pyridazin-4-yl)-1H-pyrazole-3-carbonyl]amino}-2-(trifluoromethyl)phenyl]-1-methylpiperazin-2-yl}methyl)(methyl)carbamate (4.35 g).

Preparation Example 403

To a mixture of N-{3-chloro-2-[(3R)-3-({[(3,4-dimethoxyphenyl)methyl](trifluoroacetyl)amino}methyl)-4-methylpiperazin-1-yl]-4-(2-fluorophenoxy)phenyl}-1-(2,2-difluoroethyl)-1H-pyrazole-3-carboxamide (0.27 g) and MeOH (10 mL) was added an aqueous solution obtained by dissolving potassium carbonate (0.24 g) in water (2 mL), and the resulting mixture was stirred at room temperature for 16 hours, concentrated under reduced pressure, diluted with EtOAc, and washed with water three times. The organic layer was dried over $Na_2SO_4$ and concentrated under reduced pressure. The residue was purified by silica gel column chromatography ($CH_2Cl_2$/MeOH) to give N-{3-chloro-2-[(3S)-3-({[(3,4-dimethoxyphenyl)methyl]amino}methyl)-4-methylpiperazin-1-yl]-4-(2-fluorophenoxy)phenyl}-1-(2,2-difluoroethyl)-1H-pyrazole-3-carboxamide (0.16 g) as a solid substance.

Preparation Example 404

To a mixed solution of (2R)-2-{[methyl(trifluoroacetyl)amino]methyl}-4-[3-phenoxy-6-{[2-(pyridazin-4-yl)-1,3-oxazole-4-carbonyl]amino}-2-(trifluoromethyl)phenyl]piperazine-1-carboxylate (0.414 g) and $CH_2Cl_2$ (2 mL) was added TFA (1 mL), and the resulting mixture was stirred at room temperature for 3 hours. The reaction liquid was concentrated under reduced pressure, a saturated $NaHCO_3$ aqueous solution was added to the residue, and the resulting mixture was extracted with $CH_2Cl_2$. The organic layer was dried over $Na_2SO_4$ and concentrated under reduced pressure. The residue was purified by silica gel column chromatography ($CH_2Cl_2$/MeOH) to give N-{2-[(3R)-3-1{[methyl(trifluoroacetyl)amino]methyl}piperazin-1-yl]-4-phenoxy-3-(trifluoromethyl)phenyl}-2-(pyridazin-4-yl)-1,3-oxazole-4-carboxamide (0.333 g).

Preparation Example 405

To a mixed solution of N-{2-[(3R)-3-{[methyl(trifluoroacetyl)amino]methyl}piperazin-1-yl]-4-phenoxy-3-(trifluoromethyl)phenyl}-2-(pyridazin-4-yl)-1,3-oxazole-4-carboxamide (0.318 g), $CH_2Cl_2$ (5 mL) and a 37% formaldehyde aqueous solution (0.2 mL) was added $NaBH(OAc)_3$ (0.156 g) and the resulting mixture was stirred at room temperature for 2 hours. The reaction liquid was poured into a saturated $NaHCO_3$ aqueous solution, and the resulting mixture was extracted with $CH_2Cl_2$. The organic layer was dried over $Na_2SO_4$ and concentrated under reduced pressure. The residue was purified by silica gel column chromatography (EtOAc/MeOH) to give N-{2-[(3R)-4-methyl-3-{[methyl(trifluoroacetyl)amino]methyl}piperazin-1-yl]-4-phenoxy-3-(trifluoromethyl)phenyl}-2-(pyridazin-4-yl)-1,3-oxazole-4-carboxamide (0.287 g).

The compounds shown in Table 4 below were prepared in the same manner as in the preparation methods of Preparation Examples described above. Table 4 below shows the structures of the compounds of each Preparation Example, and Table 5 shows the methods for preparing the compounds of each Preparation Example and physiochemical data. These compounds can be easily prepared by using the preparation methods of Preparation Examples above, methods obvious to those skilled in the art, or modified methods thereof.

Example 1

To a mixture of tert-butyl ({(3S)-1-[6-{[1-(2,2-difluoroethyl)-1H-pyrazole-3-carbonyl]amino}-3-(2-fluorophenoxy)-2-(trifluoromethyl)phenyl]piperidin-3-yl}methyl)carbamate (275 mg) and $CH_2Cl_2$ (3 mL) was added TFA (330 μL), and the resulting mixture was stirred at room temperature for 16 hours, and concentrated under reduced pressure. A mixed solvent (chloroform/MeOH) and a saturated $NaHCO_3$ aqueous solution were added to the residue, and the organic layer was separated, dried over $Na_2SO_4$, and concentrated under reduced pressure. The residue was purified by silica gel column chromatography (chloroform/MeOH/aqueous ammonia). The resulting substance was dissolved in EtOAc (3 mL), a 4 M HCl/EtOAc solution (500 μL) was added, and the resulting mixture was stirred at room temperature for 10 minutes, and concentrated under reduced pressure. The residue was solidified and washed with isopropyl ether, and then dried under reduced pressure to give N-{2-[(3S)-3-(aminomethyl)piperazin-1-yl]-4-(2-fluorophenoxy)-3-(trifluoromethyl)phenyl}-1-(2,2-difluoroethyl)-1H-pyrazole-3-carboxamide monohydrochloride (210 mg) as a solid substance.

Example 22

To a mixture of N-[4-(2-fluorophenoxy)-2-[(3R)-4-methyl-3-{[methyl(trifluoroacetyl)amino]methyl}piperazin-1-yl]-3-(trifluoromethyl)phenyl]-2-(pyridazin-4-yl)-1,3-oxazole-4-carboxamide (190 mg), water (630 μL) and MeOH (2 mL) was added potassium carbonate (78 mg), and the resulting mixture was stirred at room temperature for 2 hours. Water, a saturated $NH_4Cl$ aqueous solution and chloroform were added, and the aqueous layer was separated. The aqueous layer was extracted with a mixed solvent (chloroform/MeOH), and the combined organic layers were dried over $Na_2SO_4$, and concentrated under reduced pressure. The residue was purified by silica gel column chromatography (chloroform/MeOH/aqueous ammonia). The resulting substance was dissolved in EtOAc (2 mL), a 4 M HCl/EtOAc solution (350 μL) was added, and the resulting mixture was stirred at room temperature for 10 minutes, and concentrated under reduced pressure. The residue was washed with diethyl ether, and dried under reduced pressure to give N-[4-(2-fluorophenoxy)-2-{(3S)-4-methyl-3-[(methylamino)methyl]piperazin-1-yl}-3-(trifluoromethyl)phenyl]-2-(pyridazin-4-yl)-1,3-oxazole-4-carboxamide trihydrochloride (131 mg) as a solid substance.

Example 29

To a mixture of tert-butyl ({(2R)-4-[3-(2-fluorophenoxy)-6-{[1-(pyridazin-4-yl)-1H-pyrazole-3-carbonyl]amino}-2-(trifluoromethyl)phenyl]-1-methylpiperazin-2-yl}methyl)(methyl)carbamate (4.3 g) and $CH_2Cl_2$ (40 mL) was added TFA (10 mL), and the resulting mixture was stirred at room temperature for 4 hours. The reaction liquid was concentrated under reduced pressure, and the residue was basified by addition of water, chloroform and $NaHCO_3$ thereto. A liquid separation process was carried out with a separatory funnel, the aqueous layer was extracted with chloroform, and the combined organic layers were dried over $Na_2SO_4$, and concentrated under reduced pressure. The residue was purified by silica gel column chromatography (chloroform/MeOH/aqueous ammonia). The resulting amorphous substance was washed with EtOAc/Hex to give N-[4-(2-fluorophenoxy)-2-{(3S)-4-methyl-3-[(methylamino)methyl]piperazin-1-yl}-3-(trifluoromethyl)phenyl]-1-(pyridazin-4-yl)-1H-pyrazole-3-carboxamide (2.62 g) as a solid substance.

Example 86

To a mixture of N-{3-chloro-4-(2-fluorophenoxy)-2-[(3R)-4-methyl-3-{[methyl(trifluoroacetyl)amino]methyl}piperazin-1-yl]phenyl}-1-(pyridazin-4-yl)-1H-pyrazole-3-carboxamide (159 mg), MeOH (1.5 mL) and water (0.5 mL) was added potassium carbonate (68 mg), and the resulting mixture was stirred at 50° C. for 2 hours, and allowed to cool. A saturated $NH_4Cl$ aqueous solution was then added, the resulting mixture was extracted with a mixed solvent (chloroform/MeOH), and the organic layer was dried over $MgSO_4$, and concentrated under reduced pressure. The residue was purified by silica gel column chromatography (chloroform/MeOH/aqueous ammonia) to give N-[3-chloro-4-(2-fluorophenoxy)-2-{(3S)-4-methyl-3-[(methylamino)methyl]piperazin-1-yl}phenyl]-1-(pyridazin-4-yl)-1H-pyrazole-3-carboxamide (106 mg) as a solid substance.

Example 109

To a mixture of tert-butyl ({(3S)-1-[6-amino-3-phenoxy-2-(trifluoromethyl)phenyl]piperidin-3-yl}methyl)carbamate (14.0 mg), 1-(2,2,2-trifluoroethyl)-1H-pyrazole-3-carboxylic acid (7.3 mg), DIPEA (20.5 μL) and DMF (600 μL) were added HATU (17.1 mg) and DMF (100 μL), and the resulting mixture was stirred at 50° C. overnight, and allowed to cool. Chloroform and water were then added, the organic layer was separated, and concentrated under reduced pressure, and the residue was purified by LC-MS (aqueous formic acid/MeOH). The resulting substance was dissolved in $CH_2Cl_2$ (250 μL), a 4 M HCl/1,4-dioxane solution (250 μL) was added, and the resulting mixture was stirred at room temperature for 2 hours, and concentrated under reduced pressure. A mixed solvent (chloroform/MeOH) and a saturated $NaHCO_3$ aqueous solution were added to the residue, and the organic layer was separated, and concentrated under reduced pressure to give N-{2-[(3S)-3-(aminomethyl)piperidin-1-yl]-4-phenoxy-3-(trifluoromethyl)phenyl}-1-(2,2,2-trifluoroethyl)-1H-pyrazole-3-carboxamide (6.9 mg).

Example 112

To a mixture of N-{3-chloro-2-[(3S)-3-({[(3,4-dimethoxyphenyl)methyl]amino}methyl)-4-methylpiperazin-1-yl]-4-(2-fluorophenoxy)phenyl}-1-(2,2-difluoroethyl)-1H-pyrazole-3-carboxamide (0.15 g) and TFA (1 mL) was added trifluoromethanesulfonic acid (1 mL), and the resulting mixture was stirred at room temperature for 16 hours, and at 60° C. for 4 hours, and concentrated under reduced pressure. The residue was purified by preparative HPLC to give N-{2-[(3S)-3-(aminomethyl)-4-methylpiperazin-1-yl]-3-chloro-4-(2-fluorophenoxy)phenyl}-1-(2,2-difluoroethyl)-1H-pyrazole-3-carboxamide (31 mg) as a solid substance.

Example 113

To a mixed solution of N-[4-(cyclobutyloxy)-2-{2-[2-(methylamino)ethoxy]pyridin-4-yl}-3-(trifluoromethyl)phenyl]-2-(pyridazin-4-yl)-1,3-oxazole-4-carboxamide (0.110 g), $CH_2Cl_2$ (2 mL) and a 37% formaldehyde aqueous solution (81 μL) was added $NaBH(OAc)_3$ (0.064 g), and the resulting mixture was stirred at room temperature for 15 hours. The reaction liquid was poured into a saturated $NaHCO_3$ aqueous solution, and the resulting mixture was extracted with $CH_2Cl_2$. The organic layer was separated, the aqueous layer was extracted with $CH_2Cl_2$, and the combined organic layers were dried over $Na_2SO_4$, and concentrated under reduced pressure. The residue was purified by silica gel column chromatography ($CH_2Cl_2$/MeOH) to give N-[4-(cyclobutyloxy)-2-{2-[2-(dimethylamino)ethoxy]pyridin-4-yl}-3-(trifluoromethyl)phenyl]-2-(pyridazin-4-yl)-1,3-oxazole-4-carboxamide (0.098 g) as a solid substance.

Example 122

N-[4-(2-Fluorophenoxy)-2-{(3S)-4-methyl-3-[(methylamino)methyl]piperazinol-yl}-3-(trifluoromethyl)phenyl]-1-(pyridazin-4-yl)-1H-pyrazole-3-carboxamide (5 g) was dissolved in EtOH (50 mL) at 80° C., succinic acid (1.06 g) and water (2.5 mL) were added thereto, and the resulting mixture was stirred at room temperature for 48 hours. The precipitated substance was taken by filtration, and dried under reduced pressure to give a solid substance (5.50 g). A mixture of the obtained solid substance (5.45 g), EtOH (40 mL) and water (4 mL) was stirred at 70° C. to form a solution, and the solution was then stirred at room temperature for 24 hours. The precipitated substance was taken by filtration, and dried under reduced pressure at 40° C. for 2 days to give N-[4-(2-fluorophenoxy)-2-{(3S)-4-methyl-3-[(methylamino)methyl]piperazinol-yl}-3-(trifluoromethyl)phenyl]-1-(pyridazin-4-yl)-1H-pyrazole-3-carboxamide monobutanedioate (4.36 g) as a crystal.

Example 123

Succinic acid (34 mg) was added to a mixture of N-[4-(2-fluorophenoxy)-2-{(3R)-4-methyl-3-[(methylamino)methyl]piperazinol-yl}-3-(trifluoromethyl)phenyl]-1-(pyridazin-4-yl)-1H-pyrazole-3-carboxamide (150 mg) and EtOH (2 mL), water (100 μL) was added at 70° C., and the resulting mixture was stirred at room temperature for 24 hours, and concentrated under reduced pressure. MeCN (10 mL) was added to the residue, and the resulting mixture was stirred at room temperature for 24 hours. The precipitated substance was taken by filtration, and dried under reduced pressure to give N-[4-(2-fluorophenoxy)-2-{(3R)-4-methyl-3-[(methylamino)methyl]piperazinol-yl}-3-(trifluoromethyl)phenyl]-1-(pyridazin-4-yl)-1H-pyrazole-3-carboxamide monobutanedioate (165 mg) as a crystal.

Example 126

Succinic acid (22 mg) was added to a mixture of N-{2-[(3R)-3-(aminomethyl)-3-fluoropiperidin-1-yl]-4-(2-fluorophenoxy)-3-(trifluoromethyl)phenyl}-1-(pyridazin-4-yl)-1H-pyrazole-3-carboxamide (100 mg) and EtOH (1 mL), water (50 μL) was added at 70° C., and the resulting mixture was stirred at room temperature for 2 days. The precipitated solid substance was taken by filtration, and dried under reduced pressure to give N-{2-[(3R)-3-(aminomethyl)-3-fluoropiperidin-1-yl]-4-(2-fluorophenoxy)-3-(trifluoromethyl)phenyl}-1-(pyridazin-4-yl)-1H-pyrazole-3-carboxamide monobutanedioate (77 mg) as a crystal.

The compounds shown in Table 6 below were prepared in the same manner as in the preparation methods of Examples described above. Table 6 below shows the structures of the compounds of each Example, and Table 7 shows the methods for preparing the compounds of each Example and physiochemical data. These compounds can be easily prepared by using the preparation methods of Examples above, methods obvious to those skilled in the art, or modified methods thereof.

In the tables below, the following abbreviations may be used.

PEx: Number of Preparation Example

Ex: Number of Example

PSyn: Method for preparing compound of Preparation Example (the number of the PSyn field indicates that the compound concerned was prepared using the same method as that for a compound of Preparation Example whose number is identical to that of the PSyn field, and using corresponding raw materials; and for example, the compound of a PSyn field whose number is 1 was prepared using the same method as that for the compound of Preparation Example 1)

Syn: Method for preparing compound of Example (the number of the Syn field indicates that the compound concerned was prepared using the same method as that for a compound of Example whose number is identical to that of the Syn field, and using corresponding raw materials; and for example, the compound of a Syn field whose number is 1 was prepared using the same method as that for the compound of Example 1)

Str: Chemical structural formula

DAT: Physiochemical data

ESI+: m/z value in mass analysis (ionization method ESI, $[M+H]^+$ or $[M+Na]^+$ unless otherwise specified)

ESI−: m/z value in mass analysis (ionization method ESI, $[M-H]^-$ unless otherwise specified) NMR DMSO-d6 (400 MHz) or NMR DMSO-d6 (500 MHz): δ value of signal (ppm) in $^1$H-NMR in DMSO-d6

NMR DMSO-d6 (400 MHz, 80° C.): δ value of signal (ppm) in $^1$H-NMR under heating at 80° C. in DMSO-d6

NMR $CDCl_3$ (400 MHz) or NMR $CDCl_3$ (500 MHz): δ value of signal (ppm) in $^1$H-NMR in $CDCl_3$ s: Single line (spectrum)

d: Double line (spectrum)

t: Triple line (spectrum)

m: Multiple line (spectrum)

br: Broad line (spectrum)

dd: Double double line (spectrum)

Unless otherwise specified, the compound is an optical isomer having an absolute steric conformation described in a chemical structural formula. In the structural formula, HCl indicates that the compound concerned is a monohydrochloride, 2HCl indicates that the compound concerned is a dihydrochloride, and 3HCl indicates that the compound concerned is a trihydrochloride.

TABLE 4

| PEx | Str |
|---|---|
| 1 | 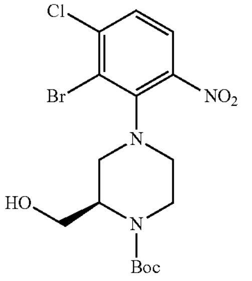 [SMILES: CC(C)(C)OC(=O)N1CCN(c2c([N+](=O)[O-])ccc(Cl)c2Br)C[C@@H]1CO] |
| 2 | 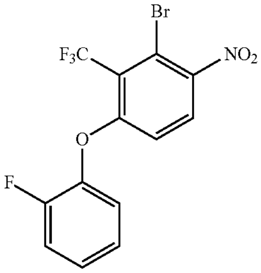 [SMILES: O=[N+]([O-])c1ccc(Oc2ccccc2F)c(C(F)(F)F)c1Br] |

TABLE 4-continued

| PEx | Str |
|---|---|
| 3 | 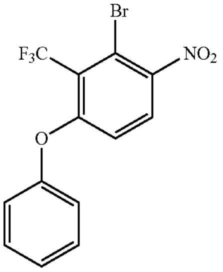 [SMILES: O=[N+]([O-])c1ccc(Oc2ccccc2)c(C(F)(F)F)c1Br] |
| 4 | 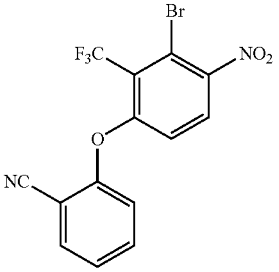 [SMILES: N#Cc1ccccc1Oc1ccc([N+](=O)[O-])c(Br)c1C(F)(F)F] |
| 5 | 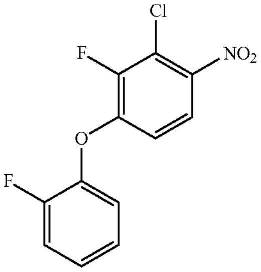 [SMILES: O=[N+]([O-])c1ccc(Oc2ccccc2F)c(F)c1Cl] |
| 6 | 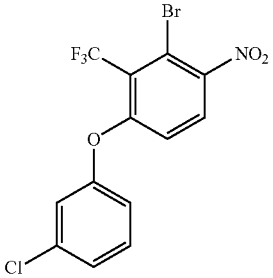 [SMILES: O=[N+]([O-])c1ccc(Oc2cccc(Cl)c2)c(C(F)(F)F)c1Br] |
| 7 | 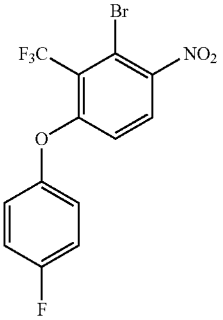 [SMILES: O=[N+]([O-])c1ccc(Oc2ccc(F)cc2)c(C(F)(F)F)c1Br] |

TABLE 4-continued
| PEx | Str |
|---|---|
| 8 | 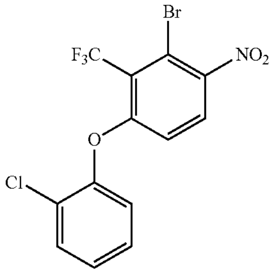 [SMILES: O=[N+]([O-])c1ccc(Oc2ccccc2Cl)c(C(F)(F)F)c1Br] |
| 9 | 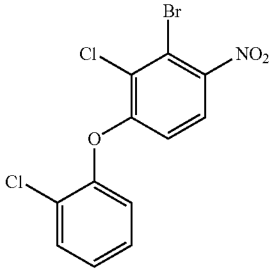 [SMILES: O=[N+]([O-])c1ccc(Oc2ccccc2Cl)c(Cl)c1Br] |
| 10 | 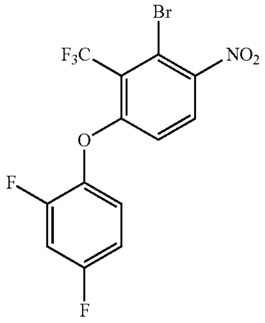 [SMILES: O=[N+]([O-])c1ccc(Oc2ccc(F)cc2F)c(C(F)(F)F)c1Br] |
| 11 | 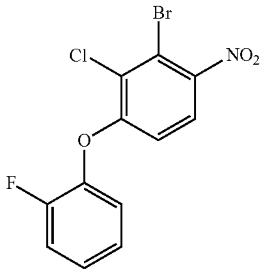 [SMILES: O=[N+]([O-])c1ccc(Oc2ccccc2F)c(Cl)c1Br] |
| 12 | 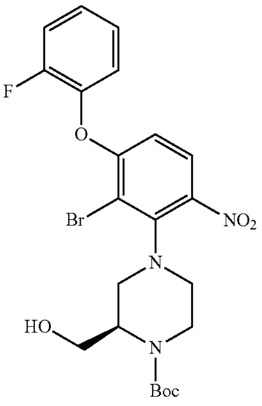 [SMILES: CC(C)(C)OC(=O)N1CCN(c2c([N+](=O)[O-])ccc(Oc3ccccc3F)c2Br)C[C@@H]1CO] |
TABLE 4-continued
| PEx | Str |
|---|---|
| 13 | 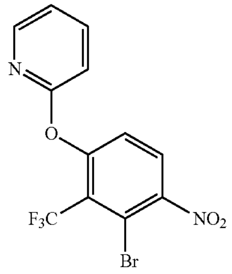 [SMILES: O=[N+]([O-])c1ccc(Oc2ccccn2)c(C(F)(F)F)c1Br] |
| 14 | 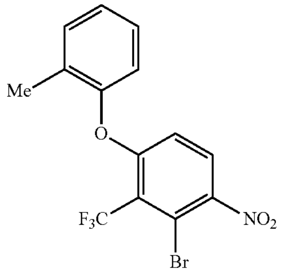 [SMILES: Cc1ccccc1Oc1ccc([N+](=O)[O-])c(Br)c1C(F)(F)F] |
| 15 | 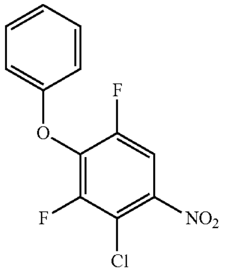 [SMILES: O=[N+]([O-])c1cc(F)c(Oc2ccccc2)c(F)c1Cl] |
| 16 | 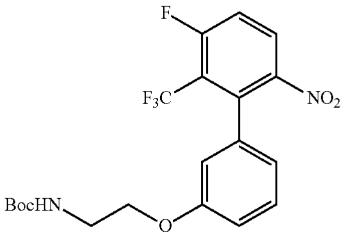 [SMILES: CC(C)(C)OC(=O)NCCOc1cccc(-c2c([N+](=O)[O-])ccc(F)c2C(F)(F)F)c1] |
| 17 | 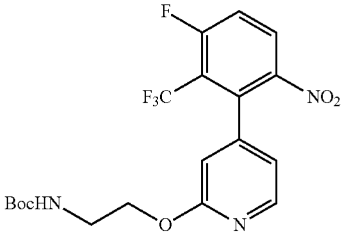 [SMILES: CC(C)(C)OC(=O)NCCOc1cc(-c2c([N+](=O)[O-])ccc(F)c2C(F)(F)F)ccn1] |

TABLE 4-continued
| PEx | Str |
|---|---|
| 18 | 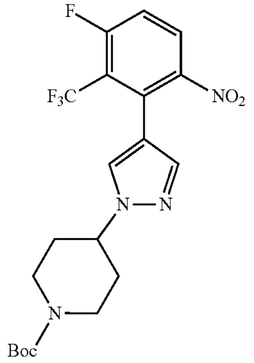 [SMILES: CC(C)(C)OC(=O)N1CCC(n2cc(-c3c([N+](=O)[O-])ccc(F)c3C(F)(F)F)cn2)CC1] |
| 19 | 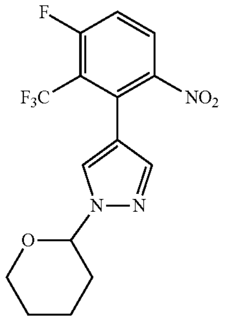 [SMILES: O=[N+]([O-])c1ccc(F)c(C(F)(F)F)c1-c1cnn(C2CCCCO2)c1] |
| 20-1 | 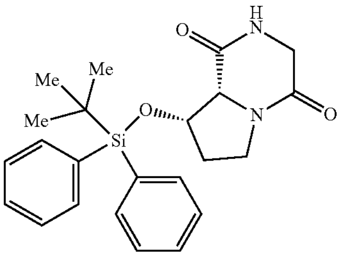 [SMILES: CC(C)(C)[Si](O[C@H]1CCN2C(=O)CNC(=O)[C@@H]12)(c1ccccc1)c1ccccc1] |
| 20-2 | 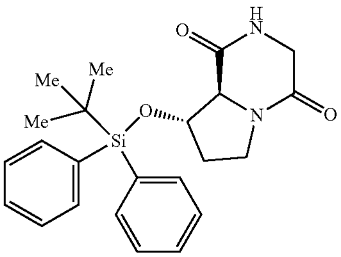 [SMILES: CC(C)(C)[Si](O[C@H]1CCN2C(=O)CNC(=O)[C@H]12)(c1ccccc1)c1ccccc1] |
| 21 | 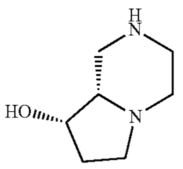 |
| 22 | 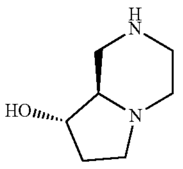 |
TABLE 4-continued
| PEx | Str |
|---|---|
| 23 | 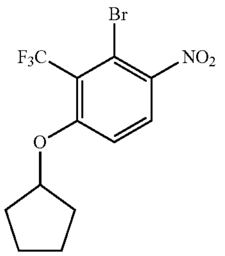 [SMILES: O=[N+]([O-])c1ccc(OC2CCCC2)c(C(F)(F)F)c1Br] |
| 24 | 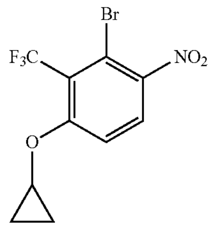 [SMILES: O=[N+]([O-])c1ccc(OC2CC2)c(C(F)(F)F)c1Br] |
| 25 | 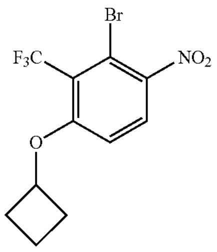 [SMILES: O=[N+]([O-])c1ccc(OC2CCC2)c(C(F)(F)F)c1Br] |
| 26 | 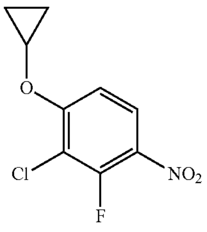 [SMILES: O=[N+]([O-])c1ccc(OC2CC2)c(Cl)c1F] |
| 27 | 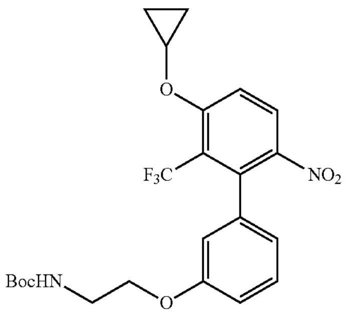 [SMILES: CC(C)(C)OC(=O)NCCOc1cccc(-c2c([N+](=O)[O-])ccc(OC3CC3)c2C(F)(F)F)c1] |

TABLE 4-continued
| PEx | Str |
|---|---|
| 28 | 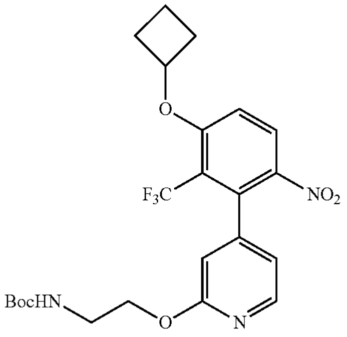 [SMILES: CC(C)(C)OC(=O)NCCOc1cc(-c2c([N+](=O)[O-])ccc(OC3CCC3)c2C(F)(F)F)ccn1] |
| 29 | 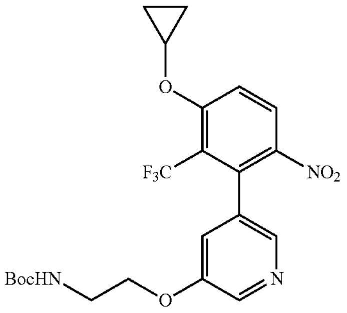 [SMILES: CC(C)(C)OC(=O)NCCOc1cncc(-c2c([N+](=O)[O-])ccc(OC3CC3)c2C(F)(F)F)c1] |
| 30 | 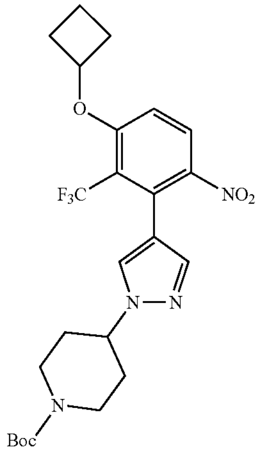 [SMILES: CC(C)(C)OC(=O)N1CCC(n2cc(-c3c([N+](=O)[O-])ccc(OC4CCC4)c3C(F)(F)F)cn2)CC1] |
| 31 | 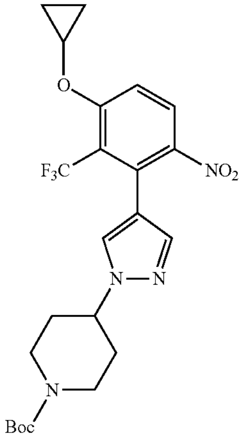 [SMILES: CC(C)(C)OC(=O)N1CCC(n2cc(-c3c([N+](=O)[O-])ccc(OC4CC4)c3C(F)(F)F)cn2)CC1] |
TABLE 4-continued
| PEx | Str |
|---|---|
| 32 | 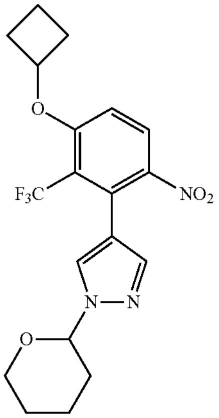 [SMILES: O=[N+]([O-])c1ccc(OC2CCC2)c(C(F)(F)F)c1-c1cnn(C2CCCCO2)c1] |
| 33 | 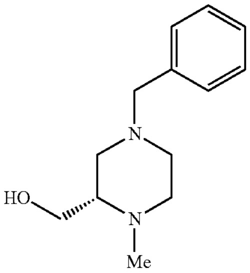 [SMILES: CN1CCN(Cc2ccccc2)C[C@H]1CO] |
| 34 | 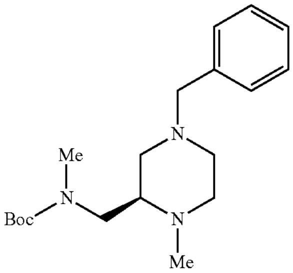 [SMILES: CN(C[C@H]1CN(Cc2ccccc2)CCN1C)C(=O)OC(C)(C)C] |
| 35 | 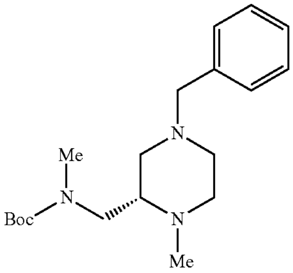 [SMILES: CN(C[C@@H]1CN(Cc2ccccc2)CCN1C)C(=O)OC(C)(C)C] |
| 36 | 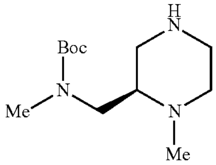 [SMILES: CN(C[C@H]1CNCCN1C)C(=O)OC(C)(C)C] |
| 37 | 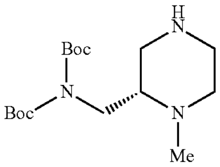 2HCl |

TABLE 4-continued
| PEx | Str |
|---|---|
| 38 | 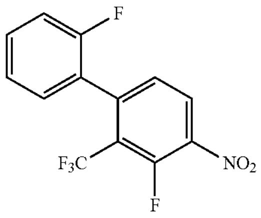 [SMILES: O=[N+]([O-])c1ccc(-c2ccccc2F)c(C(F)(F)F)c1F] |
| 39 | 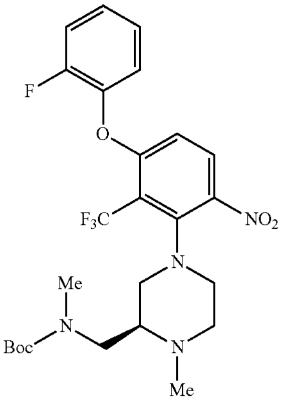 |
| 40 | 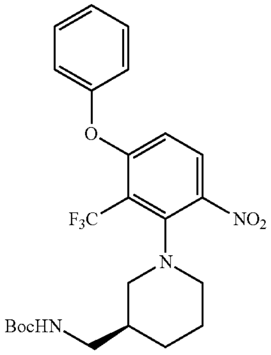 [SMILES: CC(C)(C)OC(=O)NC[C@@H]1CCCN(c2c([N+](=O)[O-])ccc(Oc3ccccc3)c2C(F)(F)F)C1] |
| 41 | 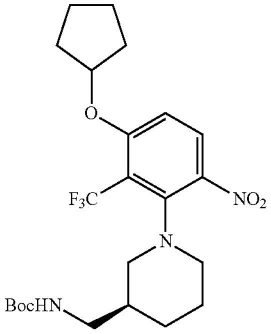 [SMILES: CC(C)(C)OC(=O)NC[C@@H]1CCCN(c2c([N+](=O)[O-])ccc(OC3CCCC3)c2C(F)(F)F)C1] |
TABLE 4-continued
| PEx | Str |
|---|---|
| 42 | 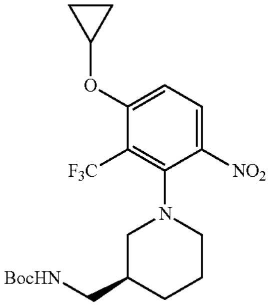 [SMILES: CC(C)(C)OC(=O)NC[C@@H]1CCCN(c2c([N+](=O)[O-])ccc(OC3CC3)c2C(F)(F)F)C1] |
| 43 | 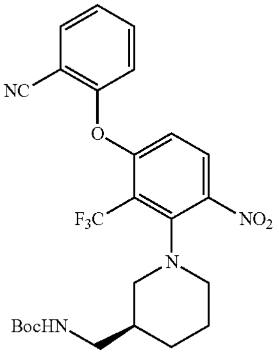 [SMILES: CC(C)(C)OC(=O)NC[C@@H]1CCCN(c2c([N+](=O)[O-])ccc(Oc3ccccc3C#N)c2C(F)(F)F)C1] |
| 44 | 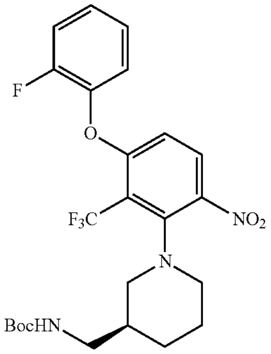 [SMILES: CC(C)(C)OC(=O)NC[C@@H]1CCCN(c2c([N+](=O)[O-])ccc(Oc3ccccc3F)c2C(F)(F)F)C1] |
| 45 | 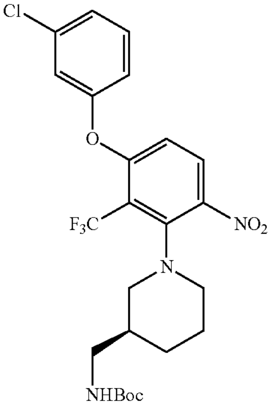 |

TABLE 4-continued
| PEx | Str |
|---|---|
| 46 | 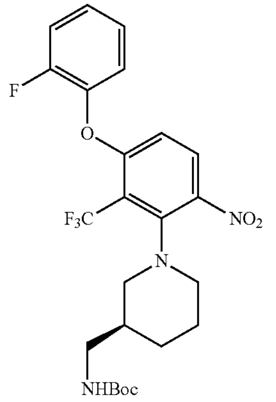 |
| 47 | 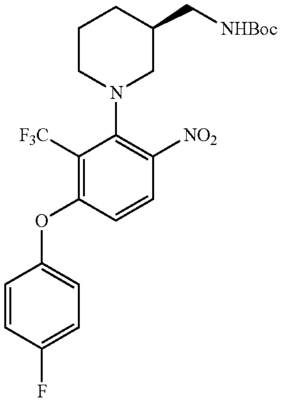 [SMILES: CC(C)(C)OC(=O)NC[C@@H]1CCCN(c2c([N+](=O)[O-])ccc(Oc3ccc(F)cc3)c2C(F)(F)F)C1] |
| 48 | 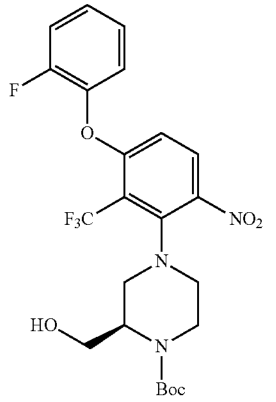 [SMILES: CC(C)(C)OC(=O)N1CCN(c2c([N+](=O)[O-])ccc(Oc3ccccc3F)c2C(F)(F)F)C[C@@H]1CO] |
| 49 | 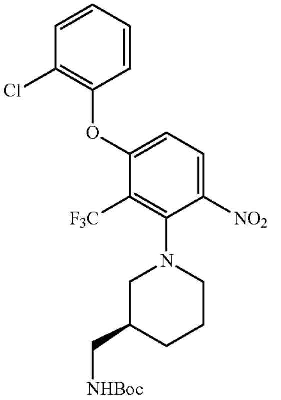 [SMILES: CC(C)(C)OC(=O)NC[C@@H]1CCCN(c2c([N+](=O)[O-])ccc(Oc3ccccc3Cl)c2C(F)(F)F)C1] |
TABLE 4-continued
| PEx | Str |
|---|---|
| 50 | 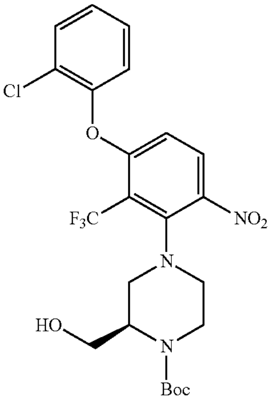 [SMILES: CC(C)(C)OC(=O)N1CCN(c2c([N+](=O)[O-])ccc(Oc3ccccc3Cl)c2C(F)(F)F)C[C@@H]1CO] |
| 51 | 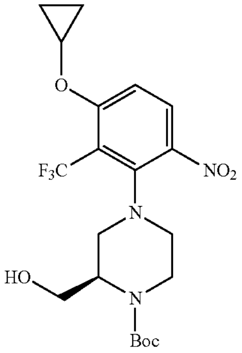 [SMILES: CC(C)(C)OC(=O)N1CCN(c2c([N+](=O)[O-])ccc(OC3CC3)c2C(F)(F)F)C[C@@H]1CO] |
| 52 | 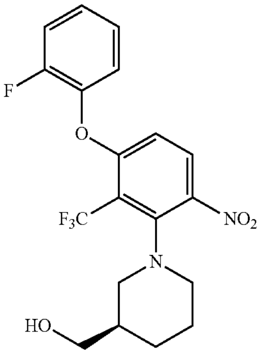 [SMILES: O=[N+]([O-])c1ccc(Oc2ccccc2F)c(C(F)(F)F)c1N1CCC[C@@H](CO)C1] |
| 53 | 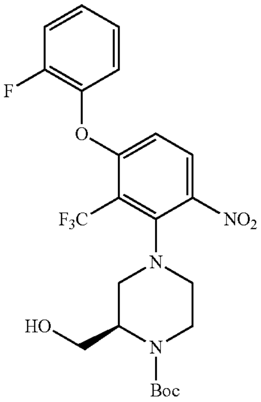 [SMILES: CC(C)(C)OC(=O)N1CCN(c2c([N+](=O)[O-])ccc(Oc3ccccc3F)c2C(F)(F)F)C[C@@H]1CO] |

TABLE 4-continued
| PEx | Str |
|---|---|
| 54 | 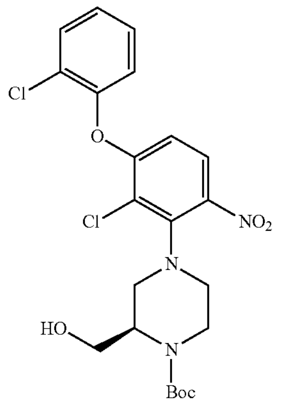 [SMILES: CC(C)(C)OC(=O)N1CCN(c2c([N+](=O)[O-])ccc(Oc3ccccc3Cl)c2Cl)C[C@@H]1CO] |
| 55 | 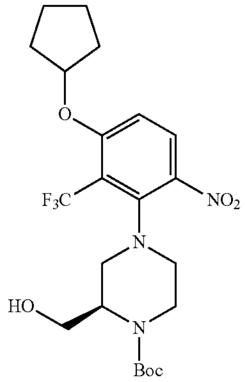 [SMILES: CC(C)(C)OC(=O)N1CCN(c2c([N+](=O)[O-])ccc(OC3CCCC3)c2C(F)(F)F)C[C@@H]1CO] |
| 56 | 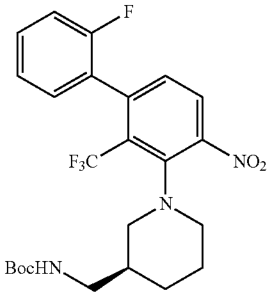 [SMILES: CC(C)(C)OC(=O)NC[C@@H]1CCCN(c2c([N+](=O)[O-])ccc(-c3ccccc3F)c2C(F)(F)F)C1] |
| 57 | 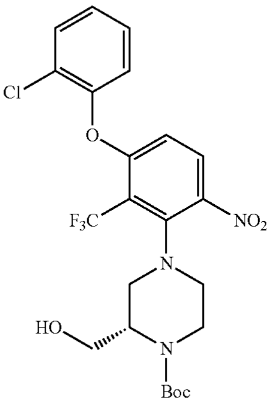 [SMILES: CC(C)(C)OC(=O)N1CCN(c2c([N+](=O)[O-])ccc(Oc3ccccc3Cl)c2C(F)(F)F)C[C@H]1CO] |
TABLE 4-continued
| PEx | Str |
|---|---|
| 58 | 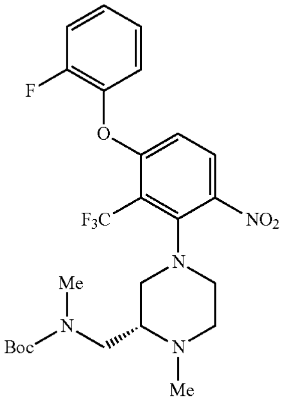 [SMILES: CN(C[C@@H]1CN(c2c([N+](=O)[O-])ccc(Oc3ccccc3F)c2C(F)(F)F)CCN1C)C(=O)OC(C)(C)C] |
| 59 | 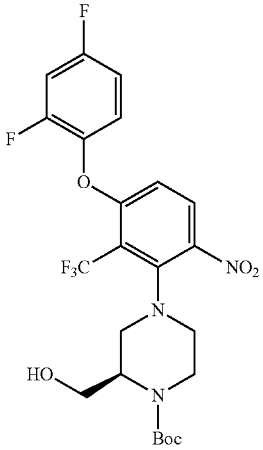 [SMILES: CC(C)(C)OC(=O)N1CCN(c2c([N+](=O)[O-])ccc(Oc3ccc(F)cc3F)c2C(F)(F)F)C[C@@H]1CO] |
| 60 | 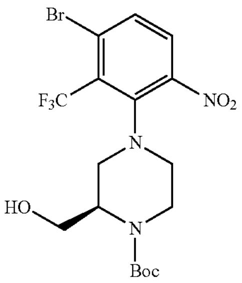 [SMILES: CC(C)(C)OC(=O)N1CCN(c2c([N+](=O)[O-])ccc(Br)c2C(F)(F)F)C[C@@H]1CO] |
| 61 | 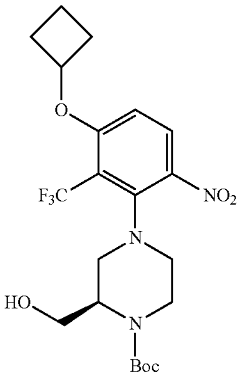 [SMILES: CC(C)(C)OC(=O)N1CCN(c2c([N+](=O)[O-])ccc(OC3CCC3)c2C(F)(F)F)C[C@@H]1CO] |

TABLE 4-continued
| PEx | Str |
| --- | --- |
| 62 | 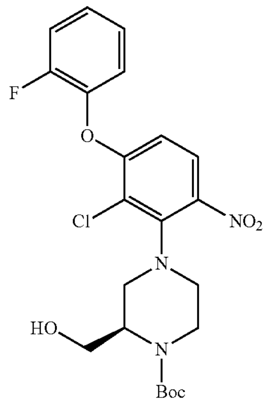 [SMILES: CC(C)(C)OC(=O)N1CCN(c2c([N+](=O)[O-])ccc(Oc3ccccc3F)c2Cl)C[C@@H]1CO] |
| 63 | 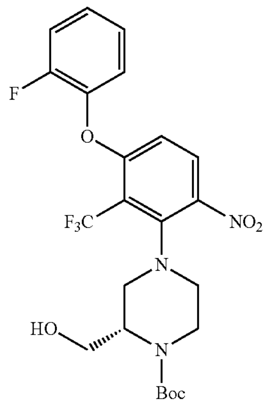 [SMILES: CC(C)(C)OC(=O)N1CCN(c2c([N+](=O)[O-])ccc(Oc3ccccc3F)c2C(F)(F)F)C[C@H]1CO] |
| 64 | 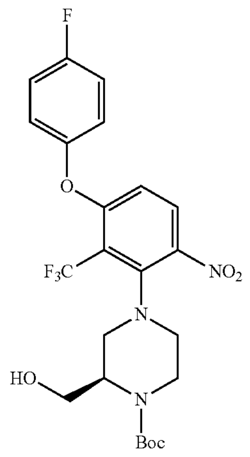 [SMILES: CC(C)(C)OC(=O)N1CCN(c2c([N+](=O)[O-])ccc(Oc3ccc(F)cc3)c2C(F)(F)F)C[C@@H]1CO] |
TABLE 4-continued
| PEx | Str |
| --- | --- |
| 65 | 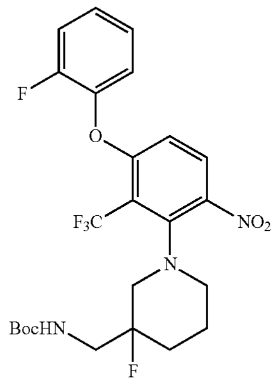 [SMILES: CC(C)(C)OC(=O)NCC1(F)CCCN(c2c([N+](=O)[O-])ccc(Oc3ccccc3F)c2C(F)(F)F)C1] |
| 66 | 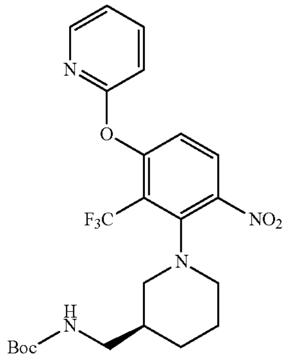 [SMILES: CC(C)(C)OC(=O)NC[C@@H]1CCCN(c2c([N+](=O)[O-])ccc(Oc3ccccn3)c2C(F)(F)F)C1] |
| 67 | 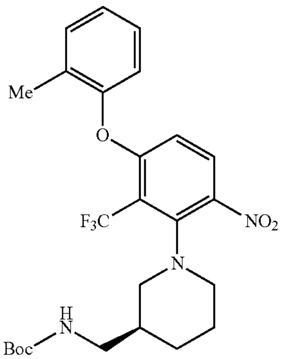 |
| 68 | 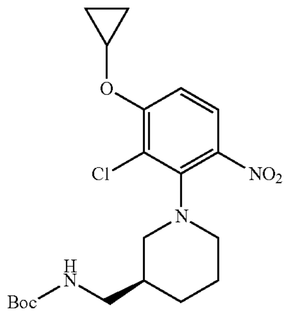 [SMILES: CC(C)(C)OC(=O)NC[C@@H]1CCCN(c2c([N+](=O)[O-])ccc(OC3CC3)c2Cl)C1] |

TABLE 4-continued
| PEx | Str |
|---|---|
| 69 | 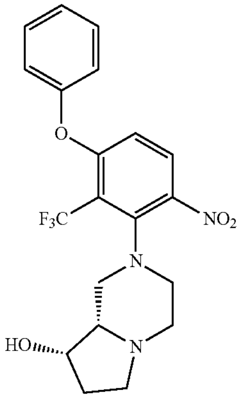 [SMILES: O=[N+]([O-])c1ccc(Oc2ccccc2)c(C(F)(F)F)c1N1CCN2CC[C@H](O)[C@@H]2C1] |
| 70 | 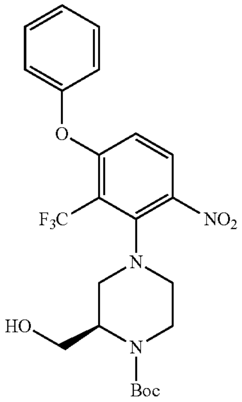 [SMILES: CC(C)(C)OC(=O)N1CCN(c2c([N+](=O)[O-])ccc(Oc3ccccc3)c2C(F)(F)F)C[C@@H]1CO] |
| 71 | 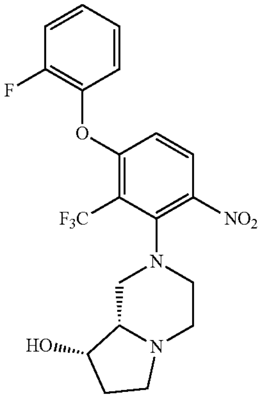 [SMILES: O=[N+]([O-])c1ccc(Oc2ccccc2F)c(C(F)(F)F)c1N1CCN2CC[C@H](O)[C@@H]2C1] |
| 72 | 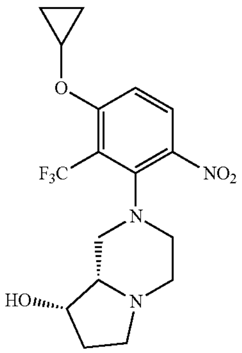 [SMILES: O=[N+]([O-])c1ccc(OC2CC2)c(C(F)(F)F)c1N1CCN2CC[C@H](O)[C@@H]2C1] |
TABLE 4-continued
| PEx | Str |
|---|---|
| 73 | 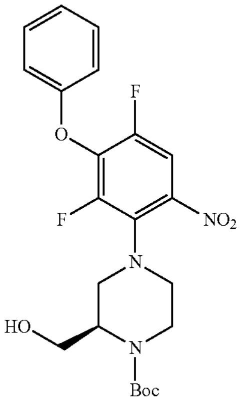 [SMILES: CC(C)(C)OC(=O)N1CCN(c2c([N+](=O)[O-])cc(F)c(Oc3ccccc3)c2F)C[C@@H]1CO] |
| 74 | 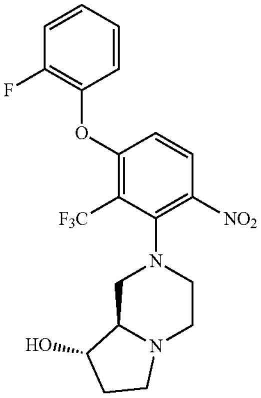 [SMILES: O=[N+]([O-])c1ccc(Oc2ccccc2F)c(C(F)(F)F)c1N1CCN2CC[C@H](O)[C@H]2C1] |
| 75 | 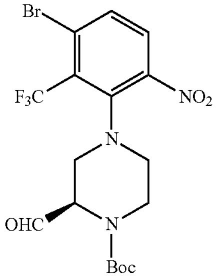 [SMILES: CC(C)(C)OC(=O)N1CCN(c2c([N+](=O)[O-])ccc(Br)c2C(F)(F)F)C[C@@H]1C=O] |
| 76 | 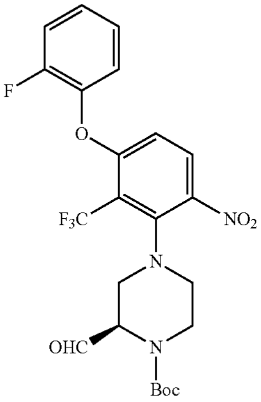 [SMILES: CC(C)(C)OC(=O)N1CCN(c2c([N+](=O)[O-])ccc(Oc3ccccc3F)c2C(F)(F)F)C[C@@H]1C=O] |

TABLE 4-continued
| PEx | Str |
| --- | --- |
| 77 | 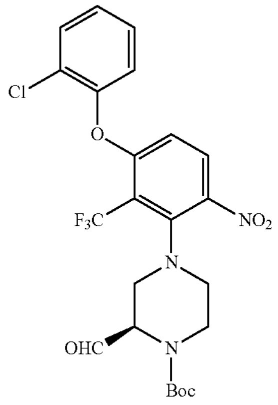 [SMILES: CC(C)(C)OC(=O)N1CCN(c2c([N+](=O)[O-])ccc(Oc3ccccc3Cl)c2C(F)(F)F)C[C@@H]1C=O] |
| 78 | 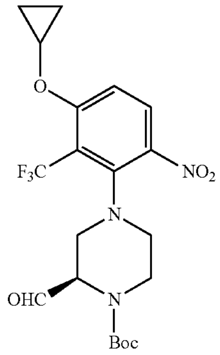 [SMILES: CC(C)(C)OC(=O)N1CCN(c2c([N+](=O)[O-])ccc(OC3CC3)c2C(F)(F)F)C[C@@H]1C=O] |
| 79 | 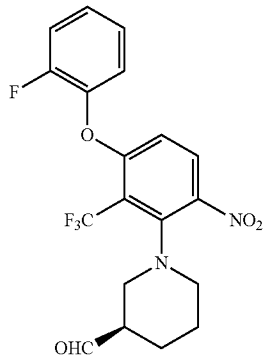 [SMILES: O=C[C@@H]1CCCN(c2c([N+](=O)[O-])ccc(Oc3ccccc3F)c2C(F)(F)F)C1] |
| 80 | 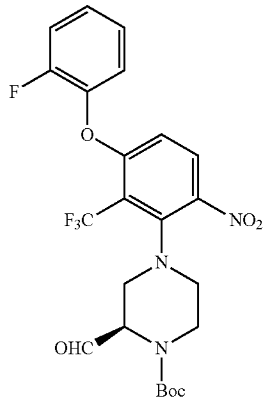 [SMILES: CC(C)(C)OC(=O)N1CCN(c2c([N+](=O)[O-])ccc(Oc3ccccc3F)c2C(F)(F)F)C[C@@H]1C=O] |
| 81 | 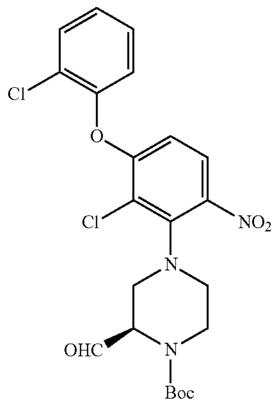 [SMILES: CC(C)(C)OC(=O)N1CCN(c2c([N+](=O)[O-])ccc(Oc3ccccc3Cl)c2Cl)C[C@@H]1C=O] |
| 82 | 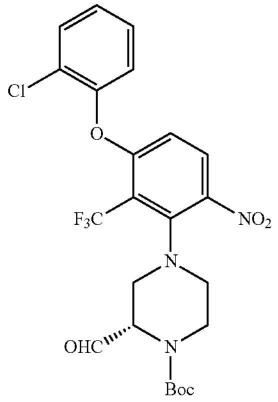 [SMILES: CC(C)(C)OC(=O)N1CCN(c2c([N+](=O)[O-])ccc(Oc3ccccc3Cl)c2C(F)(F)F)C[C@H]1C=O] |
| 83 | 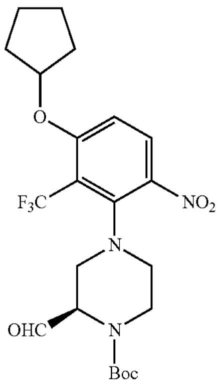 [SMILES: CC(C)(C)OC(=O)N1CCN(c2c([N+](=O)[O-])ccc(OC3CCCC3)c2C(F)(F)F)C[C@@H]1C=O] |

TABLE 4-continued
| PEx | Str |
|---|---|
| 84 | 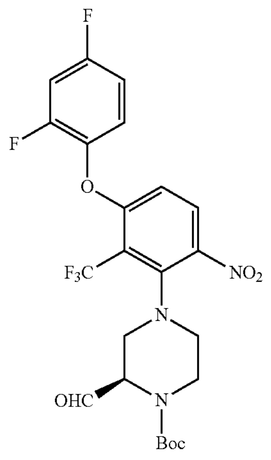 [SMILES: CC(C)(C)OC(=O)N1CCN(c2c([N+](=O)[O-])ccc(Oc3ccc(F)cc3F)c2C(F)(F)F)C[C@@H]1C=O] |
| 85 | 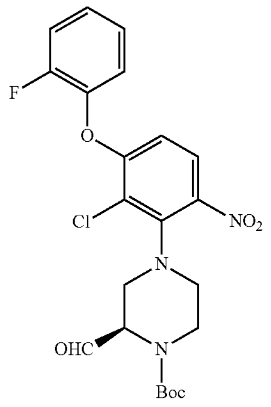 [SMILES: CC(C)(C)OC(=O)N1CCN(c2c([N+](=O)[O-])ccc(Oc3ccccc3F)c2Cl)C[C@@H]1C=O] |
| 86 | 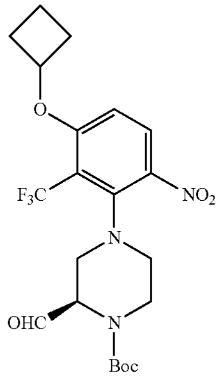 [SMILES: CC(C)(C)OC(=O)N1CCN(c2c([N+](=O)[O-])ccc(OC3CCC3)c2C(F)(F)F)C[C@@H]1C=O] |
| 87 | 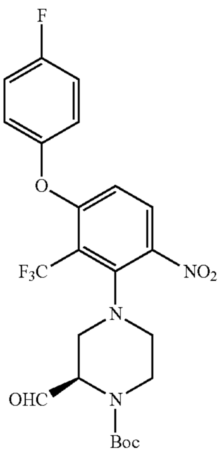 [SMILES: CC(C)(C)OC(=O)N1CCN(c2c([N+](=O)[O-])ccc(Oc3ccc(F)cc3)c2C(F)(F)F)C[C@@H]1C=O] |
| 88 | 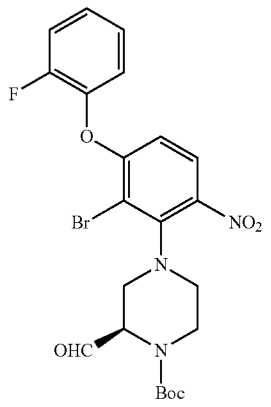 [SMILES: CC(C)(C)OC(=O)N1CCN(c2c([N+](=O)[O-])ccc(Oc3ccccc3F)c2Br)C[C@@H]1C=O] |
| 89 | 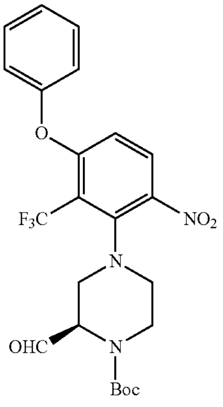 [SMILES: CC(C)(C)OC(=O)N1CCN(c2c([N+](=O)[O-])ccc(Oc3ccccc3)c2C(F)(F)F)C[C@@H]1C=O] |

TABLE 4-continued
| PEx | Str |
| --- | --- |
| 90 | 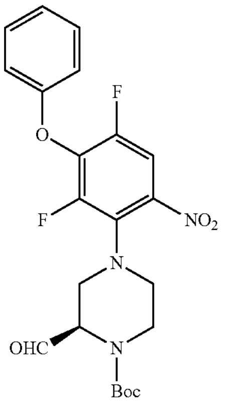 [SMILES: CC(C)(C)OC(=O)N1CCN(c2c([N+](=O)[O-])cc(F)c(Oc3ccccc3)c2F)C[C@@H]1C=O] |
| 91 | 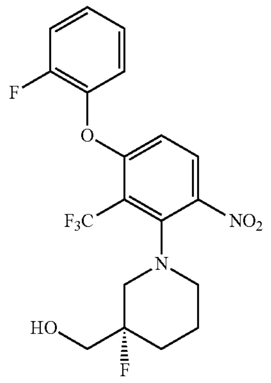 [SMILES: O=[N+]([O-])c1ccc(Oc2ccccc2F)c(C(F)(F)F)c1N1CCC[C@@](F)(CO)C1] |
| 92 | 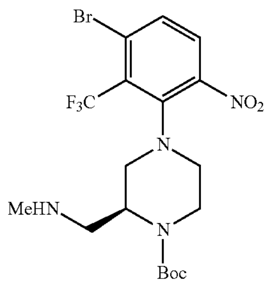 [SMILES: CNC[C@H]1CN(c2c([N+](=O)[O-])ccc(Br)c2C(F)(F)F)CCN1C(=O)OC(C)(C)C] |
| 93 | 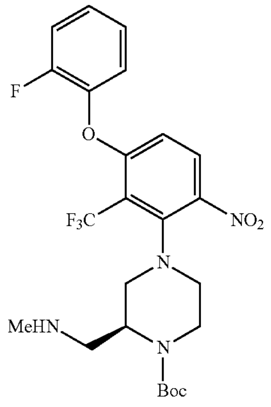 [SMILES: CNC[C@H]1CN(c2c([N+](=O)[O-])ccc(Oc3ccccc3F)c2C(F)(F)F)CCN1C(=O)OC(C)(C)C] |
TABLE 4-continued
| PEx | Str |
| --- | --- |
| 94 | 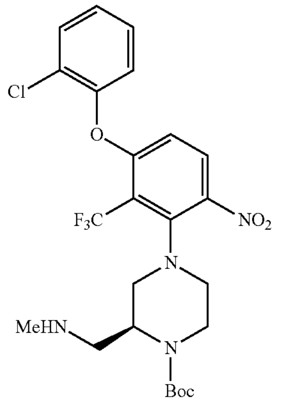 [SMILES: CNC[C@H]1CN(c2c([N+](=O)[O-])ccc(Oc3ccccc3Cl)c2C(F)(F)F)CCN1C(=O)OC(C)(C)C] |
| 95 | 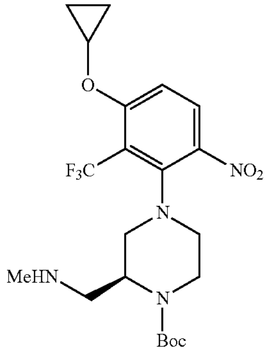 [SMILES: CNC[C@H]1CN(c2c([N+](=O)[O-])ccc(OC3CC3)c2C(F)(F)F)CCN1C(=O)OC(C)(C)C] |
| 96 | 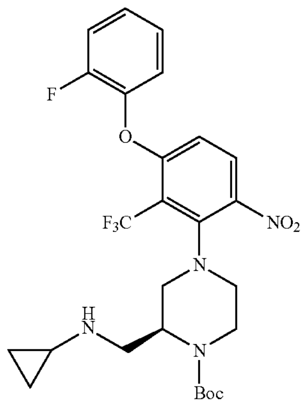 [SMILES: CC(C)(C)OC(=O)N1CCN(c2c([N+](=O)[O-])ccc(Oc3ccccc3F)c2C(F)(F)F)C[C@@H]1CNC1CC1] |
| 97 | 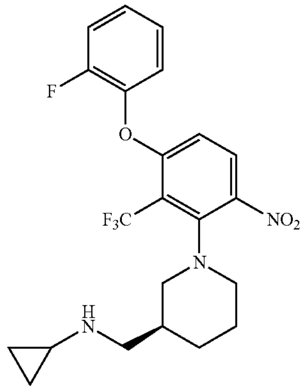 [SMILES: O=[N+]([O-])c1ccc(Oc2ccccc2F)c(C(F)(F)F)c1N1CCC[C@@H](CNC2CC2)C1] |

TABLE 4-continued
| PEx | Str |
| --- | --- |
| 98 | 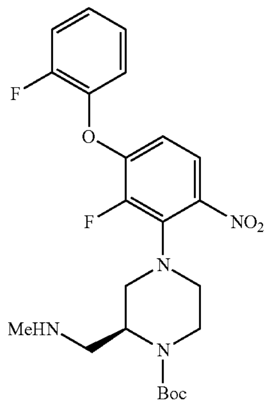 [SMILES: CNC[C@H]1CN(c2c([N+](=O)[O-])ccc(Oc3ccccc3F)c2F)CCN1C(=O)OC(C)(C)C] |
| 99 | 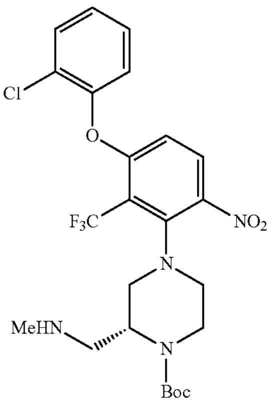 [SMILES: CNC[C@@H]1CN(c2c([N+](=O)[O-])ccc(Oc3ccccc3Cl)c2C(F)(F)F)CCN1C(=O)OC(C)(C)C] |
| 100 | 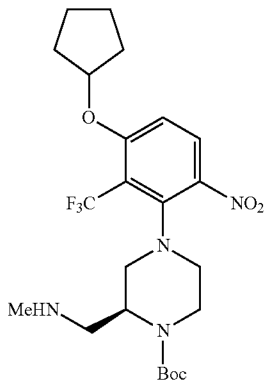 [SMILES: CNC[C@H]1CN(c2c([N+](=O)[O-])ccc(OC3CCCC3)c2C(F)(F)F)CCN1C(=O)OC(C)(C)C] |
TABLE 4-continued
| PEx | Str |
| --- | --- |
| 101 | 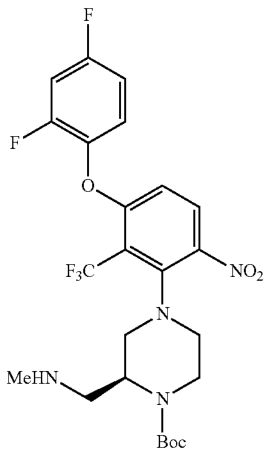 [SMILES: CNC[C@H]1CN(c2c([N+](=O)[O-])ccc(Oc3ccc(F)cc3F)c2C(F)(F)F)CCN1C(=O)OC(C)(C)C] |
| 102 | 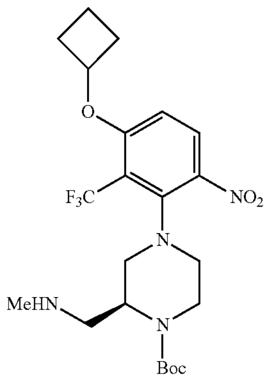 [SMILES: CNC[C@H]1CN(c2c([N+](=O)[O-])ccc(OC3CCC3)c2C(F)(F)F)CCN1C(=O)OC(C)(C)C] |
| 103 | 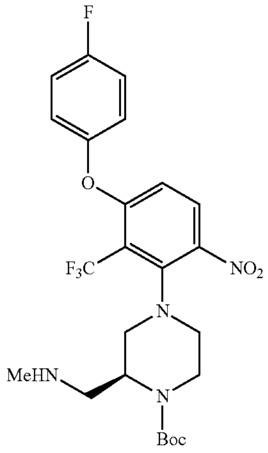 [SMILES: CNC[C@H]1CN(c2c([N+](=O)[O-])ccc(Oc3ccc(F)cc3)c2C(F)(F)F)CCN1C(=O)OC(C)(C)C] |

TABLE 4-continued
| PEx | Str |
| --- | --- |
| 104 | 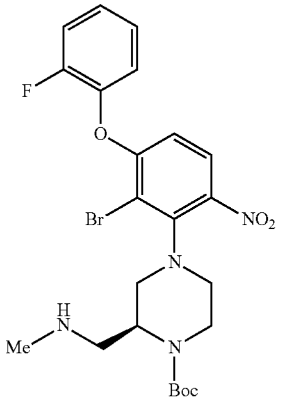 [SMILES: CNC[C@H]1CN(c2c([N+](=O)[O-])ccc(Oc3ccccc3F)c2Br)CCN1C(=O)OC(C)(C)C] |
| 105 | 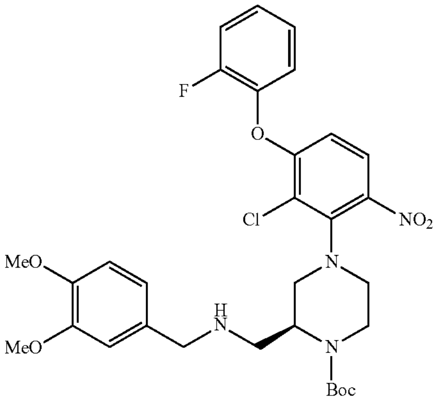 [SMILES: COc1ccc(CNC[C@H]2CN(c3c([N+](=O)[O-])ccc(Oc4ccccc4F)c3Cl)CCN2C(=O)OC(C)(C)C)cc1OC] |
| 106 | 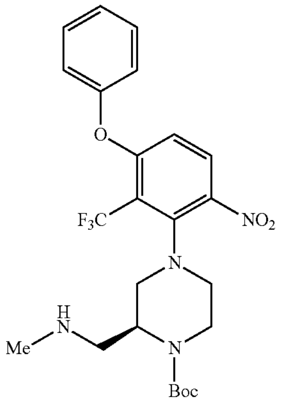 [SMILES: CNC[C@H]1CN(c2c([N+](=O)[O-])ccc(Oc3ccccc3)c2C(F)(F)F)CCN1C(=O)OC(C)(C)C] |
| 107 | 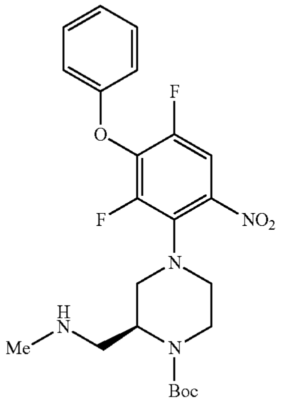 [SMILES: CNC[C@H]1CN(c2c([N+](=O)[O-])cc(F)c(Oc3ccccc3)c2F)CCN1C(=O)OC(C)(C)C] |
TABLE 4-continued
| PEx | Str |
| --- | --- |
| 108 | 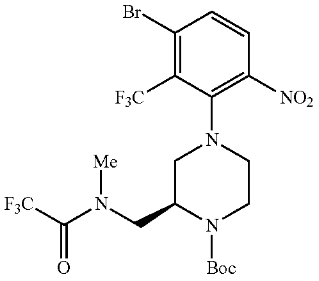 [SMILES: CN(C[C@H]1CN(c2c([N+](=O)[O-])ccc(Br)c2C(F)(F)F)CCN1C(=O)OC(C)(C)C)C(=O)C(F)(F)F] |
| 109 | 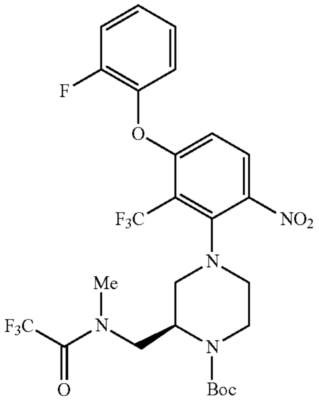 [SMILES: CN(C[C@H]1CN(c2c([N+](=O)[O-])ccc(Oc3ccccc3F)c2C(F)(F)F)CCN1C(=O)OC(C)(C)C)C(=O)C(F)(F)F] |
| 110 | 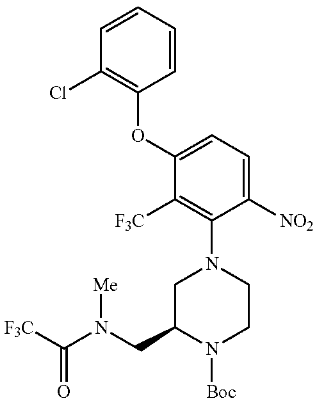 [SMILES: CN(C[C@H]1CN(c2c([N+](=O)[O-])ccc(Oc3ccccc3Cl)c2C(F)(F)F)CCN1C(=O)OC(C)(C)C)C(=O)C(F)(F)F] |
| 111 | 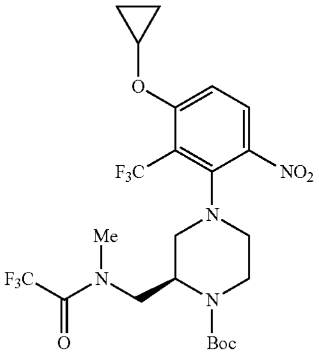 [SMILES: CN(C[C@H]1CN(c2c([N+](=O)[O-])ccc(OC3CC3)c2C(F)(F)F)CCN1C(=O)OC(C)(C)C)C(=O)C(F)(F)F] |

TABLE 4-continued
| PEx | Str |
| --- | --- |
| 112 | 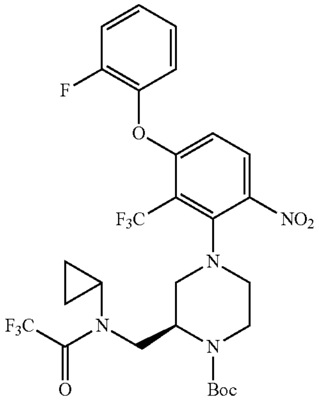 [SMILES: CC(C)(C)OC(=O)N1CCN(c2c([N+](=O)[O-])ccc(Oc3ccccc3F)c2C(F)(F)F)C[C@@H]1CN(C(=O)C(F)(F)F)C1CC1] |
| 113 | 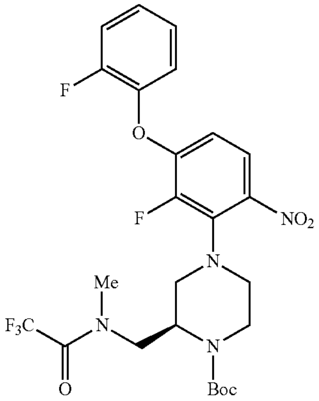 [SMILES: CN(C[C@H]1CN(c2c([N+](=O)[O-])ccc(Oc3ccccc3F)c2F)CCN1C(=O)OC(C)(C)C)C(=O)C(F)(F)F] |
| 114 | 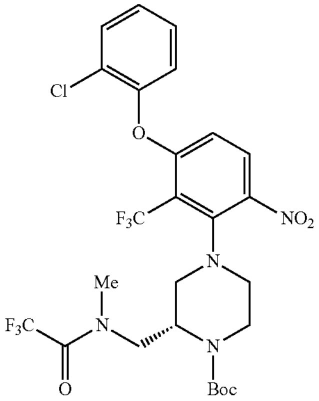 [SMILES: CN(C[C@@H]1CN(c2c([N+](=O)[O-])ccc(Oc3ccccc3Cl)c2C(F)(F)F)CCN1C(=O)OC(C)(C)C)C(=O)C(F)(F)F] |
| 115 | 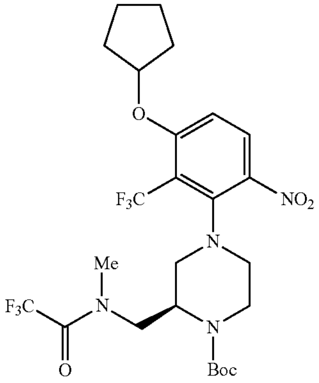 [SMILES: CN(C[C@H]1CN(c2c([N+](=O)[O-])ccc(OC3CCCC3)c2C(F)(F)F)CCN1C(=O)OC(C)(C)C)C(=O)C(F)(F)F] |
TABLE 4-continued
| PEx | Str |
| --- | --- |
| 116 | 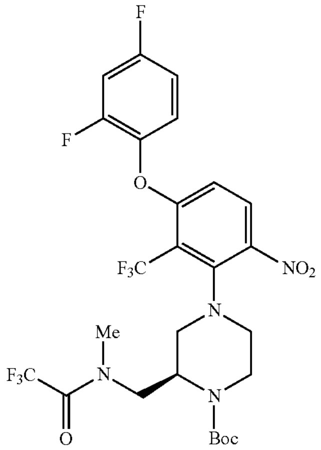 [SMILES: CN(C[C@H]1CN(c2c([N+](=O)[O-])ccc(Oc3ccc(F)cc3F)c2C(F)(F)F)CCN1C(=O)OC(C)(C)C)C(=O)C(F)(F)F] |
| 117 | 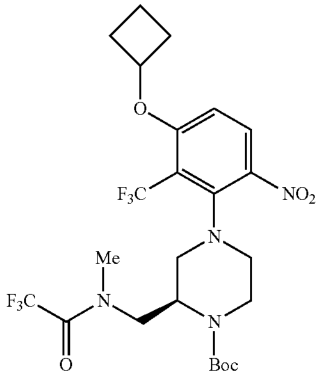 [SMILES: CN(C[C@H]1CN(c2c([N+](=O)[O-])ccc(OC3CCC3)c2C(F)(F)F)CCN1C(=O)OC(C)(C)C)C(=O)C(F)(F)F] |
| 118 | 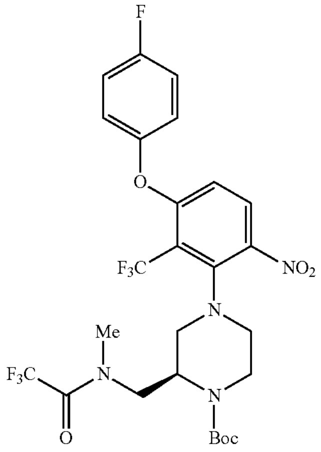 [SMILES: CN(C[C@H]1CN(c2c([N+](=O)[O-])ccc(Oc3ccc(F)cc3)c2C(F)(F)F)CCN1C(=O)OC(C)(C)C)C(=O)C(F)(F)F] |

TABLE 4-continued
| PEx | Str |
|---|---|
| 119 | 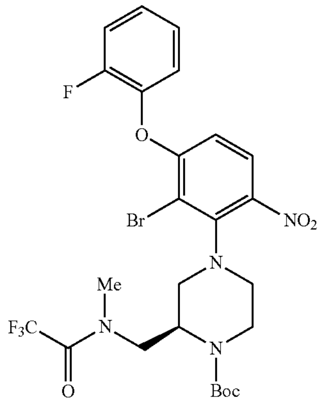 [SMILES: CN(C[C@H]1CN(c2c([N+](=O)[O-])ccc(Oc3ccccc3F)c2Br)CCN1C(=O)OC(C)(C)C)C(=O)C(F)(F)F] |
| 120 | 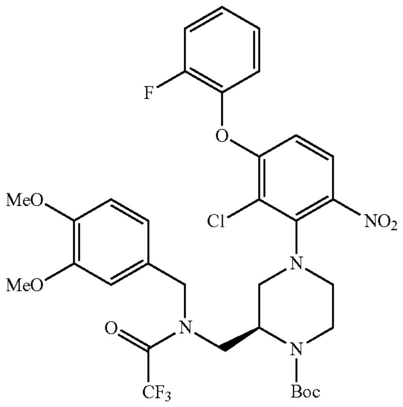 |
| 121 | 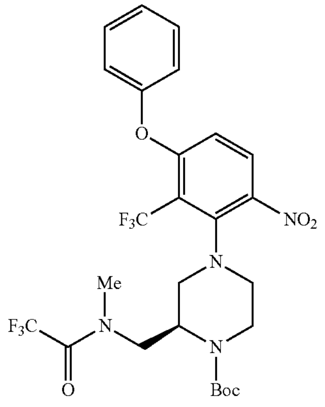 [SMILES: CN(C[C@H]1CN(c2c([N+](=O)[O-])ccc(Oc3ccccc3)c2C(F)(F)F)CCN1C(=O)OC(C)(C)C)C(=O)C(F)(F)F] |
| 122 | 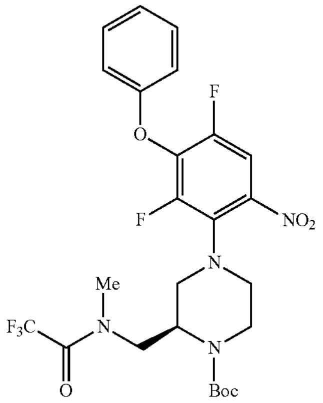 [SMILES: CN(C[C@H]1CN(c2c([N+](=O)[O-])cc(F)c(Oc3ccccc3)c2F)CCN1C(=O)OC(C)(C)C)C(=O)C(F)(F)F] |
| 123 | 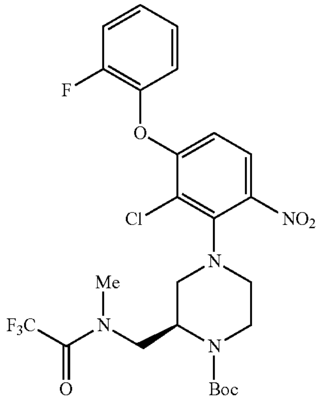 [SMILES: CN(C[C@H]1CN(c2c([N+](=O)[O-])ccc(Oc3ccccc3F)c2Cl)CCN1C(=O)OC(C)(C)C)C(=O)C(F)(F)F] |
| 124 | 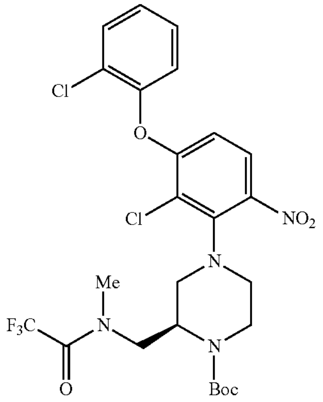 [SMILES: CN(C[C@H]1CN(c2c([N+](=O)[O-])ccc(Oc3ccccc3Cl)c2Cl)CCN1C(=O)OC(C)(C)C)C(=O)C(F)(F)F] |
| 125 | 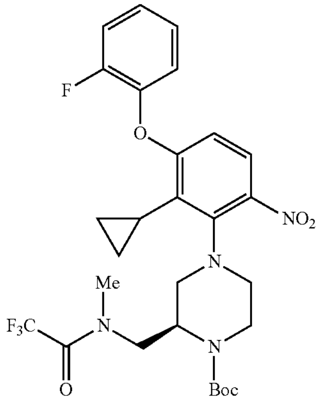 [SMILES: CN(C[C@H]1CN(c2c([N+](=O)[O-])ccc(Oc3ccccc3F)c2C2CC2)CCN1C(=O)OC(C)(C)C)C(=O)C(F)(F)F] |

TABLE 4-continued
| PEx | Str |
|---|---|
| 126 | 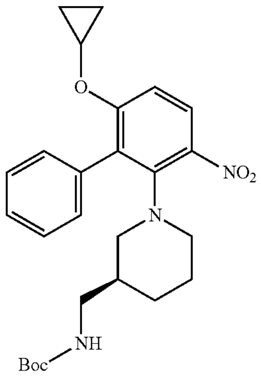 |
| 127 | 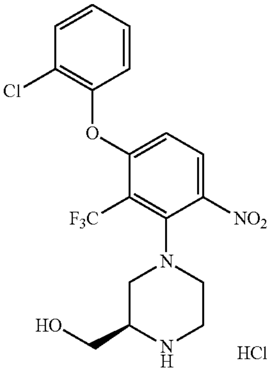 [SMILES: O=[N+]([O-])c1ccc(Oc2ccccc2Cl)c(C(F)(F)F)c1N1CCN[C@@H](CO)C1 ; Cl] |
| 128 | 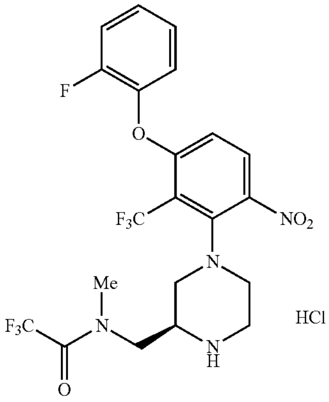 [SMILES: CN(C[C@H]1CN(c2c([N+](=O)[O-])ccc(Oc3ccccc3F)c2C(F)(F)F)CCN1)C(=O)C(F)(F)F ; Cl] |
| 129 | 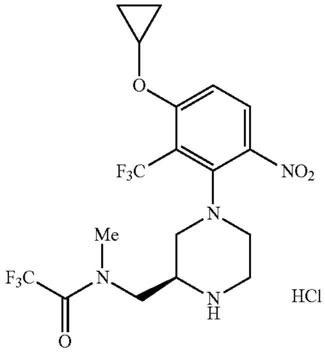 [SMILES: CN(C[C@H]1CN(c2c([N+](=O)[O-])ccc(OC3CC3)c2C(F)(F)F)CCN1)C(=O)C(F)(F)F ; Cl] |
TABLE 4-continued
| PEx | Str |
|---|---|
| 130 | 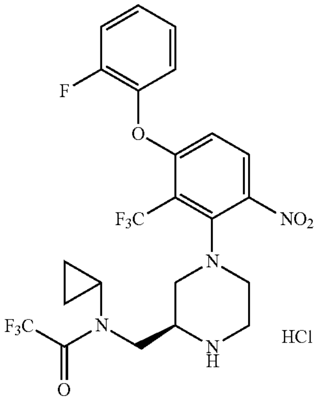 [SMILES: O=C(N(C[C@H]1CN(c2c([N+](=O)[O-])ccc(Oc3ccccc3F)c2C(F)(F)F)CCN1)C1CC1)C(F)(F)F ; Cl] |
| 131 | 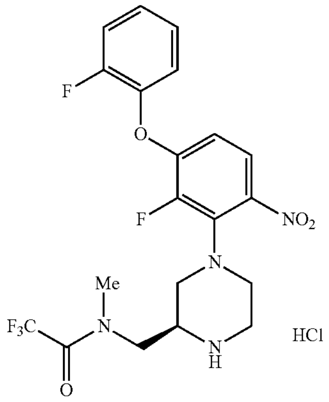 [SMILES: CN(C[C@H]1CN(c2c([N+](=O)[O-])ccc(Oc3ccccc3F)c2F)CCN1)C(=O)C(F)(F)F ; Cl] |
| 132 | 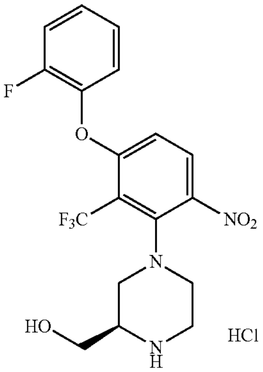 [SMILES: O=[N+]([O-])c1ccc(Oc2ccccc2F)c(C(F)(F)F)c1N1CCN[C@@H](CO)C1 ; Cl] |
| 133 | 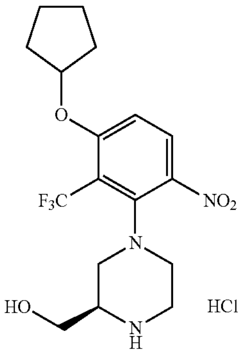 [SMILES: O=[N+]([O-])c1ccc(OC2CCCC2)c(C(F)(F)F)c1N1CCN[C@@H](CO)C1 ; Cl] |

TABLE 4-continued
| PEx | Str |
|---|---|
| 134 | 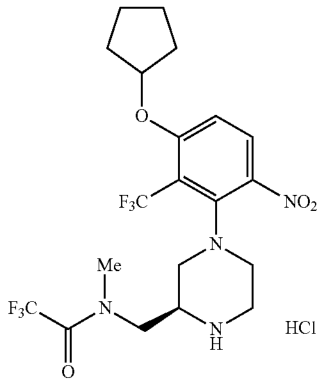 [SMILES: CN(C[C@H]1CN(c2c([N+](=O)[O-])ccc(OC3CCCC3)c2C(F)(F)F)CCN1)C(=O)C(F)(F)F ; Cl] |
| 135 | 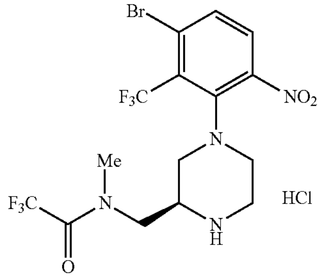 [SMILES: CN(C[C@H]1CN(c2c([N+](=O)[O-])ccc(Br)c2C(F)(F)F)CCN1)C(=O)C(F)(F)F ; Cl] |
| 136 | 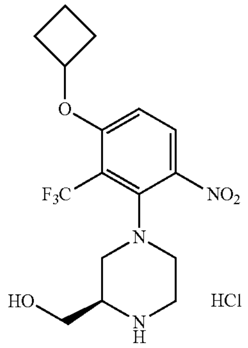 [SMILES: O=[N+]([O-])c1ccc(OC2CCC2)c(C(F)(F)F)c1N1CCN[C@@H](CO)C1 ; Cl] |
| 137 | 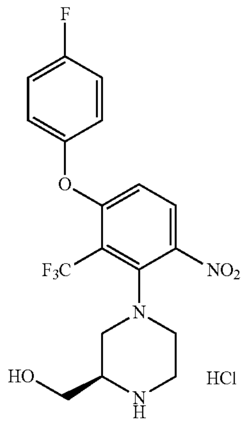 [SMILES: O=[N+]([O-])c1ccc(Oc2ccc(F)cc2)c(C(F)(F)F)c1N1CCN[C@@H](CO)C1 ; Cl] |
TABLE 4-continued
| PEx | Str |
|---|---|
| 138 | 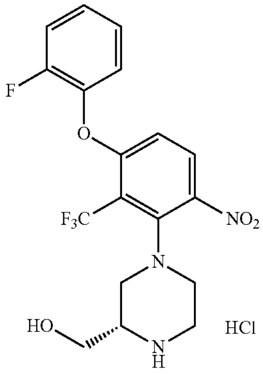 [SMILES: O=[N+]([O-])c1ccc(Oc2ccccc2F)c(C(F)(F)F)c1N1CCN[C@H](CO)C1 ; Cl] |
| 139 | 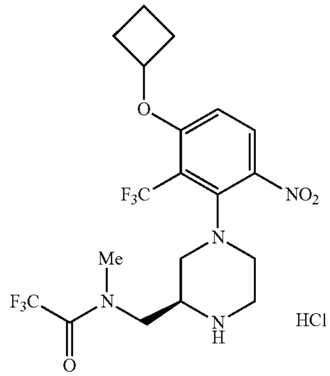 [SMILES: CN(C[C@H]1CN(c2c([N+](=O)[O-])ccc(OC3CCC3)c2C(F)(F)F)CCN1)C(=O)C(F)(F)F ; Cl] |
| 140 | 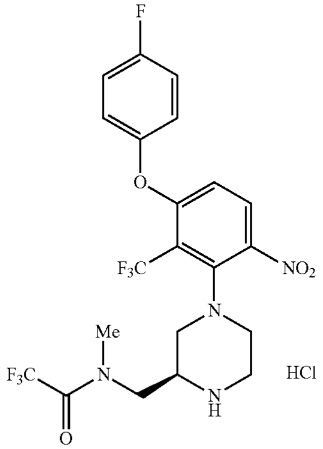 [SMILES: CN(C[C@H]1CN(c2c([N+](=O)[O-])ccc(Oc3ccc(F)cc3)c2C(F)(F)F)CCN1)C(=O)C(F)(F)F ; Cl] |
| 141 | 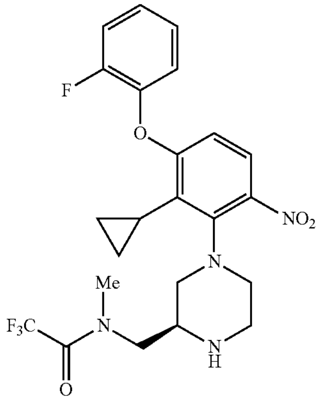 [SMILES: CN(C[C@H]1CN(c2c([N+](=O)[O-])ccc(Oc3ccccc3F)c2C2CC2)CCN1)C(=O)C(F)(F)F] |

TABLE 4-continued
| PEx | Str |
| --- | --- |
| 142 | 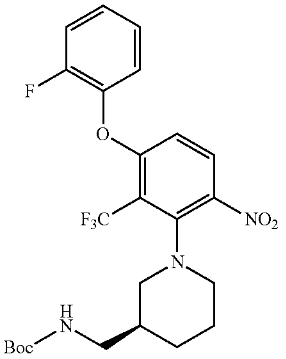 [SMILES: CC(C)(C)OC(=O)NC[C@@H]1CCCN(c2c([N+](=O)[O-])ccc(Oc3ccccc3F)c2C(F)(F)F)C1] |
| 143 | 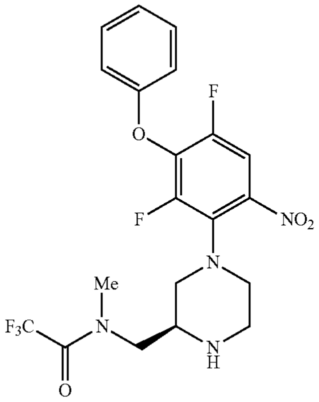 [SMILES: CN(C[C@H]1CN(c2c([N+](=O)[O-])cc(F)c(Oc3ccccc3)c2F)CCN1)C(=O)C(F)(F)F] |
| 144 | 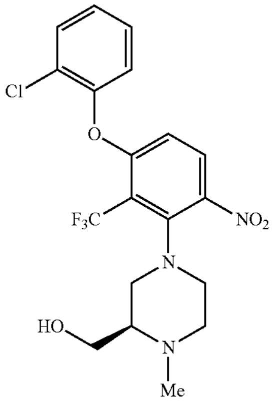 [SMILES: CN1CCN(c2c([N+](=O)[O-])ccc(Oc3ccccc3Cl)c2C(F)(F)F)C[C@@H]1CO] |
| 145 | 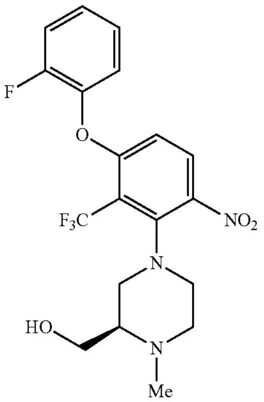 [SMILES: CN1CCN(c2c([N+](=O)[O-])ccc(Oc3ccccc3F)c2C(F)(F)F)C[C@@H]1CO] |
TABLE 4-continued
| PEx | Str |
| --- | --- |
| 146 | 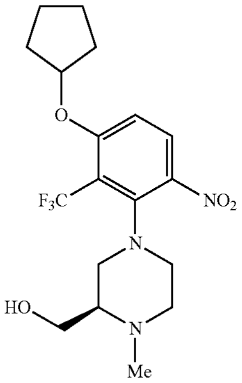 [SMILES: CN1CCN(c2c([N+](=O)[O-])ccc(OC3CCCC3)c2C(F)(F)F)C[C@@H]1CO] |
| 147 | 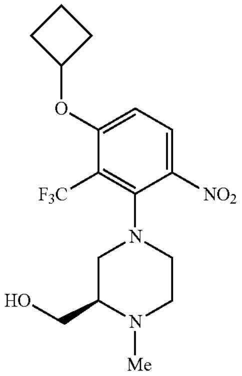 [SMILES: CN1CCN(c2c([N+](=O)[O-])ccc(OC3CCC3)c2C(F)(F)F)C[C@@H]1CO] |
| 148 | 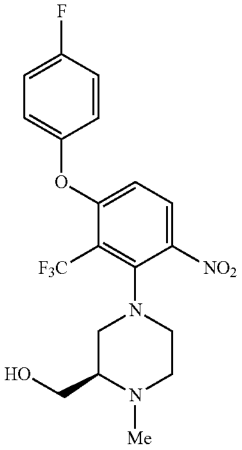 [SMILES: CN1CCN(c2c([N+](=O)[O-])ccc(Oc3ccc(F)cc3)c2C(F)(F)F)C[C@@H]1CO] |
| 149 | 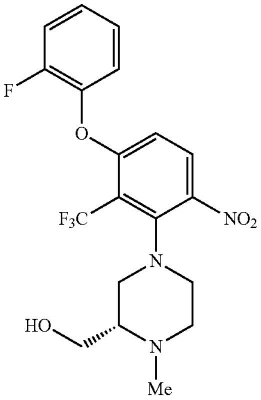 [SMILES: CN1CCN(c2c([N+](=O)[O-])ccc(Oc3ccccc3F)c2C(F)(F)F)C[C@H]1CO] |

TABLE 4-continued
| PEx | Str |
|---|---|
| 150 | 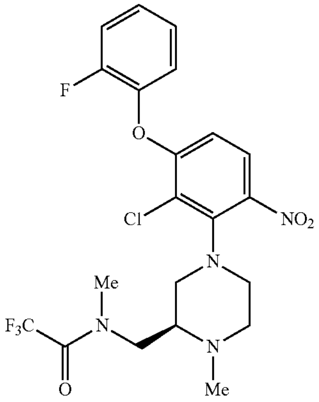 [SMILES: CN(C[C@H]1CN(c2c([N+](=O)[O-])ccc(Oc3ccccc3F)c2Cl)CCN1C)C(=O)C(F)(F)F] |
| 151 | 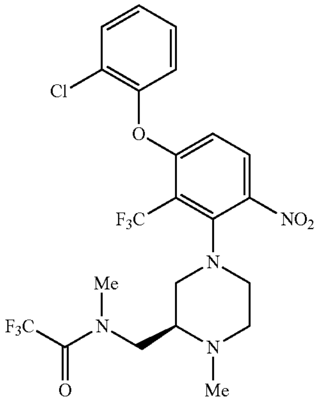 [SMILES: CN(C[C@H]1CN(c2c([N+](=O)[O-])ccc(Oc3ccccc3Cl)c2C(F)(F)F)CCN1C)C(=O)C(F)(F)F] |
| 152 | 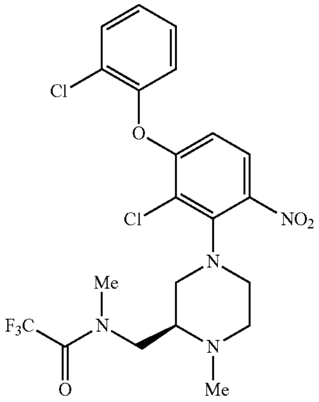 [SMILES: CN(C[C@H]1CN(c2c([N+](=O)[O-])ccc(Oc3ccccc3Cl)c2Cl)CCN1C)C(=O)C(F)(F)F] |
TABLE 4-continued
| PEx | Str |
|---|---|
| 153 | 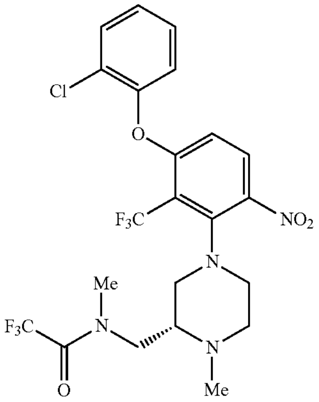 [SMILES: CN(C[C@@H]1CN(c2c([N+](=O)[O-])ccc(Oc3ccccc3Cl)c2C(F)(F)F)CCN1C)C(=O)C(F)(F)F] |
| 154 | 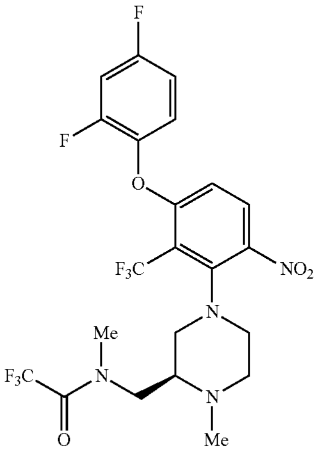 [SMILES: CN(C[C@H]1CN(c2c([N+](=O)[O-])ccc(Oc3ccc(F)cc3F)c2C(F)(F)F)CCN1C)C(=O)C(F)(F)F] |
| 155 | 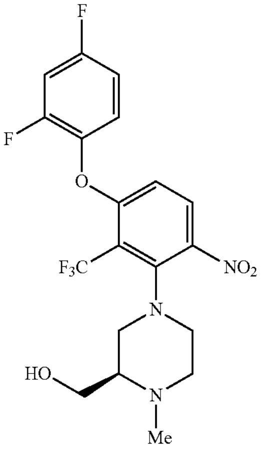 [SMILES: CN1CCN(c2c([N+](=O)[O-])ccc(Oc3ccc(F)cc3F)c2C(F)(F)F)C[C@@H]1CO] |

TABLE 4-continued
| PEx | Str |
| --- | --- |
| 156 | 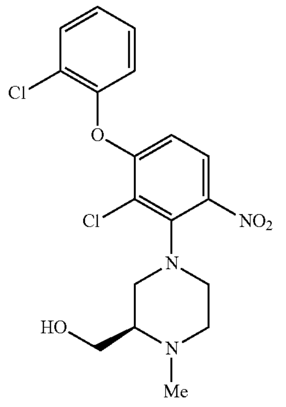 [SMILES: CN1CCN(c2c([N+](=O)[O-])ccc(Oc3ccccc3Cl)c2Cl)C[C@@H]1CO] |
| 157 | 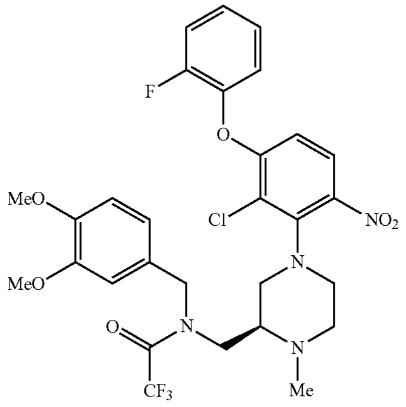 |
| 158 | 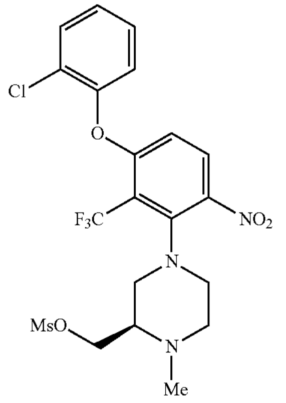 [SMILES: CN1CCN(c2c([N+](=O)[O-])ccc(Oc3ccccc3Cl)c2C(F)(F)F)C[C@@H]1COS(C)(=O)=O] |
| 159 | 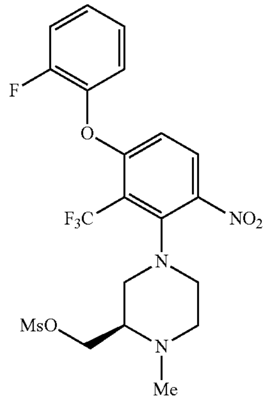 [SMILES: CN1CCN(c2c([N+](=O)[O-])ccc(Oc3ccccc3F)c2C(F)(F)F)C[C@@H]1COS(C)(=O)=O] |
TABLE 4-continued
| PEx | Str |
| --- | --- |
| 160 | 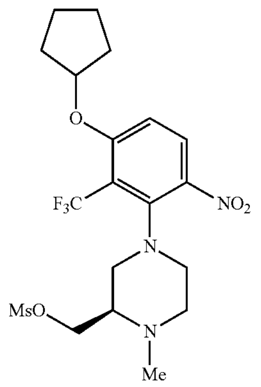 [SMILES: CN1CCN(c2c([N+](=O)[O-])ccc(OC3CCCC3)c2C(F)(F)F)C[C@@H]1COS(C)(=O)=O] |
| 161 | 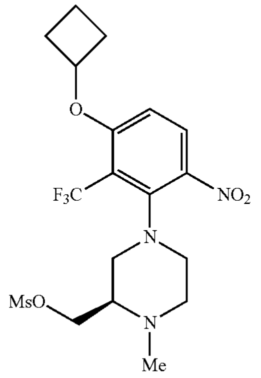 [SMILES: CN1CCN(c2c([N+](=O)[O-])ccc(OC3CCC3)c2C(F)(F)F)C[C@@H]1COS(C)(=O)=O] |
| 162 | 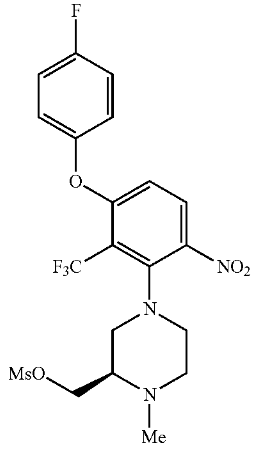 [SMILES: CN1CCN(c2c([N+](=O)[O-])ccc(Oc3ccc(F)cc3)c2C(F)(F)F)C[C@@H]1COS(C)(=O)=O] |

TABLE 4-continued
| PEx | Str |
|---|---|
| 163 | 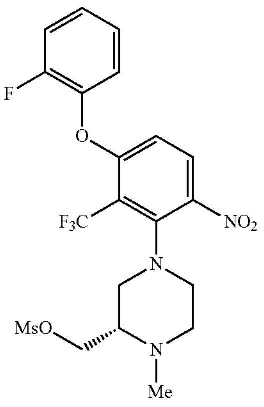 [SMILES: CN1CCN(c2c([N+](=O)[O-])ccc(Oc3ccccc3F)c2C(F)(F)F)C[C@H]1COS(C)(=O)=O] |
| 164 | 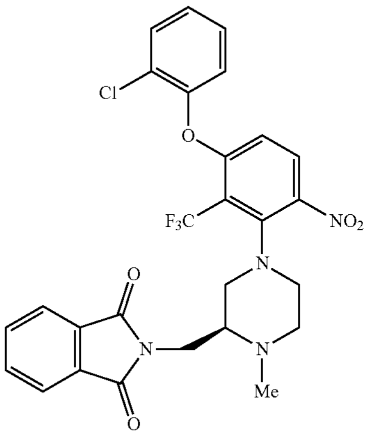 [SMILES: CN1CCN(c2c([N+](=O)[O-])ccc(Oc3ccccc3Cl)c2C(F)(F)F)C[C@@H]1CN1C(=O)c2ccccc2C1=O] |
| 165 | 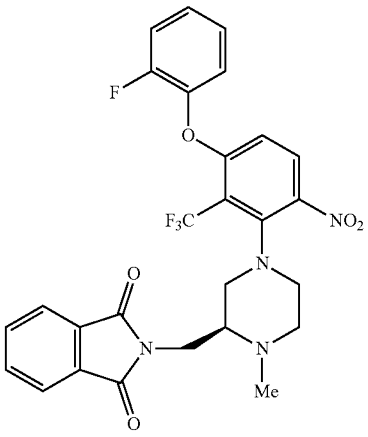 [SMILES: CN1CCN(c2c([N+](=O)[O-])ccc(Oc3ccccc3F)c2C(F)(F)F)C[C@@H]1CN1C(=O)c2ccccc2C1=O] |
TABLE 4-continued
| PEx | Str |
|---|---|
| 166 | 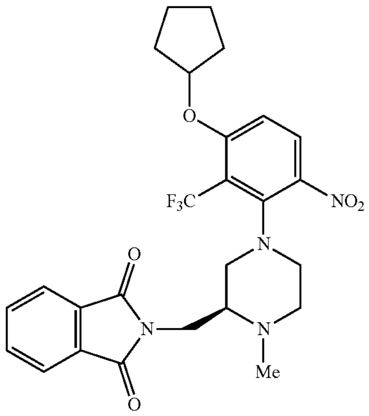 [SMILES: CN1CCN(c2c([N+](=O)[O-])ccc(OC3CCCC3)c2C(F)(F)F)C[C@@H]1CN1C(=O)c2ccccc2C1=O] |
| 167 | 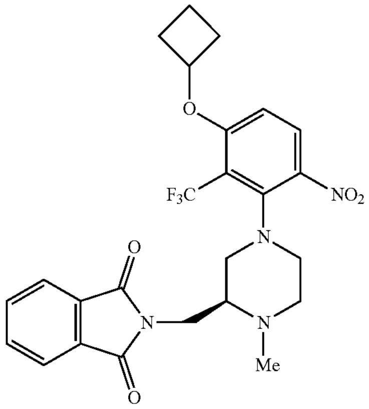 [SMILES: CN1CCN(c2c([N+](=O)[O-])ccc(OC3CCC3)c2C(F)(F)F)C[C@@H]1CN1C(=O)c2ccccc2C1=O] |
| 168 | 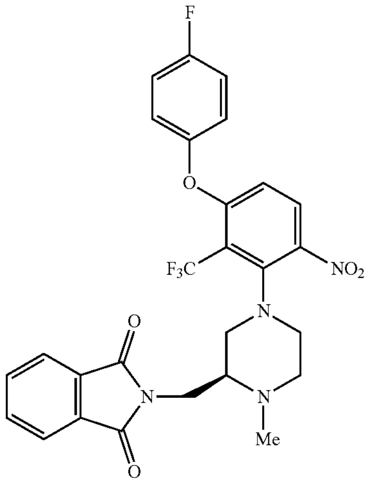 [SMILES: CN1CCN(c2c([N+](=O)[O-])ccc(Oc3ccc(F)cc3)c2C(F)(F)F)C[C@@H]1CN1C(=O)c2ccccc2C1=O] |

TABLE 4-continued
| PEx | Str |
| --- | --- |
| 169 | 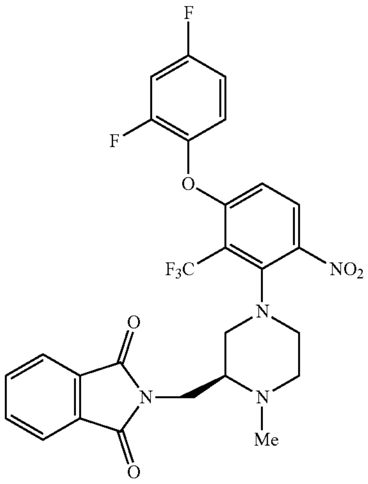 [SMILES: CN1CCN(c2c([N+](=O)[O-])ccc(Oc3ccc(F)cc3F)c2C(F)(F)F)C[C@@H]1CN1C(=O)c2ccccc2C1=O] |
| 170 | 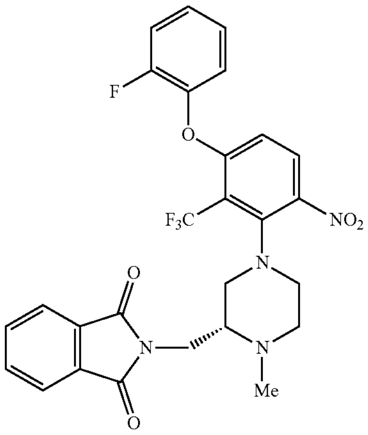 [SMILES: CN1CCN(c2c([N+](=O)[O-])ccc(Oc3ccccc3F)c2C(F)(F)F)C[C@H]1CN1C(=O)c2ccccc2C1=O] |
| 171 | 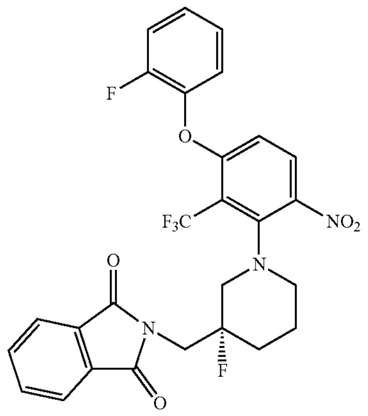 [SMILES: O=C1c2ccccc2C(=O)N1C[C@]1(F)CCCN(c2c([N+](=O)[O-])ccc(Oc3ccccc3F)c2C(F)(F)F)C1] |
| 172 | 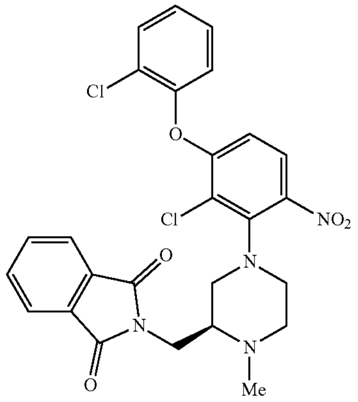 [SMILES: CN1CCN(c2c([N+](=O)[O-])ccc(Oc3ccccc3Cl)c2Cl)C[C@@H]1CN1C(=O)c2ccccc2C1=O] |
| 173 | 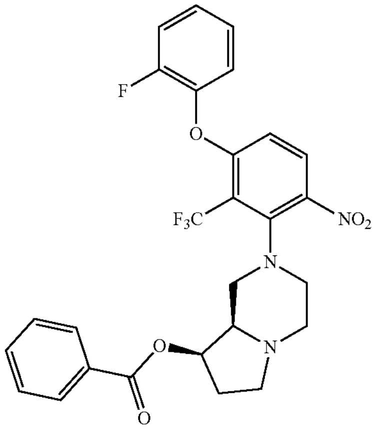 [SMILES: O=C(O[C@@H]1CCN2CCN(c3c([N+](=O)[O-])ccc(Oc4ccccc4F)c3C(F)(F)F)C[C@H]12)c1ccccc1] |
| 174 | 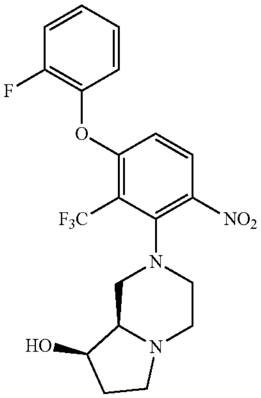 [SMILES: O=[N+]([O-])c1ccc(Oc2ccccc2F)c(C(F)(F)F)c1N1CCN2CC[C@@H](O)[C@H]2C1] |

TABLE 4-continued
| PEx | Str |
|---|---|
| 175 | 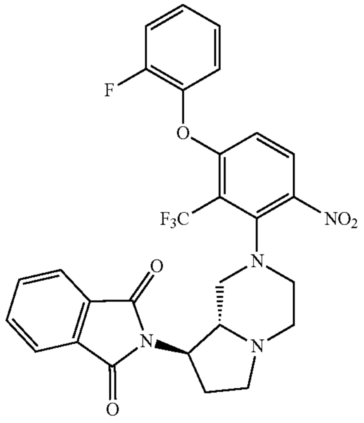 [SMILES: O=C1c2ccccc2C(=O)N1[C@@H]1CCN2CCN(c3c([N+](=O)[O-])ccc(Oc4ccccc4F)c3C(F)(F)F)C[C@@H]12] |
| 176 | 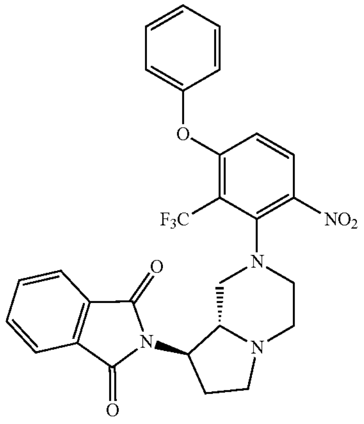 [SMILES: O=C1c2ccccc2C(=O)N1[C@@H]1CCN2CCN(c3c([N+](=O)[O-])ccc(Oc4ccccc4)c3C(F)(F)F)C[C@@H]12] |
| 177 | 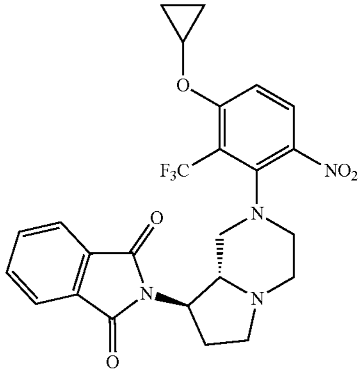 [SMILES: O=C1c2ccccc2C(=O)N1[C@@H]1CCN2CCN(c3c([N+](=O)[O-])ccc(OC4CC4)c3C(F)(F)F)C[C@@H]12] |
TABLE 4-continued
| PEx | Str |
|---|---|
| 178 | 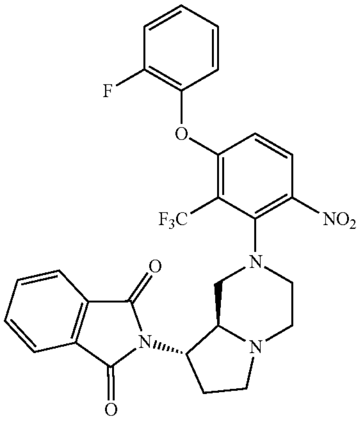 [SMILES: O=C1c2ccccc2C(=O)N1[C@H]1CCN2CCN(c3c([N+](=O)[O-])ccc(Oc4ccccc4F)c3C(F)(F)F)C[C@H]12] |
| 179 | 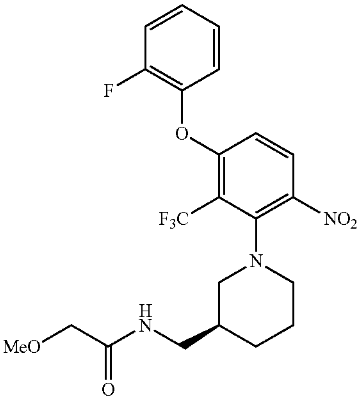 [SMILES: COCC(=O)NC[C@@H]1CCCN(c2c([N+](=O)[O-])ccc(Oc3ccccc3F)c2C(F)(F)F)C1] |
| 180 | 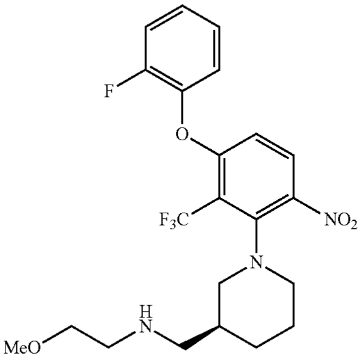 [SMILES: COCCNC[C@@H]1CCCN(c2c([N+](=O)[O-])ccc(Oc3ccccc3F)c2C(F)(F)F)C1] |
| 181 | 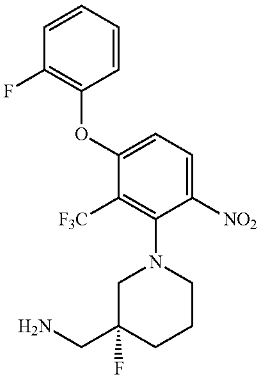 [SMILES: NC[C@]1(F)CCCN(c2c([N+](=O)[O-])ccc(Oc3ccccc3F)c2C(F)(F)F)C1] |

TABLE 4-continued
| PEx | Str |
|---|---|
| 182 | 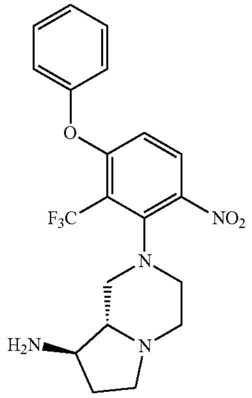 [SMILES: N[C@@H]1CCN2CCN(c3c([N+](=O)[O-])ccc(Oc4ccccc4)c3C(F)(F)F)C[C@@H]12] |
| 183 | 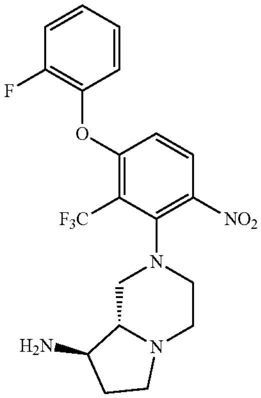 [SMILES: N[C@@H]1CCN2CCN(c3c([N+](=O)[O-])ccc(Oc4ccccc4F)c3C(F)(F)F)C[C@@H]12] |
| 184 | 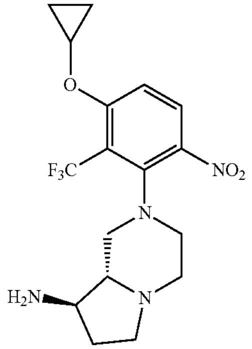 [SMILES: N[C@@H]1CCN2CCN(c3c([N+](=O)[O-])ccc(OC4CC4)c3C(F)(F)F)C[C@@H]12] |
| 185 | 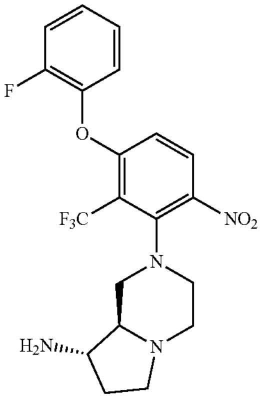 [SMILES: N[C@H]1CCN2CCN(c3c([N+](=O)[O-])ccc(Oc4ccccc4F)c3C(F)(F)F)C[C@H]12] |
TABLE 4-continued
| PEx | Str |
|---|---|
| 186 | 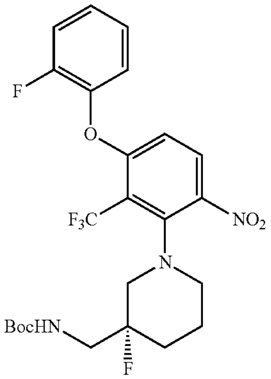 [SMILES: CC(C)(C)OC(=O)NC[C@]1(F)CCCN(c2c([N+](=O)[O-])ccc(Oc3ccccc3F)c2C(F)(F)F)C1] |
| 187 | 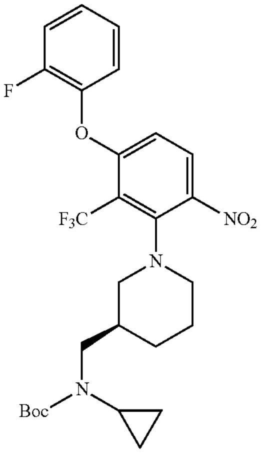 [SMILES: CC(C)(C)OC(=O)N(C[C@@H]1CCCN(c2c([N+](=O)[O-])ccc(Oc3ccccc3F)c2C(F)(F)F)C1)C1CC1] |
| 188 | 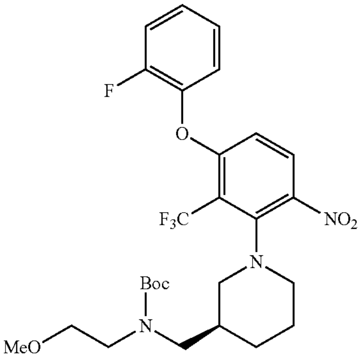 |
| 189 | 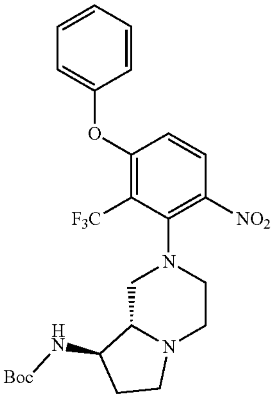 [SMILES: CC(C)(C)OC(=O)N[C@@H]1CCN2CCN(c3c([N+](=O)[O-])ccc(Oc4ccccc4)c3C(F)(F)F)C[C@@H]12] |

TABLE 4-continued
| PEx | Str |
| --- | --- |
| 190 | 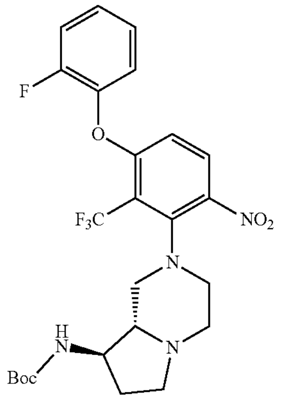 [SMILES: CC(C)(C)OC(=O)N[C@@H]1CCN2CCN(c3c([N+](=O)[O-])ccc(Oc4ccccc4F)c3C(F)(F)F)C[C@@H]12] |
| 191 | 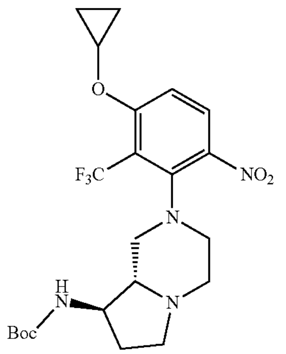 [SMILES: CC(C)(C)OC(=O)N[C@@H]1CCN2CCN(c3c([N+](=O)[O-])ccc(OC4CC4)c3C(F)(F)F)C[C@@H]12] |
| 192 | 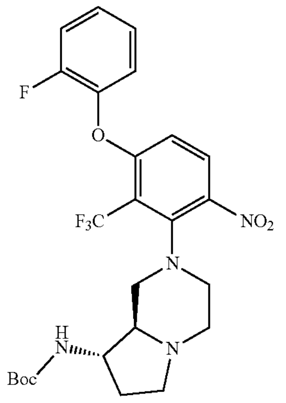 [SMILES: CC(C)(C)OC(=O)N[C@H]1CCN2CCN(c3c([N+](=O)[O-])ccc(Oc4ccccc4F)c3C(F)(F)F)C[C@H]12] |
| 193 | 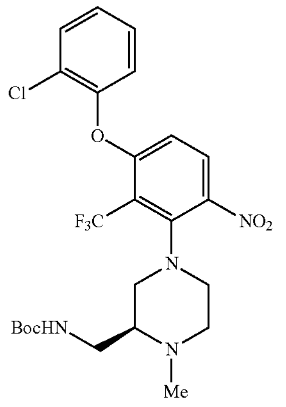 [SMILES: CN1CCN(c2c([N+](=O)[O-])ccc(Oc3ccccc3Cl)c2C(F)(F)F)C[C@@H]1CNC(=O)OC(C)(C)C] |
TABLE 4-continued
| PEx | Str |
| --- | --- |
| 194 | 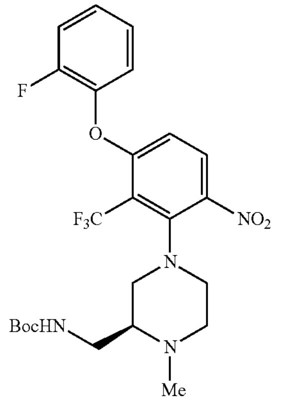 [SMILES: CN1CCN(c2c([N+](=O)[O-])ccc(Oc3ccccc3F)c2C(F)(F)F)C[C@@H]1CNC(=O)OC(C)(C)C] |
| 195 | 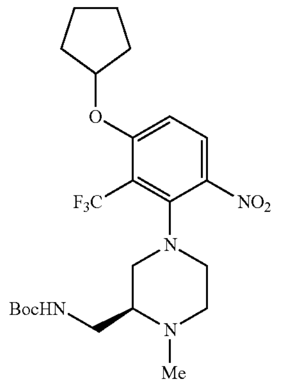 [SMILES: CN1CCN(c2c([N+](=O)[O-])ccc(OC3CCCC3)c2C(F)(F)F)C[C@@H]1CNC(=O)OC(C)(C)C] |
| 196 | 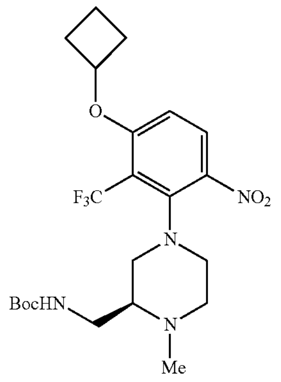 |
| 197 | 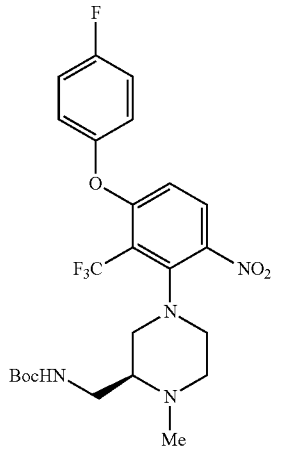 |

TABLE 4-continued
| PEx | Str |
| --- | --- |
| 198 | 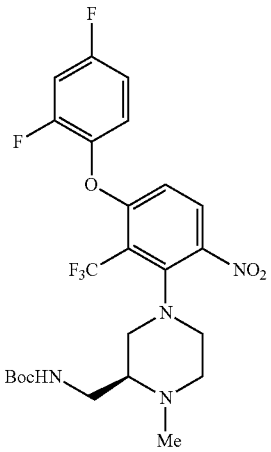 |
| 199 | 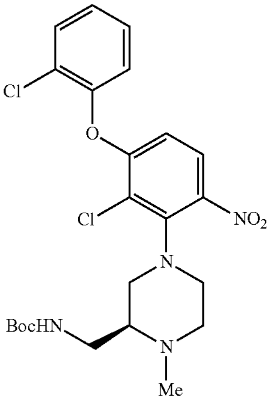 [SMILES: CN1CCN(c2c([N+](=O)[O-])ccc(Oc3ccccc3Cl)c2Cl)C[C@@H]1CNC(=O)OC(C)(C)C] |
| 200 | 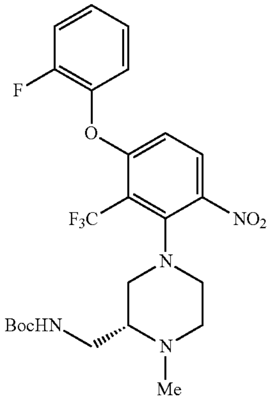 |
| 201 | 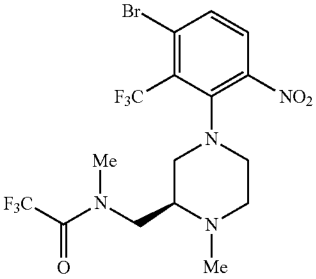 [SMILES: CN(C[C@H]1CN(c2c([N+](=O)[O-])ccc(Br)c2C(F)(F)F)CCN1C)C(=O)C(F)(F)F] |
TABLE 4-continued
| PEx | Str |
| --- | --- |
| 202 | 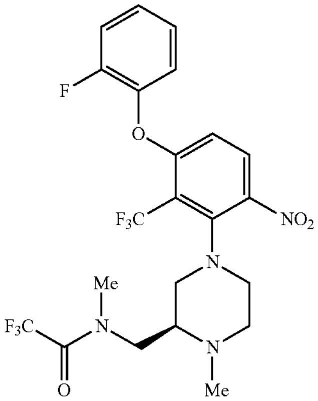 [SMILES: CN(C[C@H]1CN(c2c([N+](=O)[O-])ccc(Oc3ccccc3F)c2C(F)(F)F)CCN1C)C(=O)C(F)(F)F] |
| 203 | 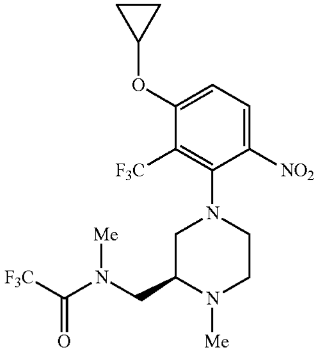 [SMILES: CN(C[C@H]1CN(c2c([N+](=O)[O-])ccc(OC3CC3)c2C(F)(F)F)CCN1C)C(=O)C(F)(F)F] |
| 204 | 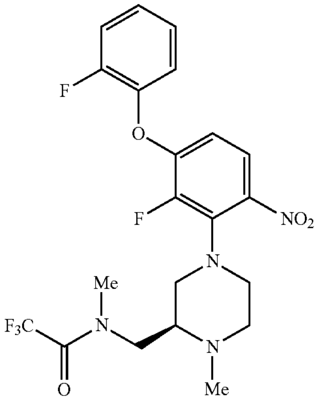 |
| 205 | 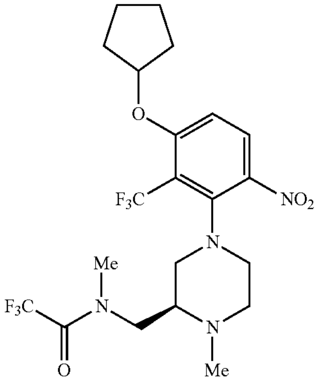 [SMILES: CN(C[C@H]1CN(c2c([N+](=O)[O-])ccc(OC3CCCC3)c2C(F)(F)F)CCN1C)C(=O)C(F)(F)F] |

TABLE 4-continued
| PEx | Str |
| --- | --- |
| 206 | 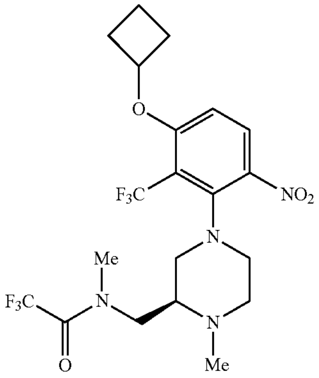 [SMILES: CN(C[C@H]1CN(c2c([N+](=O)[O-])ccc(OC3CCC3)c2C(F)(F)F)CCN1C)C(=O)C(F)(F)F] |
| 207 | 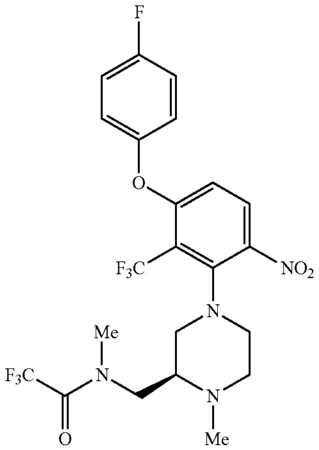 [SMILES: CN(C[C@H]1CN(c2c([N+](=O)[O-])ccc(Oc3ccc(F)cc3)c2C(F)(F)F)CCN1C)C(=O)C(F)(F)F] |
| 208 | 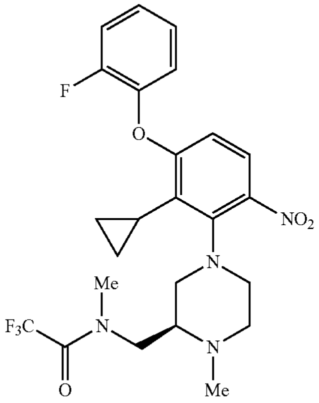 [SMILES: CN(C[C@H]1CN(c2c([N+](=O)[O-])ccc(Oc3ccccc3F)c2C2CC2)CCN1C)C(=O)C(F)(F)F] |
TABLE 4-continued
| PEx | Str |
| --- | --- |
| 209 | 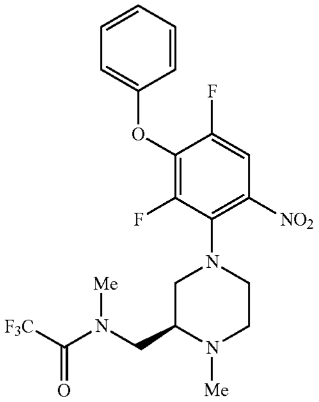 |
| 210 | 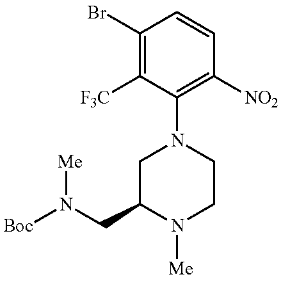 [SMILES: CN(C[C@H]1CN(c2c([N+](=O)[O-])ccc(Br)c2C(F)(F)F)CCN1C)C(=O)OC(C)(C)C] |
| 211 | 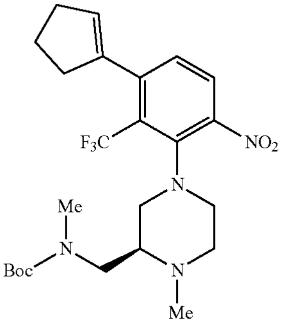 [SMILES: CN(C[C@H]1CN(c2c([N+](=O)[O-])ccc(C3=CCCC3)c2C(F)(F)F)CCN1C)C(=O)OC(C)(C)C] |
| 212 | 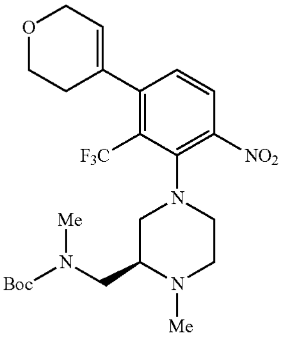 [SMILES: CN(C[C@H]1CN(c2c([N+](=O)[O-])ccc(C3=CCOCC3)c2C(F)(F)F)CCN1C)C(=O)OC(C)(C)C] |

TABLE 4-continued
| PEx | Str |
|---|---|
| 213 | 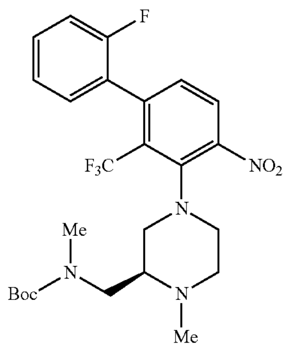 [SMILES: CN(C[C@H]1CN(c2c([N+](=O)[O-])ccc(-c3ccccc3F)c2C(F)(F)F)CCN1C)C(=O)OC(C)(C)C] |
| 214 | 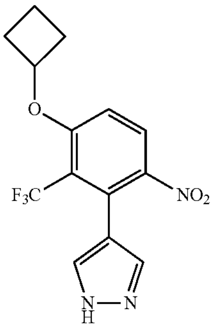 [SMILES: O=[N+]([O-])c1ccc(OC2CCC2)c(C(F)(F)F)c1-c1cn[nH]c1] |
| 215 | 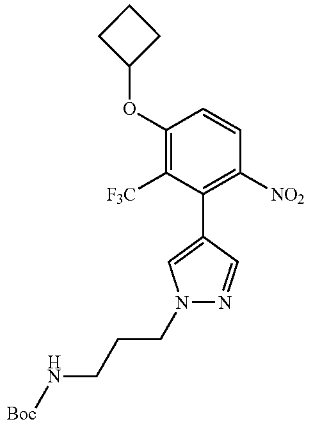 [SMILES: CC(C)(C)OC(=O)NCCCn1cc(-c2c([N+](=O)[O-])ccc(OC3CCC3)c2C(F)(F)F)cn1] |
| 216 | 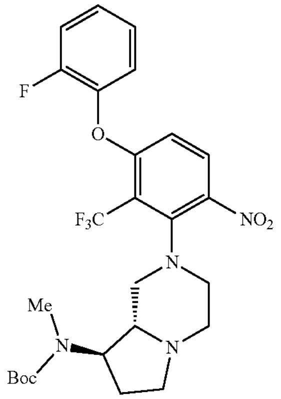 [SMILES: CN(C(=O)OC(C)(C)C)[C@@H]1CCN2CCN(c3c([N+](=O)[O-])ccc(Oc4ccccc4F)c3C(F)(F)F)C[C@@H]12] |
TABLE 4-continued
| PEx | Str |
|---|---|
| 217 | 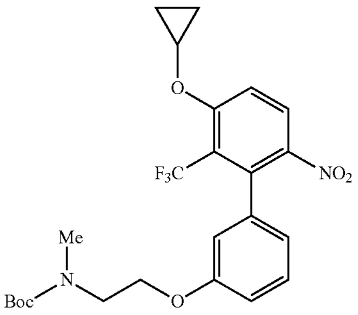 [SMILES: CN(CCOc1cccc(-c2c([N+](=O)[O-])ccc(OC3CC3)c2C(F)(F)F)c1)C(=O)OC(C)(C)C] |
| 218 | 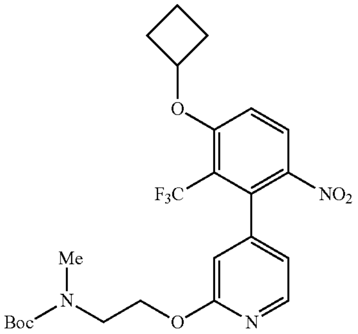 [SMILES: CN(CCOc1cc(-c2c([N+](=O)[O-])ccc(OC3CCC3)c2C(F)(F)F)ccn1)C(=O)OC(C)(C)C] |
| 219 | 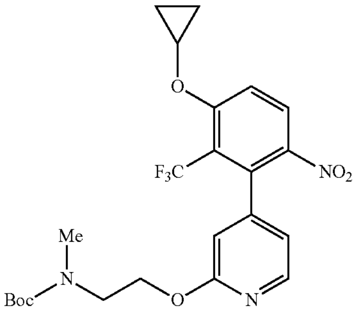 [SMILES: CN(CCOc1cc(-c2c([N+](=O)[O-])ccc(OC3CC3)c2C(F)(F)F)ccn1)C(=O)OC(C)(C)C] |
| 220 | 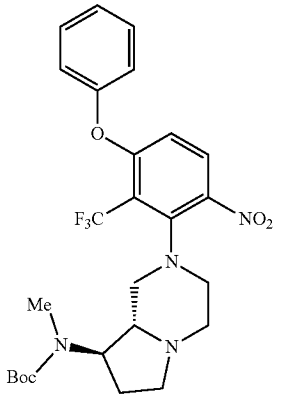 [SMILES: CN(C(=O)OC(C)(C)C)[C@@H]1CCN2CCN(c3c([N+](=O)[O-])ccc(Oc4ccccc4)c3C(F)(F)F)C[C@@H]12] |

TABLE 4-continued
| PEx | Str |
|---|---|
| 221 | 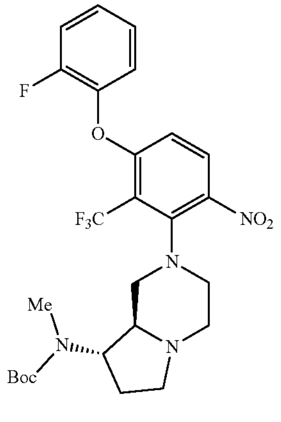 [SMILES: CN(C(=O)OC(C)(C)C)[C@H]1CCN2CCN(c3c([N+](=O)[O-])ccc(Oc4ccccc4F)c3C(F)(F)F)C[C@H]12] |
| 222 | 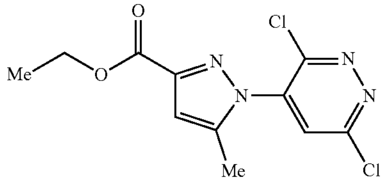 [SMILES: CCOC(=O)c1cc(C)n(-c2cc(Cl)nnc2Cl)n1] |
| 223 | 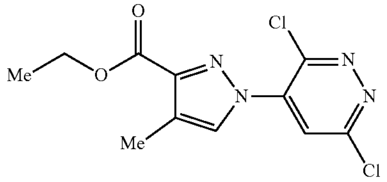 [SMILES: CCOC(=O)c1nn(-c2cc(Cl)nnc2Cl)cc1C] |
| 224 | 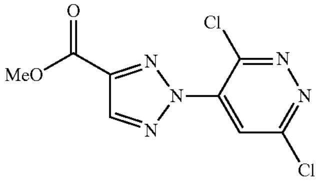 [SMILES: COC(=O)c1cnn(-c2cc(Cl)nnc2Cl)n1] |
| 225 | 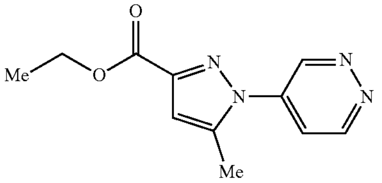 [SMILES: CCOC(=O)c1cc(C)n(-c2ccnnc2)n1] |
| 226 | 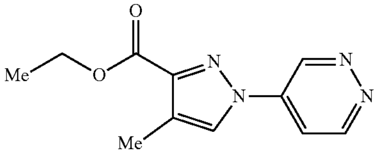 [SMILES: CCOC(=O)c1nn(-c2ccnnc2)cc1C] |
| 227 | 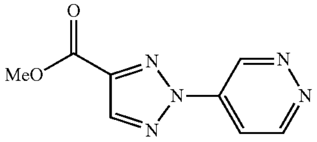 [SMILES: COC(=O)c1cnn(-c2ccnnc2)n1] |
TABLE 4-continued
| PEx | Str |
|---|---|
| 228 | 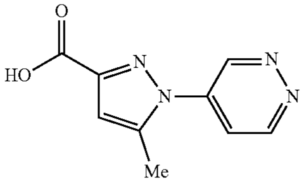 [SMILES: Cc1cc(C(=O)O)nn1-c1ccnnc1] |
| 229 | 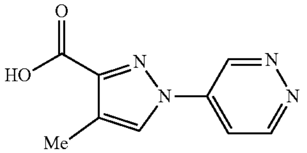 [SMILES: Cc1cn(-c2ccnnc2)nc1C(=O)O] |
| 230 | 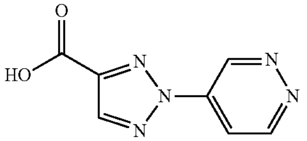 [SMILES: O=C(O)c1cnn(-c2ccnnc2)n1] |
| 231 | 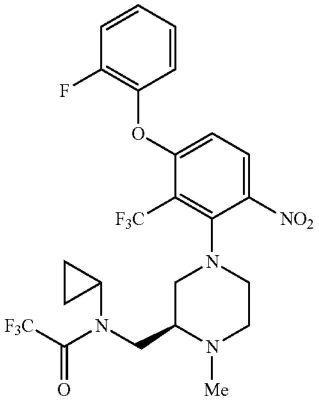 [SMILES: CN1CCN(c2c([N+](=O)[O-])ccc(Oc3ccccc3F)c2C(F)(F)F)C[C@@H]1CN(C(=O)C(F)(F)F)C1CC1] |
| 232 | 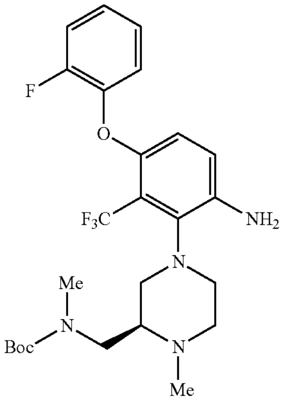 [SMILES: CN(C[C@H]1CN(c2c(N)ccc(Oc3ccccc3F)c2C(F)(F)F)CCN1C)C(=O)OC(C)(C)C] |

TABLE 4-continued
| PEx | Str |
|---|---|
| 233 | 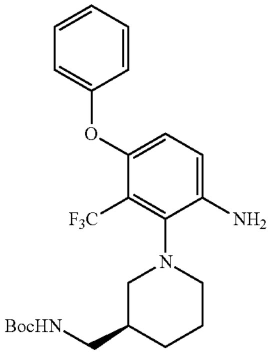 |
| 234 | 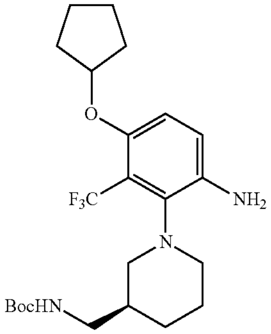 |
| 235 | 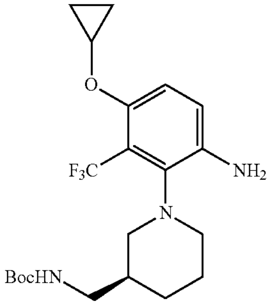 |
| 236 | 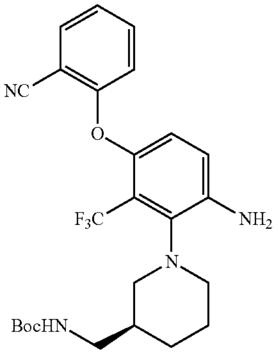 |
| 237 | 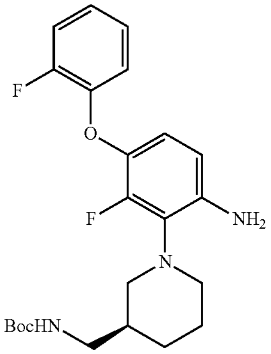 [SMILES: CC(C)(C)OC(=O)NC[C@@H]1CCCN(c2c(N)ccc(Oc3ccccc3F)c2F)C1] |
| 238 | 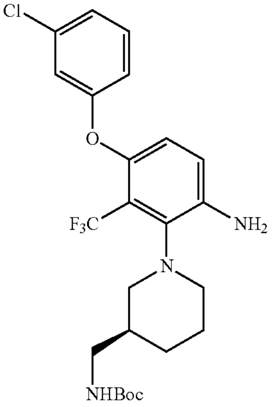 [SMILES: CC(C)(C)OC(=O)NC[C@@H]1CCCN(c2c(N)ccc(Oc3cccc(Cl)c3)c2C(F)(F)F)C1] |
| 239 | 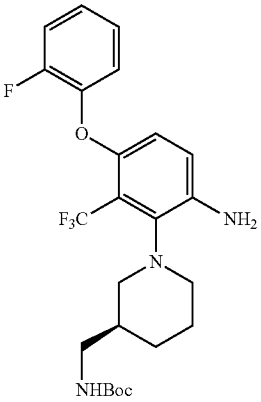 [SMILES: CC(C)(C)OC(=O)NC[C@@H]1CCCN(c2c(N)ccc(Oc3ccccc3F)c2C(F)(F)F)C1] |
| 240 | 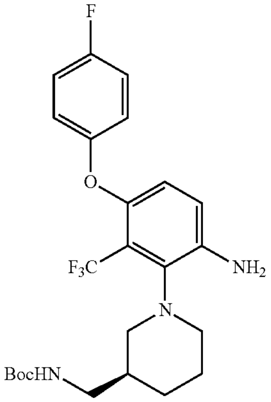 [SMILES: CC(C)(C)OC(=O)NC[C@@H]1CCCN(c2c(N)ccc(Oc3ccc(F)cc3)c2C(F)(F)F)C1] |

TABLE 4-continued
| PEx | Str |
| --- | --- |
| 241 | 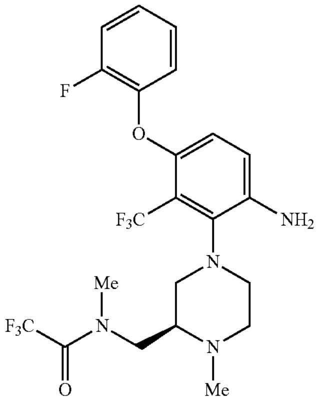 [SMILES: CN(C[C@H]1CN(c2c(N)ccc(Oc3ccccc3F)c2C(F)(F)F)CCN1C)C(=O)C(F)(F)F] |
| 242 | 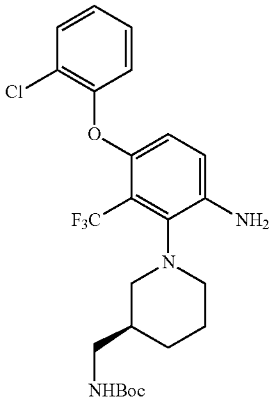 |
| 243 | 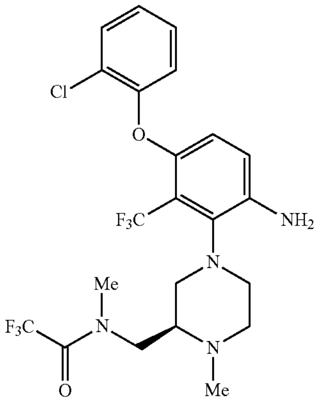 |
| 244 | 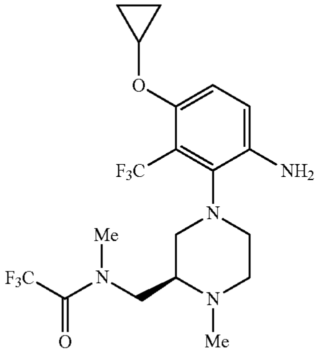 [SMILES: CN(C[C@H]1CN(c2c(N)ccc(OC3CC3)c2C(F)(F)F)CCN1C)C(=O)C(F)(F)F] |
TABLE 4-continued
| PEx | Str |
| --- | --- |
| 245 | 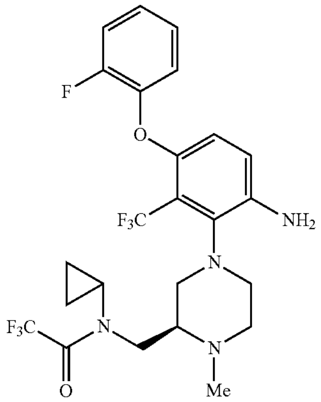 |
| 246 | 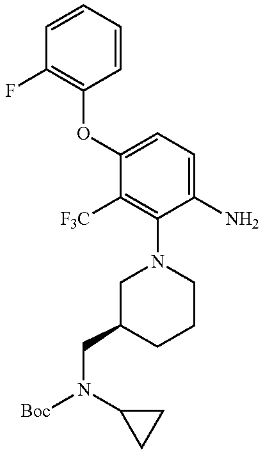 |
| 247 | 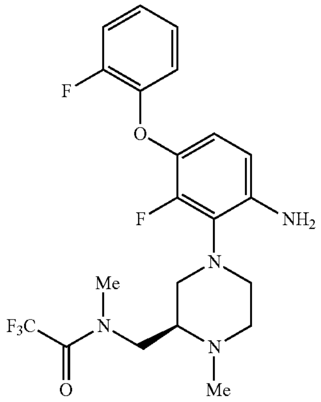 |

TABLE 4-continued
| PEx | Str |
| --- | --- |
| 248 | 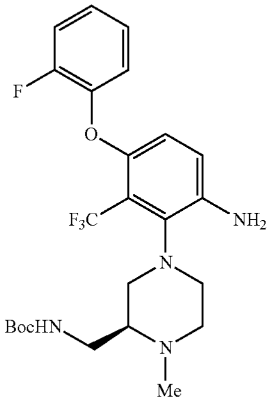 |
| 249 | 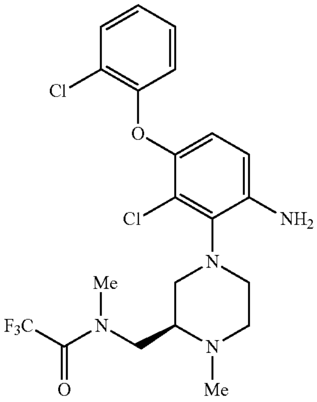 [SMILES: CN(C[C@H]1CN(c2c(N)ccc(Oc3ccccc3Cl)c2Cl)CCN1C)C(=O)C(F)(F)F] |
| 250 | 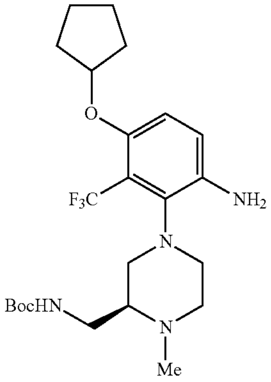 |
| 251 | 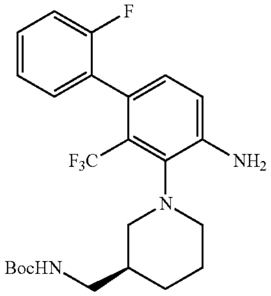 |
TABLE 4-continued
| PEx | Str |
| --- | --- |
| 252 | 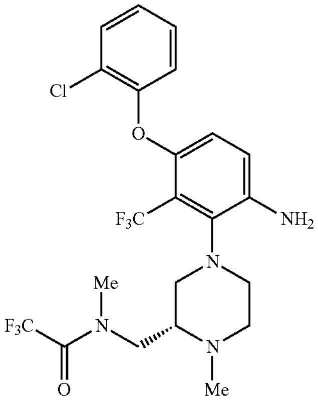 |
| 253 | 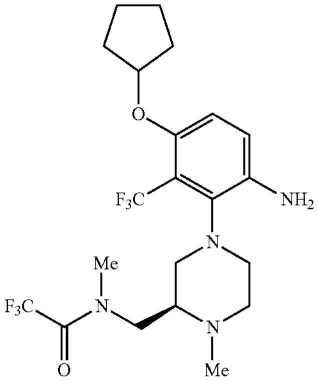 |
| 254 | 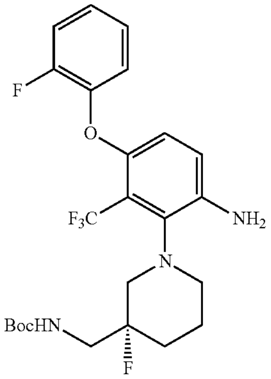 [SMILES: CC(C)(C)OC(=O)NC[C@]1(F)CCCN(c2c(N)ccc(Oc3ccccc3F)c2C(F)(F)F)C1] |
| 255 | 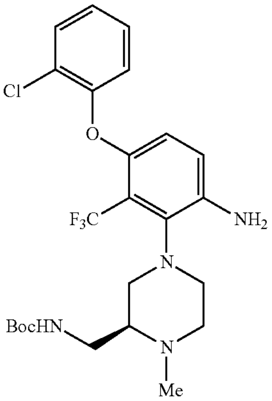 |

TABLE 4-continued
| PEx | Str |
|---|---|
| 256 | 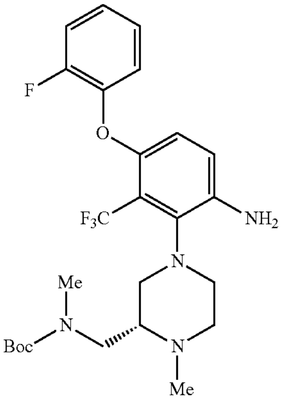 |
| 257 | 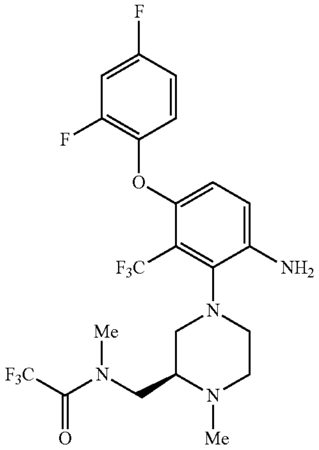 |
| 258 | 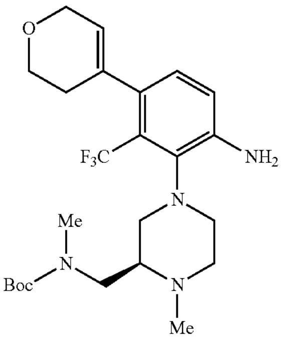 |
| 259 | 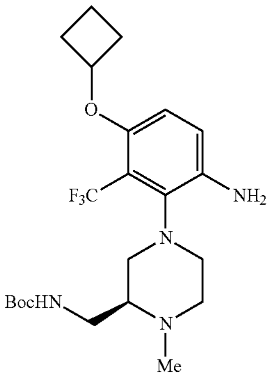 |
TABLE 4-continued
| PEx | Str |
|---|---|
| 260 | 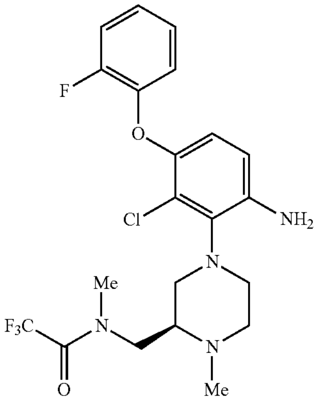 |
| 261 | 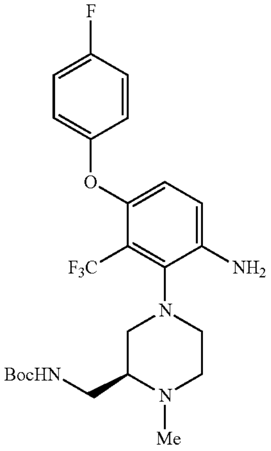 [SMILES: CN1CCN(c2c(N)ccc(Oc3ccc(F)cc3)c2C(F)(F)F)C[C@@H]1CNC(=O)OC(C)(C)C] |
| 262 | 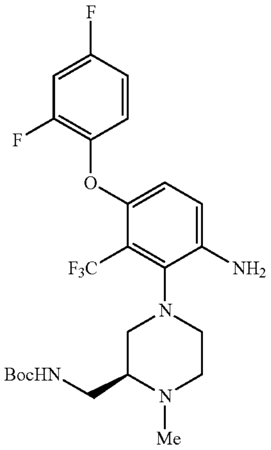 [SMILES: CN1CCN(c2c(N)ccc(Oc3ccc(F)cc3F)c2C(F)(F)F)C[C@@H]1CNC(=O)OC(C)(C)C] |

TABLE 4-continued
| PEx | Str |
|---|---|
| 263 | 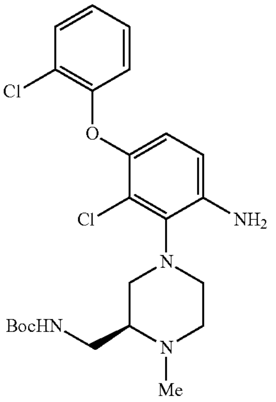 |
| 264 | 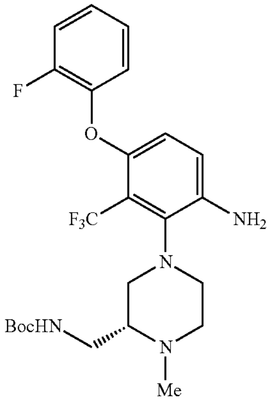 [SMILES: CN1CCN(c2c(N)ccc(Oc3ccccc3F)c2C(F)(F)F)C[C@H]1CNC(=O)OC(C)(C)C] |
| 265 | 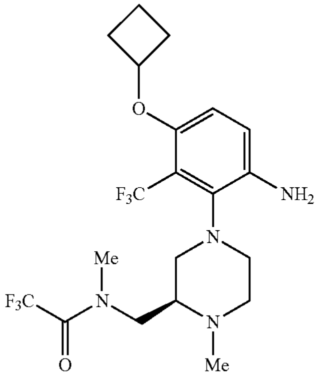 |
TABLE 4-continued
| PEx | Str |
|---|---|
| 266 | 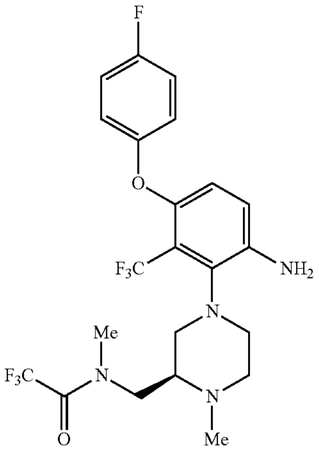 |
| 267 | 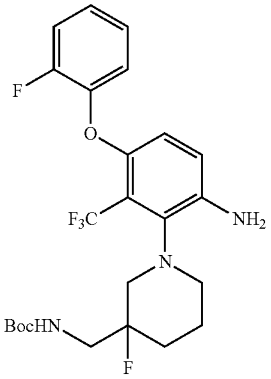 |
| 268 | 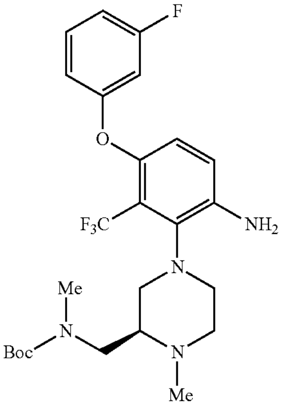 [SMILES: CN(C[C@H]1CN(c2c(N)ccc(Oc3cccc(F)c3)c2C(F)(F)F)CCN1C)C(=O)OC(C)(C)C] |

TABLE 4-continued
| PEx | Str |
|---|---|
| 269 | 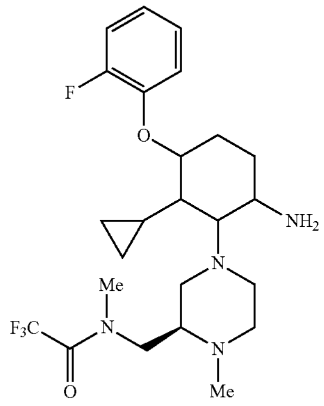 [SMILES: CN(C[C@H]1CN(C2C(N)CCC(Oc3ccccc3F)C2C2CC2)CCN1C)C(=O)C(F)(F)F] |
| 270 | 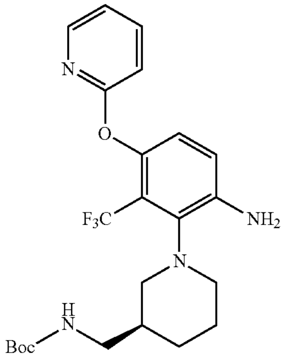 |
| 271 | 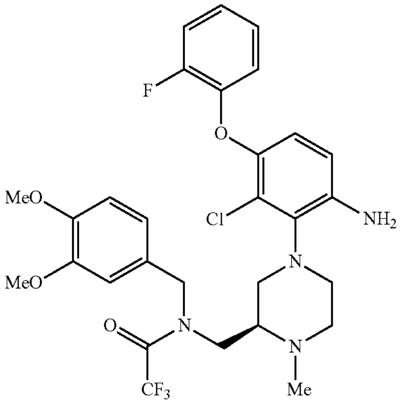 [SMILES: COc1ccc(CN(C[C@H]2CN(c3c(N)ccc(Oc4ccccc4F)c3Cl)CCN2C)C(=O)C(F)(F)F)cc1OC] |
| 272 | 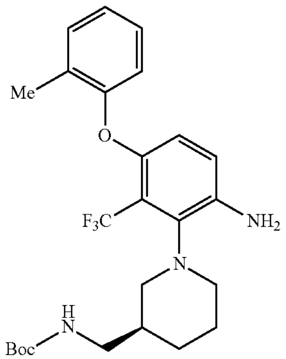 [SMILES: Cc1ccccc1Oc1ccc(N)c(N2CCC[C@@H](CNC(=O)OC(C)(C)C)C2)c1C(F)(F)F] |
| 273 | 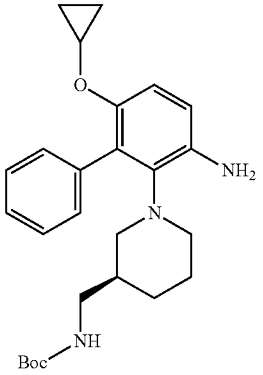 [SMILES: CC(C)(C)OC(=O)NC[C@@H]1CCCN(c2c(N)ccc(OC3CC3)c2-c2ccccc2)C1] |
| 274 | 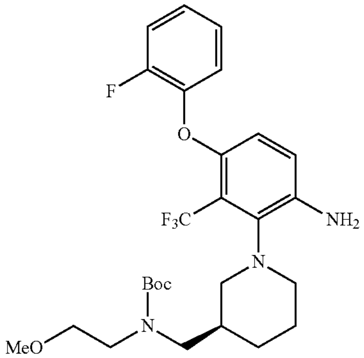 [SMILES: COCCN(C[C@@H]1CCCN(c2c(N)ccc(Oc3ccccc3F)c2C(F)(F)F)C1)C(=O)OC(C)(C)C] |
| 275 | 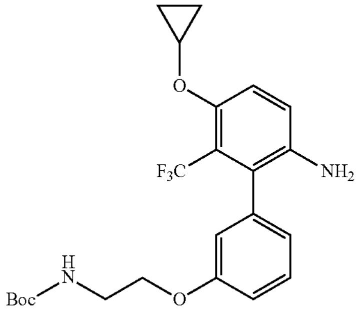 [SMILES: CC(C)(C)OC(=O)NCCOc1cccc(-c2c(N)ccc(OC3CC3)c2C(F)(F)F)c1] |
| 276 | 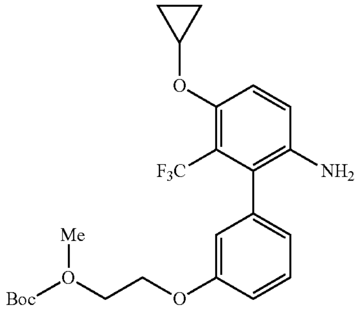 |

TABLE 4-continued
| PEx | Str |
| --- | --- |
| 277 | 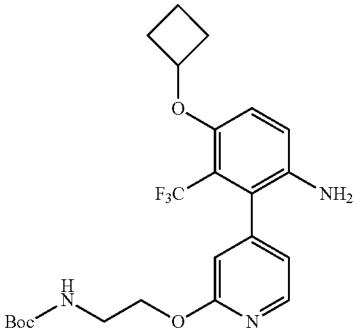 [SMILES: CC(C)(C)OC(=O)NCCOc1cc(-c2c(N)ccc(OC3CCC3)c2C(F)(F)F)ccn1] |
| 278 | 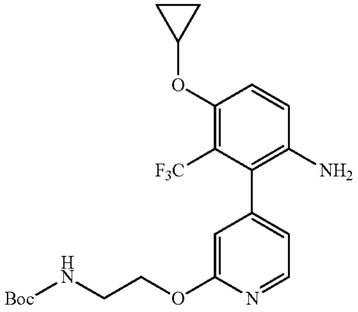 [SMILES: CC(C)(C)OC(=O)NCCOc1cc(-c2c(N)ccc(OC3CC3)c2C(F)(F)F)ccn1] |
| 279 | 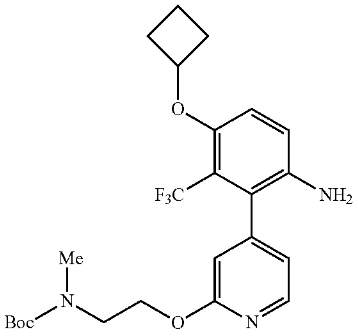 |
| 280 | 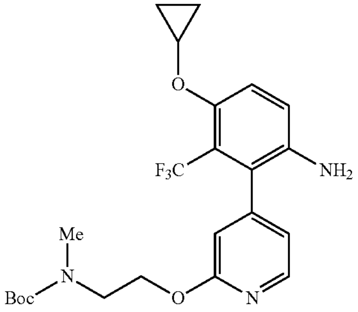 |
TABLE 4-continued
| PEx | Str |
| --- | --- |
| 281 | 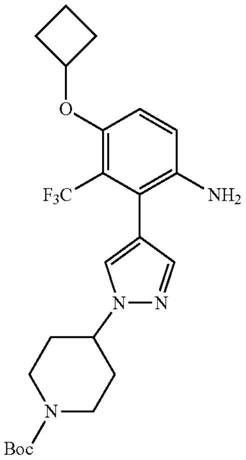 [SMILES: CC(C)(C)OC(=O)N1CCC(n2cc(-c3c(N)ccc(OC4CCC4)c3C(F)(F)F)cn2)CC1] |
| 282 | 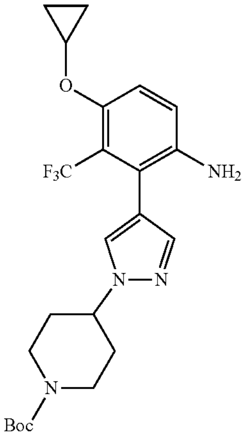 [SMILES: CC(C)(C)OC(=O)N1CCC(n2cc(-c3c(N)ccc(OC4CC4)c3C(F)(F)F)cn2)CC1] |
| 283 | 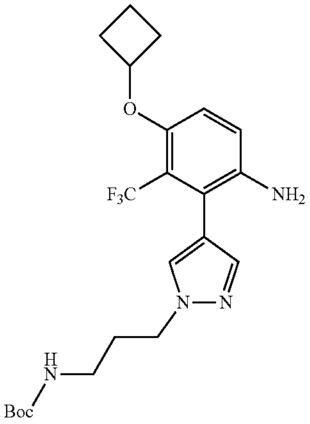 [SMILES: CC(C)(C)OC(=O)NCCCn1cc(-c2c(N)ccc(OC3CCC3)c2C(F)(F)F)cn1] |

TABLE 4-continued
| PEx | Str |
| --- | --- |
| 284 | 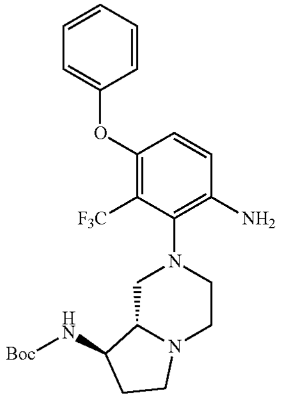 [SMILES: CC(C)(C)OC(=O)N[C@@H]1CCN2CCN(c3c(N)ccc(Oc4ccccc4)c3C(F)(F)F)C[C@@H]12] |
| 285 | 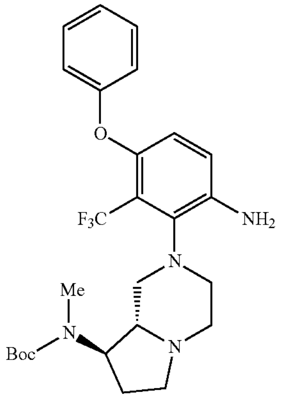 [SMILES: CN(C(=O)OC(C)(C)C)[C@@H]1CCN2CCN(c3c(N)ccc(Oc4ccccc4)c3C(F)(F)F)C[C@@H]12] |
| 286 | 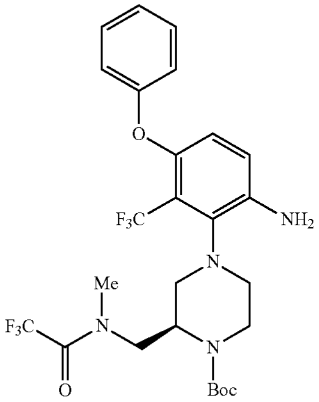 |
| 287 | 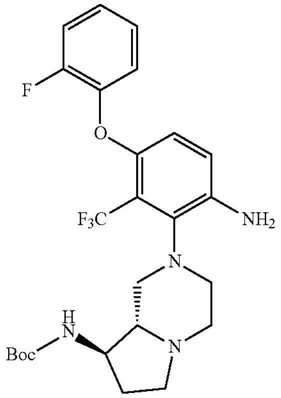 [SMILES: CC(C)(C)OC(=O)N[C@@H]1CCN2CCN(c3c(N)ccc(Oc4ccccc4F)c3C(F)(F)F)C[C@@H]12] |
TABLE 4-continued
| PEx | Str |
| --- | --- |
| 288 | 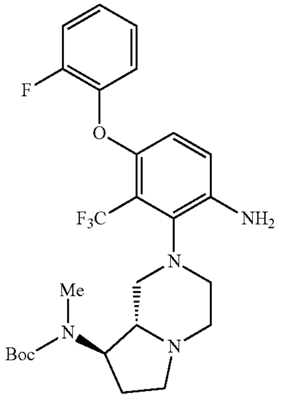 [SMILES: CN(C(=O)OC(C)(C)C)[C@@H]1CCN2CCN(c3c(N)ccc(Oc4ccccc4F)c3C(F)(F)F)C[C@@H]12] |
| 289 | 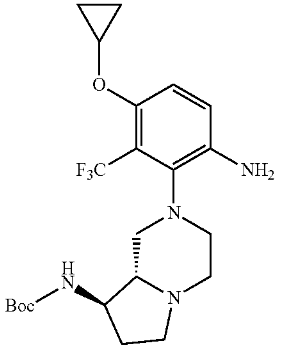 [SMILES: CC(C)(C)OC(=O)N[C@@H]1CCN2CCN(c3c(N)ccc(OC4CC4)c3C(F)(F)F)C[C@@H]12] |
| 290 | 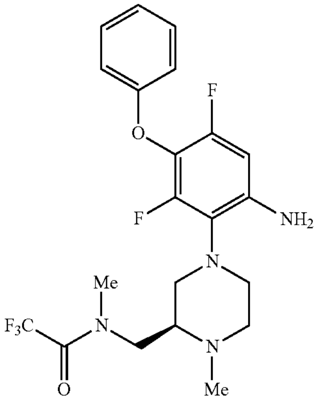 [SMILES: CN(C[C@H]1CN(c2c(N)cc(F)c(Oc3ccccc3)c2F)CCN1C)C(=O)C(F)(F)F] |
| 291 | 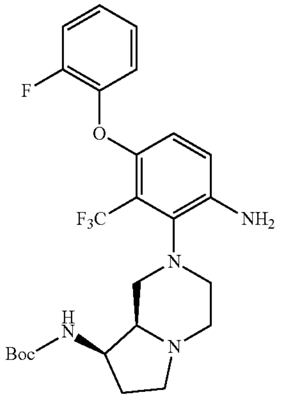 [SMILES: CC(C)(C)OC(=O)N[C@@H]1CCN2CCN(c3c(N)ccc(Oc4ccccc4F)c3C(F)(F)F)C[C@H]12] |

TABLE 4-continued
| PEx | Str |
|---|---|
| 292 | 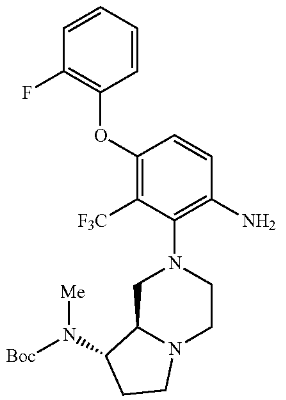 [SMILES: CN(C(=O)OC(C)(C)C)[C@H]1CCN2CCN(c3c(N)ccc(Oc4ccccc4F)c3C(F)(F)F)C[C@H]12] |
| 293 | 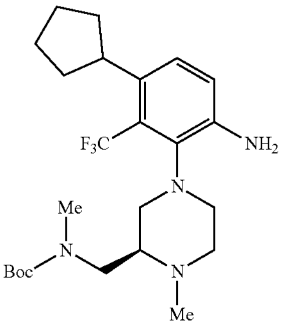 [SMILES: CN(C[C@H]1CN(c2c(N)ccc(C3CCCC3)c2C(F)(F)F)CCN1C)C(=O)OC(C)(C)C] |
| 294 | 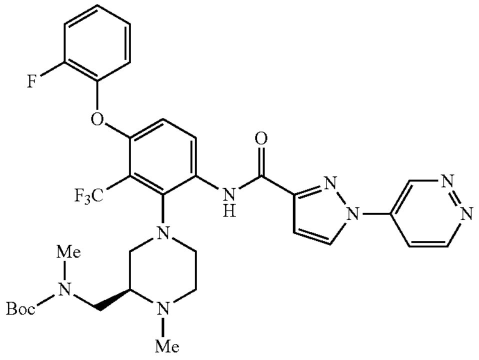 [SMILES: CN(C[C@H]1CN(c2c(NC(=O)c3ccn(-c4ccnnc4)n3)ccc(Oc3ccccc3F)c2C(F)(F)F)CCN1C)C(=O)OC(C)(C)C] |
| 295 | 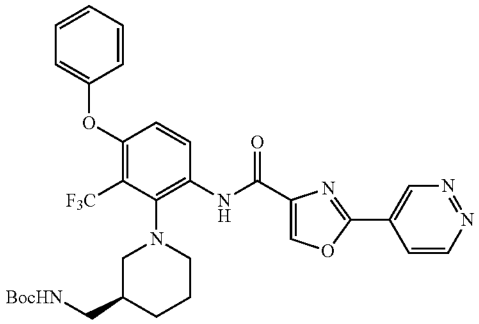 [SMILES: CC(C)(C)OC(=O)NC[C@@H]1CCCN(c2c(NC(=O)c3coc(-c4ccnnc4)n3)ccc(Oc3ccccc3)c2C(F)(F)F)C1] |
TABLE 4-continued
| PEx | Str |
|---|---|
| 296 | 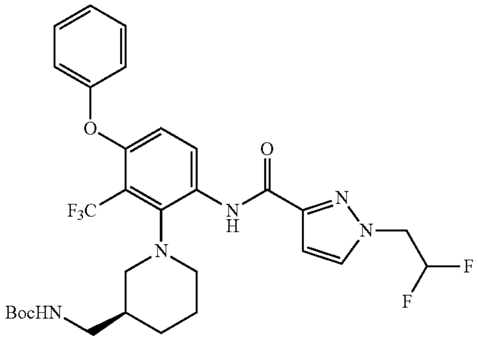 [SMILES: CC(C)(C)OC(=O)NC[C@@H]1CCCN(c2c(NC(=O)c3ccn(CC(F)F)n3)ccc(Oc3ccccc3)c2C(F)(F)F)C1] |
| 297 | 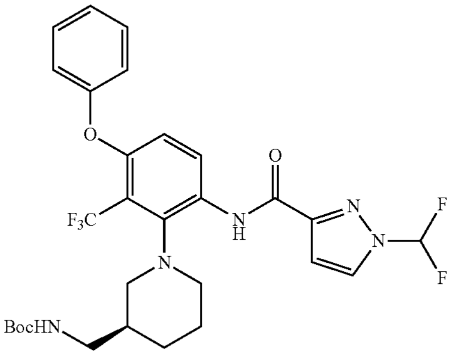 [SMILES: CC(C)(C)OC(=O)NC[C@@H]1CCCN(c2c(NC(=O)c3ccn(C(F)F)n3)ccc(Oc3ccccc3)c2C(F)(F)F)C1] |
| 298 | 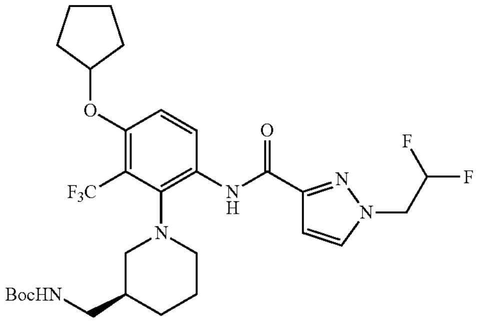 [SMILES: CC(C)(C)OC(=O)NC[C@@H]1CCCN(c2c(NC(=O)c3ccn(CC(F)F)n3)ccc(OC3CCCC3)c2C(F)(F)F)C1] |
| 299 | 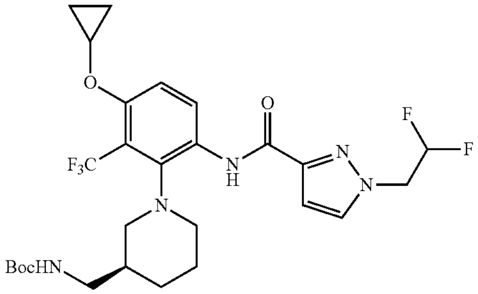 [SMILES: CC(C)(C)OC(=O)NC[C@@H]1CCCN(c2c(NC(=O)c3ccn(CC(F)F)n3)ccc(OC3CC3)c2C(F)(F)F)C1] |

TABLE 4-continued
| PEx | Str |
| --- | --- |
| 300 | 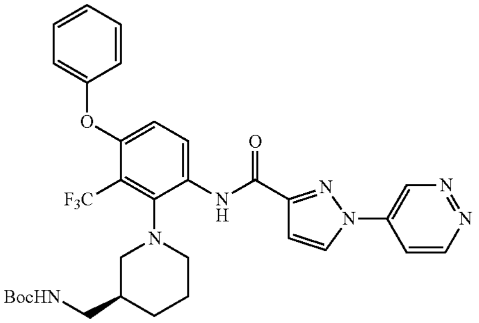 [SMILES: CC(C)(C)OC(=O)NC[C@@H]1CCCN(c2c(NC(=O)c3ccn(-c4ccnnc4)n3)ccc(Oc3ccccc3)c2C(F)(F)F)C1] |
| 301 | 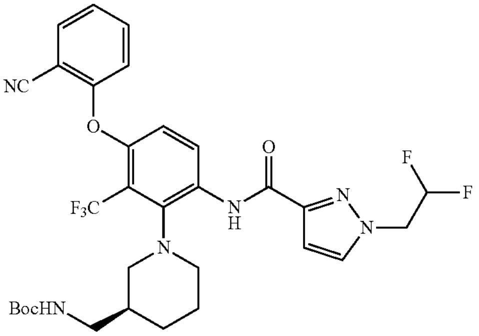 [SMILES: CC(C)(C)OC(=O)NC[C@@H]1CCCN(c2c(NC(=O)c3ccn(CC(F)F)n3)ccc(Oc3ccccc3C#N)c2C(F)(F)F)C1] |
| 302 | 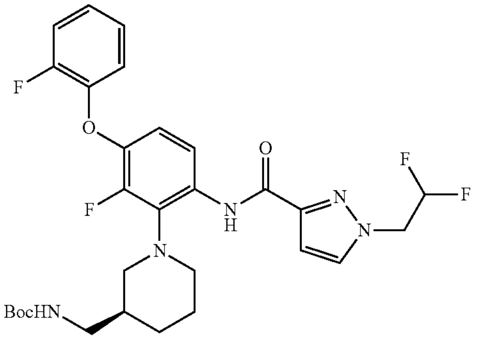 [SMILES: CC(C)(C)OC(=O)NC[C@@H]1CCCN(c2c(NC(=O)c3ccn(CC(F)F)n3)ccc(Oc3ccccc3F)c2F)C1] |
| 303 | 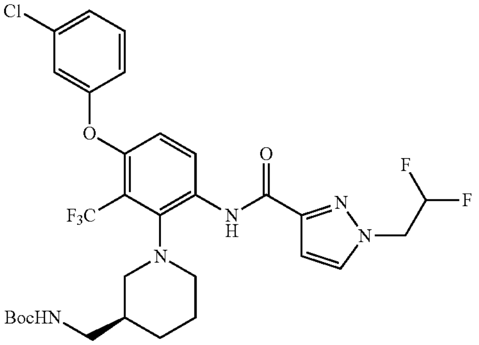 [SMILES: CC(C)(C)OC(=O)NC[C@@H]1CCCN(c2c(NC(=O)c3ccn(CC(F)F)n3)ccc(Oc3cccc(Cl)c3)c2C(F)(F)F)C1] |
TABLE 4-continued
| PEx | Str |
| --- | --- |
| 304 | 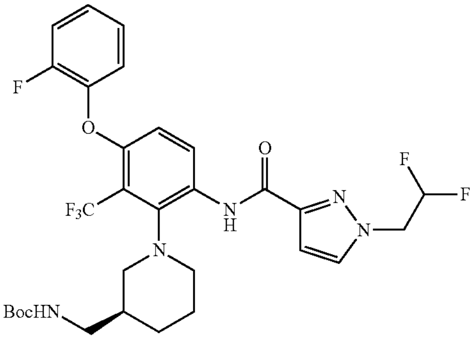 [SMILES: CC(C)(C)OC(=O)NC[C@@H]1CCCN(c2c(NC(=O)c3ccn(CC(F)F)n3)ccc(Oc3ccccc3F)c2C(F)(F)F)C1] |
| 305 | 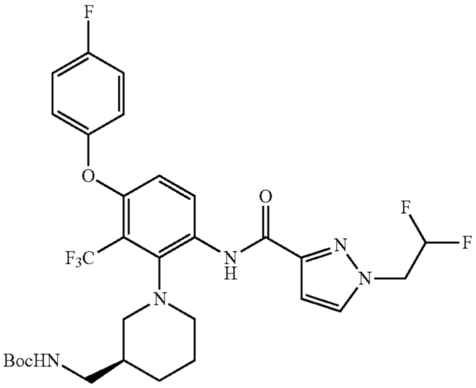 [SMILES: CC(C)(C)OC(=O)NC[C@@H]1CCCN(c2c(NC(=O)c3ccn(CC(F)F)n3)ccc(Oc3ccc(F)cc3)c2C(F)(F)F)C1] |
| 306 | 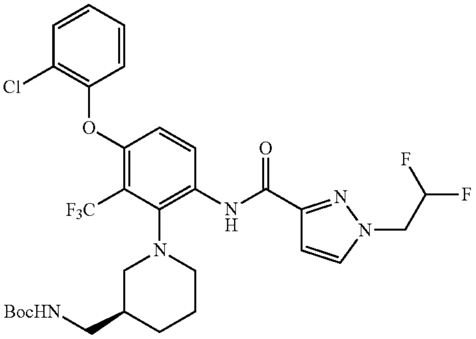 |
| 307 | 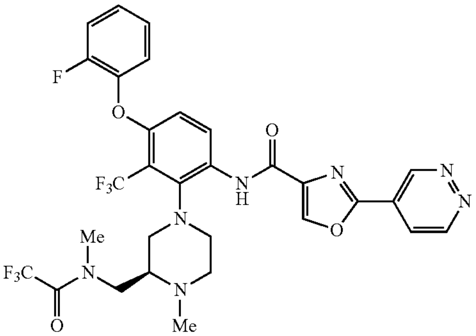 [SMILES: CN(C[C@H]1CN(c2c(NC(=O)c3coc(-c4ccnnc4)n3)ccc(Oc3ccccc3F)c2C(F)(F)F)CCN1C)C(=O)C(F)(F)F] |

TABLE 4-continued
| PEx | Str |
| --- | --- |
| 308 | 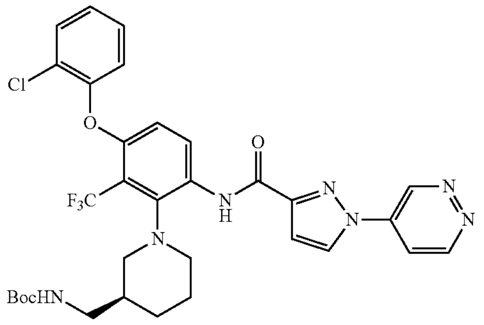 [SMILES: CC(C)(C)OC(=O)NC[C@@H]1CCCN(c2c(NC(=O)c3ccn(-c4ccnnc4)n3)ccc(Oc3ccccc3Cl)c2C(F)(F)F)C1] |
| 309 | 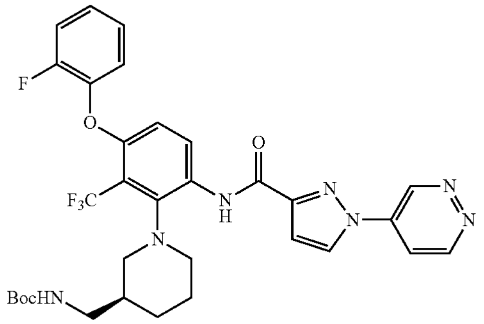 |
| 310 | 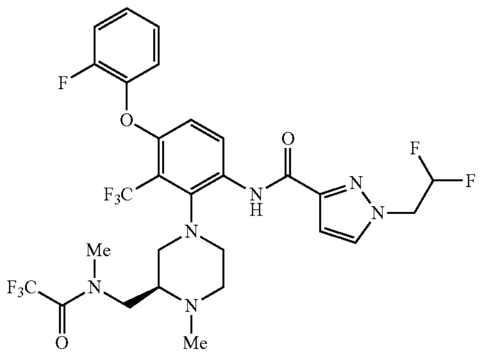 [SMILES: CN(C[C@H]1CN(c2c(NC(=O)c3ccn(CC(F)F)n3)ccc(Oc3ccccc3F)c2C(F)(F)F)CCN1C)C(=O)C(F)(F)F] |
| 311 | 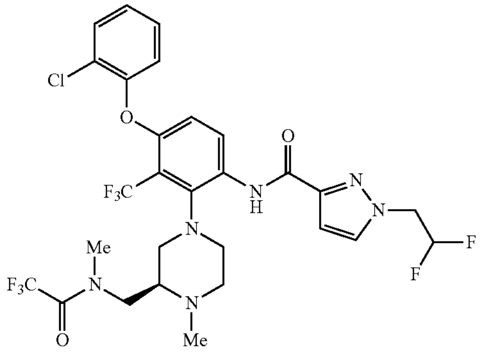 [SMILES: CN(C[C@H]1CN(c2c(NC(=O)c3ccn(CC(F)F)n3)ccc(Oc3ccccc3Cl)c2C(F)(F)F)CCN1C)C(=O)C(F)(F)F] |
| 312 | 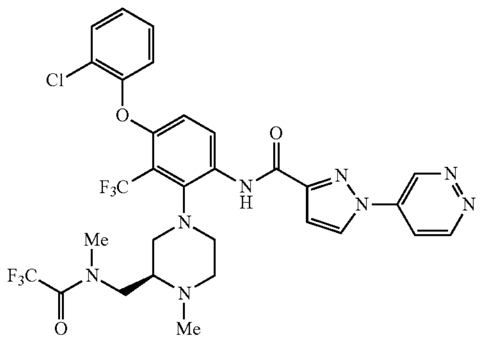 [SMILES: CN(C[C@H]1CN(c2c(NC(=O)c3ccn(-c4ccnnc4)n3)ccc(Oc3ccccc3Cl)c2C(F)(F)F)CCN1C)C(=O)C(F)(F)F] |
| 313 | 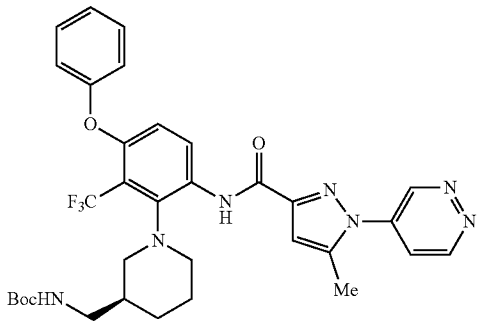 [SMILES: Cc1cc(C(=O)Nc2ccc(Oc3ccccc3)c(C(F)(F)F)c2N2CCC[C@@H](CNC(=O)OC(C)(C)C)C2)nn1-c1ccnnc1] |
| 314 | 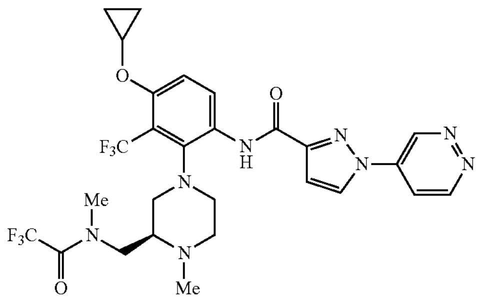 [SMILES: CN(C[C@H]1CN(c2c(NC(=O)c3ccn(-c4ccnnc4)n3)ccc(OC3CC3)c2C(F)(F)F)CCN1C)C(=O)C(F)(F)F] |
| 315 | 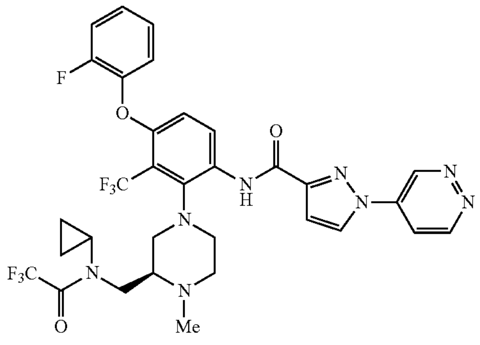 [SMILES: CN1CCN(c2c(NC(=O)c3ccn(-c4ccnnc4)n3)ccc(Oc3ccccc3F)c2C(F)(F)F)C[C@@H]1CN(C(=O)C(F)(F)F)C1CC1] |

TABLE 4-continued
| PEx | Str |
|---|---|
| 316 | 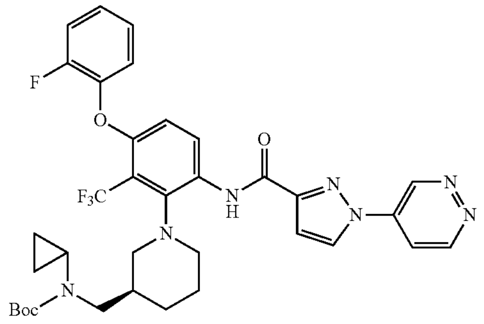 [SMILES: CC(C)(C)OC(=O)N(C[C@@H]1CCCN(c2c(NC(=O)c3ccn(-c4ccnnc4)n3)ccc(Oc3ccccc3F)c2C(F)(F)F)C1)C1CC1] |
| 317 | 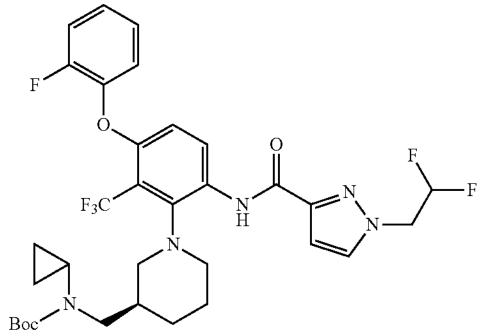 [SMILES: CC(C)(C)OC(=O)N(C[C@@H]1CCCN(c2c(NC(=O)c3ccn(CC(F)F)n3)ccc(Oc3ccccc3F)c2C(F)(F)F)C1)C1CC1] |
| 318 | 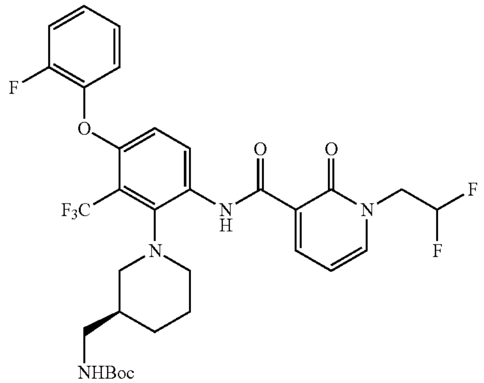 [SMILES: CC(C)(C)OC(=O)NC[C@@H]1CCCN(c2c(NC(=O)c3cccn(CC(F)F)c3=O)ccc(Oc3ccccc3F)c2C(F)(F)F)C1] |
| 319 | 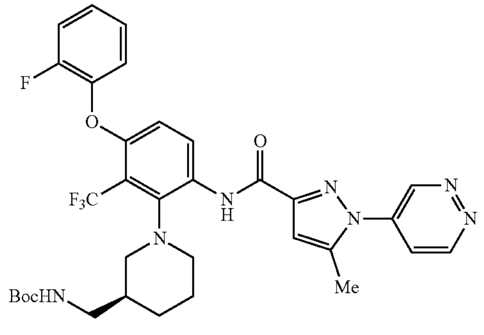 [SMILES: Cc1cc(C(=O)Nc2ccc(Oc3ccccc3F)c(C(F)(F)F)c2N2CCC[C@@H](CNC(=O)OC(C)(C)C)C2)nn1-c1ccnnc1] |
| 320 | 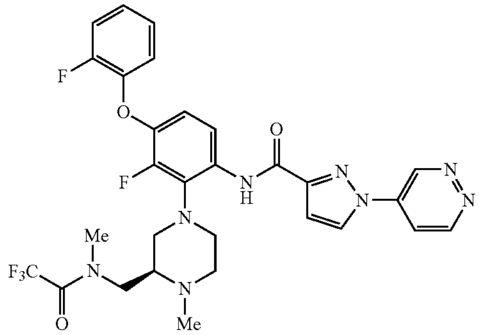 |
| 321 | 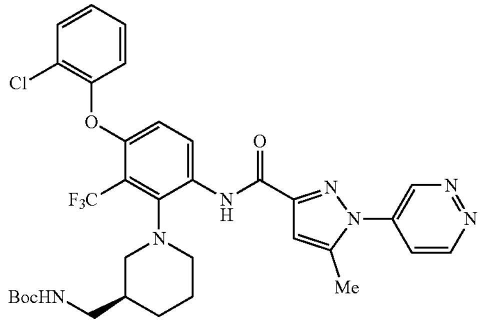 [SMILES: Cc1cc(C(=O)Nc2ccc(Oc3ccccc3Cl)c(C(F)(F)F)c2N2CCC[C@@H](CNC(=O)OC(C)(C)C)C2)nn1-c1ccnnc1] |
| 322 | 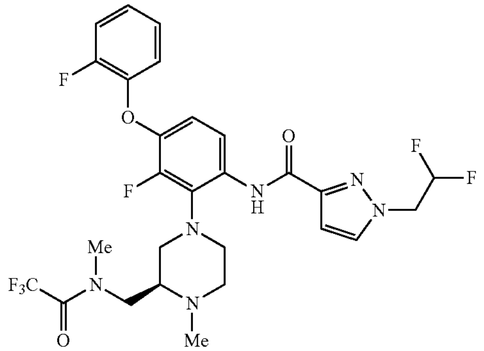 [SMILES: CN(C[C@H]1CN(c2c(NC(=O)c3ccn(CC(F)F)n3)ccc(Oc3ccccc3F)c2F)CCN1C)C(=O)C(F)(F)F] |
| 323 | 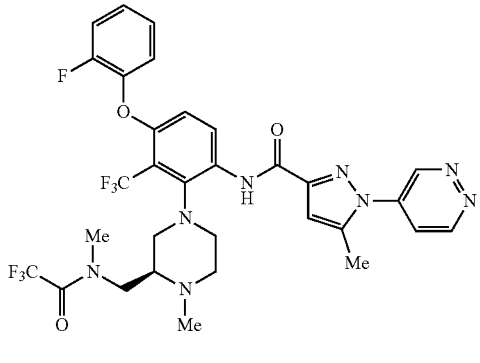 [SMILES: Cc1cc(C(=O)Nc2ccc(Oc3ccccc3F)c(C(F)(F)F)c2N2CCN(C)[C@@H](CN(C)C(=O)C(F)(F)F)C2)nn1-c1ccnnc1] |

TABLE 4-continued
| PEx | Str |
|---|---|
| 324 | 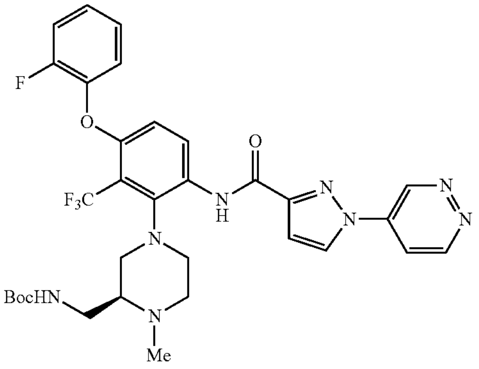 [SMILES: CN1CCN(c2c(NC(=O)c3ccn(-c4ccnnc4)n3)ccc(Oc3ccccc3F)c2C(F)(F)F)C[C@@H]1CNC(=O)OC(C)(C)C] |
| 325 | 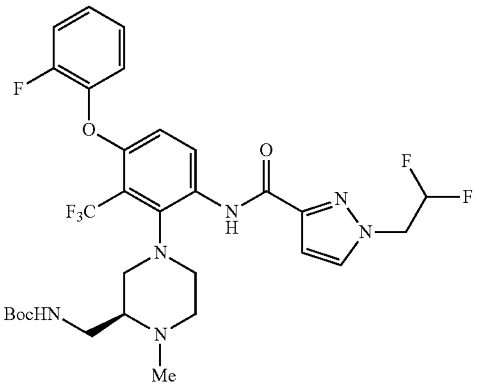 [SMILES: CN1CCN(c2c(NC(=O)c3ccn(CC(F)F)n3)ccc(Oc3ccccc3F)c2C(F)(F)F)C[C@@H]1CNC(=O)OC(C)(C)C] |
| 326 | 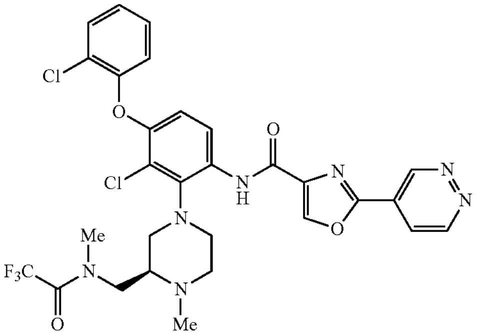 |
| 327 | 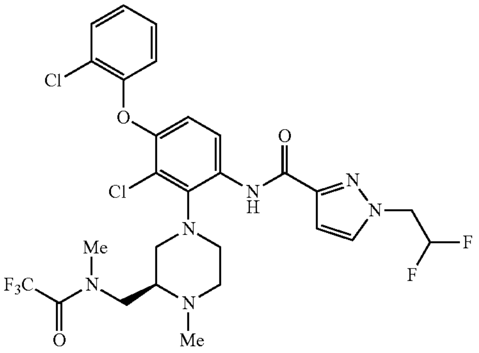 [SMILES: CN(C[C@H]1CN(c2c(NC(=O)c3ccn(CC(F)F)n3)ccc(Oc3ccccc3Cl)c2Cl)CCN1C)C(=O)C(F)(F)F] |
TABLE 4-continued
| PEx | Str |
|---|---|
| 328 | 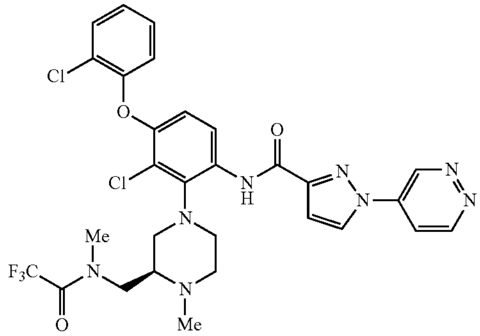 [SMILES: CN(C[C@H]1CN(c2c(NC(=O)c3ccn(-c4ccnnc4)n3)ccc(Oc3ccccc3Cl)c2Cl)CCN1C)C(=O)C(F)(F)F] |
| 329 | 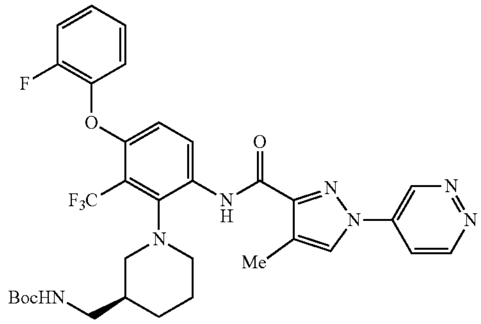 [SMILES: Cc1cn(-c2ccnnc2)nc1C(=O)Nc1ccc(Oc2ccccc2F)c(C(F)(F)F)c1N1CCC[C@@H](CNC(=O)OC(C)(C)C)C1] |
| 330 | 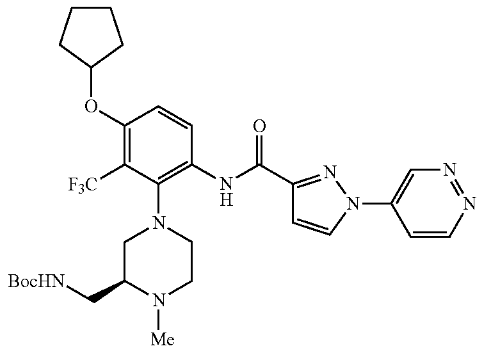 [SMILES: CN1CCN(c2c(NC(=O)c3ccn(-c4ccnnc4)n3)ccc(OC3CCCC3)c2C(F)(F)F)C[C@@H]1CNC(=O)OC(C)(C)C] |
| 331 | 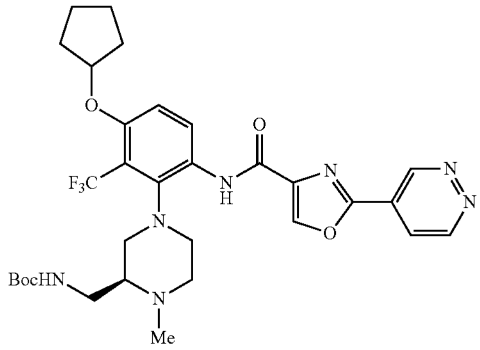 [SMILES: CN1CCN(c2c(NC(=O)c3coc(-c4ccnnc4)n3)ccc(OC3CCCC3)c2C(F)(F)F)C[C@@H]1CNC(=O)OC(C)(C)C] |

TABLE 4-continued
| PEx | Str |
|---|---|
| 332 | 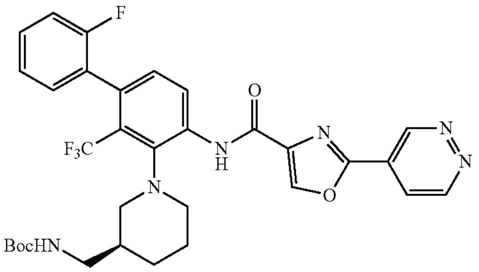 [SMILES: CC(C)(C)OC(=O)NC[C@@H]1CCCN(c2c(NC(=O)c3coc(-c4ccnnc4)n3)ccc(-c3ccccc3F)c2C(F)(F)F)C1] |
| 333 | 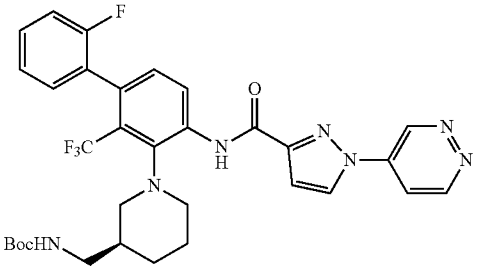 [SMILES: CC(C)(C)OC(=O)NC[C@@H]1CCCN(c2c(NC(=O)c3ccn(-c4ccnnc4)n3)ccc(-c3ccccc3F)c2C(F)(F)F)C1] |
| 334 | 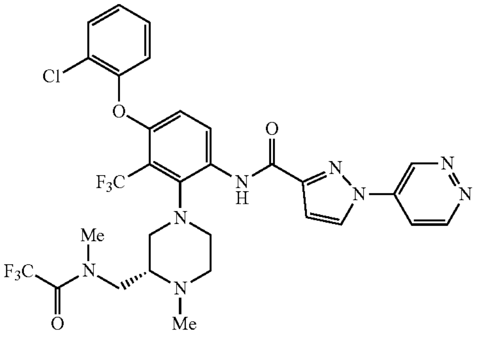 [SMILES: CN(C[C@@H]1CN(c2c(NC(=O)c3ccn(-c4ccnnc4)n3)ccc(Oc3ccccc3Cl)c2C(F)(F)F)CCN1C)C(=O)C(F)(F)F] |
| 335 | 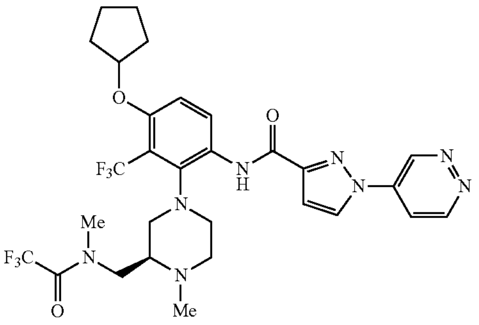 [SMILES: CN(C[C@H]1CN(c2c(NC(=O)c3ccn(-c4ccnnc4)n3)ccc(OC3CCCC3)c2C(F)(F)F)CCN1C)C(=O)C(F)(F)F] |
| 336 | 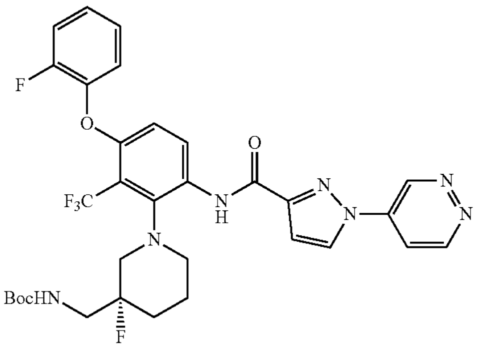 [SMILES: CC(C)(C)OC(=O)NC[C@]1(F)CCCN(c2c(NC(=O)c3ccn(-c4ccnnc4)n3)ccc(Oc3ccccc3F)c2C(F)(F)F)C1] |
TABLE 4-continued
| PEx | Str |
|---|---|
| 337 | 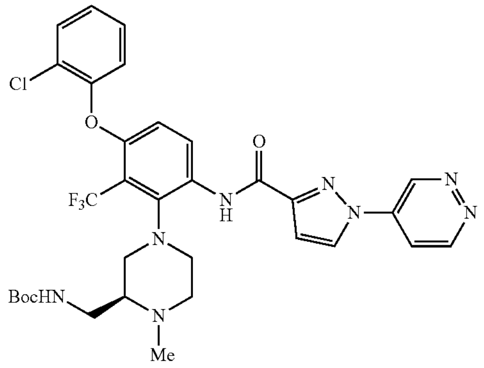 [SMILES: CN1CCN(c2c(NC(=O)c3ccn(-c4ccnnc4)n3)ccc(Oc3ccccc3Cl)c2C(F)(F)F)C[C@@H]1CNC(=O)OC(C)(C)C] |
| 338 | 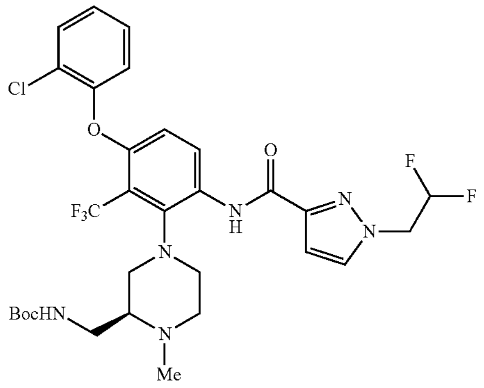 [SMILES: CN1CCN(c2c(NC(=O)c3ccn(CC(F)F)n3)ccc(Oc3ccccc3Cl)c2C(F)(F)F)C[C@@H]1CNC(=O)OC(C)(C)C] |
| 339 | 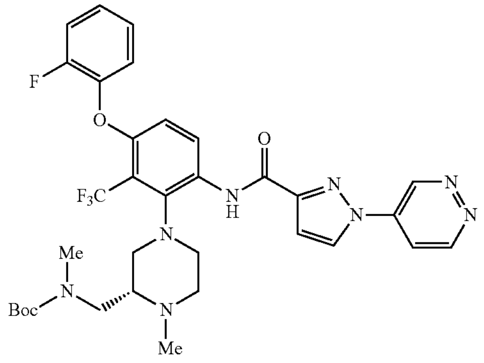 [SMILES: CN(C[C@@H]1CN(c2c(NC(=O)c3ccn(-c4ccnnc4)n3)ccc(Oc3ccccc3F)c2C(F)(F)F)CCN1C)C(=O)OC(C)(C)C] |
| 340 | 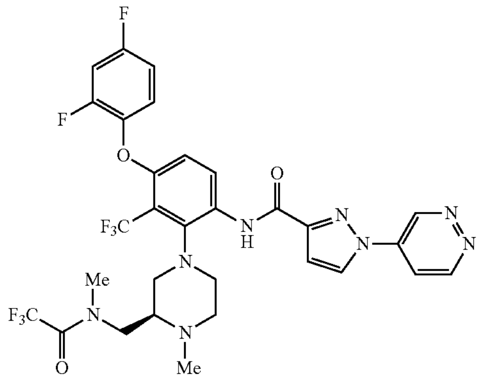 [SMILES: CN(C[C@H]1CN(c2c(NC(=O)c3ccn(-c4ccnnc4)n3)ccc(Oc3ccc(F)cc3F)c2C(F)(F)F)CCN1C)C(=O)C(F)(F)F] |

TABLE 4-continued
| PEx | Str |
| --- | --- |
| 341 | 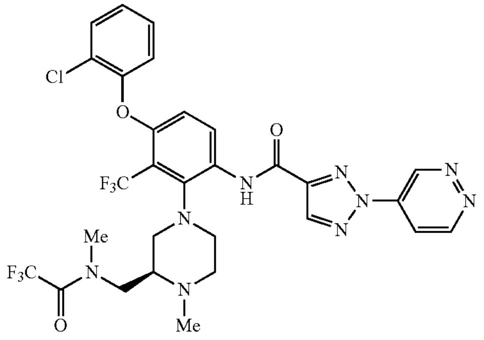 |
| 342 | 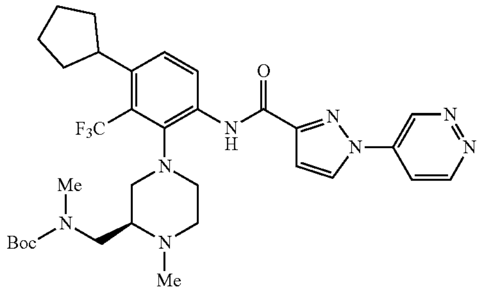 [SMILES: CN(C[C@H]1CN(c2c(NC(=O)c3ccn(-c4ccnnc4)n3)ccc(C3CCCC3)c2C(F)(F)F)CCN1C)C(=O)OC(C)(C)C] |
| 343 | 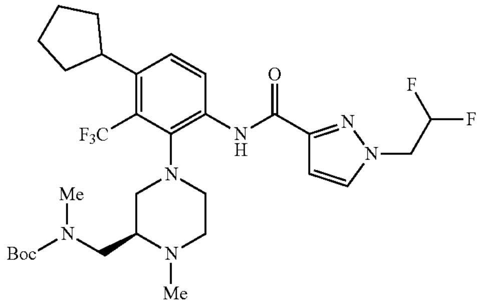 [SMILES: CN(C[C@H]1CN(c2c(NC(=O)c3ccn(CC(F)F)n3)ccc(C3CCCC3)c2C(F)(F)F)CCN1C)C(=O)OC(C)(C)C] |
| 344 | 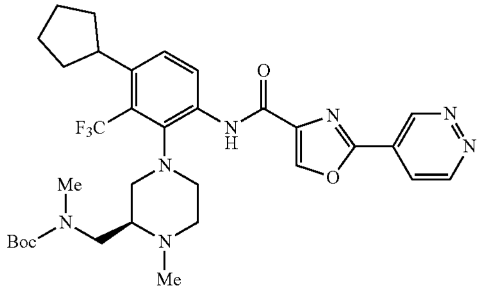 [SMILES: CN(C[C@H]1CN(c2c(NC(=O)c3coc(-c4ccnnc4)n3)ccc(C3CCCC3)c2C(F)(F)F)CCN1C)C(=O)OC(C)(C)C] |
| 345 | 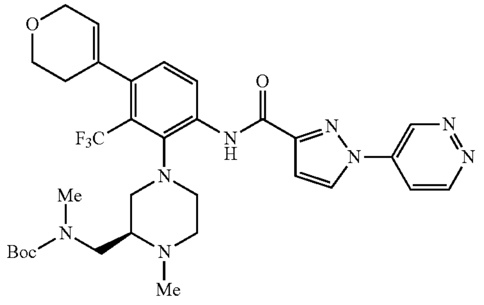 [SMILES: CN(C[C@H]1CN(c2c(NC(=O)c3ccn(-c4ccnnc4)n3)ccc(C3=CCOCC3)c2C(F)(F)F)CCN1C)C(=O)OC(C)(C)C] |
TABLE 4-continued
| PEx | Str |
| --- | --- |
| 346 | 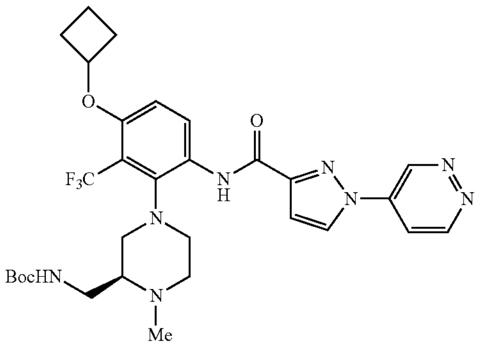 [SMILES: CN1CCN(c2c(NC(=O)c3ccn(-c4ccnnc4)n3)ccc(OC3CCC3)c2C(F)(F)F)C[C@@H]1CNC(=O)OC(C)(C)C] |
| 347 | 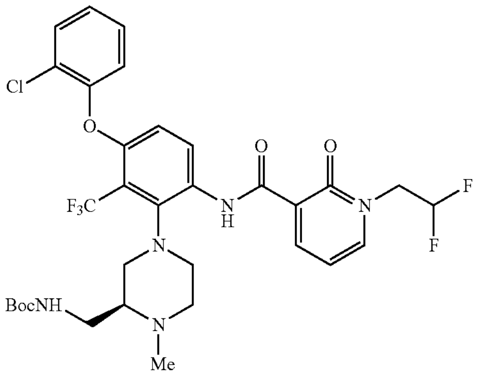 |
| 348 | 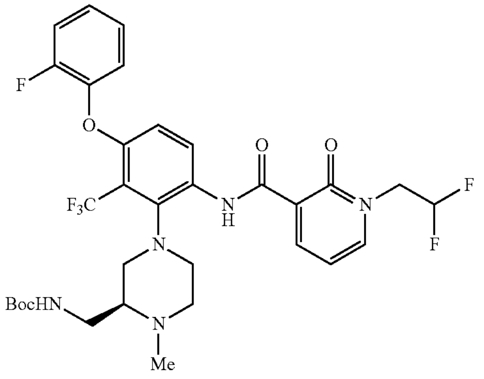 |
| 349 | 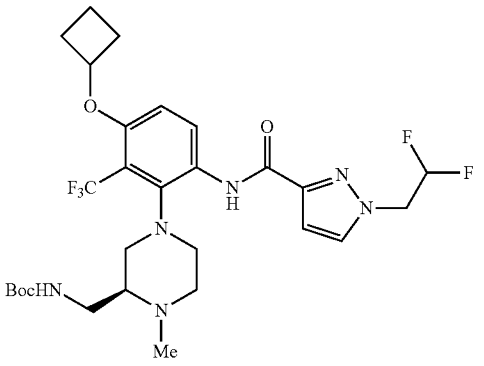 [SMILES: CN1CCN(c2c(NC(=O)c3ccn(CC(F)F)n3)ccc(OC3CCC3)c2C(F)(F)F)C[C@@H]1CNC(=O)OC(C)(C)C] |

TABLE 4-continued
| PEx | Str |
|---|---|
| 350 | 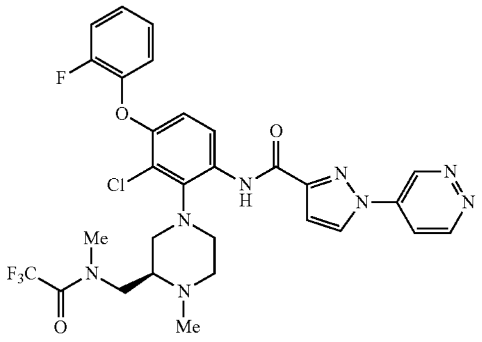 |
| 351 | 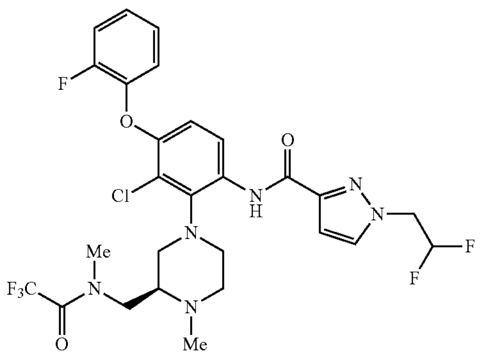 [SMILES: CN(C[C@H]1CN(c2c(NC(=O)c3ccn(CC(F)F)n3)ccc(Oc3ccccc3F)c2Cl)CCN1C)C(=O)C(F)(F)F] |
| 352 | 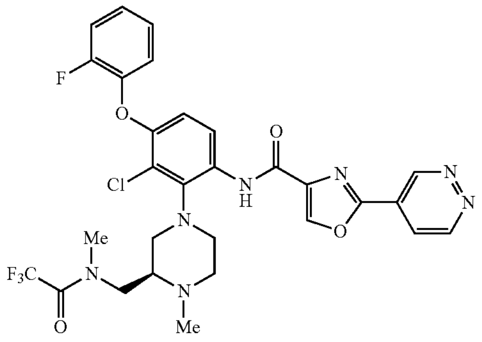 [SMILES: CN(C[C@H]1CN(c2c(NC(=O)c3coc(-c4ccnnc4)n3)ccc(Oc3ccccc3F)c2Cl)CCN1C)C(=O)C(F)(F)F] |
| 353 | 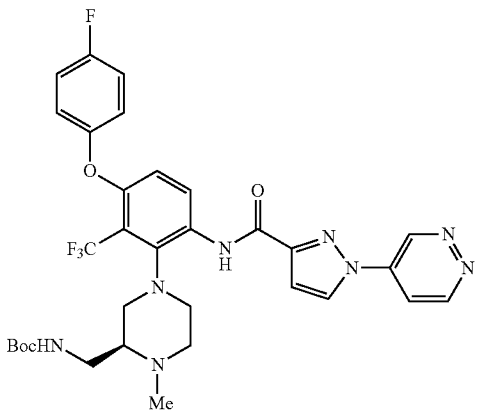 [SMILES: CN1CCN(c2c(NC(=O)c3ccn(-c4ccnnc4)n3)ccc(Oc3ccc(F)cc3)c2C(F)(F)F)C[C@@H]1CNC(=O)OC(C)(C)C] |
| 354 | 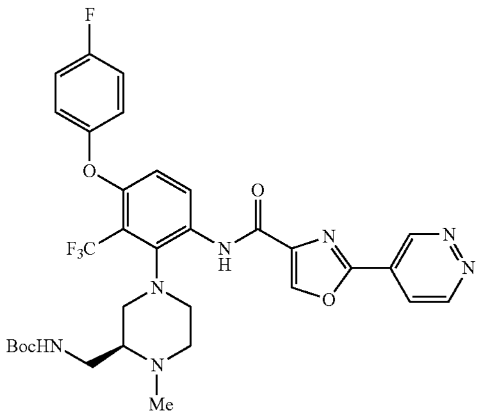 [SMILES: CN1CCN(c2c(NC(=O)c3coc(-c4ccnnc4)n3)ccc(Oc3ccc(F)cc3)c2C(F)(F)F)C[C@@H]1CNC(=O)OC(C)(C)C] |
| 355 | 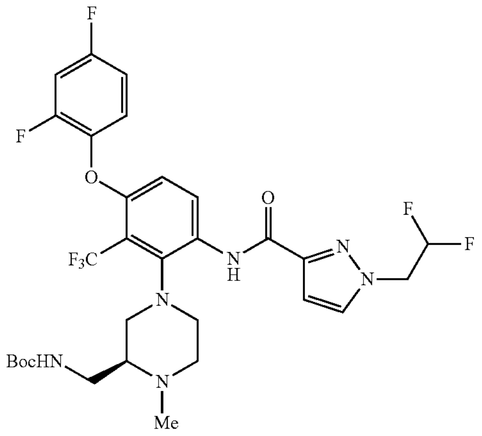 [SMILES: CN1CCN(c2c(NC(=O)c3ccn(CC(F)F)n3)ccc(Oc3ccc(F)cc3F)c2C(F)(F)F)C[C@@H]1CNC(=O)OC(C)(C)C] |
| 356 | 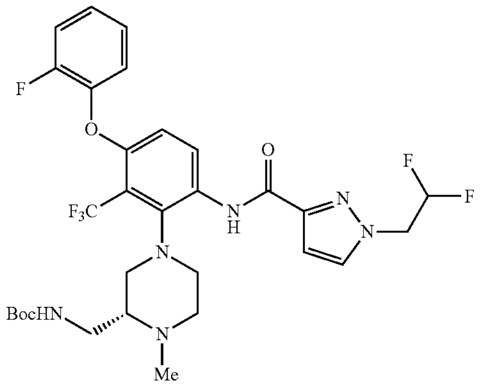 [SMILES: CN1CCN(c2c(NC(=O)c3ccn(CC(F)F)n3)ccc(Oc3ccccc3F)c2C(F)(F)F)C[C@H]1CNC(=O)OC(C)(C)C] |
| 357 | 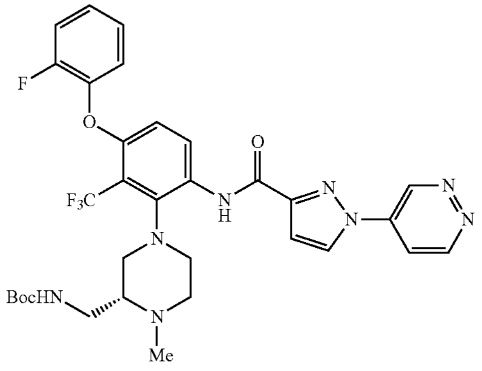 [SMILES: CN1CCN(c2c(NC(=O)c3ccn(-c4ccnnc4)n3)ccc(Oc3ccccc3F)c2C(F)(F)F)C[C@H]1CNC(=O)OC(C)(C)C] |

TABLE 4-continued
| PEx | Str |
|---|---|
| 358 | 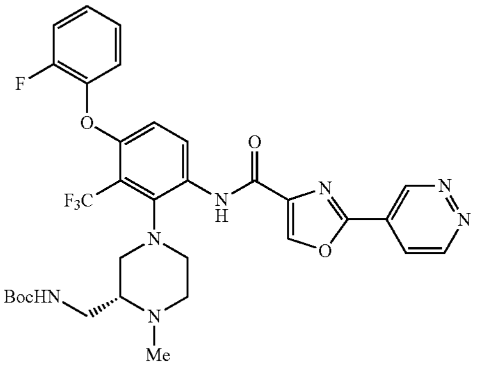 [SMILES: CN1CCN(c2c(NC(=O)c3coc(-c4ccnnc4)n3)ccc(Oc3ccccc3F)c2C(F)(F)F)C[C@H]1CNC(=O)OC(C)(C)C] |
| 359 | 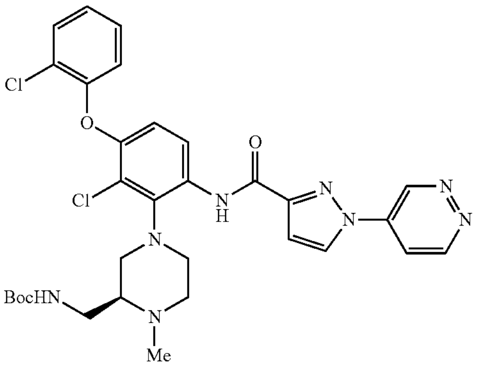 [SMILES: CN1CCN(c2c(NC(=O)c3ccn(-c4ccnnc4)n3)ccc(Oc3ccccc3Cl)c2Cl)C[C@@H]1CNC(=O)OC(C)(C)C] |
| 360 | 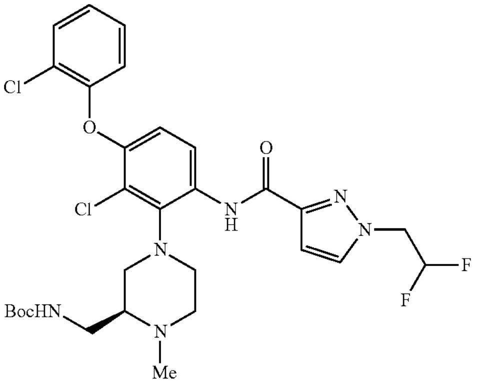 [SMILES: CN1CCN(c2c(NC(=O)c3ccn(CC(F)F)n3)ccc(Oc3ccccc3Cl)c2Cl)C[C@@H]1CNC(=O)OC(C)(C)C] |
| 361 | 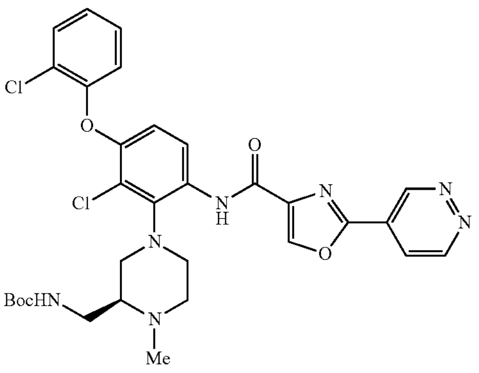 [SMILES: CN1CCN(c2c(NC(=O)c3coc(-c4ccnnc4)n3)ccc(Oc3ccccc3Cl)c2Cl)C[C@@H]1CNC(=O)OC(C)(C)C] |
TABLE 4-continued
| PEx | Str |
|---|---|
| 362 | 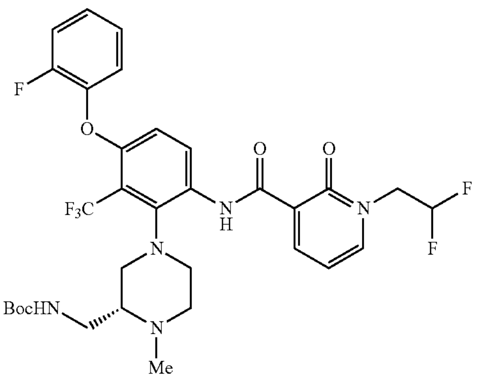 |
| 363 | 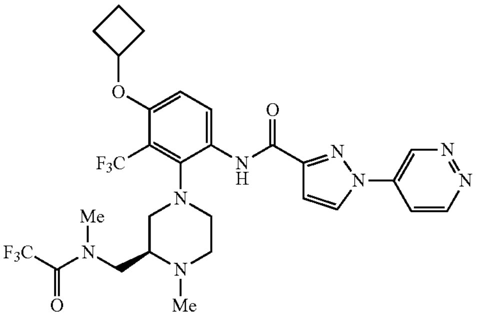 [SMILES: CN(C[C@H]1CN(c2c(NC(=O)c3ccn(-c4ccnnc4)n3)ccc(OC3CCC3)c2C(F)(F)F)CCN1C)C(=O)C(F)(F)F] |
| 364 | 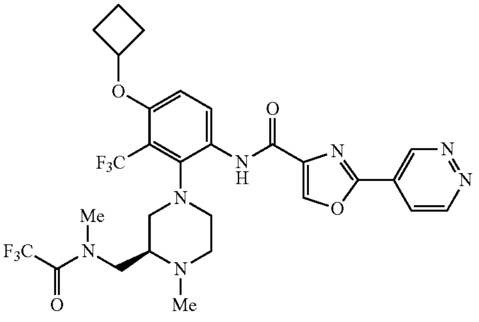 [SMILES: CN(C[C@H]1CN(c2c(NC(=O)c3coc(-c4ccnnc4)n3)ccc(OC3CCC3)c2C(F)(F)F)CCN1C)C(=O)C(F)(F)F] |
| 365 | 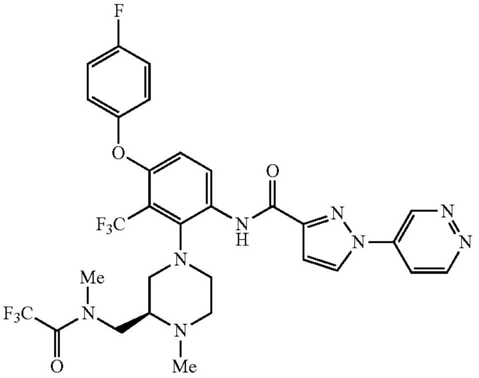 [SMILES: CN(C[C@H]1CN(c2c(NC(=O)c3ccn(-c4ccnnc4)n3)ccc(Oc3ccc(F)cc3)c2C(F)(F)F)CCN1C)C(=O)C(F)(F)F] |

TABLE 4-continued
| PEx | Str |
|---|---|
| 366 | 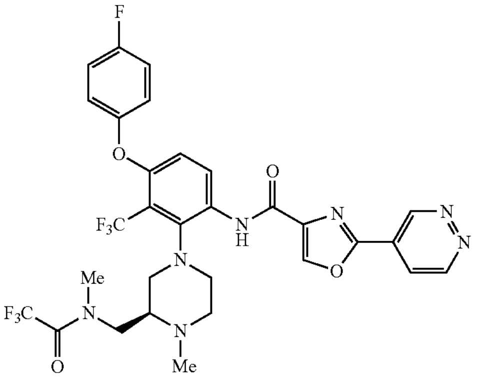 [SMILES: CN(C[C@H]1CN(c2c(NC(=O)c3coc(-c4ccnnc4)n3)ccc(Oc3ccc(F)cc3)c2C(F)(F)F)CCN1C)C(=O)C(F)(F)F] |
| 367 | 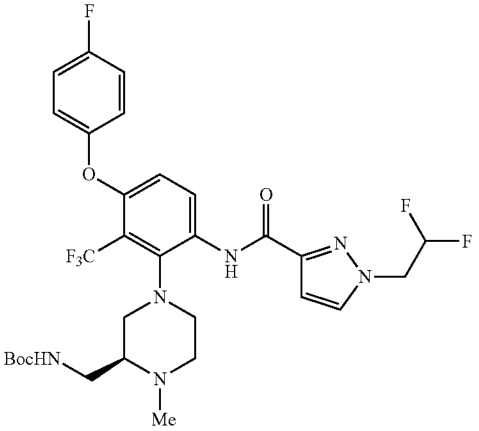 [SMILES: CN1CCN(c2c(NC(=O)c3ccn(CC(F)F)n3)ccc(Oc3ccc(F)cc3)c2C(F)(F)F)C[C@@H]1CNC(=O)OC(C)(C)C] |
| 368 | 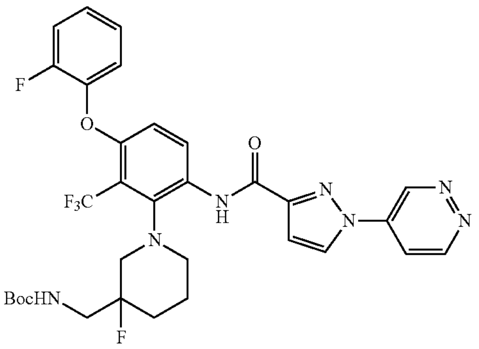 [SMILES: CC(C)(C)OC(=O)NCC1(F)CCCN(c2c(NC(=O)c3ccn(-c4ccnnc4)n3)ccc(Oc3ccccc3F)c2C(F)(F)F)C1] |
| 369 | 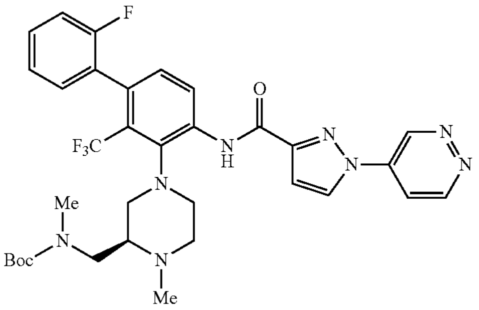 [SMILES: CN(C[C@H]1CN(c2c(NC(=O)c3ccn(-c4ccnnc4)n3)ccc(-c3ccccc3F)c2C(F)(F)F)CCN1C)C(=O)OC(C)(C)C] |
TABLE 4-continued
| PEx | Str |
|---|---|
| 370 | 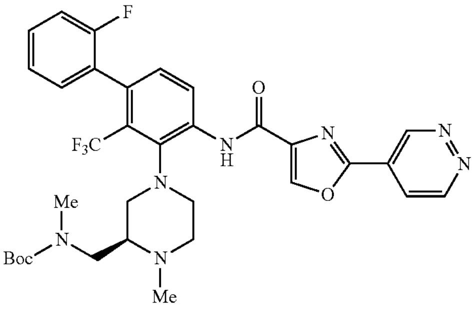 [SMILES: CN(C[C@H]1CN(c2c(NC(=O)c3coc(-c4ccnnc4)n3)ccc(-c3ccccc3F)c2C(F)(F)F)CCN1C)C(=O)OC(C)(C)C] |
| 371 | 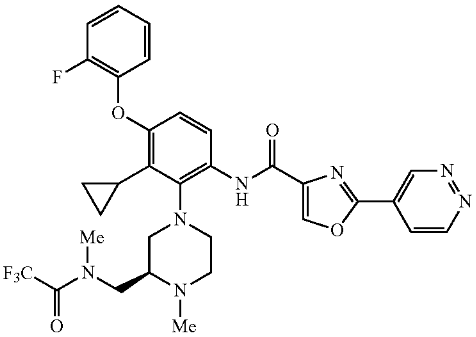 [SMILES: CN(C[C@H]1CN(c2c(NC(=O)c3coc(-c4ccnnc4)n3)ccc(Oc3ccccc3F)c2C2CC2)CCN1C)C(=O)C(F)(F)F] |
| 372 | 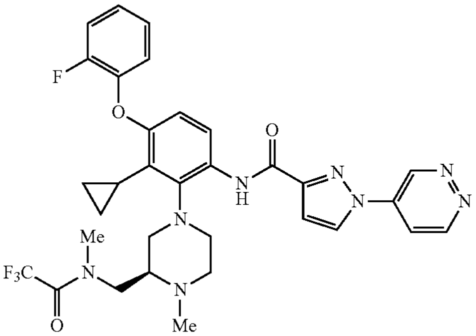 [SMILES: CN(C[C@H]1CN(c2c(NC(=O)c3ccn(-c4ccnnc4)n3)ccc(Oc3ccccc3F)c2C2CC2)CCN1C)C(=O)C(F)(F)F] |
| 373 | 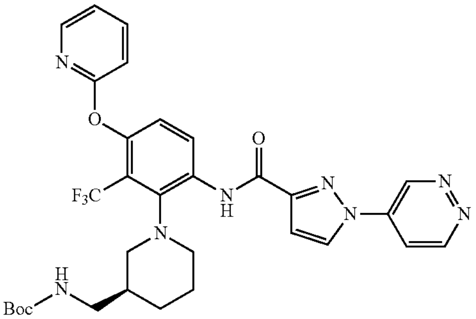 [SMILES: CC(C)(C)OC(=O)NC[C@@H]1CCCN(c2c(NC(=O)c3ccn(-c4ccnnc4)n3)ccc(Oc3ccccn3)c2C(F)(F)F)C1] |

TABLE 4-continued
| PEx | Str |
|---|---|
| 374 | 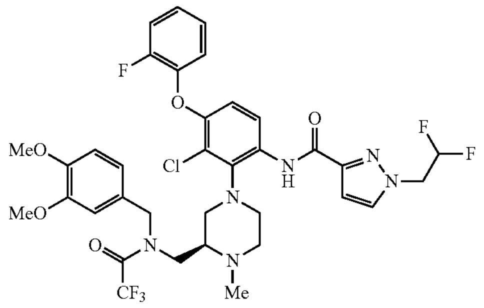 [SMILES: COc1ccc(CN(C[C@H]2CN(c3c(NC(=O)c4ccn(CC(F)F)n4)ccc(Oc4ccccc4F)c3Cl)CCN2C)C(=O)C(F)(F)F)cc1OC] |
| 375 | 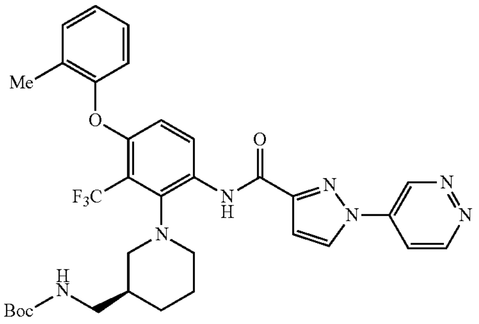 [SMILES: Cc1ccccc1Oc1ccc(NC(=O)c2ccn(-c3ccnnc3)n2)c(N2CCC[C@@H](CNC(=O)OC(C)(C)C)C2)c1C(F)(F)F] |
| 376 | 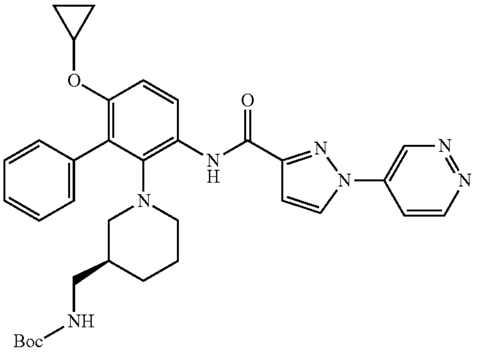 [SMILES: CC(C)(C)OC(=O)NC[C@@H]1CCCN(c2c(NC(=O)c3ccn(-c4ccnnc4)n3)ccc(OC3CC3)c2-c2ccccc2)C1] |
| 377 | 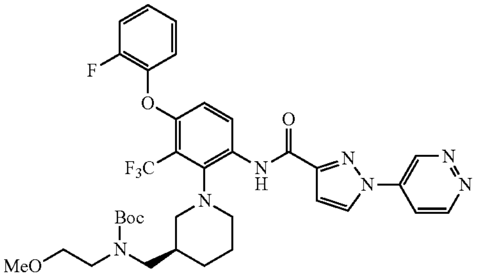 [SMILES: COCCN(C[C@@H]1CCCN(c2c(NC(=O)c3ccn(-c4ccnnc4)n3)ccc(Oc3ccccc3F)c2C(F)(F)F)C1)C(=O)OC(C)(C)C] |
| 378 | 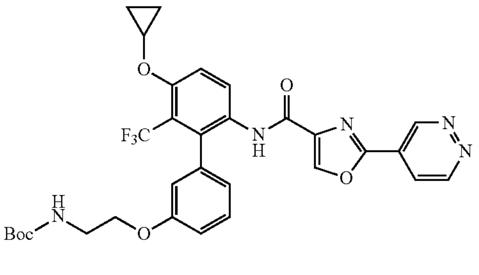 [SMILES: CC(C)(C)OC(=O)NCCOc1cccc(-c2c(NC(=O)c3coc(-c4ccnnc4)n3)ccc(OC3CC3)c2C(F)(F)F)c1] |
| 379 | 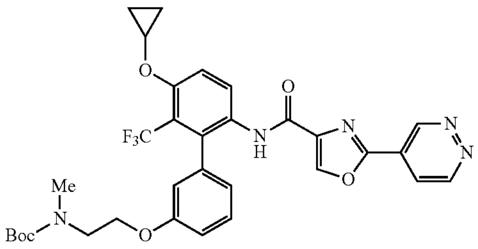 [SMILES: CN(CCOc1cccc(-c2c(NC(=O)c3coc(-c4ccnnc4)n3)ccc(OC3CC3)c2C(F)(F)F)c1)C(=O)OC(C)(C)C] |
| 380 | 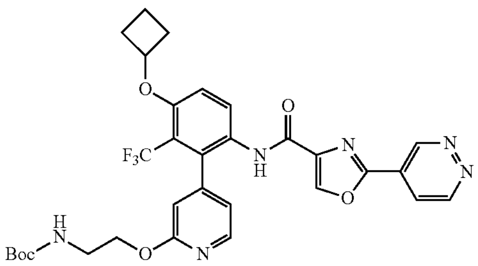 [SMILES: CC(C)(C)OC(=O)NCCOc1cc(-c2c(NC(=O)c3coc(-c4ccnnc4)n3)ccc(OC3CCC3)c2C(F)(F)F)ccn1] |
| 381 | 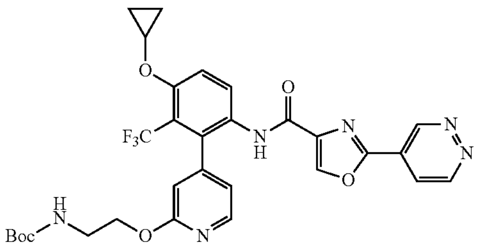 [SMILES: CC(C)(C)OC(=O)NCCOc1cc(-c2c(NC(=O)c3coc(-c4ccnnc4)n3)ccc(OC3CC3)c2C(F)(F)F)ccn1] |
| 382 | 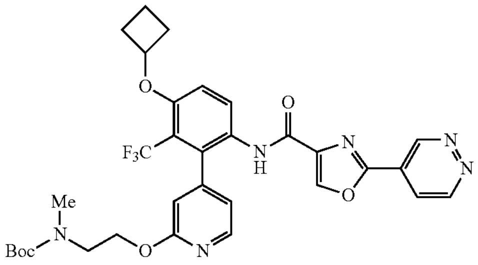 [SMILES: CN(CCOc1cc(-c2c(NC(=O)c3coc(-c4ccnnc4)n3)ccc(OC3CCC3)c2C(F)(F)F)ccn1)C(=O)OC(C)(C)C] |
| 383 | 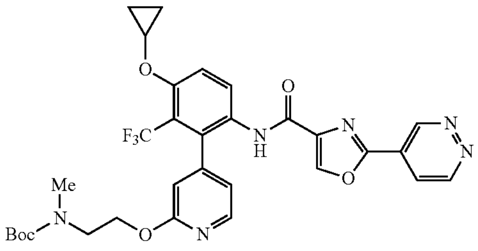 [SMILES: CN(CCOc1cc(-c2c(NC(=O)c3coc(-c4ccnnc4)n3)ccc(OC3CC3)c2C(F)(F)F)ccn1)C(=O)OC(C)(C)C] |

TABLE 4-continued
| PEx | Str |
|---|---|
| 384 | 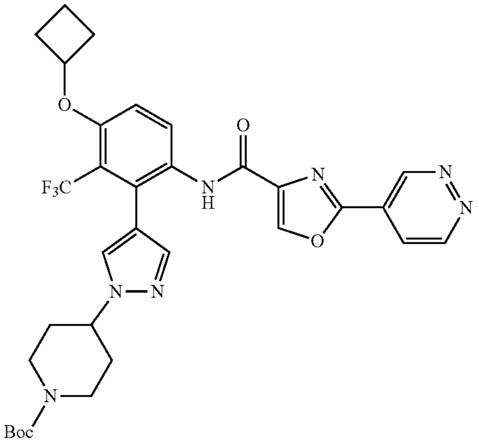 [SMILES: CC(C)(C)OC(=O)N1CCC(n2cc(-c3c(NC(=O)c4coc(-c5ccnnc5)n4)ccc(OC4CCC4)c3C(F)(F)F)cn2)CC1] |
| 385 | 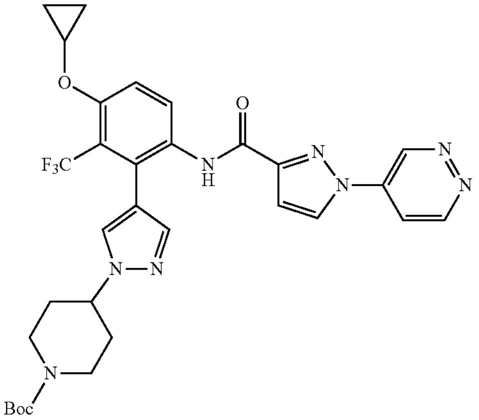 [SMILES: CC(C)(C)OC(=O)N1CCC(n2cc(-c3c(NC(=O)c4ccn(-c5ccnnc5)n4)ccc(OC4CC4)c3C(F)(F)F)cn2)CC1] |
| 386 | 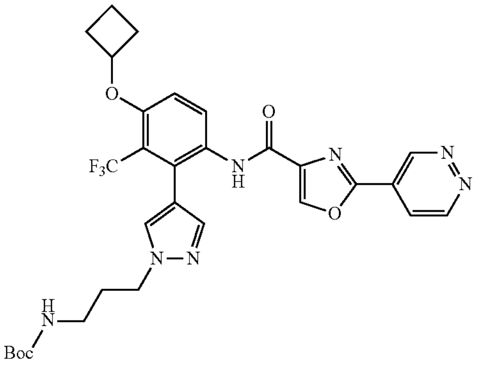 [SMILES: CC(C)(C)OC(=O)NCCCn1cc(-c2c(NC(=O)c3coc(-c4ccnnc4)n3)ccc(OC3CCC3)c2C(F)(F)F)cn1] |
| 387 | 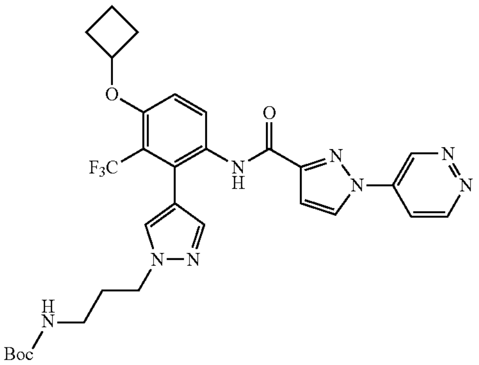 [SMILES: CC(C)(C)OC(=O)NCCCn1cc(-c2c(NC(=O)c3ccn(-c4ccnnc4)n3)ccc(OC3CCC3)c2C(F)(F)F)cn1] |
TABLE 4-continued
| PEx | Str |
|---|---|
| 388 | 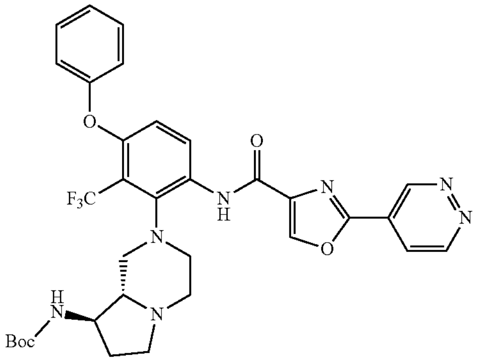 [SMILES: CC(C)(C)OC(=O)N[C@@H]1CCN2CCN(c3c(NC(=O)c4coc(-c5ccnnc5)n4)ccc(Oc4ccccc4)c3C(F)(F)F)C[C@@H]12] |
| 389 | 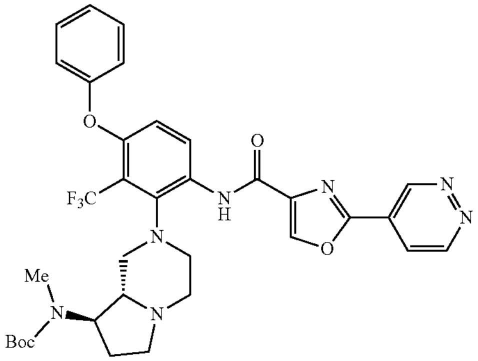 [SMILES: CN(C(=O)OC(C)(C)C)[C@@H]1CCN2CCN(c3c(NC(=O)c4coc(-c5ccnnc5)n4)ccc(Oc4ccccc4)c3C(F)(F)F)C[C@@H]12] |
| 390 | 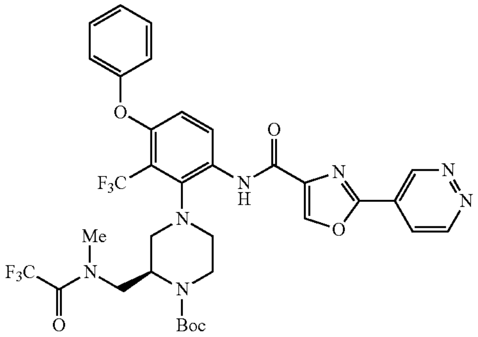 |
| 391 | 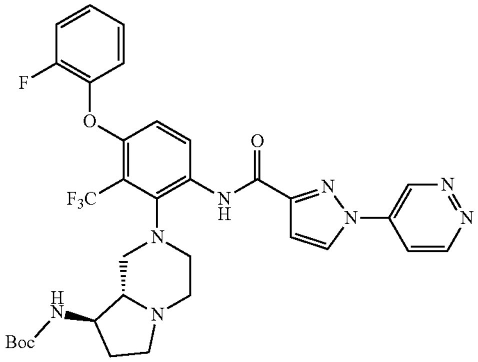 [SMILES: CC(C)(C)OC(=O)N[C@@H]1CCN2CCN(c3c(NC(=O)c4ccn(-c5ccnnc5)n4)ccc(Oc4ccccc4F)c3C(F)(F)F)C[C@@H]12] |

TABLE 4-continued
| PEx | Str |
| --- | --- |
| 392 | 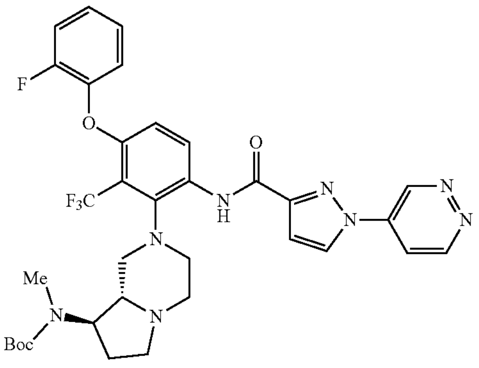 [SMILES: CN(C(=O)OC(C)(C)C)[C@@H]1CCN2CCN(c3c(NC(=O)c4ccn(-c5ccnnc5)n4)ccc(Oc4ccccc4F)c3C(F)(F)F)C[C@@H]12] |
| 393 | 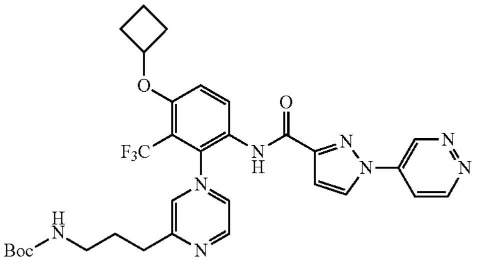 |
| 394 | 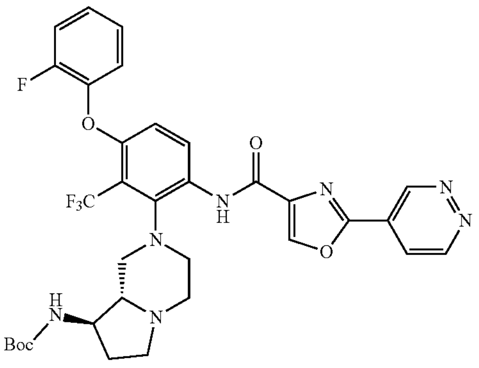 [SMILES: CC(C)(C)OC(=O)N[C@@H]1CCN2CCN(c3c(NC(=O)c4coc(-c5ccnnc5)n4)ccc(Oc4ccccc4F)c3C(F)(F)F)C[C@@H]12] |
| 395 | 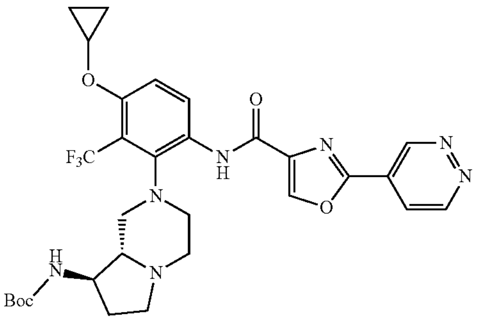 [SMILES: CC(C)(C)OC(=O)N[C@@H]1CCN2CCN(c3c(NC(=O)c4coc(-c5ccnnc5)n4)ccc(OC4CC4)c3C(F)(F)F)C[C@@H]12] |
TABLE 4-continued
| PEx | Str |
| --- | --- |
| 396 | 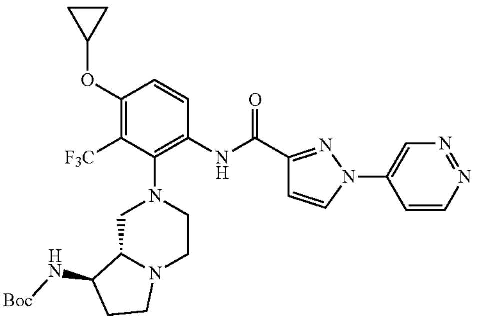 [SMILES: CC(C)(C)OC(=O)N[C@@H]1CCN2CCN(c3c(NC(=O)c4ccn(-c5ccnnc5)n4)ccc(OC4CC4)c3C(F)(F)F)C[C@@H]12] |
| 397 | 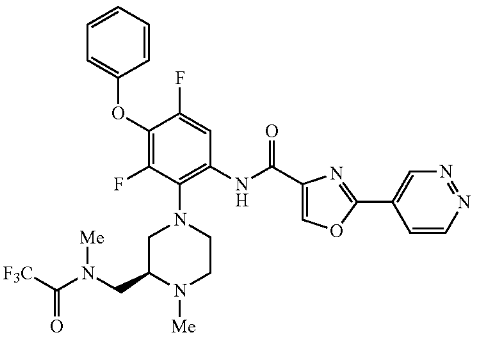 [SMILES: CN(C[C@H]1CN(c2c(NC(=O)c3coc(-c4ccnnc4)n3)cc(F)c(Oc3ccccc3)c2F)CCN1C)C(=O)C(F)(F)F] |
| 398 | 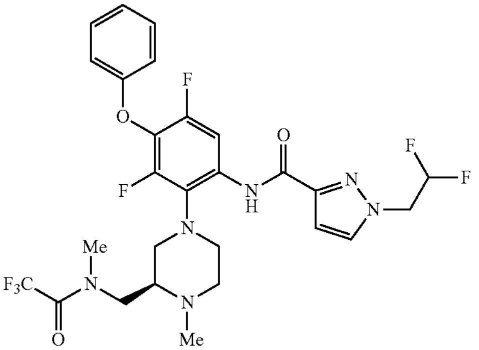 [SMILES: CN(C[C@H]1CN(c2c(NC(=O)c3ccn(CC(F)F)n3)cc(F)c(Oc3ccccc3)c2F)CCN1C)C(=O)C(F)(F)F] |
| 399 | 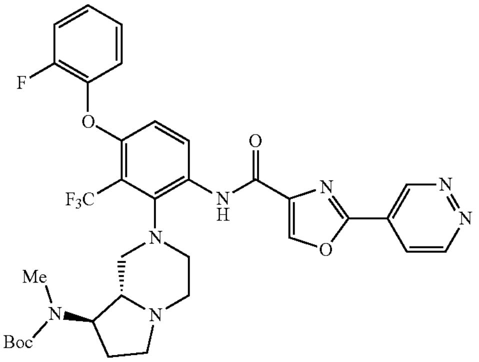 [SMILES: CN(C(=O)OC(C)(C)C)[C@@H]1CCN2CCN(c3c(NC(=O)c4coc(-c5ccnnc5)n4)ccc(Oc4ccccc4F)c3C(F)(F)F)C[C@@H]12] |

TABLE 4-continued

| PEx | Str |
|---|---|
| 400 | 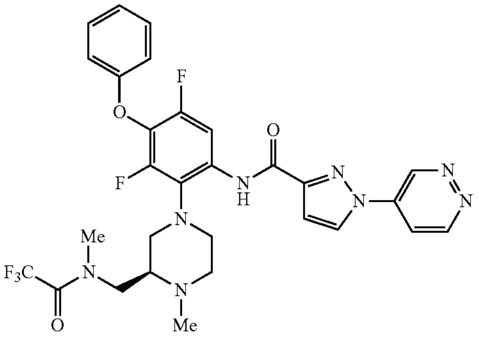 [SMILES: CN(C[C@H]1CN(c2c(NC(=O)c3ccn(-c4ccnnc4)n3)cc(F)c(Oc3ccccc3)c2F)CCN1C)C(=O)C(F)(F)F] |
| 401 | 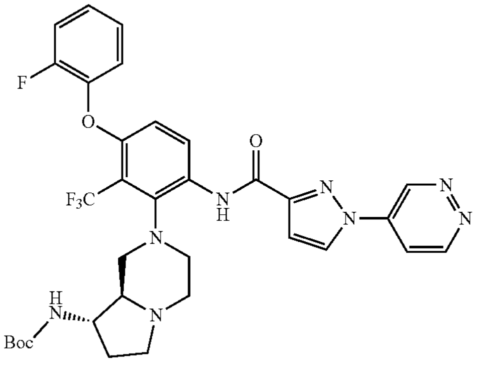 [SMILES: CC(C)(C)OC(=O)N[C@H]1CCN2CCN(c3c(NC(=O)c4ccn(-c5ccnnc5)n4)ccc(Oc4ccccc4F)c3C(F)(F)F)C[C@H]12] |
| 402 | 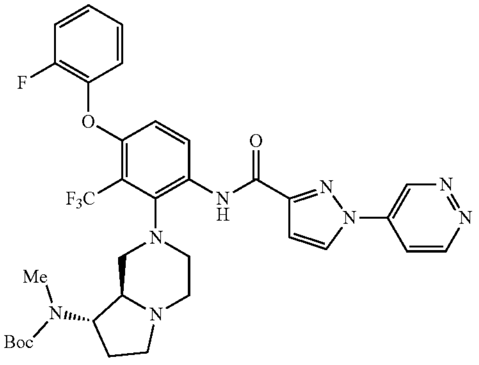 [SMILES: CN(C(=O)OC(C)(C)C)[C@H]1CCN2CCN(c3c(NC(=O)c4ccn(-c5ccnnc5)n4)ccc(Oc4ccccc4F)c3C(F)(F)F)C[C@H]12] |
| 403 | 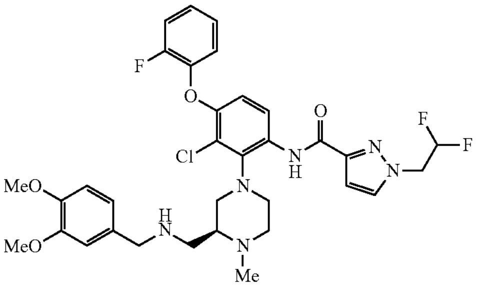 [SMILES: COc1ccc(CNC[C@H]2CN(c3c(NC(=O)c4ccn(CC(F)F)n4)ccc(Oc4ccccc4F)c3Cl)CCN2C)cc1OC] |

TABLE 4-continued

| PEx | Str |
|---|---|
| 404 | 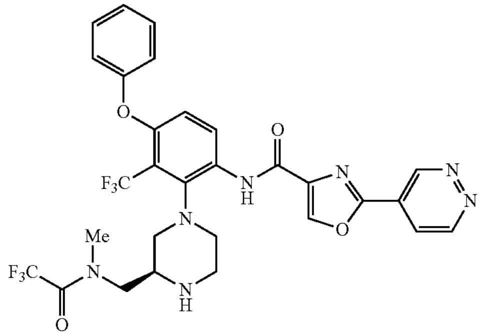 [SMILES: CN(C[C@H]1CN(c2c(NC(=O)c3coc(-c4ccnnc4)n3)ccc(Oc3ccccc3)c2C(F)(F)F)CCN1)C(=O)C(F)(F)F] |
| 405 | 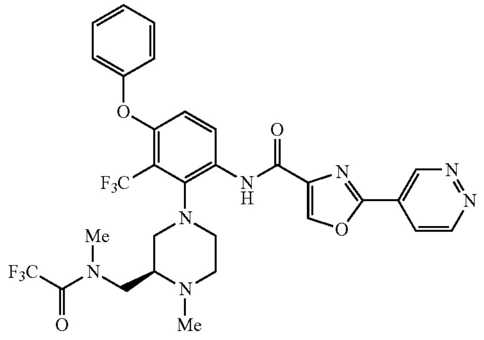 [SMILES: CN(C[C@H]1CN(c2c(NC(=O)c3coc(-c4ccnnc4)n3)ccc(Oc3ccccc3)c2C(F)(F)F)CCN1C)C(=O)C(F)(F)F] |

TABLE 5

| PEx | PSyn | DAT |
|---|---|---|
| 1 | 1 | — |
| 2 | 2 | NMR DMSO-d6 (500 MHz): 7.20 (1H, d), 7.28-7.43 (3H, m), 7.44-7.52 (1H, m), 8.18 (1H, dd) |
| 3 | 2 | NMR CDCl3 (500 MHz): 6.94 (1H, dd), 7.02-7.07 (2H, m), 7.24-7.29 (1H, m), 7.40-7.46 (2H, m), 7.65 (1H, dd) |
| 4 | 2 | ESI+: 409.0 |
| 5 | 2 | NMR DMSO-d6 (500 MHz): 7.11 (1H, ddd), 7.28-7.55 (4H, m), 8.01 (1H, dd) |
| 6 | 2 | NMR DMSO-d6 (500 MHz): 7.17 (1H, ddd), 7.30-7.40 (3H, m), 7.49 (1H, dd), 8.21 (1H, dd) |
| 7 | 2 | NMR DMSO-d6 (500 MHz): 7.18 (1H, dd), 7.23-7.29 (2H, m), 7.29-7.37 (2H, m), 8.16 (1H, dd) |
| 8 | 2 | NMR DMSO-d6 (500 MHz): 7.06 (1H, dd), 7.35-7.41 (2H, m), 7.44-7.51 (1H, m), 7.67-7.72 (1H, m), 8.16 (1H, dd) |
| 9 | 2 | ESI+: 362.0, 364.1 |
| 10 | 2 | NMR DMSO-d6 (500 MHz): 7.17-7.28 (2H, m), 7.46-7.54 (1H, m), 7.54-7.62 (1H, m), 8.17 (1H, d) |
| 11 | 2 | NMR DMSO-d6 (500 MHz): 7.06 (1H, dd), 7.28-7.44 (3H, m), 7.45-7.54 (1H, m), 7.99 (1H, d) |
| 12 | 2 | ESI+: 549.8 |
| 13 | 2 | ESI+: 362.6 |
| 14 | 2 | — |
| 15 | 2 | NMR $CDCl_3$ (400 MHz): 6.98 (2H, d), 7.15-7.19 (1H, m), 7.33-7.39 (2H, m), 7.74 (1H, dd) |
| 16 | 16 | ESI+: 467.3 |
| 17 | 16 | NMR $CDCl_3$ (400 MHz): 1.46 (9H, s), 3.55-3.56 (2H, m), 4.39-4.42 (2H, m), 4.99 (1H, br s), 6.62 (1H, s), 6.81 (1H, dd), 7.45 (1H, t), 8.05 (1H, dd), 8.19 (1H, d) |
| 18 | 16 | NMR $CDCl_3$ (400 MHz): 1.48 (9H, s), 1.90-1.96 (2H, m), 2.14-2.17 (2H, m), 2.88-2.94 (2H, m), 4.22-4.33 (3H, m), 7.31-7.35 (1H, m), 7.46 (1H, s), 7.48 (1H, s), 7.83 (1H, dd) |
| 19 | 16 | NMR $CDCl_3$ (400 MHz): 1.60-1.77 (3H, m), 1.98-2.15 (3H, m), 3.68-3.74 (1H, m), 3.99-4.03 (1H, m), 5.42-5.45 (1H, m), 7.34 (1H, t), 7.53 (1H, s), 7.66 (1H, s), 7.84 (1H, dd) |
| 20-1 | 20 | NMR $CDCl_3$ (400 MHz): 1.00 (9H, s), 1.60-1.69 (2H, m), 3.37-3.43 (1H, m), 3.95-4.20 (4H, m), 4.81 (1H, br s), 6.43 (1H, br s), 7.37-7.46 (6H, m), 7.64-7.76 (4H, m) |

TABLE 5-continued

| PEx | PSyn | DAT |
|---|---|---|
| 20-2 | 20 | NMR $CDCl_3$ (400 MHz): 1.09 (9H, s), 1.61-1.70 (1H, m), 1.75-1.84 (1H, m), 3.47-3.54 (1H, m), 3.69-3.80 (2H, m), 4.01-4.07 (2H, m), 4.84-4.87 (1H, m), 6.00-6.01 (1H, m), 7.37-7.46 (6H, m), 7.67-7.74 (4H, m) |
| 21 | 21 | ESI+: 143.1 |
| 22 | 21 | ESI+: 143.1 |
| 23 | 23 | NMR DMSO-d6 (500 MHz): 1.56-1.81 (6H, m), 1.88-2.01 (2H, m), 5.12-5.17 (1H, m), 7.51 (1H, d), 8.18 (1H, dd) |
| 24 | 23 | ESI+: 326.2 |
| 25 | 23 | NMR DMSO-d6 (500 MHz): 1.57-1.72 (1H, m), 1.76-1.89 (1H, m), 2.01-2.14 (2H, m), 2.41-2.51 (2H, m), 4.90-5.02 (1H, m), 7.31 (1H, d), 8.17 (1H, d) |
| 26 | 23 | — |
| 27 | 23 | NMR CDCl3 (400 MHz): 0.91-0.94 (4H, m), 1.45 (9H, s), 3.51-3.55 (2H, m), 3.93-4.02 (3H, m), 4.99 (1H, br s), 6.73-6.74 (1H, m), 6.81 (1H, d), 6.91 (1H, dd), 7.26-7.30 (1H, m), 7.51 (1H, d), 7.94 (1H, d) |
| 28 | 23 | NMR CDCl3 (400 MHz): 1.46 (9H, s), 1.74-1.81 (1H, m), 1.96-2.05 (1H, m), 2.27-2.32 (2H, m), 2.51-2.57 (2H, m), 3.54-3.55 (2H, m), 4.38-4.41 (2H, m), 4.81-4.88 (1H, m), 5.02 (1H, br s), 6.59 (1H, s), 6.80 (1H, dd), 6.97 (1H, d), 8.01 (1H, d), 8.15 (1H, d) |
| 29 | 23 | NMR CDCl3 (400 MHz): 0.94-0.97 (4H, m), 1.47 (9H, s), 3.55-3.56 (2H, m), 3.97-4.00 (1H, m), 4.40 (2H, t), 5.02 (1H, br s), 6.60 (1H, s), 6.80 (1H, dd), 7.58 (1H, d), 8.08 (1H, d), 8.16 (1H, d) |
| 30 | 23 | NMR CDCl3 (400 MHz): 1.48 (9H, s), 1.72-1.79 (1H, m), 1.91-1.96 (3H, m), 2.14-2.18 (2H, m), 2.25-2.30 (2H, m), 2.48-2.52 (2H, m), 2.90-2.92 (2H, m), 4.25-4.28 (3H, m), 4.78-4.82 (1H, m), 6.89 (1H, d), 7.41 (1H, s), 7.44 (1H, s), 7.79 (1H, d) |
| 31 | 23 | NMR $CDCl_3$ (400 MHz): 0.86-0.93 (4H, m), 1.47 (9H, s), 1.90-1.97 (2H, m), 2.13-2.17 (2H, m), 2.88-2.94 (2H, m), 3.91-3.94 (1H, m), 4.13-4.28 (3H, m), 7.40 (1H, s), 7.43 (1H, s), 7.48 (1H, d), 7.84 (1H, d) |
| 32 | 23 | NMR $CDCl_3$ (400 MHz): 1.59-1.81 (4H, m), 1.90-2.32 (6H, m), 2.48-2.55 (2H, m), 3.67-3.73 (1H, m), 3.99-4.03 (1H, m), 4.76-4.83 (1H, m), 5.43 (1H, dd), 6.89 (1H, d), 7.49 (1H, s), 7.60 (1H, s), 7.80 (1H, d) |
| 33 | 33 | ESI+: 221.2 |
| 34 | 34 | ESI+: 334.3 |
| 35 | 34 | ESI+: 334.3 |
| 36 | 36 | ESI+: 244.2 |
| 37 | 36 | ESI+: 244.2 |
| 38 | 38 | NMR DMSO-d6 (500 MHz): 7.33-7.41 (2H, m), 7.41-7.47 (1H, m), 7.51-7.62 (2H, m), 8.51 (1H, dd) |
| 39 | 39 | ESI+: 543.4 |
| 40 | 39 | ESI+: 496.3 |
| 41 | 39 | ESI+: 488.3 |
| 42 | 39 | ESI+: 460.3 |
| 43 | 39 | ESI+: 543.4 |
| 44 | 39 | ESI+: 464.4 |
| 45 | 39 | ESI+: 552.3, 554.3 |
| 46 | 39 | ESI+: 536.4 |
| 47 | 39 | ESI+: 514.3 |
| 48 | 39 | ESI+: 538.2 |
| 49 | 39 | ESI+: 552.2, 554.2 |
| 50 | 39 | ESI+: 554.3, 556.2 |
| 51 | 39 | ESI+: 484.2 |
| 52 | 39 | ESI+: 415.3 |
| 53 | 39 | ESI+: 488.3 |
| 54 | 39 | ESI+: 520.3, 522.3 |
| 55 | 39 | ESI+: 512.4 |
| 56 | 39 | ESI+: 520.3 |
| 57 | 39 | ESI+: 554.3, 556.3 |
| 58 | 39 | ESI+: 543.4 |
| 59 | 39 | ESI+: 556.3 |
| 60 | 60 | ESI+: 508.1 |
| 61 | 39 | ESI+: 498.3 |
| 62 | 39 | ESI+: 504.2, 506.2 |
| 63 | 39 | ESI+: 538.2 |
| 64 | 39 | ESI+: 538.2 |
| 65 | 39 | ESI+: 554.3 |
| 66 | 39 | ESI+: 497.2 |
| 67 | 39 | ESI+: 532.0 |
| 68 | 39 | ESI+: 426.1 |
| 69 | 39 | ESI+: 424.3 |
| 70 | 39 | NMR $CDCl_3$ (400 MHz): 1.49 (9H, s), 3.03-3.06 (1H, m), 3.24-3.26 (4H, m), 3.84-3.90 (3H, m), 4.20 (1H, br s), 6.74 (1H, d), 7.05 (2H, d), 7.23-7.26 (1H, m), 7.41-7.45 (2H, m), 7.59 (1H, d) |
| 71 | 39 | ESI+: 442.2 |
| 72 | 39 | ESI+: 388.2 |
| 73 | 39 | NMR CDCl3 (400 MHz): 1.45-1.47 (9H, m), 2.94-3.03 (1H, m), 3.12-3.25 (3H, m), 3.29-3.37 (1H, m), 3.74-4.04 (3H, m), 4.16-4.29 (1H, m), 6.85-6.97 (2H, m), 7.10-7.18 (1H, m), 7.31-7.42 (3H, m) |
| 74 | 39 | ESI+: 442.3 |
| 75 | 75 | NMR CDCl3 (500 MHz): 1.38-1.57 (9H, m), 2.99-3.58 (5H, m), 3.80-4.08 (1H, m), 4.32-4.91 (1H, m), 7.51 (1H, d), 7.71 (1H, d), 9.59 (1H, br s) |
| 76 | 75 | ESI+: 536.2 |
| 77 | 75 | ESI+: 552.1 |
| 78 | 75 | NMR DMSO-d6 (500 MHz): 0.63-0.79 (2H, m), 0.82-0.92 (2H, m), 1.29-1.48 (9H, m), 2.79-3.26 (4H, m), 3.61 (1H, d), 3.64-3.76 (1H, m), 4.07-4.17 (1H, m), 4.45-4.65 (1H, m), 7.49-7.61 (1H, m), 8.03-8.17 (1H, m), 9.46 (1H, br s) |
| 79 | 75 | ESI+: 413.3 |
| 80 | 75 | NMR DMSO-d6 (500 MHz): 1.31-1.50 (9H, m); 2.79-3.42 (4H, m), 3.72-3.87 (2H, m), 4.52-4.80 (1H, m), 6.87 (1H, dd), 7.23-7.41 (3H, m), 7.42-7.51 (1H, m), 7.68 (1H, dd), 9.55 (1H, d) |
| 81 | 75 | ESI+: 518.2 |
| 82 | 75 | ESI+: 552.2 |
| 83 | 75 | ESI+: 510.3 |
| 84 | 75 | ESI+: 554.3 |
| 85 | 75 | ESI+: 502.3 |
| 86 | 75 | ESI -: 472.3 |
| 87 | 75 | ESI+: 536.2 |
| 88 | 75 | — |
| 89 | 75 | NMR $CDCl_3$ (400 MHz): 1.47-1.51 (9H, m), 3.13-3.54 (5H, m), 3.88-4.05 (1H, m), 4.43-4.71 (1H, m), 6.76 (1H, d), 7.05 (2H, d), 7.23-7.27 (1H, m), 7.40-7.45 (2H, m), 7.63 (1H, d), 9.63-9.66 (1H, m) |
| 90 | 75 | NMR $CDCl_3$ (400 MHz): 1.46-1.49 (9H, m), 2.90-3.34 (3H, m), 3.40-3.50 (1H, m), 3.56-3.69 (1H, m), 3.71-4.10 (1H, m), 4.42-4.71 (1H, m), 6.96 (2H, d), 7.11-7.18 (1H, m), 7.31-7.39 (2H, m), 7.40 (1H, dd), 9.63-9.66 (1H, m) |
| 91 | 91 | ESI+: 433.2 |
| 92 | 92 | ESI+: 499.2 |
| 93 | 92 | ESI+: 529.2 |
| 94 | 92 | ESI+: 545.3, 547.2 |
| 95 | 92 | ESI+: 475.4 |
| 96 | 92 | ESI+: 555.2 |
| 97 | 92 | ESI+: 454.3 |
| 98 | 92 | ESI+: 479.4 |
| 99 | 92 | ESI+: 545.3, 547.3 |
| 100 | 92 | ESI+: 503.3 |
| 101 | 92 | ESI+: 547.3 |
| 102 | 92 | ESI+: 489.3 |
| 103 | 92 | ESI+: 529.3 |
| 104 | 92 | ESI+: 538.9 |
| 105 | 92 | ESI+: 631.4 |
| 106 | 92 | NMR CDCl3 (400 MHz): 1.49 (9H, s), 2.44 (3H, s), 2.80-2.83 (1H, m), 2.92-3.02 (2H, m), 3.20-3.25 (4H, m), 3.92-4.16 (2H, m), 6.72 (1H, d), 7.04-7.06 (2H, m), 7.22-7.26 (1H, m), 7.40-7.44 (2H, m), 7.58 (1H, d) |
| 107 | 92 | NMR $CDCl_3$ (400 MHz): 1.47 (9H, s), 2.46 (3H, s), 2.77-3.37 (7H, m), 3.86-4.03 (1H, m), 4.13-4.29 (1H, m), 6.96 (2H, d), 7.10-7.17 (1H, m), 7.31-7.41 (3H, m) |
| 108 | 108 | ESI+: 617.2 |
| 109 | 108 | ESI+: 647.3 |
| 110 | 108 | ESI+: 663.3, 665.3 |
| 111 | 108 | ESI+: 593.3 |
| 112 | 108 | ESI+: 673.2 |
| 113 | 108 | NMR DMSO-d6 (500 MHz): 1.38 (9H, s), 2.91-3.49 (9H, m), 3.68-3.98 (1H, m), 4.28-4.62 (2H, m), 6.84 (1H, dd), 7.25-7.39 (3H, m), 7.42-7.53 (1H, m), 7.64-7.74 (1H, m) |
| 114 | 108 | ESI+: 663.3, 665.2 |
| 115 | 108 | ESI+: 621.2 |
| 116 | 108 | ESI+: 665.3 |
| 117 | 108 | ESI+: 607.3 |
| 118 | 108 | ESI+: 647.3 |
| 119 | 108 | — |

TABLE 5-continued

| PEx | PSyn | DAT |
|---|---|---|
| 120 | 108 | — |
| 121 | 108 | ESI+: 629.3 |
| 122 | 108 | NMR CDCl3 (400 MHz): 1.42 (9H, s), 2.86-3.58 (9H, m), 3.65-3.90 (1H, m), 4.43-4.60 (2H, m), 6.92-6.98 (2H, m), 7.10-7.17 (1H, m), 7.30-7.44 (3H, m) |
| 123 | 123 | ESI+: 613.2, 615.2 |
| 124 | 123 | ESI+: 629.3, 631.2, 633.3 |
| 125 | 125 | — |
| 126 | 125 | — |
| 127 | 127 | ESI+: 432.3, 434.3 |
| 128 | 127 | ESI+: 525.3 |
| 129 | 127 | ESI+: 471.3 |
| 130 | 127 | ESI+: 551.3 |
| 131 | 127 | ESI+: 475.3 |
| 132 | 127 | ESI+: 416.3 |
| 133 | 127 | ESI+: 390.3 |
| 134 | 127 | — |
| 135 | 127 | ESI+: 493.1 |
| 136 | 127 | ESI+: 376.3 |
| 137 | 127 | ESI+: 416.2 |
| 138 | 127 | ESI+: 416.2 |
| 139 | 127 | ESI+: 485.2 |
| 140 | 127 | ESI+: 525.2 |
| 141 | 127 | — |
| 142 | 127 | — |
| 143 | 127 | NMR $CDCl_3$ (400 MHz): 2.80-3.26 (10H, m), 3.38-3.53 (2H, m), 6.93-7.00 (2H, m), 7.10-7.18 (1H, m), 7.31-7.38 (2H, m), 7.41 (1H, dd) |
| 144 | 144 | ESI+: 446.3, 448.2 |
| 145 | 144 | ESI+: 430.3 |
| 146 | 144 | ESI+: 404.3 |
| 147 | 144 | ESI+: 390.3 |
| 148 | 144 | ESI+: 430.2 |
| 149 | 144 | ESI+: 430.2 |
| 150 | 150 | ESI+: 505.1, 507.1 |
| 151 | 150 | ESI+: 555.3, 557.3 |
| 152 | 150 | ESI+: 521.2, 523.2 |
| 153 | 150 | ESI+: 555.3, 557.2 |
| 154 | 150 | ESI+: 557.2 |
| 155 | 150 | ESI+: 448.2 |
| 156 | 150 | ESI+: 412.1, 414.1 |
| 157 | 150 | ESI+: 641.1 |
| 158 | 158 | ESI+: 524.2, 526.2 |
| 159 | 158 | ESI+: 508.3 |
| 160 | 158 | ESI+: 482.3 |
| 161 | 158 | ESI+: 468.3 |
| 162 | 158 | ESI+: 508.1 |
| 163 | 158 | ESI+: 508.2 |
| 164 | 164 | ESI+: 575.3, 577.3 |
| 165 | 164 | ESI+: 559.3 |
| 166 | 164 | ESI+: 533.4 |
| 167 | 164 | ESI+: 519.4 |
| 168 | 164 | ESI+: 559.2 |
| 169 | 171 | ESI+: 577.2 |
| 170 | 164 | ESI+: 559.3 |
| 171 | 171 | ESI+: 584.3 |
| 172 | 171 | ESI+: 541.1, 543.1 |
| 173 | 173 | ESI+: 546.2 |
| 174 | 174 | ESI+: 442.3 |
| 175 | 175 | ESI+: 571.3 |
| 176 | 175 | ESI+: 553.3 |
| 177 | 175 | ESI+: 517.3 |
| 178 | 175 | ESI+: 571.5 |
| 179 | 179 | ESI+: 485.9 |
| 180 | 180 | — |
| 181 | 181 | ESI+: 432.3 |
| 182 | 181 | ESI+: 423.3 |
| 183 | 181 | ESI+: 441.4 |
| 184 | 181 | ESI+: 387.3 |
| 185 | 181 | ESI+: 441.4 |
| 186 | 186 | ESI+: 554.3 |
| 187 | 186 | ESI+: 576.4 |

TABLE 5-continued

| PEx | PSyn | DAT |
|---|---|---|
| 188 | 186 | NMR DMSO-d6 (400 MHz): 0.97-1.00 (1H, m), 1.37 (9H, s), 1.52-1.55 (1H, m), 1.64-1.70 (2H, m), 1.94-1.98 (1H, m), 2.61 (1H, t), 2.88-2.91 (1H, m), 2.97-3.12 (4H, m), 3.20 (3H, s), 3.25-3.29 (2H, m), 3.39-3.45 (2H, m), 6.79 (1H, m), 7.27-7.37 (3H, m), 7.43-7.48 (1H, m), 7.94-7.96 (1H, m) |
| 189 | 186 | ESI+: 523.4 |
| 190 | 186 | ESI+: 541.4 |
| 191 | 186 | ESI+: 487.3 |
| 192 | 186 | ESI+: 541.5 |
| 193 | 193 | ESI+: 545.3, 547.3 |
| 194 | 193 | ESI+: 529.3 |
| 195 | 193 | ESI+: 503.4 |
| 196 | 193 | ESI+: 489.3 |
| 197 | 193 | ESI+: 529.3 |
| 198 | 193 | ESI+: 547.3 |
| 199 | 193 | ESI+: 511.2, 513.2 |
| 200 | 193 | ESI+: 529.3 |
| 201 | 201 | ESI+: 509.1 |
| 202 | 201 | ESI+: 539.3 |
| 203 | 201 | ESI+: 485.3 |
| 204 | 201 | ESI+: 489.3 |
| 205 | 201 | ESI+: 513.3 |
| 206 | 201 | ESI+: 499.3 |
| 207 | 201 | ESI+: 539.2 |
| 208 | 201 | — |
| 209 | 201 | NMR $CDCl_3$: (400 MHz): 2.36-2.52 (4H, m), 2.61-2.70 (1H, m), 2.82-3.36 (8H, m), 3.59-3.69 (2H, m), 6.94-7.01 (2H, m), 7.11-7.17 (1H, m), 7.31-7.44 (3H, m) |
| 210 | 210 | ESI+: 513.3 |
| 211 | 211 | ESI+: 499.3 |
| 212 | 211 | ESI+: 515.3 |
| 213 | 211 | ESI+: 527.3 |
| 214 | 214 | NMR $CDCl_3$ (400 MHz): 1.70-1.82 (1H, m), 1.89-2.00 (1H, m), 2.20-2.33 (2H, m), 2.48-2.56 (2H m), 4.77-4.84 (1H, m), 6.91 (1H, d), 7.58 (2H, s), 7.81 (1H, d) |
| 215 | 215 | ESI+: 507.1 |
| 216 | 216 | ESI+: 555.3 |
| 217 | 216 | NMR CDCl3 (400 MHz): 0.91-0.94 (4H, m), 1.45 (9H, s), 2.96 (3H, s), 3.58 (2H, br s), 3.93-3.97 (1H, m), 4.07 (2H, br s), 6.73-6.74 (1H, m), 6.80 (1H, d), 6.91 (1H, dd), 7.26-7.29 (1H, m), 7.51 (1H, d), 7.93 (1H, d) |
| 218 | 216 | NMR CDCl3 (400 MHz): 1.46 (9H, s), 1.76-1.81 (1H, m), 1.96-1.98 (1H, m), 2.27-2.32 (2H, m), 2.53-2.55 (2H, m), 2.95 (3H, s), 3.60-3.62 (2H, m), 4.39-4.46 (2H, m), 4.82-4.86 (1H, m), 6.59 (1H, d), 6.79-6.80 (1H, m), 6.97 (1H, d), 8.01 (1H, d), 8.15 (1H, d) |
| 219 | 216 | NMR CDCl3 (400 MHz): 0.92-0.96 (4H, m), 1.46 (9H, s), 2.94 (3H, s), 3.61 (2H, br s), 3.96-3.97 (1H, m), 4.46 (2H, br s), 6.58 (1H, s), 6.78 (1H, d), 7.56 (1H, d), 8.06 (1H, d), 8.15 (1H, d) |
| 220 | 216 | ESI+: 537.3 |
| 221 | 216 | ESI+: 555.5 |
| 222 | 222 | ESI+: 301.1 |
| 223 | 222 | ESI+: 301.2, 303.2, 305.2 |
| 224 | 222 | ESI+: 274.2, 276.1 |
| 225 | 225 | ESI+: 233.3 |
| 226 | 225 | ESI+: 233.3 |
| 227 | 225 | ESI+: 206.1 |
| 228 | 228 | ESI+: 205.3 |
| 229 | 228 | ESI+: 205.1 |
| 230 | 228 | ESI+: 192.0 |
| 231 | 231 | ESI+: 565.3 |
| 232 | 232 | ESI+: 513.4 |
| 233 | 232 | ESI+: 466.3 |
| 234 | 232 | ESI+: 458.3 |
| 235 | 232 | ESI+: 430.3 |
| 236 | 232 | ESI+: 491.4 |
| 237 | 232 | ESI+: 434.4 |
| 238 | 232 | ESI+: 500.4, 502.3 |
| 239 | 232 | ESI+: 484.3 |
| 240 | 232 | ESI+: 484.3 |
| 241 | 232 | ESI+: 509.4 |
| 242 | 232 | ESI+: 500.3, 502.2 |
| 243 | 232 | ESI+: 525.2, 527.1 |
| 244 | 232 | ESI+: 455.4 |
| 245 | 232 | ESI+: 535.3 |

TABLE 5-continued

| PEx | PSyn | DAT |
|---|---|---|
| 246 | 232 | ESI+: 524.4 |
| 247 | 232 | ESI+: 459.4 |
| 248 | 232 | ESI+: 499.4 |
| 249 | 232 | ESI+: 491.3, 493.2 |
| 250 | 232 | ESI+: 473.4 |
| 251 | 232 | ESI+: 468.4 |
| 252 | 232 | ESI+: 525.3, 527.2 |
| 253 | 232 | ESI+: 483.3 |
| 254 | 232 | ESI+: 502.3 |
| 255 | 232 | ESI+: 515.4, 517.3 |
| 256 | 232 | ESI+: 513.4 |
| 257 | 232 | ESI+: 527.2 |
| 258 | 232 | ESI+: 485.3 |
| 259 | 232 | ESI+: 459.3 |
| 260 | 232 | ESI+: 475.2, 477.2 |
| 261 | 232 | ESI+: 499.3 |
| 262 | 232 | ESI+: 517.3 |
| 263 | 232 | ESI+: 481.2, 483.2 |
| 264 | 232 | ESI+: 499.3 |
| 265 | 232 | ESI+: 469.3 |
| 266 | 232 | ESI+: 509.3 |
| 267 | 232 | ESI+: 502.3 |
| 268 | 232 | ESI+: 497.4 |
| 269 | 232 | ESI+: 481.0 |
| 270 | 232 | ESI+: 467.1 |
| 271 | 232 | ESI+: 611.0 |
| 272 | 232 | ESI+: 480.2 |
| 273 | 232 | ESI+: 438.3 |
| 274 | 232 | ESI+: 542.2 |
| 275 | 232 | ESI+: 475.3 |
| 276 | 232 | ESI+: 489.4 |
| 277 | 232 | NMR CDCl3 (400 MHz): 1.45 (9H, s), 1.60-2.05 (2H, m), 2.19-2.24 (2H, m), 2.38-2.42 (2H, m), 3.22 (2H, br s), 3.55-3.56 (2H, m), 4.39-4.41 (2H, m), 4.60-4.63 (1H, m), 5.03 (1H, br s), 6.62 (1H, s), 6.76-6.85 (3H, m), 8.21 (1H, d) |
| 278 | 232 | NMR CDCl3 (400 MHz): 0.77-0.82 (4H, m), 1.45 (9H, s), 3.26 (2H, br s), 3.55-3.56 (2H, m), 3.80-3.83 (1H, m), 4.40 (2H, t), 5.03 (1H, br s), 6.62 (1H, s), 6.77 (1H, dd), 6.90 (1H, d), 7.29 (1H, d), 8.21 (1H, d) |
| 279 | 232 | NMR CDCl3 (400 MHz): 1.45 (9H, s), 1.61-1.86 (2H, m), 2.18-2.23 (2H, m), 2.37-2.42 (2H, m), 2.95 (3H, s), 3.60-3.62 (4H, m), 4.45 (2H, br s), 4.59-4.63 (1H, m), 6.62 (1H, d), 6.76-6.85 (3H, m), 8.21 (1H, d) |
| 280 | 232 | NMR $CDCl_3$ (400 MHz): 0.76-0.81 (4H, m), 1.46 (9H, s), 2.95 (3H, s), 3.22 (2H, br s), 3.60-3.63 (2H, m), 3.80-3.82 (1H, m), 4.45 (2H, br s), 6.61 (1H, s), 6.75 (1H, d), 6.90 (1H, d), 7.26-7.29 (1H, m), 8.21 (1H, d) |
| 281 | 232 | NMR $CDCl_3$ (400 MHz): 1.48 (9H, s), 1.58-1.64 (1H, m), 1.79-2.00 (3H, m), 2.17-2.22 (4H, m), 2.36-2.42 (2H, m), 2.89-2.94 (2H, m), 3.44 (2H, br s), 4.11-4.34 (3H, m), 4.54-4.61 (1H, m), 6.76 (1H, d), 6.82 (1H, d), 7.37 (1H, s), 7.45 (1H, s) |
| 282 | 232 | NMR $CDCl_3$: (400 MHz): 0.74-0.90 (4H, m), 1.48 (9H, s), 1.92-1.99 (2H, m), 2.16-2.19 (2H, m), 2.90-2.93 (2H, m), 3.46 (2H, br s), 3.77-3.81 (1H, m), 4.15-4.33 (3H, m), 6.88 (1H, d), 7.24 (1H, d), 7.37 (1H, s), 7.45 (1H, s) |
| 283 | 232 | NMR $CDCl_3$ (400 MHz): 1.44 (9H, s), 1.57-1.68 (1H, m), 1.79-1.87 (1H, m), 2.05-2.11 (2H, m), 2.15-2.25 (2H, m), 2.36-2.43 (2H, m), 3.11-3.12 (2H, m), 3.47 (2H, br s), 4.24 (2H, t), 4.54-4.61 (1H, m), 4.78 (1H, br s), 6.75-6.83 (2H, m), 7.36 (1H, s), 7.44 (1H, s) |
| 284 | 232 | ESI+: 493.5 |
| 285 | 232 | ESI+: 507.4 |
| 286 | 232 | ESI+: 577.1 |
| 287 | 232 | ESI -: 509.0 |
| 288 | 232 | ESI+: 525.3 |
| 289 | 232 | ESI+: 457.4 |
| 290 | 232 | NMR CDCl3 (400 MHz): 2.36-3.47 (14H, m), 3.76-4.06 (1H, m), 4.19-4.52 (2H, m), 6.33 (1H, dd), 6.93 (2H, d), 6.99-7.07 (1H, m), 7.23-7.33 (2H, m) |
| 291 | 232 | ESI+: 511.5 |
| 292 | 232 | ESI+: 525.7 |
| 293 | 293 | ESI+: 471.3 |
| 294 | 294 | ESI+: 685.5 |
| 295 | 294 | ESI+: 639.3 |
| 296 | 294 | ESI+: 646.5 |
| 297 | 294 | ESI+: 610.4 |

TABLE 5-continued

| PEx | PSyn | DAT |
|---|---|---|
| 298 | 294 | ESI+: 616.4 |
| 299 | 294 | ESI+: 588.5 |
| 300 | 294 | ESI+: 660.4 |
| 301 | 294 | ESI+: 671.4 |
| 302 | 294 | ESI+: 592.5 |
| 303 | 294 | ESI+: 658.3 |
| 304 | 294 | ESI+: 664.4 |
| 305 | 294 | ESI+: 642.3 |
| 306 | 294 | ESI+: 680.3, 682.3 |
| 307 | 294 | ESI+: 682.4 |
| 308 | 294 | ESI+: 672.2 |
| 309 | 294 | ESI+: 656.3 |
| 310 | 294 | ESI+: 667.4 |
| 311 | 294 | ESI+: 683.3, 685.2 |
| 312 | 294 | ESI+: 697.2, 699.2 |
| 313 | 294 | ESI+: 674.4 |
| 314 | 294 | ESI+: 627.4 |
| 315 | 294 | ESI+: 707.4 |
| 316 | 294 | ESI+: 696.5 |
| 317 | 294 | ESI+: 704.4 |
| 318 | 294 | ESI+: 691.4 |
| 319 | 294 | ESI+: 692.5 |
| 320 | 294 | ESI+: 631.4 |
| 321 | 294 | ESI+: 686.3 |
| 322 | 294 | ESI+: 617.4 |
| 323 | 294 | ESI+: 695.3 |
| 324 | 294 | ESI+: 671.4 |
| 325 | 294 | ESI+: 657.4 |
| 326 | 294 | ESI+: 664.3, 666.3 |
| 327 | 294 | ESI+: 649.3, 651.2 |
| 328 | 294 | ESI+: 663.3, 665.3 |
| 329 | 294 | ESI+: 692.4 |
| 330 | 294 | ESI+: 645.5 |
| 331 | 294 | ESI+: 646.5 |
| 332 | 294 | ESI+: 663.4 |
| 333 | 294 | ESI+: 662.4 |
| 334 | 294 | ESI+: 697.3, 699.3 |
| 335 | 294 | ESI+: 655.4 |
| 336 | 294 | ESI+: 674.4 |
| 337 | 294 | ESI+: 687.3, 689.3 |
| 338 | 294 | ESI+: 673.3, 675.3 |
| 339 | 294 | ESI+: 685.5 |
| 340 | 294 | ESI+: 699.3 |
| 341 | 294 | ESI+: 698.2, 700.2 |
| 342 | 294 | ESI+: 643.4 |
| 343 | 294 | ESI+: 629.4 |
| 344 | 294 | ESI+: 644.4 |
| 345 | 294 | ESI+: 657.4 |
| 346 | 294 | ESI+: 631.4 |
| 347 | 294 | ESI+: 700.3, 702.3 |
| 348 | 294 | ESI+: 684.3 |
| 349 | 294 | ESI+: 617.4 |
| 350 | 294 | ESI+: 647.3, 649.2 |
| 351 | 294 | ESI+: 633.2, 635.2 |
| 352 | 294 | ESI+: 648.2, 650.2 |
| 353 | 294 | ESI+: 671.4 |
| 354 | 294 | ESI+: 672.4 |
| 355 | 294 | ESI+: 675.4 |
| 356 | 294 | ESI+: 657.4 |
| 357 | 294 | ESI+: 671.4 |
| 358 | 294 | ESI+: 672.4 |
| 359 | 294 | ESI+: 653.4, 655.3 |
| 360 | 294 | ESI+: 639.3, 641.4 |
| 361 | 294 | ESI+: 654.3, 656.3 |
| 362 | 294 | ESI+: 684.4 |
| 363 | 294 | ESI+: 641.4 |
| 364 | 294 | ESI+: 642.4 |
| 365 | 294 | ESI+: 681.4 |
| 366 | 294 | ESI+: 682.3 |
| 367 | 294 | ESI+: 657.4 |
| 368 | 294 | ESI+: 674.4 |
| 369 | 294 | ESI+: 669.5 |
| 370 | 294 | ESI+: 670.5 |
| 371 | 294 | ESI+: 654.0 |
| 372 | 294 | ESI+: 653.1 |
| 373 | 294 | ESI+: 639.3 |
| 374 | 294 | ESI+: 769.0 |
| 375 | 294 | ESI+: 652.2 |

TABLE 5-continued
| PEx | PSyn | DAT |
|---|---|---|
| 376 | 294 | ESI+: 610.1 |
| 377 | 294 | ESI+: 712.7 |
| 378 | 294 | ESI+: 648.4 |
| 379 | 294 | ESI+: 662.3 |
| 380 | 294 | ESI+: 663.2 |
| 381 | 294 | ESI+: 649.4 |
| 382 | 294 | ESI+: 677.5 |
| 383 | 294 | ESI+: 663.3 |
| 384 | 294 | ESI+: 676.4 |
| 385 | 294 | ESI+: 639.5 |
| 386 | 294 | ESI+: 650.3 |
| 387 | 294 | ESI+: 627.4 |
| 388 | 294 | ESI+: 666.3 |
| 389 | 294 | ESI+: 680.3 |
| 390 | 294 | ESI+: 772.4 |
| 391 | 294 | ESI+: 683.2 |
TABLE 5-continued
| PEx | PSyn | DAT |
|---|---|---|
| 392 | 294 | ESI+: 697.4 |
| 393 | 294 | ESI+: 640.4 |
| 394 | 294 | ESI+: 684.4 |
| 395 | 294 | ESI+: 630.4 |
| 396 | 294 | ESI+: 629.3 |
| 397 | 294 | ESI+: 632.3 |
| 398 | 294 | ESI+: 617.4 |
| 399 | 294 | ESI+: 698.6 |
| 400 | 294 | ESI+: 631.6 |
| 401 | 294 | ESI+: 683.5 |
| 402 | 294 | ESI+: 697.5 |
| 403 | 403 | ESI+: 673.1 |
| 404 | 404 | ESI+: 650.3 |
| 405 | 405 | ESI+: 664.3 |
TABLE 6
| Ex | Str |
|---|---|
| 1 | 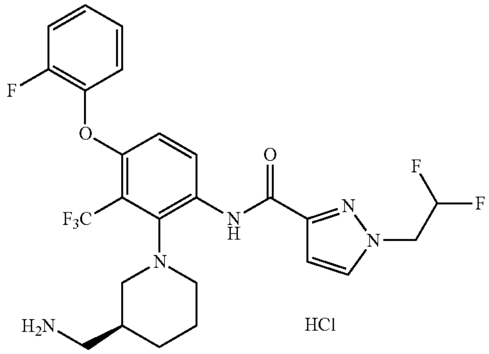 [SMILES: NC[C@@H]1CCCN(c2c(NC(=O)c3ccn(CC(F)F)n3)ccc(Oc3ccccc3F)c2C(F)(F)F)C1 ; Cl] |
| 2 | 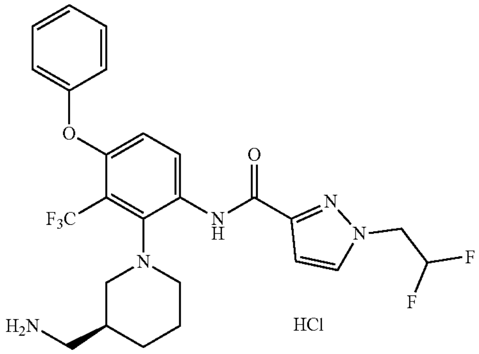 [SMILES: NC[C@@H]1CCCN(c2c(NC(=O)c3ccn(CC(F)F)n3)ccc(Oc3ccccc3)c2C(F)(F)F)C1 ; Cl] |
| 3 | 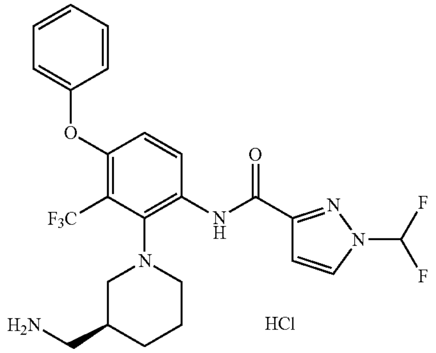 [SMILES: NC[C@@H]1CCCN(c2c(NC(=O)c3ccn(C(F)F)n3)ccc(Oc3ccccc3)c2C(F)(F)F)C1 ; Cl] |

TABLE 6-continued
| Ex | Str |
| --- | --- |
| 4 | 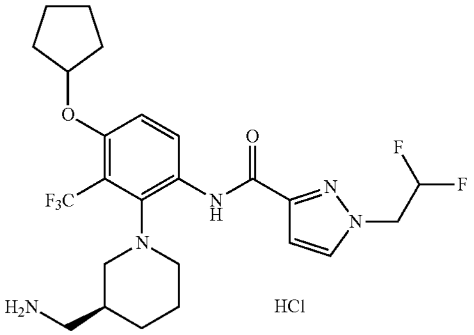 [SMILES: NC[C@@H]1CCCN(c2c(NC(=O)c3ccn(CC(F)F)n3)ccc(OC3CCCC3)c2C(F)(F)F)C1 ; Cl] HCl |
| 5 | 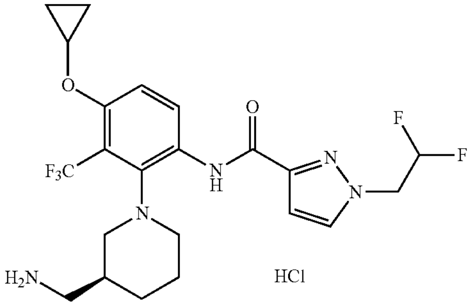 [SMILES: NC[C@@H]1CCCN(c2c(NC(=O)c3ccn(CC(F)F)n3)ccc(OC3CC3)c2C(F)(F)F)C1 ; Cl] HCl |
| 6 | 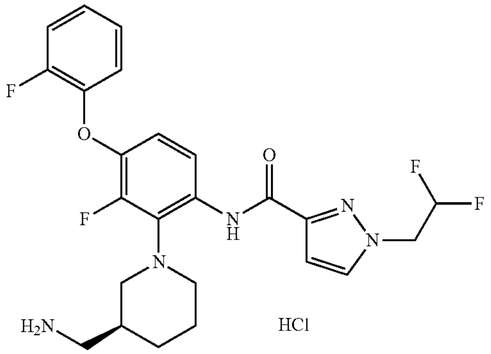 [SMILES: NC[C@@H]1CCCN(c2c(NC(=O)c3ccn(CC(F)F)n3)ccc(Oc3ccccc3F)c2F)C1 ; Cl] HCl |
| 7 | 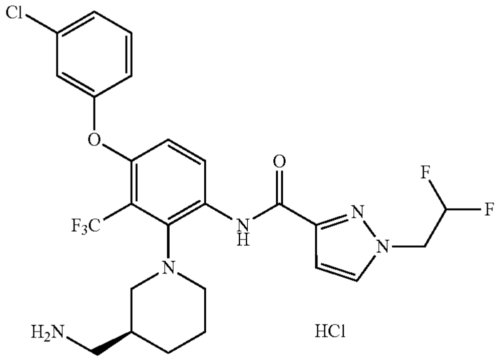 [SMILES: NC[C@@H]1CCCN(c2c(NC(=O)c3ccn(CC(F)F)n3)ccc(Oc3cccc(Cl)c3)c2C(F)(F)F)C1 ; Cl] HCl |

TABLE 6-continued
| Ex | Str |
|---|---|
| 8 | 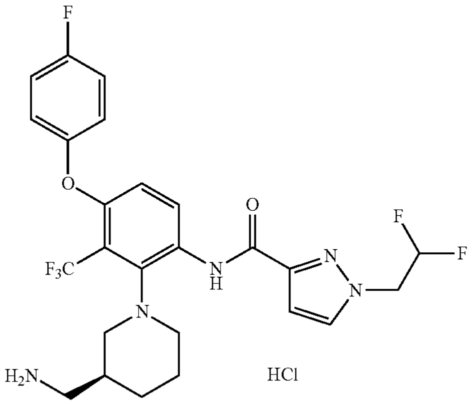 [SMILES: NC[C@@H]1CCCN(c2c(NC(=O)c3ccn(CC(F)F)n3)ccc(Oc3ccc(F)cc3)c2C(F)(F)F)C1 ; Cl] HCl |
| 9 | 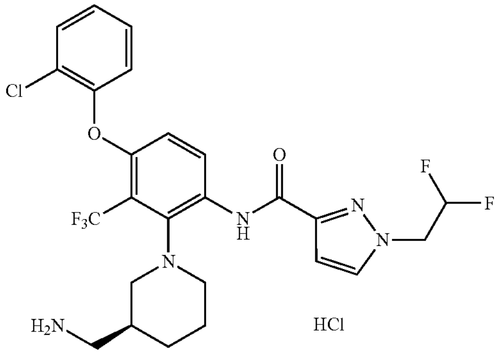 [SMILES: NC[C@@H]1CCCN(c2c(NC(=O)c3ccn(CC(F)F)n3)ccc(Oc3ccccc3Cl)c2C(F)(F)F)C1 ; Cl] HCl |
| 10 | 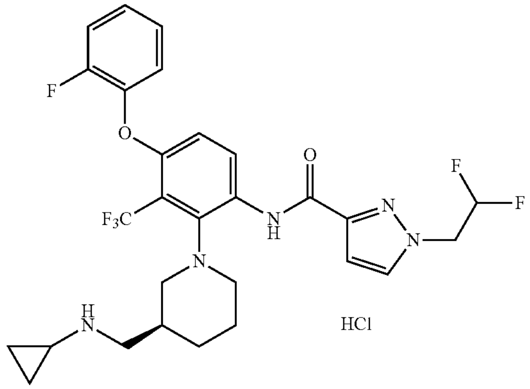 [SMILES: O=C(Nc1ccc(Oc2ccccc2F)c(C(F)(F)F)c1N1CCC[C@@H](CNC2CC2)C1)c1ccn(CC(F)F)n1 ; Cl] HCl |
| 11 | 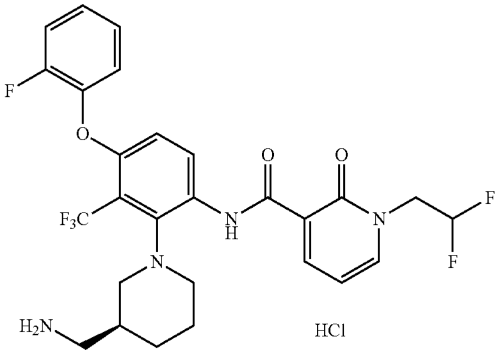 [SMILES: NC[C@@H]1CCCN(c2c(NC(=O)c3cccn(CC(F)F)c3=O)ccc(Oc3ccccc3F)c2C(F)(F)F)C1 ; Cl] HCl |

TABLE 6-continued
| Ex | Str |
| --- | --- |
| 12 | 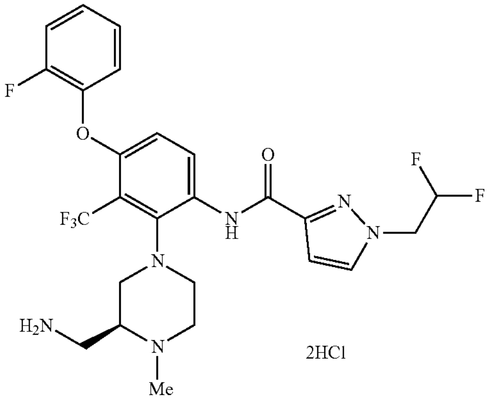 [SMILES: CN1CCN(c2c(NC(=O)c3ccn(CC(F)F)n3)ccc(Oc3ccccc3F)c2C(F)(F)F)C[C@@H]1CN] 2HCl |
| 13 | 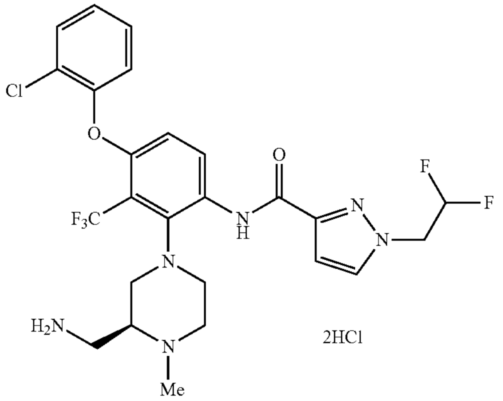 [SMILES: CN1CCN(c2c(NC(=O)c3ccn(CC(F)F)n3)ccc(Oc3ccccc3Cl)c2C(F)(F)F)C[C@@H]1CN] 2HCl |
| 14 | 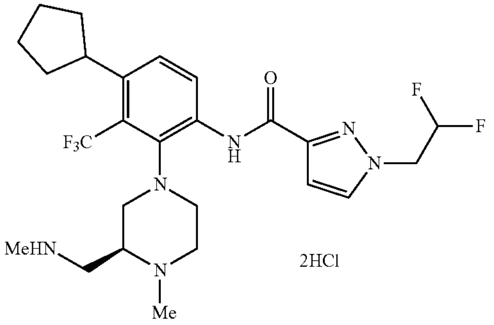 [SMILES: CNC[C@H]1CN(c2c(NC(=O)c3ccn(CC(F)F)n3)ccc(C3CCCC3)c2C(F)(F)F)CCN1C] 2HCl |
| 15 | 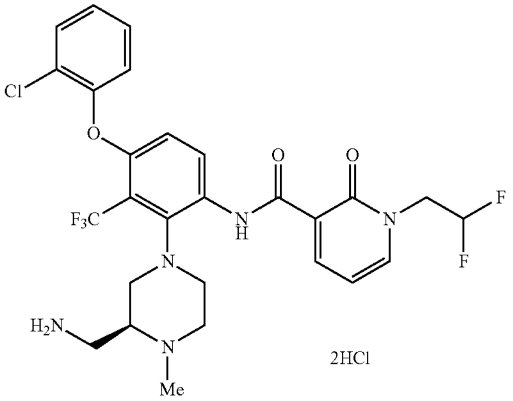 [SMILES: CN1CCN(c2c(NC(=O)c3cccn(CC(F)F)c3=O)ccc(Oc3ccccc3Cl)c2C(F)(F)F)C[C@@H]1CN] 2HCl |

TABLE 6-continued
| Ex | Str |
|---|---|
| 16 | 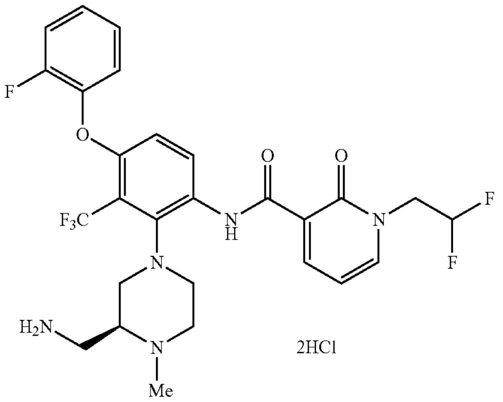 [SMILES: CN1CCN(c2c(NC(=O)c3cccn(CC(F)F)c3=O)ccc(Oc3ccccc3F)c2C(F)(F)F)C[C@@H]1CN] 2HCl |
| 17 | 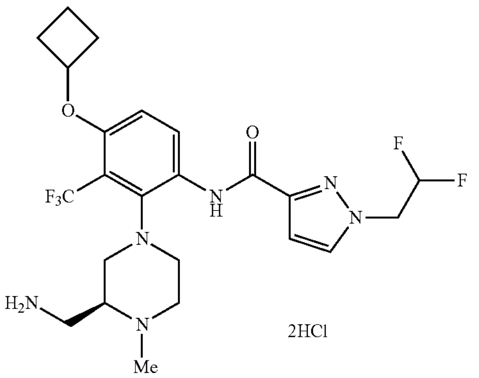 [SMILES: CN1CCN(c2c(NC(=O)c3ccn(CC(F)F)n3)ccc(OC3CCC3)c2C(F)(F)F)C[C@@H]1CN] 2HCl |
| 18 | 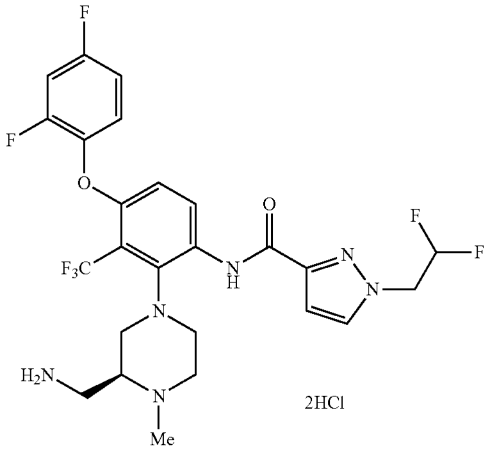 [SMILES: CN1CCN(c2c(NC(=O)c3ccn(CC(F)F)n3)ccc(Oc3ccc(F)cc3F)c2C(F)(F)F)C[C@@H]1CN] 2HCl |

TABLE 6-continued
| Ex | Str |
|---|---|
| 19 | 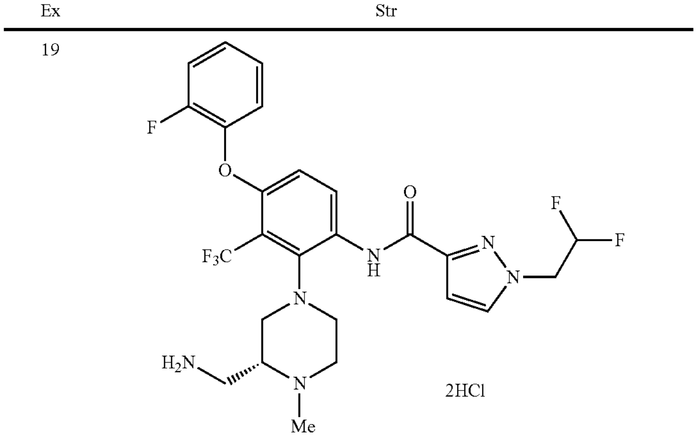 2HCl |
| 20 | 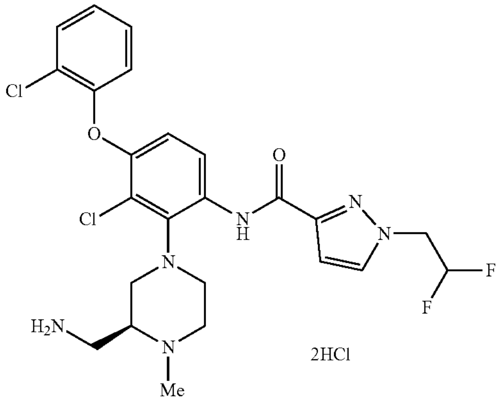 [SMILES: CN1CCN(c2c(NC(=O)c3ccn(CC(F)F)n3)ccc(Oc3ccccc3Cl)c2Cl)C[C@@H]1CN] 2HCl |
| 21 | 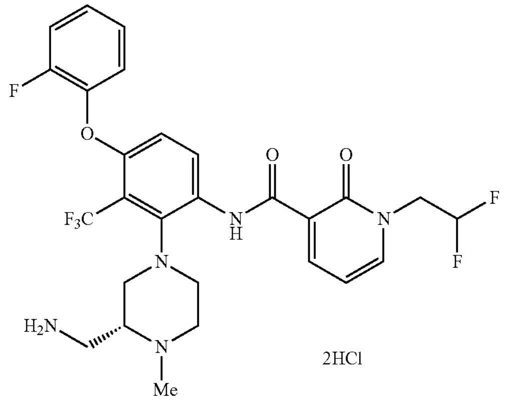 [SMILES: CN1CCN(c2c(NC(=O)c3cccn(CC(F)F)c3=O)ccc(Oc3ccccc3F)c2C(F)(F)F)C[C@H]1CN] 2HCl |
| 22 | 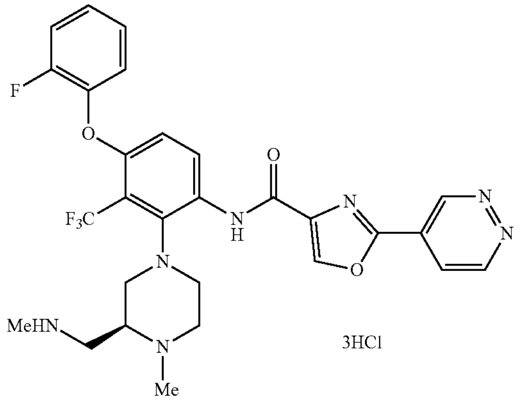 [SMILES: CNC[C@H]1CN(c2c(NC(=O)c3coc(-c4ccnnc4)n3)ccc(Oc3ccccc3F)c2C(F)(F)F)CCN1C] 3HCl |

TABLE 6-continued
| Ex | Str |
|---|---|
| 23 | 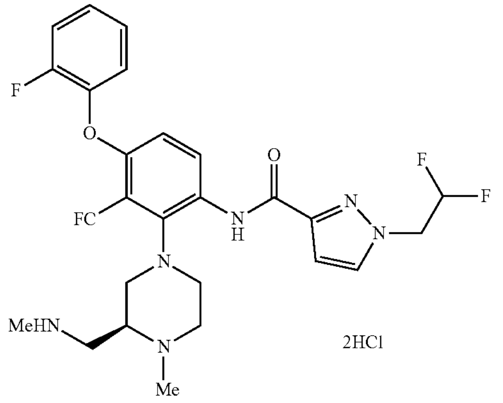 |
| 24 | 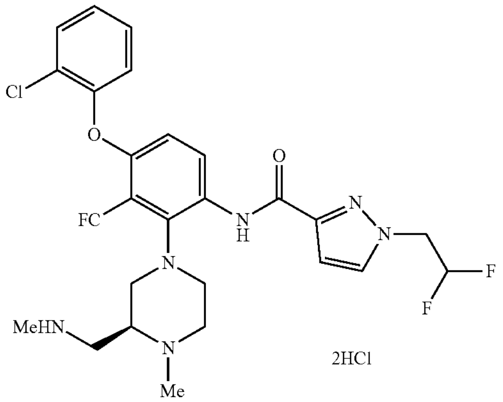 |
| 25 | 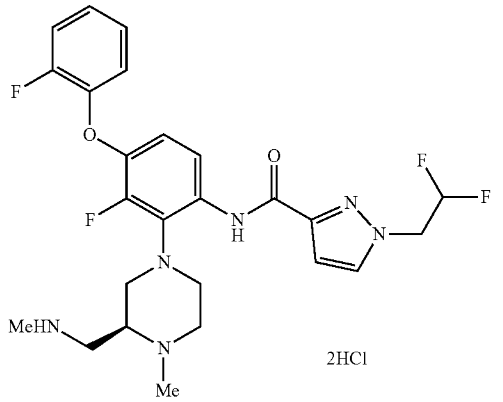 [SMILES: CNC[C@H]1CN(c2c(NC(=O)c3ccn(CC(F)F)n3)ccc(Oc3ccccc3F)c2F)CCN1C] |

TABLE 6-continued
| Ex | Str |
|---|---|
| 26 | 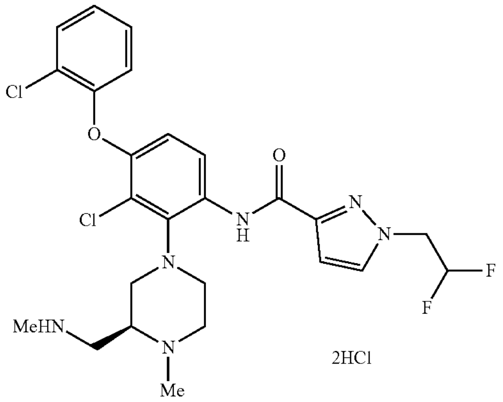 [SMILES: CNC[C@H]1CN(c2c(NC(=O)c3ccn(CC(F)F)n3)ccc(Oc3ccccc3Cl)c2Cl)CCN1C] |
| 27 | 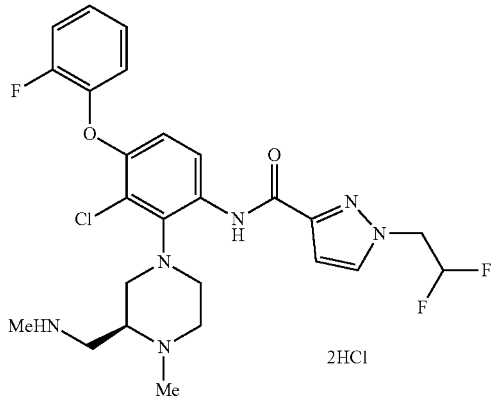 [SMILES: CNC[C@H]1CN(c2c(NC(=O)c3ccn(CC(F)F)n3)ccc(Oc3ccccc3F)c2Cl)CCN1C] |
| 28 | 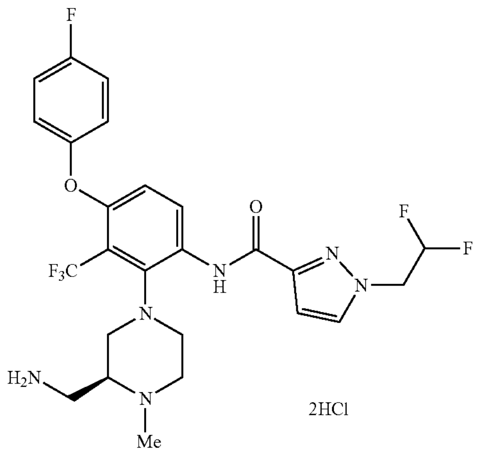 [SMILES: CN1CCN(c2c(NC(=O)c3ccn(CC(F)F)n3)ccc(Oc3ccc(F)cc3)c2C(F)(F)F)C[C@@H]1CN] |

TABLE 6-continued
| Ex | Str |
|---|---|
| 29 | 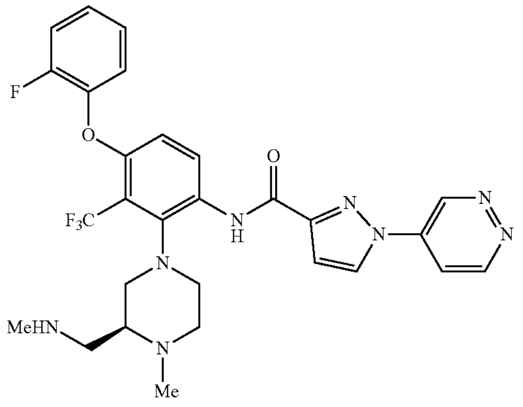 [SMILES: CNC[C@H]1CN(c2c(NC(=O)c3ccn(-c4ccnnc4)n3)ccc(Oc3ccccc3F)c2C(F)(F)F)CCN1C] |
| 30 | 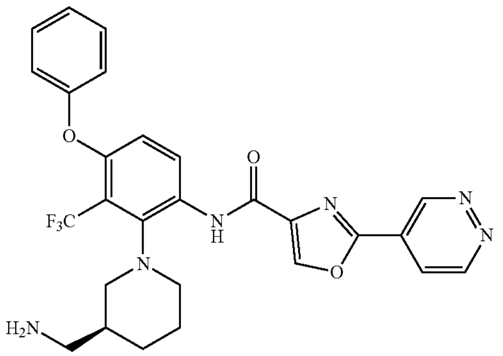 [SMILES: NC[C@@H]1CCCN(c2c(NC(=O)c3coc(-c4ccnnc4)n3)ccc(Oc3ccccc3)c2C(F)(F)F)C1] |
| 31 | 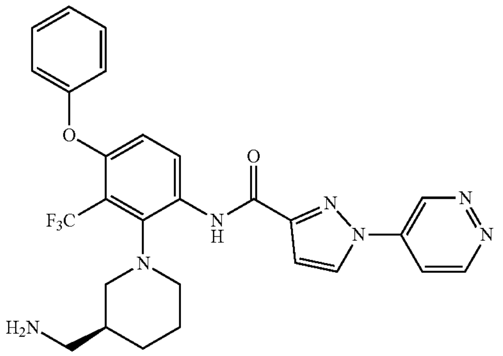 [SMILES: NC[C@@H]1CCCN(c2c(NC(=O)c3ccn(-c4ccnnc4)n3)ccc(Oc3ccccc3)c2C(F)(F)F)C1] |
| 32 | 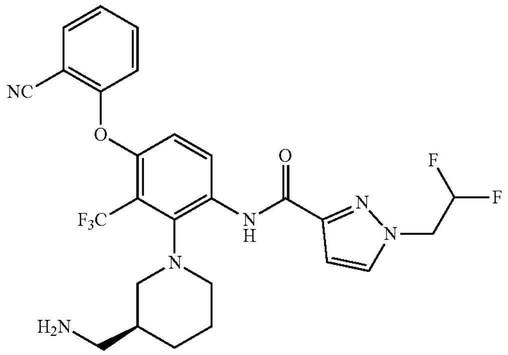 [SMILES: N#Cc1ccccc1Oc1ccc(NC(=O)c2ccn(CC(F)F)n2)c(N2CCC[C@@H](CN)C2)c1C(F)(F)F] |

TABLE 6-continued
| Ex | Str |
|---|---|
| 33 | 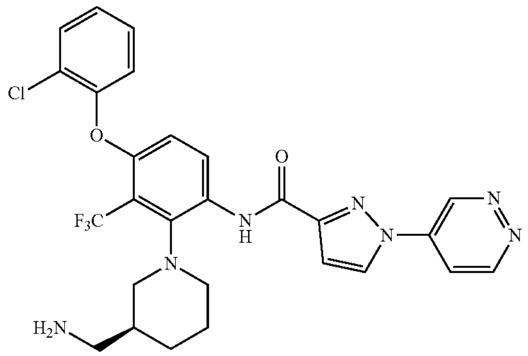 [SMILES: NC[C@@H]1CCCN(c2c(NC(=O)c3ccn(-c4ccnnc4)n3)ccc(Oc3ccccc3Cl)c2C(F)(F)F)C1] |
| 34 | 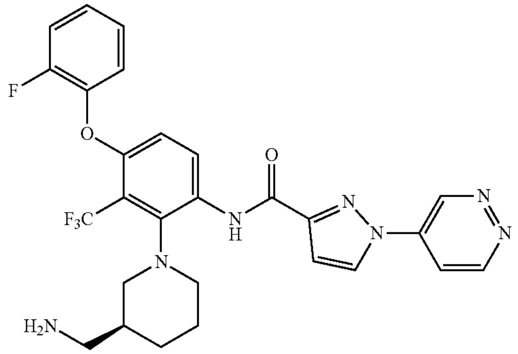 [SMILES: NC[C@@H]1CCCN(c2c(NC(=O)c3ccn(-c4ccnnc4)n3)ccc(Oc3ccccc3F)c2C(F)(F)F)C1] |
| 35 | 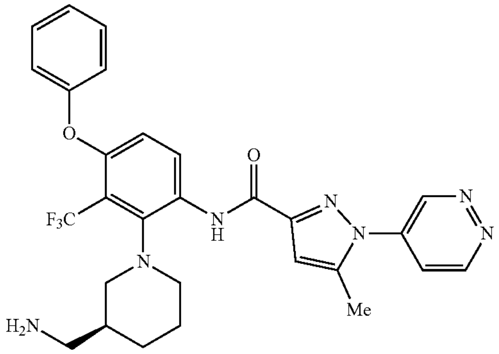 [SMILES: Cc1cc(C(=O)Nc2ccc(Oc3ccccc3)c(C(F)(F)F)c2N2CCC[C@@H](CN)C2)nn1-c1ccnnc1] |
| 36 | 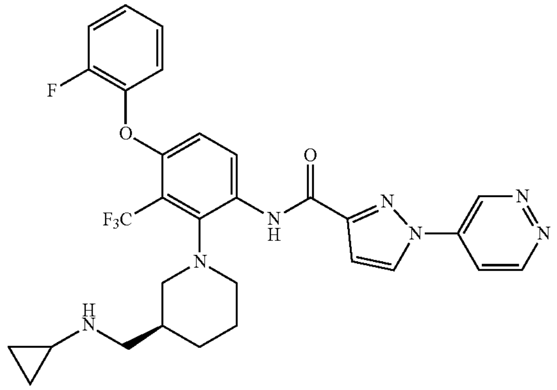 [SMILES: O=C(Nc1ccc(Oc2ccccc2F)c(C(F)(F)F)c1N1CCC[C@@H](CNC2CC2)C1)c1ccn(-c2ccnnc2)n1] |

TABLE 6-continued
| Ex | Str |
| --- | --- |
| 37 | 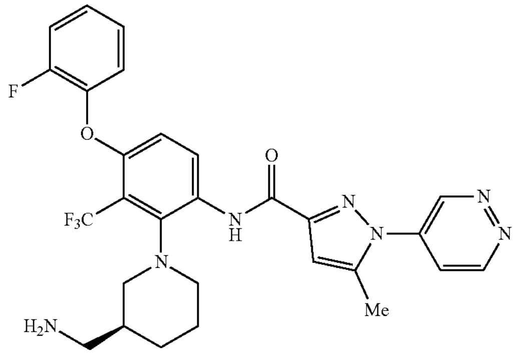 [SMILES: Cc1cc(C(=O)Nc2ccc(Oc3ccccc3F)c(C(F)(F)F)c2N2CCC[C@@H](CN)C2)nn1-c1ccnnc1] |
| 38 | 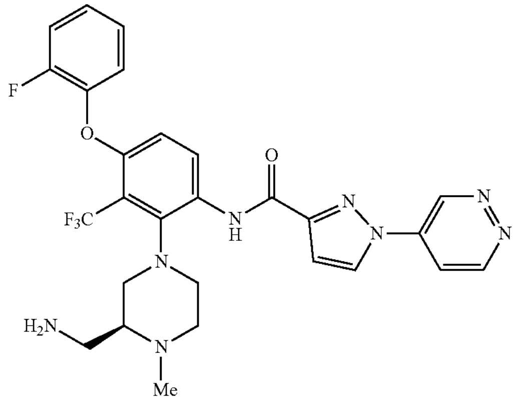 [SMILES: CN1CCN(c2c(NC(=O)c3ccn(-c4ccnnc4)n3)ccc(Oc3ccccc3F)c2C(F)(F)F)C[C@@H]1CN] |
| 39 | 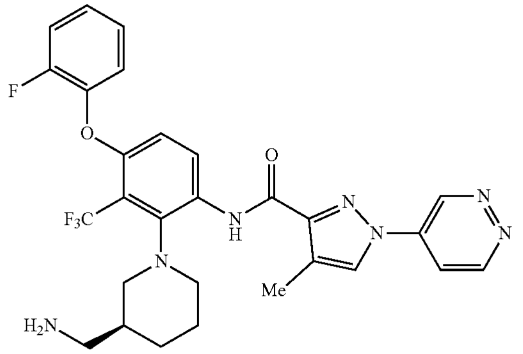 [SMILES: Cc1cn(-c2ccnnc2)nc1C(=O)Nc1ccc(Oc2ccccc2F)c(C(F)(F)F)c1N1CCC[C@@H](CN)C1] |
| 40 | 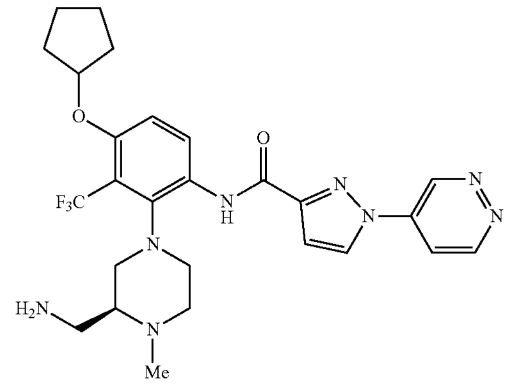 [SMILES: CN1CCN(c2c(NC(=O)c3ccn(-c4ccnnc4)n3)ccc(OC3CCCC3)c2C(F)(F)F)C[C@@H]1CN] |

TABLE 6-continued
| Ex | Str |
|---|---|
| 41 | 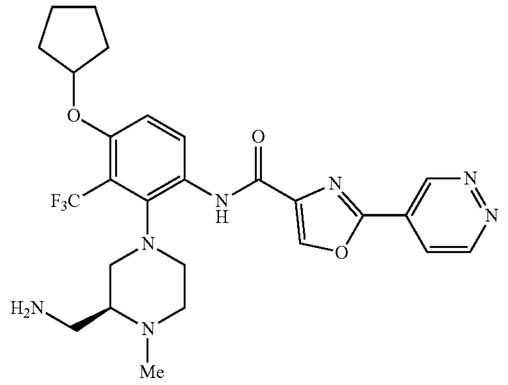 [SMILES: CN1CCN(c2c(NC(=O)c3coc(-c4ccnnc4)n3)ccc(OC3CCCC3)c2C(F)(F)F)C[C@@H]1CN] |
| 42 | 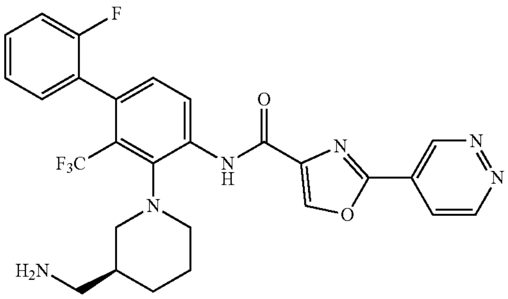 [SMILES: NC[C@@H]1CCCN(c2c(NC(=O)c3coc(-c4ccnnc4)n3)ccc(-c3ccccc3F)c2C(F)(F)F)C1] |
| 43 | 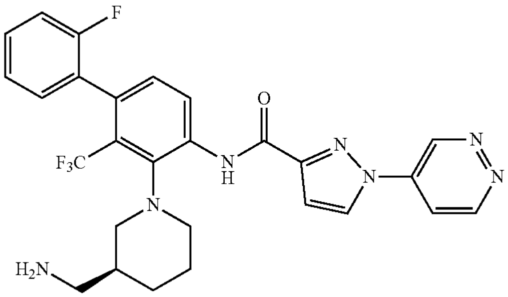 [SMILES: NC[C@@H]1CCCN(c2c(NC(=O)c3ccn(-c4ccnnc4)n3)ccc(-c3ccccc3F)c2C(F)(F)F)C1] |
| 44 | 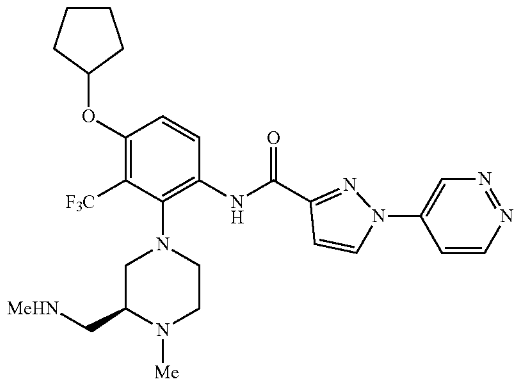 [SMILES: CNC[C@H]1CN(c2c(NC(=O)c3ccn(-c4ccnnc4)n3)ccc(OC3CCCC3)c2C(F)(F)F)CCN1C] |

TABLE 6-continued
| Ex | Str |
|---|---|
| 45 | 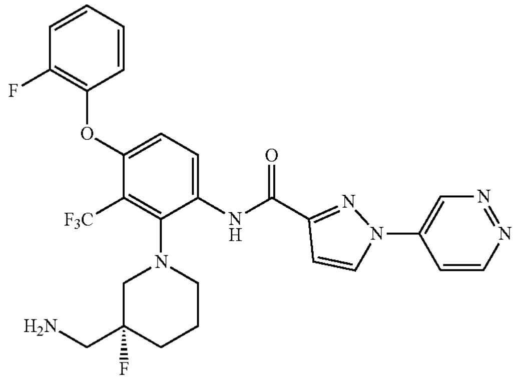 [SMILES: NC[C@]1(F)CCCN(c2c(NC(=O)c3ccn(-c4ccnnc4)n3)ccc(Oc3ccccc3F)c2C(F)(F)F)C1] |
| 46 | 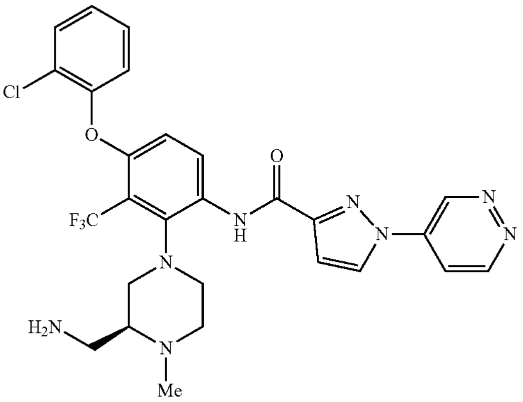 [SMILES: CN1CCN(c2c(NC(=O)c3ccn(-c4ccnnc4)n3)ccc(Oc3ccccc3Cl)c2C(F)(F)F)C[C@@H]1CN] |
| 47 | 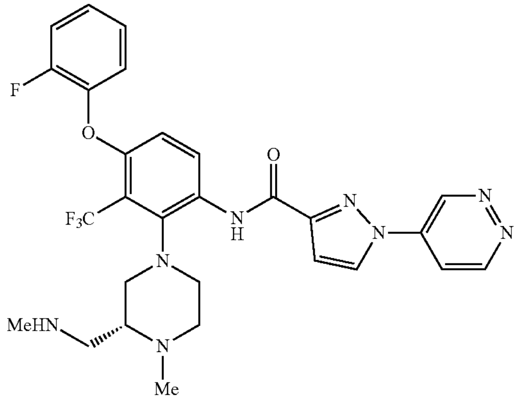 [SMILES: CNC[C@@H]1CN(c2c(NC(=O)c3ccn(-c4ccnnc4)n3)ccc(Oc3ccccc3F)c2C(F)(F)F)CCN1C] |
| 48 | 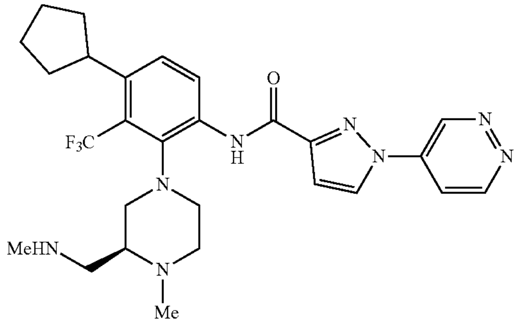 [SMILES: CNC[C@H]1CN(c2c(NC(=O)c3ccn(-c4ccnnc4)n3)ccc(C3CCCC3)c2C(F)(F)F)CCN1C] |

TABLE 6-continued
| Ex | Str |
| --- | --- |
| 49 | 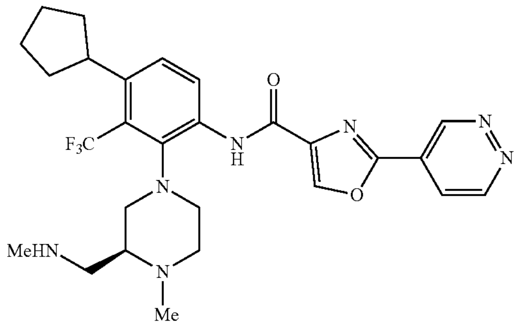 [SMILES: CNC[C@H]1CN(c2c(NC(=O)c3coc(-c4ccnnc4)n3)ccc(C3CCCC3)c2C(F)(F)F)CCN1C] |
| 50 | 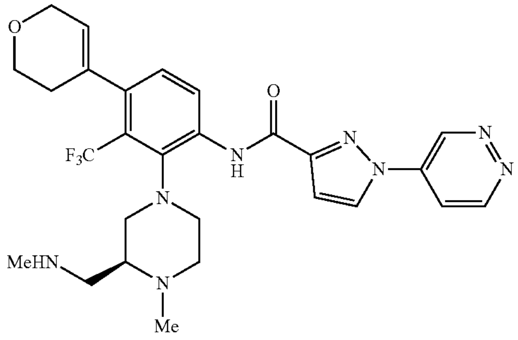 [SMILES: CNC[C@H]1CN(c2c(NC(=O)c3ccn(-c4ccnnc4)n3)ccc(C3=CCOCC3)c2C(F)(F)F)CCN1C] |
| 51 | 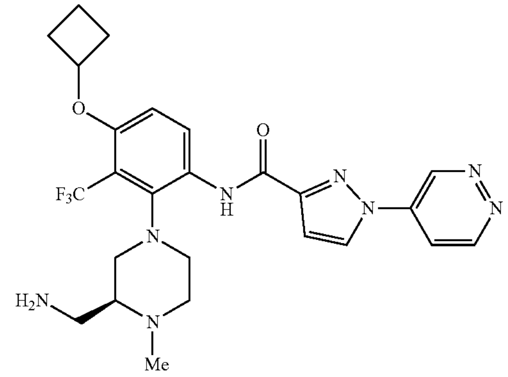 [SMILES: CN1CCN(c2c(NC(=O)c3ccn(-c4ccnnc4)n3)ccc(OC3CCC3)c2C(F)(F)F)C[C@@H]1CN] |
| 52 | 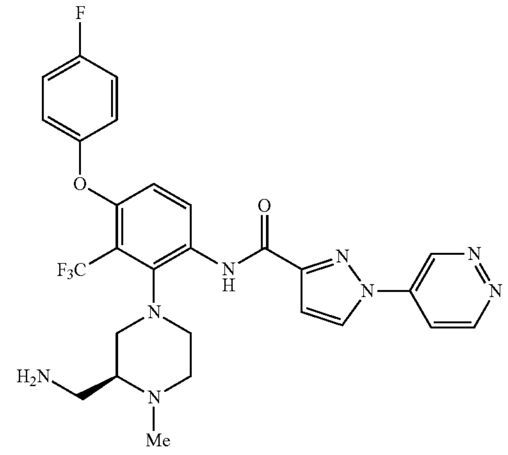 [SMILES: CN1CCN(c2c(NC(=O)c3ccn(-c4ccnnc4)n3)ccc(Oc3ccc(F)cc3)c2C(F)(F)F)C[C@@H]1CN] |

TABLE 6-continued
| Ex | Str |
| --- | --- |
| 53 | 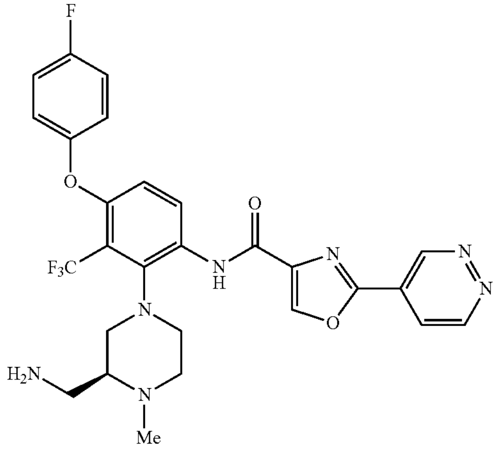 [SMILES: CN1CCN(c2c(NC(=O)c3coc(-c4ccnnc4)n3)ccc(Oc3ccc(F)cc3)c2C(F)(F)F)C[C@@H]1CN] |
| 54 | 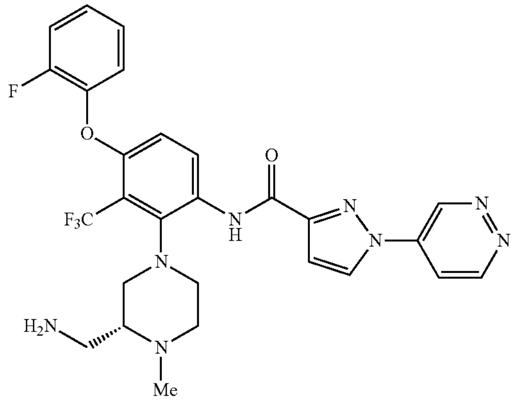 [SMILES: CN1CCN(c2c(NC(=O)c3ccn(-c4ccnnc4)n3)ccc(Oc3ccccc3F)c2C(F)(F)F)C[C@H]1CN] |
| 55 | 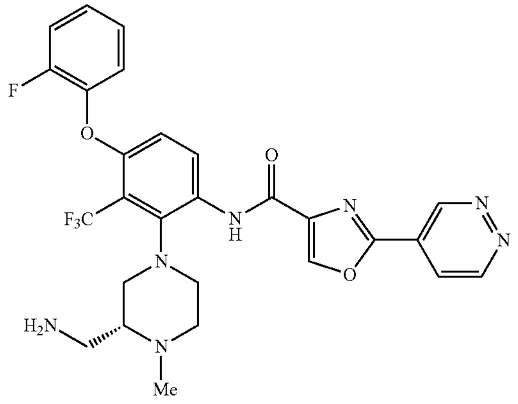 [SMILES: CN1CCN(c2c(NC(=O)c3coc(-c4ccnnc4)n3)ccc(Oc3ccccc3F)c2C(F)(F)F)C[C@H]1CN] |

TABLE 6-continued
| Ex | Str |
|---|---|
| 56 | 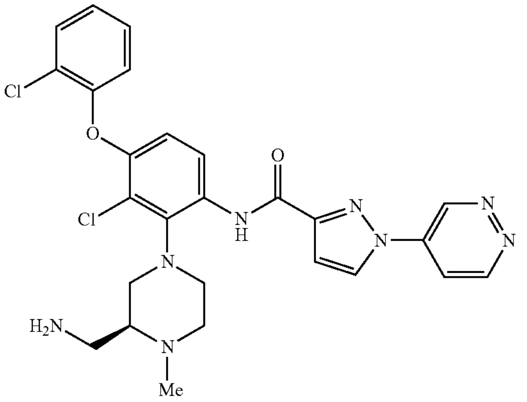 [SMILES: CN1CCN(c2c(NC(=O)c3ccn(-c4ccnnc4)n3)ccc(Oc3ccccc3Cl)c2Cl)C[C@@H]1CN] |
| 57 | 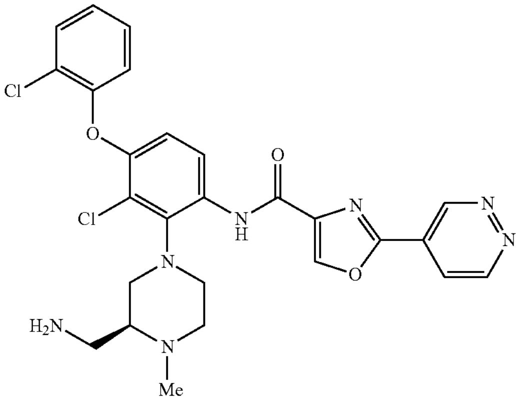 [SMILES: CN1CCN(c2c(NC(=O)c3coc(-c4ccnnc4)n3)ccc(Oc3ccccc3Cl)c2Cl)C[C@@H]1CN] |
| 58 | 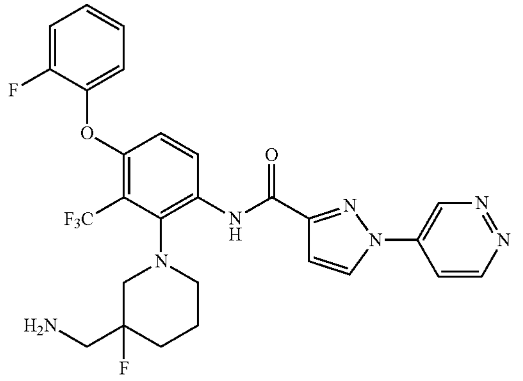 [SMILES: NCC1(F)CCCN(c2c(NC(=O)c3ccn(-c4ccnnc4)n3)ccc(Oc3ccccc3F)c2C(F)(F)F)C1] |
| 59 | 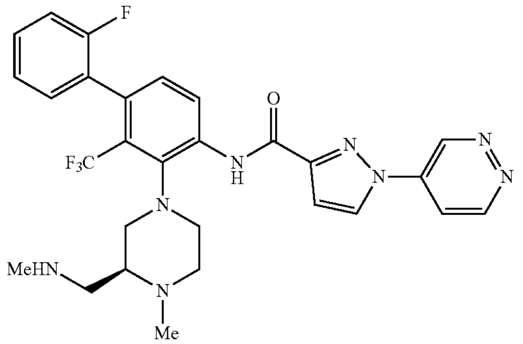 [SMILES: CNC[C@H]1CN(c2c(NC(=O)c3ccn(-c4ccnnc4)n3)ccc(-c3ccccc3F)c2C(F)(F)F)CCN1C] |

TABLE 6-continued
| Ex | Str |
| --- | --- |
| 60 | 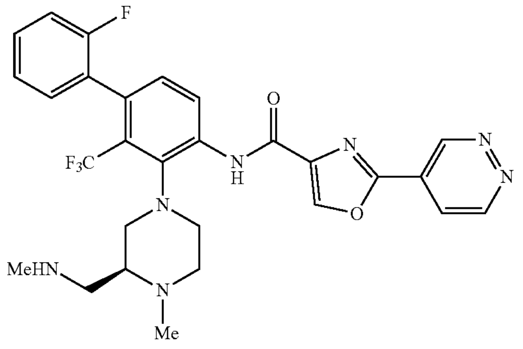 [SMILES: CNC[C@H]1CN(c2c(NC(=O)c3coc(-c4ccnnc4)n3)ccc(-c3ccccc3F)c2C(F)(F)F)CCN1C] |
| 61 | 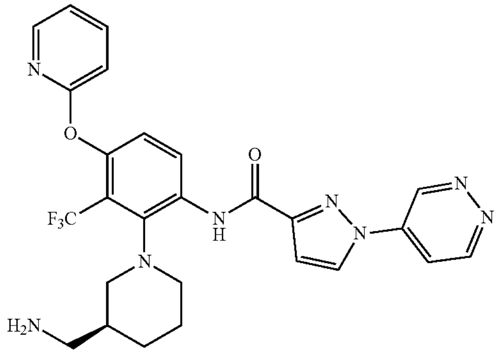 [SMILES: NC[C@@H]1CCCN(c2c(NC(=O)c3ccn(-c4ccnnc4)n3)ccc(Oc3ccccn3)c2C(F)(F)F)C1] |
| 62 | 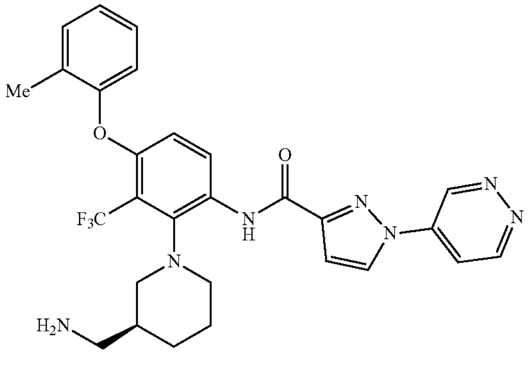 [SMILES: Cc1ccccc1Oc1ccc(NC(=O)c2ccn(-c3ccnnc3)n2)c(N2CCC[C@@H](CN)C2)c1C(F)(F)F] |
| 63 | 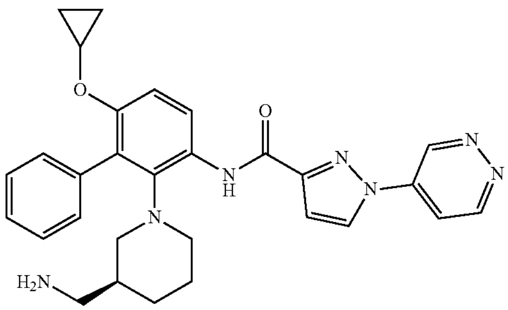 [SMILES: NC[C@@H]1CCCN(c2c(NC(=O)c3ccn(-c4ccnnc4)n3)ccc(OC3CC3)c2-c2ccccc2)C1] |

TABLE 6-continued
| Ex | Str |
|---|---|
| 64 | 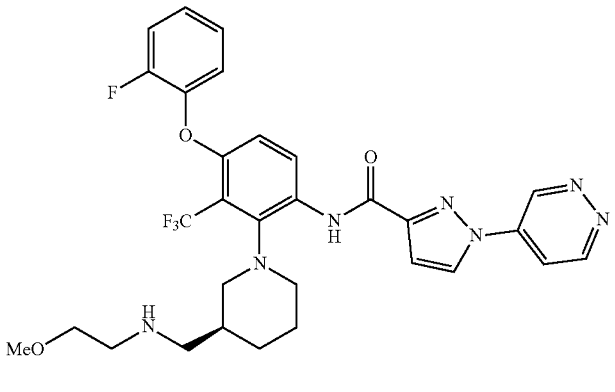 [SMILES: COCCNC[C@@H]1CCCN(c2c(NC(=O)c3ccn(-c4ccnnc4)n3)ccc(Oc3ccccc3F)c2C(F)(F)F)C1] |
| 65 | 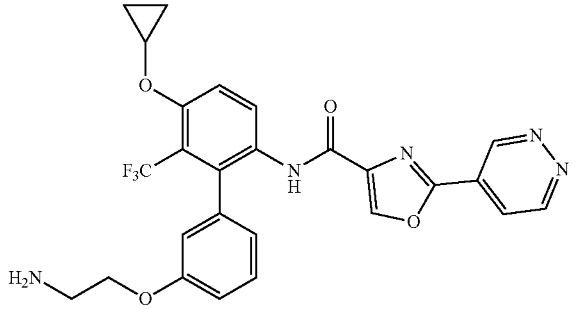 [SMILES: NCCOc1cccc(-c2c(NC(=O)c3coc(-c4ccnnc4)n3)ccc(OC3CC3)c2C(F)(F)F)c1] |
| 66 | 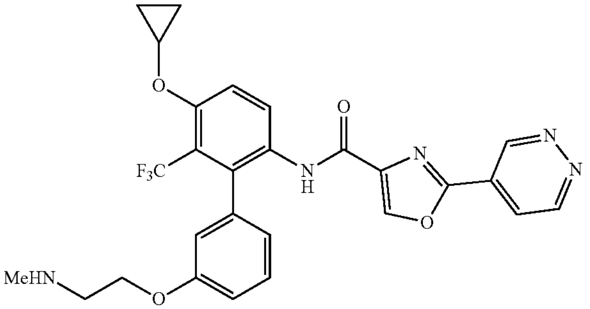 [SMILES: CNCCOc1cccc(-c2c(NC(=O)c3coc(-c4ccnnc4)n3)ccc(OC3CC3)c2C(F)(F)F)c1] |
| 67 | 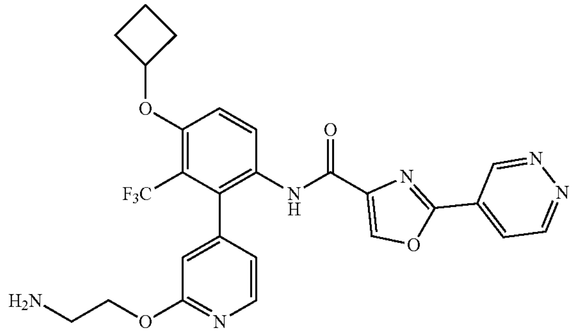 [SMILES: NCCOc1cc(-c2c(NC(=O)c3coc(-c4ccnnc4)n3)ccc(OC3CCC3)c2C(F)(F)F)ccn1] |

TABLE 6-continued
| Ex | Str |
|---|---|
| 68 | 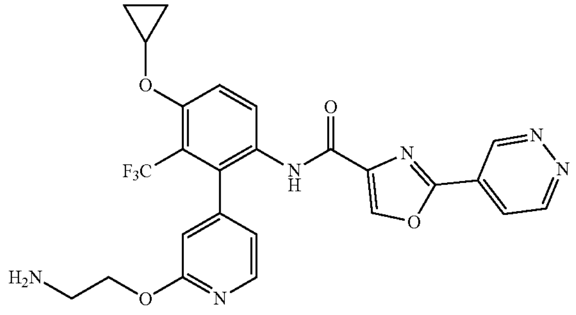 [SMILES: NCCOc1cc(-c2c(NC(=O)c3coc(-c4ccnnc4)n3)ccc(OC3CC3)c2C(F)(F)F)ccn1] |
| 69 | 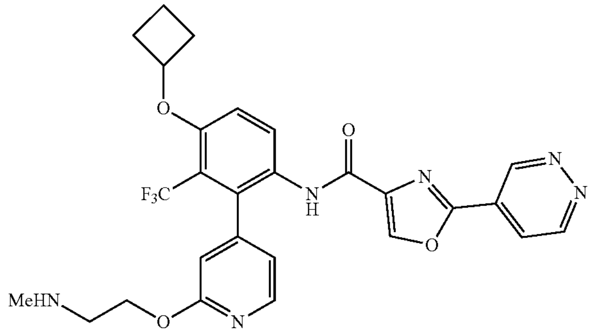 [SMILES: CNCCOc1cc(-c2c(NC(=O)c3coc(-c4ccnnc4)n3)ccc(OC3CCC3)c2C(F)(F)F)ccn1] |
| 70 | 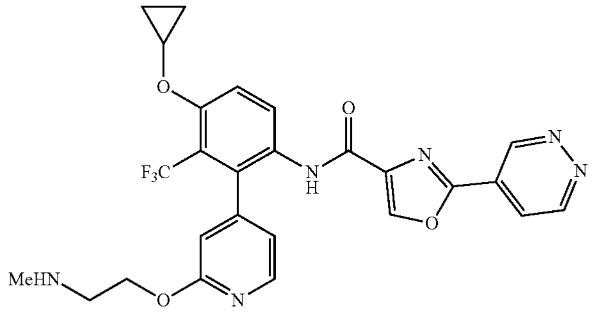 [SMILES: CNCCOc1cc(-c2c(NC(=O)c3coc(-c4ccnnc4)n3)ccc(OC3CC3)c2C(F)(F)F)ccn1] |
| 71 | 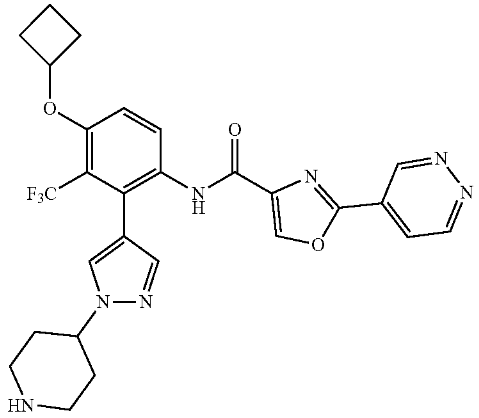 [SMILES: O=C(Nc1ccc(OC2CCC2)c(C(F)(F)F)c1-c1cnn(C2CCNCC2)c1)c1coc(-c2ccnnc2)n1] |

TABLE 6-continued
| Ex | Str |
| --- | --- |
| 72 | 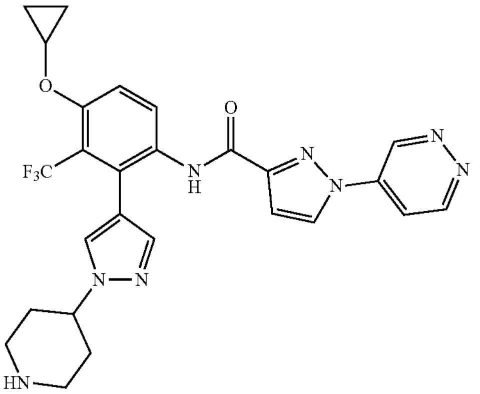 [SMILES: O=C(Nc1ccc(OC2CC2)c(C(F)(F)F)c1-c1cnn(C2CCNCC2)c1)c1ccn(-c2ccnnc2)n1] |
| 73 | 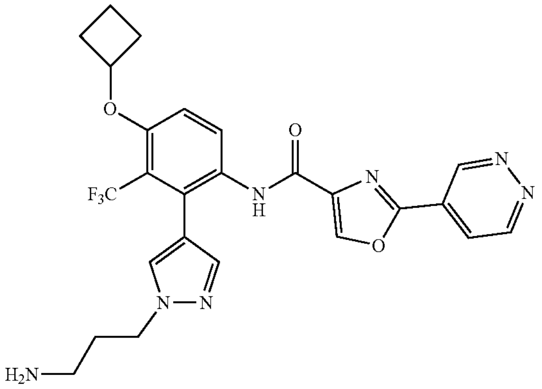 [SMILES: NCCCn1cc(-c2c(NC(=O)c3coc(-c4ccnnc4)n3)ccc(OC3CCC3)c2C(F)(F)F)cn1] |
| 74 | 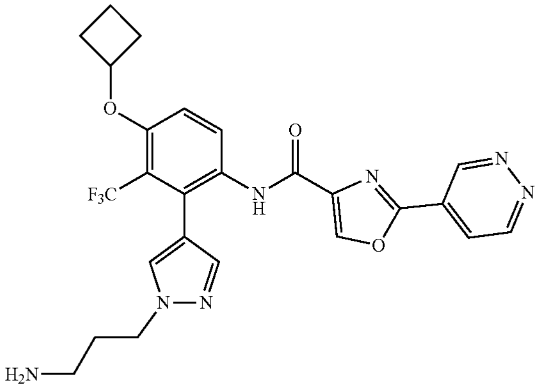 [SMILES: NCCCn1cc(-c2c(NC(=O)c3coc(-c4ccnnc4)n3)ccc(OC3CCC3)c2C(F)(F)F)cn1] |
| 75 | 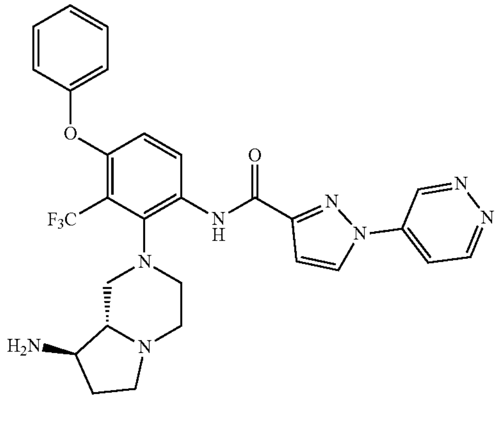 [SMILES: N[C@@H]1CCN2CCN(c3c(NC(=O)c4ccn(-c5ccnnc5)n4)ccc(Oc4ccccc4)c3C(F)(F)F)C[C@@H]12] |

TABLE 6-continued
| Ex | Str |
|---|---|
| 76 | 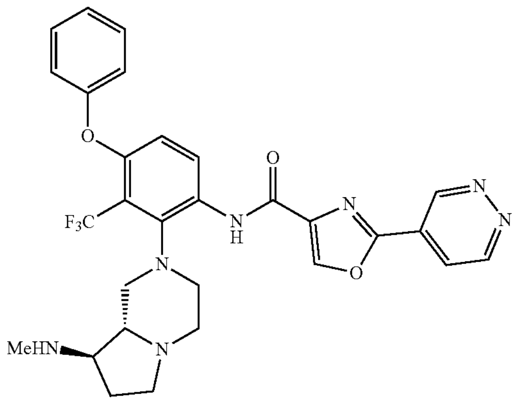 [SMILES: CN[C@@H]1CCN2CCN(c3c(NC(=O)c4coc(-c5ccnnc5)n4)ccc(Oc4ccccc4)c3C(F)(F)F)C[C@@H]12] |
| 77 | 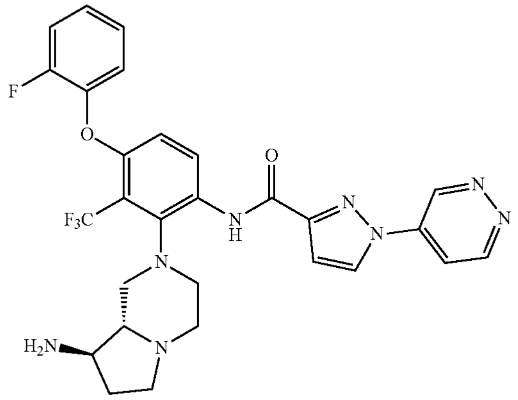 [SMILES: N[C@@H]1CCN2CCN(c3c(NC(=O)c4ccn(-c5ccnnc5)n4)ccc(Oc4ccccc4F)c3C(F)(F)F)C[C@@H]12] |
| 78 | 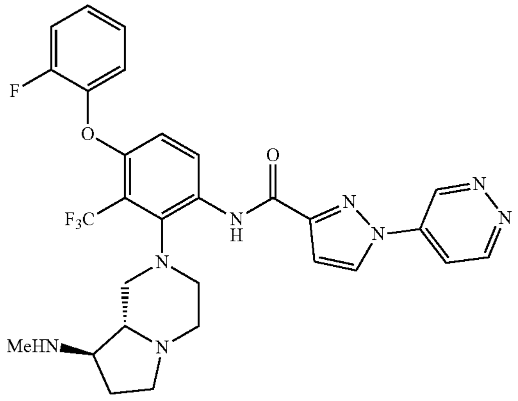 [SMILES: CN[C@@H]1CCN2CCN(c3c(NC(=O)c4ccn(-c5ccnnc5)n4)ccc(Oc4ccccc4F)c3C(F)(F)F)C[C@@H]12] |
| 79 | 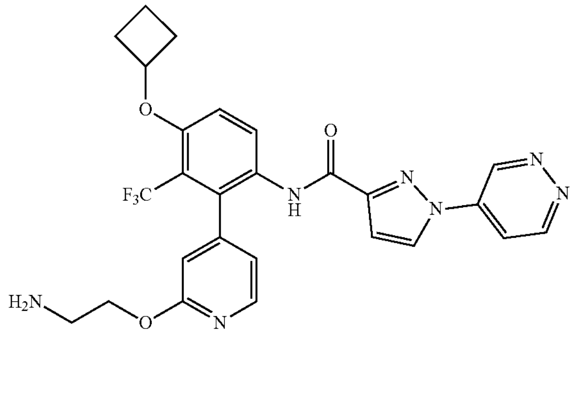 [SMILES: NCCOc1cc(-c2c(NC(=O)c3ccn(-c4ccnnc4)n3)ccc(OC3CCC3)c2C(F)(F)F)ccn1] |

TABLE 6-continued
| Ex | Str |
|---|---|
| 80 | 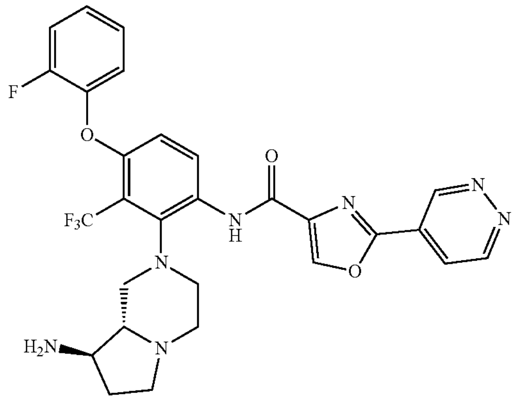 [SMILES: N[C@@H]1CCN2CCN(c3c(NC(=O)c4coc(-c5ccnnc5)n4)ccc(Oc4ccccc4F)c3C(F)(F)F)C[C@@H]12] |
| 81 | 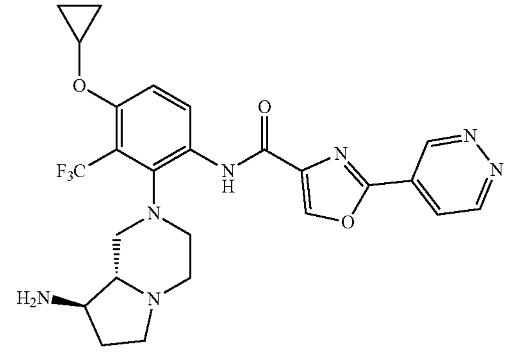 [SMILES: N[C@@H]1CCN2CCN(c3c(NC(=O)c4coc(-c5ccnnc5)n4)ccc(OC4CC4)c3C(F)(F)F)C[C@@H]12] |
| 82 | 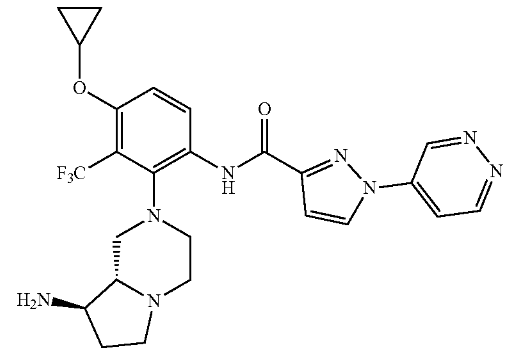 [SMILES: N[C@@H]1CCN2CCN(c3c(NC(=O)c4ccn(-c5ccnnc5)n4)ccc(OC4CC4)c3C(F)(F)F)C[C@@H]12] |
| 83 | 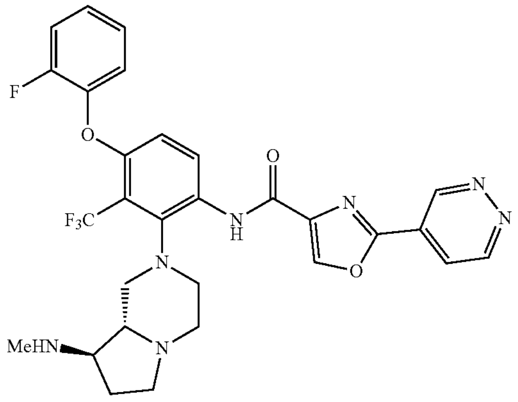 [SMILES: CN[C@@H]1CCN2CCN(c3c(NC(=O)c4coc(-c5ccnnc5)n4)ccc(Oc4ccccc4F)c3C(F)(F)F)C[C@@H]12] |

TABLE 6-continued
| Ex | Str |
|---|---|
| 84 | 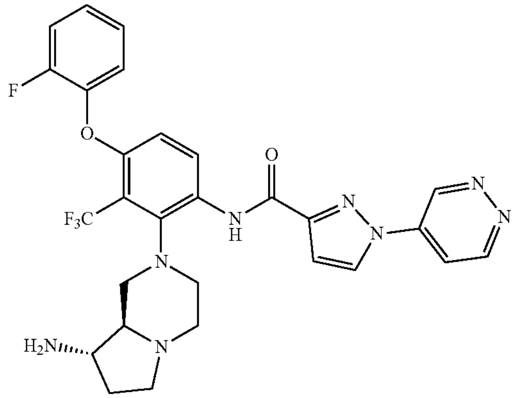 [SMILES: N[C@H]1CCN2CCN(c3c(NC(=O)c4ccn(-c5ccnnc5)n4)ccc(Oc4ccccc4F)c3C(F)(F)F)C[C@H]12] |
| 85 | 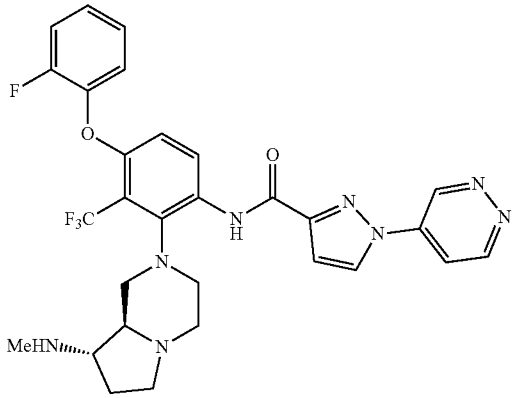 [SMILES: CN[C@H]1CCN2CCN(c3c(NC(=O)c4ccn(-c5ccnnc5)n4)ccc(Oc4ccccc4F)c3C(F)(F)F)C[C@H]12] |
| 86 | 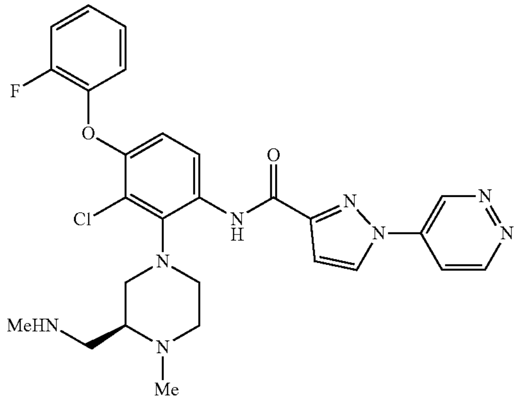 [SMILES: CNC[C@H]1CN(c2c(NC(=O)c3ccn(-c4ccnnc4)n3)ccc(Oc3ccccc3F)c2Cl)CCN1C] |
| 87 | 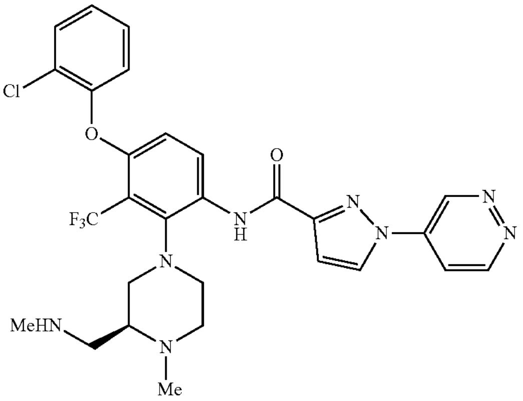 [SMILES: CNC[C@H]1CN(c2c(NC(=O)c3ccn(-c4ccnnc4)n3)ccc(Oc3ccccc3Cl)c2C(F)(F)F)CCN1C] |

TABLE 6-continued
| Ex | Str |
|---|---|
| 88 | 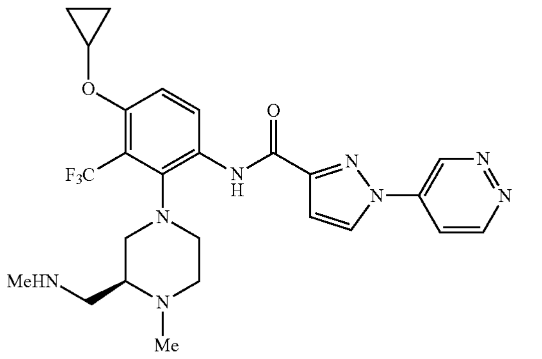 [SMILES: CNC[C@H]1CN(c2c(NC(=O)c3ccn(-c4ccnnc4)n3)ccc(OC3CC3)c2C(F)(F)F)CCN1C] |
| 89 | 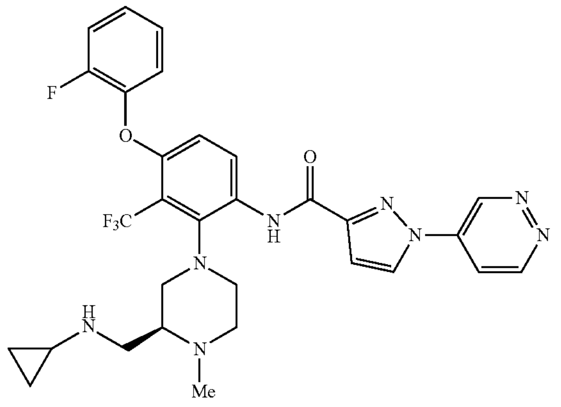 [SMILES: CN1CCN(c2c(NC(=O)c3ccn(-c4ccnnc4)n3)ccc(Oc3ccccc3F)c2C(F)(F)F)C[C@@H]1CNC1CC1] |
| 90 | 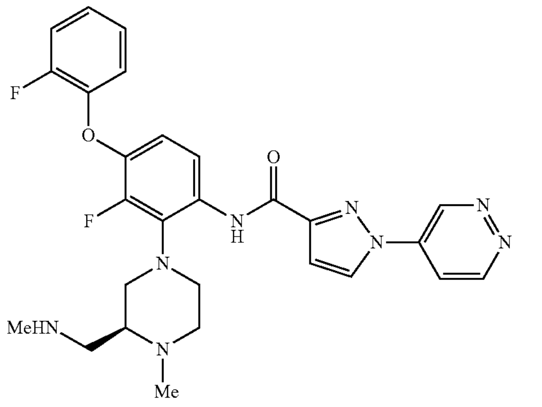 [SMILES: CNC[C@H]1CN(c2c(NC(=O)c3ccn(-c4ccnnc4)n3)ccc(Oc3ccccc3F)c2F)CCN1C] |
| 91 | 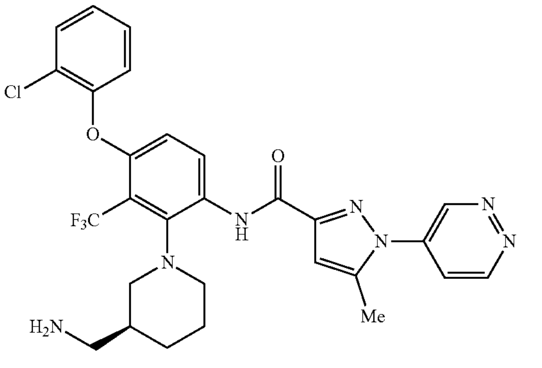 [SMILES: Cc1cc(C(=O)Nc2ccc(Oc3ccccc3Cl)c(C(F)(F)F)c2N2CCC[C@@H](CN)C2)nn1-c1ccnnc1] |

TABLE 6-continued
| Ex | Str |
|---|---|
| 92 | 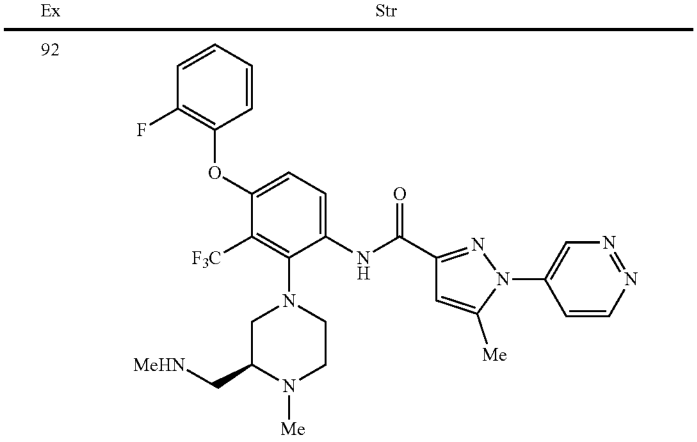 |
| 93 | 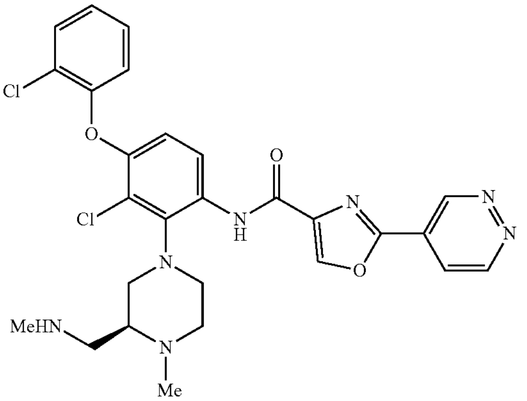 [SMILES: CNC[C@H]1CN(c2c(NC(=O)c3coc(-c4ccnnc4)n3)ccc(Oc3ccccc3Cl)c2Cl)CCN1C] |
| 94 | 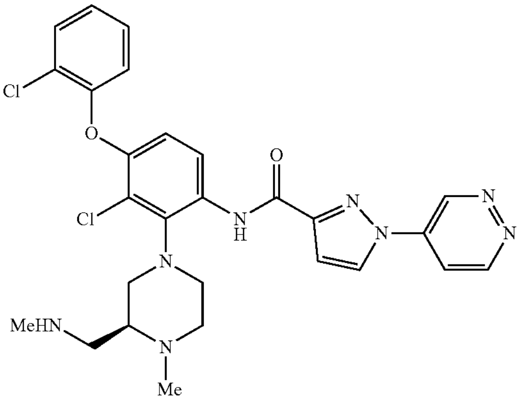 [SMILES: CNC[C@H]1CN(c2c(NC(=O)c3ccn(-c4ccnnc4)n3)ccc(Oc3ccccc3Cl)c2Cl)CCN1C] |
| 95 | 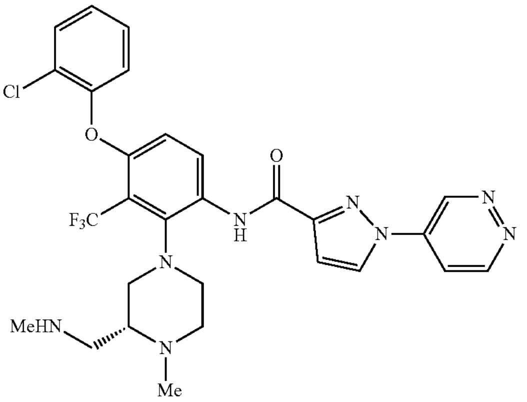 [SMILES: CNC[C@@H]1CN(c2c(NC(=O)c3ccn(-c4ccnnc4)n3)ccc(Oc3ccccc3Cl)c2C(F)(F)F)CCN1C] |

TABLE 6-continued
| Ex | Str |
| --- | --- |
| 96 | 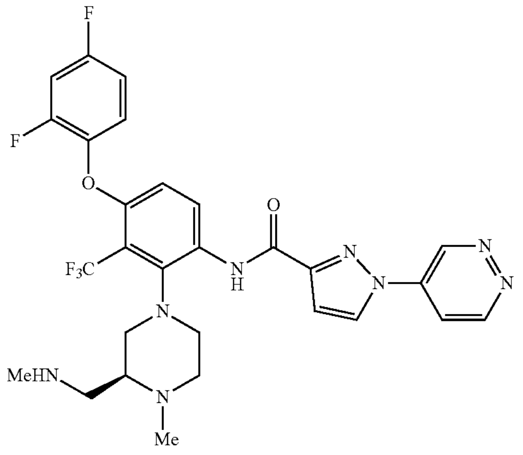 [SMILES: CNC[C@H]1CN(c2c(NC(=O)c3ccn(-c4ccnnc4)n3)ccc(Oc3ccc(F)cc3F)c2C(F)(F)F)CCN1C] |
| 97 | 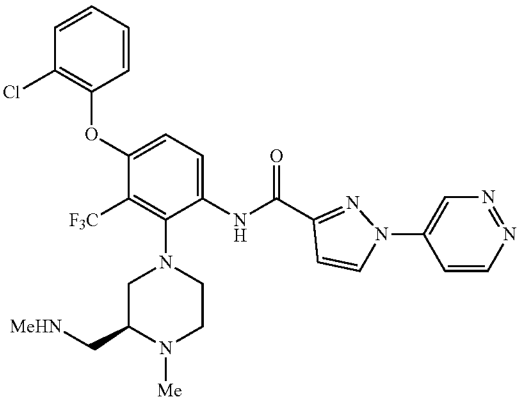 |
| 98 | 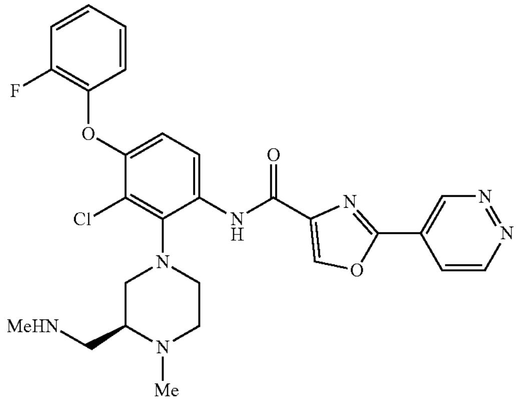 [SMILES: CNC[C@H]1CN(c2c(NC(=O)c3coc(-c4ccnnc4)n3)ccc(Oc3ccccc3F)c2Cl)CCN1C] |

TABLE 6-continued
| Ex | Str |
| --- | --- |
| 99 | 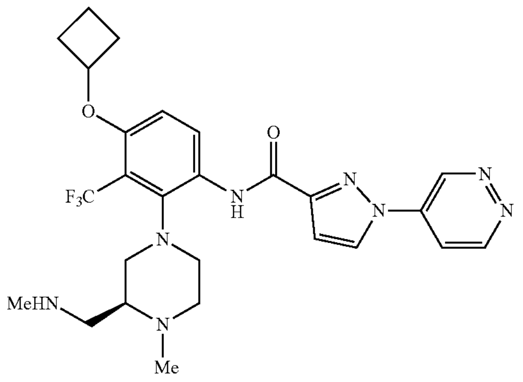 [SMILES: CNC[C@H]1CN(c2c(NC(=O)c3ccn(-c4ccnnc4)n3)ccc(OC3CCC3)c2C(F)(F)F)CCN1C] |
| 100 | 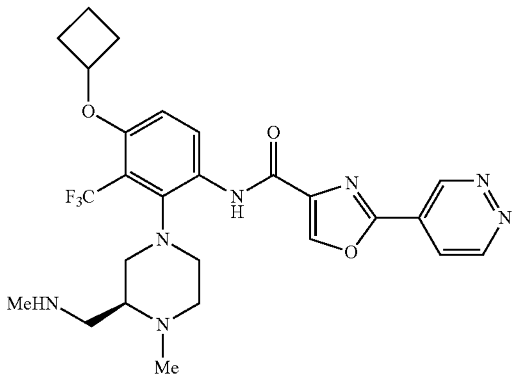 [SMILES: CNC[C@H]1CN(c2c(NC(=O)c3coc(-c4ccnnc4)n3)ccc(OC3CCC3)c2C(F)(F)F)CCN1C] |
| 101 | 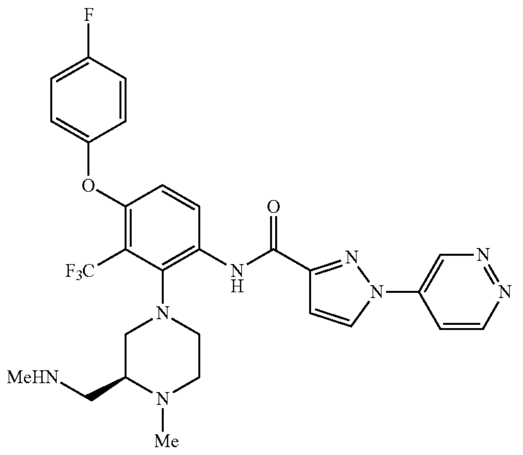 [SMILES: CNC[C@H]1CN(c2c(NC(=O)c3ccn(-c4ccnnc4)n3)ccc(Oc3ccc(F)cc3)c2C(F)(F)F)CCN1C] |

TABLE 6-continued
| Ex | Str |
| --- | --- |
| 102 | 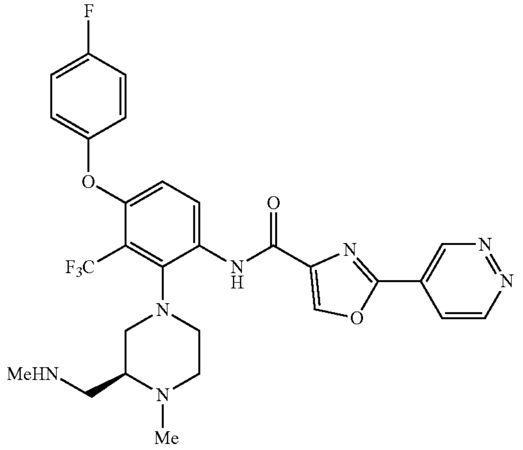 [SMILES: CNC[C@H]1CN(c2c(NC(=O)c3coc(-c4ccnnc4)n3)ccc(Oc3ccc(F)cc3)c2C(F)(F)F)CCN1C] |
| 103 | 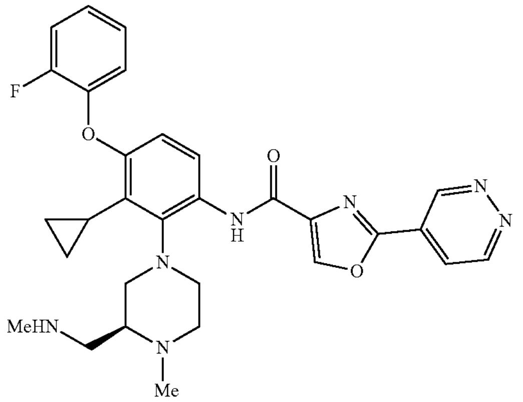 [SMILES: CNC[C@H]1CN(c2c(NC(=O)c3coc(-c4ccnnc4)n3)ccc(Oc3ccccc3F)c2C2CC2)CCN1C] |
| 104 | 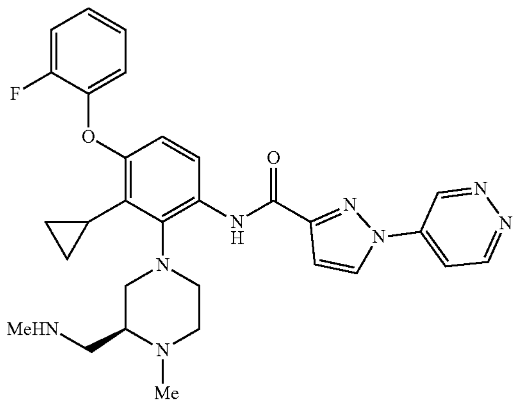 [SMILES: CNC[C@H]1CN(c2c(NC(=O)c3ccn(-c4ccnnc4)n3)ccc(Oc3ccccc3F)c2C2CC2)CCN1C] |

TABLE 6-continued
| Ex | Str |
| --- | --- |
| 105 | 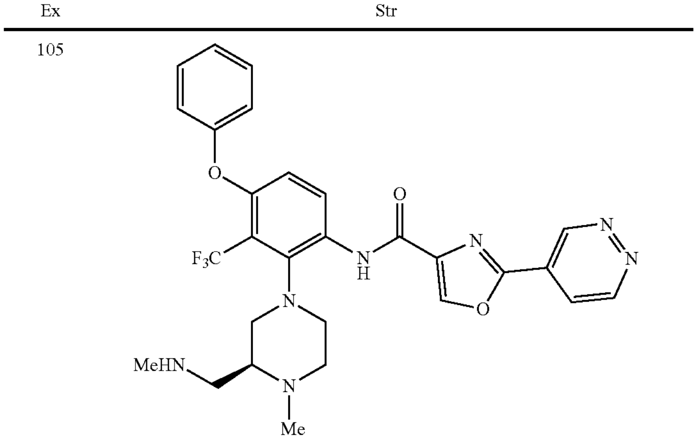 |
| 106 | 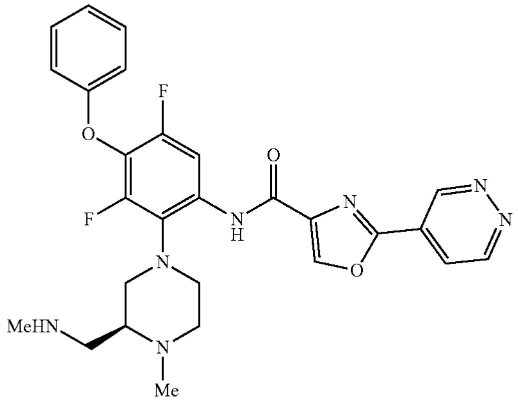 [SMILES: CNC[C@H]1CN(c2c(NC(=O)c3coc(-c4ccnnc4)n3)cc(F)c(Oc3ccccc3)c2F)CCN1C] |
| 107 | 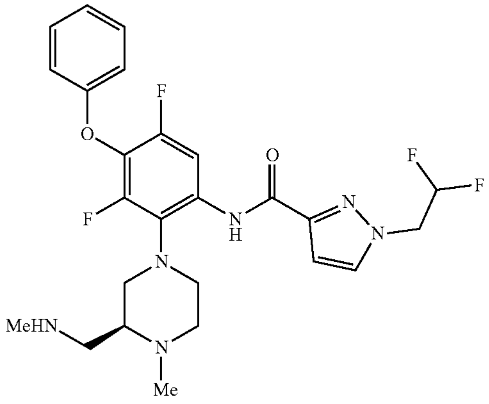 [SMILES: CNC[C@H]1CN(c2c(NC(=O)c3ccn(CC(F)F)n3)cc(F)c(Oc3ccccc3)c2F)CCN1C] |
| 108 | 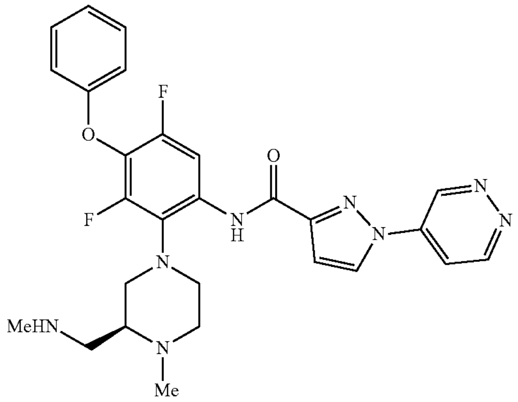 [SMILES: CNC[C@H]1CN(c2c(NC(=O)c3ccn(-c4ccnnc4)n3)cc(F)c(Oc3ccccc3)c2F)CCN1C] |

TABLE 6-continued
| Ex | Str |
|---|---|
| 109 | 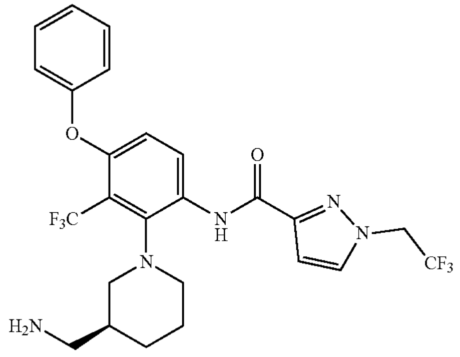 [SMILES: NC[C@@H]1CCCN(c2c(NC(=O)c3ccn(CC(F)(F)F)n3)ccc(Oc3ccccc3)c2C(F)(F)F)C1] |
| 110 | 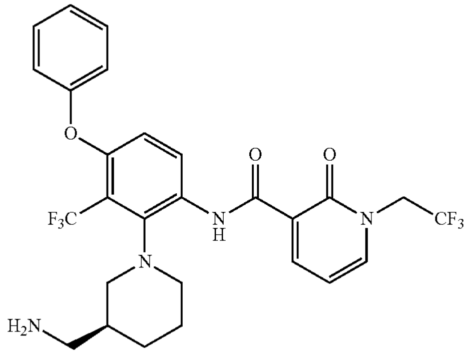 [SMILES: NC[C@@H]1CCCN(c2c(NC(=O)c3cccn(CC(F)(F)F)c3=O)ccc(Oc3ccccc3)c2C(F)(F)F)C1] |
| 111 | 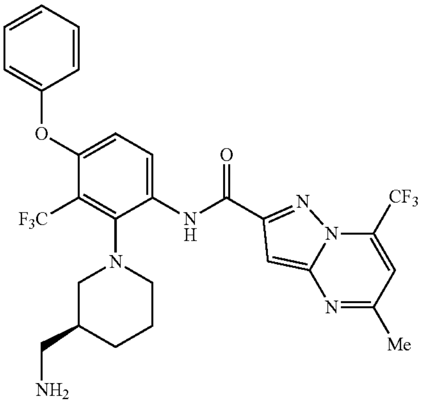 [SMILES: Cc1cc(C(F)(F)F)n2nc(C(=O)Nc3ccc(Oc4ccccc4)c(C(F)(F)F)c3N3CCC[C@@H](CN)C3)cc2n1] |
| 112 | 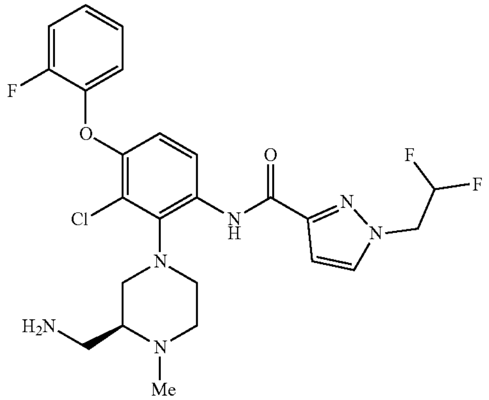 [SMILES: CN1CCN(c2c(NC(=O)c3ccn(CC(F)F)n3)ccc(Oc3ccccc3F)c2Cl)C[C@@H]1CN] |

TABLE 6-continued
| Ex | Str |
| --- | --- |
| 113 | 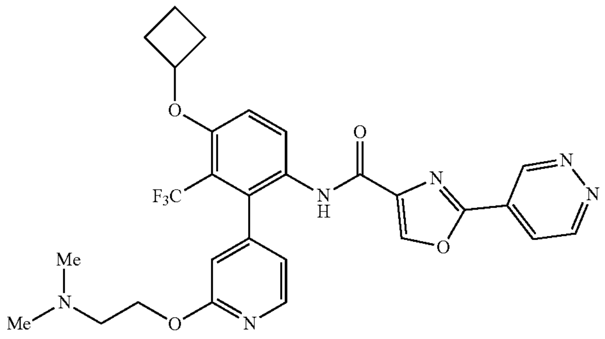 [SMILES: CN(C)CCOc1cc(-c2c(NC(=O)c3coc(-c4ccnnc4)n3)ccc(OC3CCC3)c2C(F)(F)F)ccn1] |
| 114 | 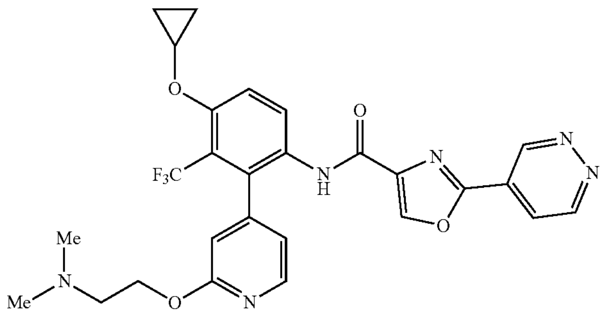 [SMILES: CN(C)CCOc1cc(-c2c(NC(=O)c3coc(-c4ccnnc4)n3)ccc(OC3CC3)c2C(F)(F)F)ccn1] |
| 115 | 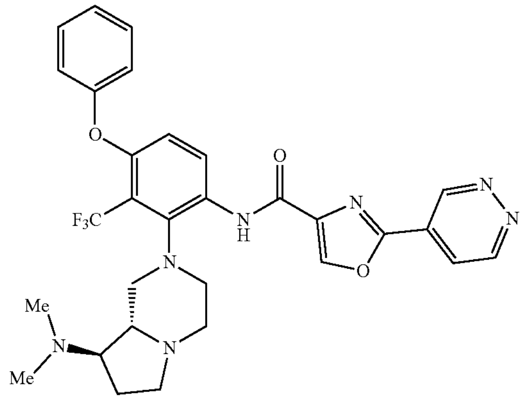 [SMILES: CN(C)[C@@H]1CCN2CCN(c3c(NC(=O)c4coc(-c5ccnnc5)n4)ccc(Oc4ccccc4)c3C(F)(F)F)C[C@@H]12] |
| 116 | 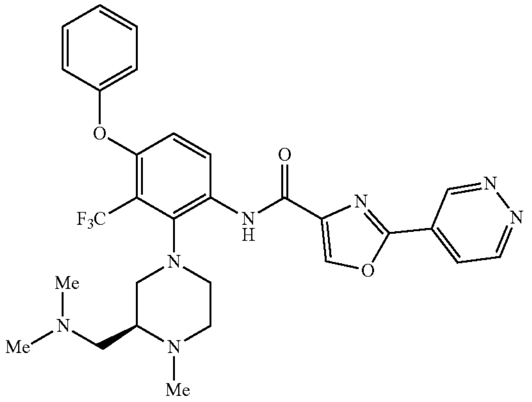 [SMILES: CN(C)C[C@H]1CN(c2c(NC(=O)c3coc(-c4ccnnc4)n3)ccc(Oc3ccccc3)c2C(F)(F)F)CCN1C] |

TABLE 6-continued
| Ex | Str |
| --- | --- |
| 117 | 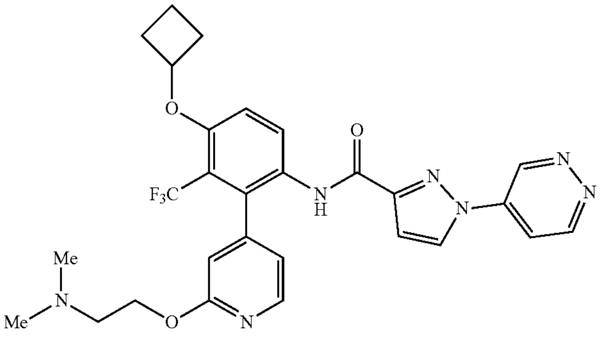 [SMILES: CN(C)CCOc1cc(-c2c(NC(=O)c3ccn(-c4ccnnc4)n3)ccc(OC3CCC3)c2C(F)(F)F)ccn1] |
| 118 | 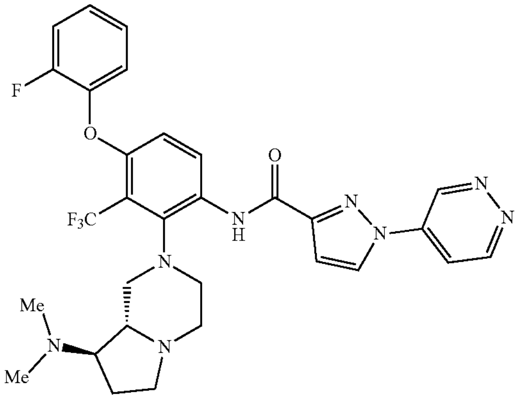 [SMILES: CN(C)[C@@H]1CCN2CCN(c3c(NC(=O)c4ccn(-c5ccnnc5)n4)ccc(Oc4ccccc4F)c3C(F)(F)F)C[C@@H]12] |
| 119 | 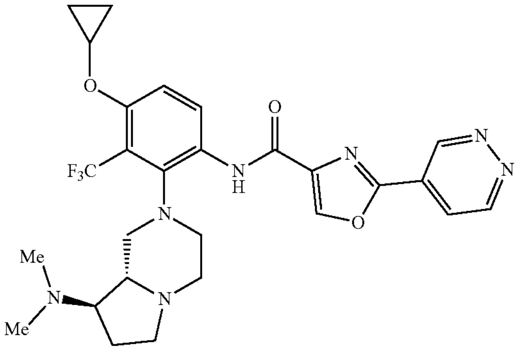 [SMILES: CN(C)[C@@H]1CCN2CCN(c3c(NC(=O)c4coc(-c5ccnnc5)n4)ccc(OC4CC4)c3C(F)(F)F)C[C@@H]12] |
| 120 | 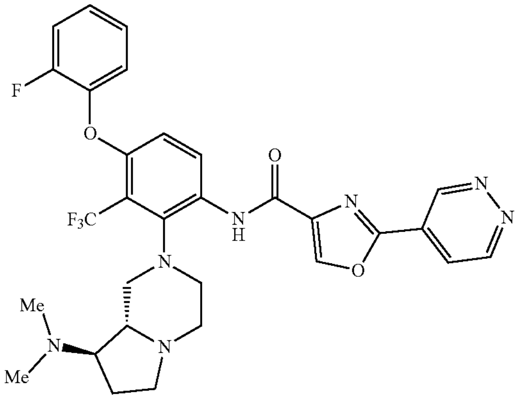 [SMILES: CN(C)[C@@H]1CCN2CCN(c3c(NC(=O)c4coc(-c5ccnnc5)n4)ccc(Oc4ccccc4F)c3C(F)(F)F)C[C@@H]12] |

TABLE 6-continued
| Ex | Str |
| --- | --- |
| 121 | 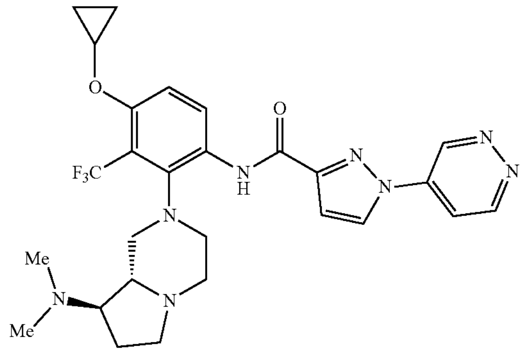 [SMILES: CN(C)[C@@H]1CCN2CCN(c3c(NC(=O)c4ccn(-c5ccnnc5)n4)ccc(OC4CC4)c3C(F)(F)F)C[C@@H]12] |
| 122 | 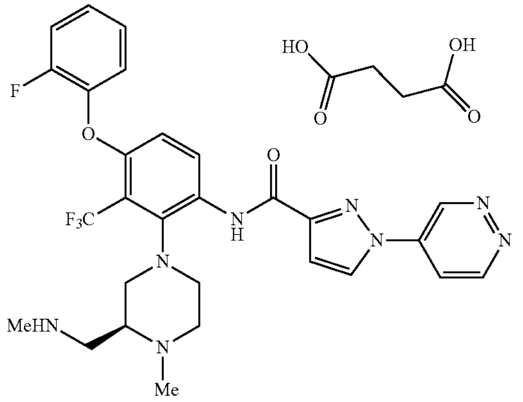 |
| 123 | 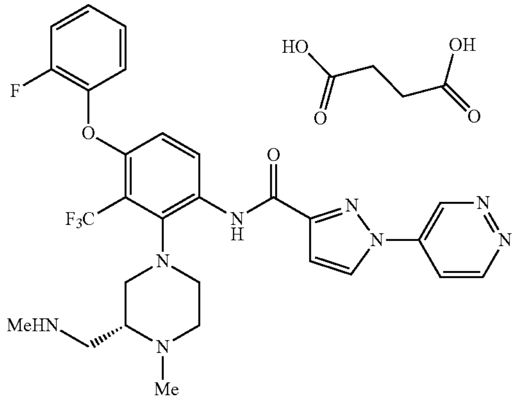 |
| 124 | 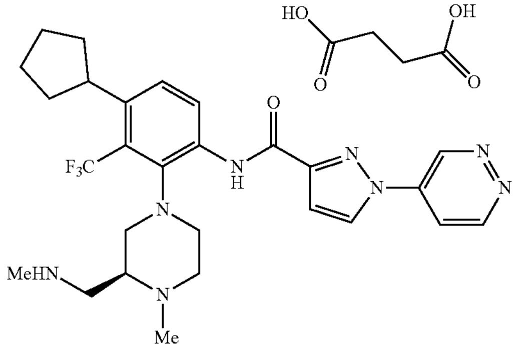 |

TABLE 6-continued

| Ex | Str |
|---|---|
| 125 | 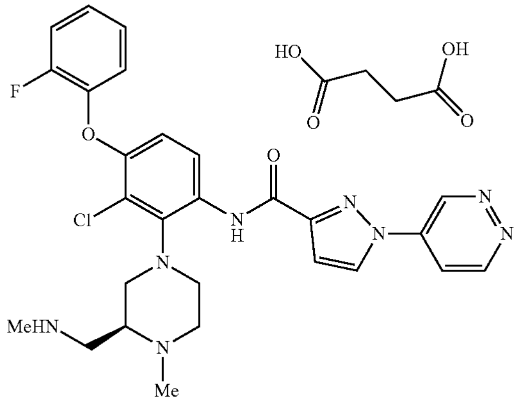 |
| 126 | 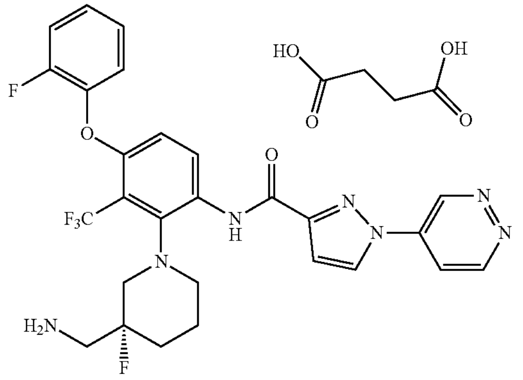 |

TABLE 7

| Ex | Syn | DAT |
|---|---|---|
| 1 | 1 | ESI+: 542.4<br>NMR DMSO-d6 (500 MHz): 1.07-1.21 (1H, m), 1.39-2.33 (3H, m), 2.61-3.19 (6H, m), 3.34-3.67 (1H, m), 4.74-4.93 (2H, m), 6.26-6.62 (1H, m), 6.86-6.90 (1H, m), 6.95-7.02 (1H, m), 7.04-7.11 (1H, m), 7.19-7.26 (2H, m), 7.36-7.44 (1H, m), 7.91 (3H, br s), 8.00-8.05 (1H, m), 8.39-10.30 (2H, m) |
| 2 | 1 | ESI+: 524.4 |
| 3 | 1 | ESI+: 510.3 |
| 4 | 1 | ESI+: 516.4 |
| 5 | 1 | ESI+: 488.4 |
| 6 | 1 | ESI+: 492.4 |
| 7 | 1 | ESI+: 558.4, 560.4 |
| 8 | 1 | ESI+: 542.2 |
| 9 | 1 | ESI+: 558.3, 560.3 |
| 10 | 1 | ESI+: 582.4 |
| 11 | 1 | ESI+: 569.3 |
| 12 | 1 | ESI+: 557.4 |
| 13 | 1 | ESI+: 573.2, 575.2<br>NMR DMSO-d6 (500 MHz): 2.78-4.07 (12H, m), 4.76-5.33 (2H, m), 6.34-6.70 (1H, m), 6.87-7.12 (3H, m), 7.19-7.30 (1H, m), 7.33-7.45 (1H, m), 7.63 (1H, dd), 7.96-8.10 (1H, m), 8.13-8.70 (4H, m), 9.40-10.04 (1H, m), 11.82-12.65 (1H, m) |
| 14 | 1 | ESI+: 529.3 |
| 15 | 1 | ESI+: 600.2, 602.2 |
| 16 | 1 | ESI+: 584.3 |
| 17 | 1 | ESI+: 517.3 |
| 18 | 1 | ESI+: 575.3 |
| 19 | 1 | ESI+: 557.3 |

TABLE 7-continued

| Ex | Syn | DAT |
|---|---|---|
| 20 | 1 | ESI+: 539.3, 541.3<br>NMR DMSO-d6 (500 MHz): 2.76-4.49 (12H, m), 4.79-5.19 (2H, m), 6.32-6.69 (1H, m), 6.83-6.97 (2H, m), 6.97-7.11 (1H, m), 7.17-7.27 (1H, m), 7.31-7.41 (1H, m), 7.62 (1H, dd), 8.02 (1H, d), 8.09-8.57 (4H, m), 9.71-10.43 (1H, m), 11.50-12.37 (1H, m) |
| 21 | 1 | ESI+: 584.4 |
| 22 | 22 | ESI+: 586.4 |
| 23 | 22 | ESI+: 571.4 |
| 24 | 22 | ESI+: 587.3, 589.3 |
| 25 | 22 | ESI+: 521.4 |
| 26 | 22 | ESI+: 553.3, 555.3 |
| 27 | 22 | ESI+: 537.2, 539.3 |
| 28 | 1 | ESI+: 557.3 |
| 29 | 29 | ESI+: 585.4<br>NMR DMSO-d6 (500 MHz): 1.47 (1H, br s), 2.13-2.19 (3H, m), 2.23-2.58 (5H, m), 2.60-2.72 (2H, m), 2.81-2.93 (2H, m), 3.00-3.46 (3H, m), 7.00 (1H, d), 7.05-7.15 (1H, m), 7.19-7.27 (3H, m), 7.37-7.44 (1H, m), 8.15-8.70 (2H, m), 8.96-9.04 (1H, m), 9.39-9.49 (1H, m), 10.01-10.17 (2H, m) |
| 30 | 29 | ESI+: 539.3 |
| 31 | 29 | ESI+: 538.3 |
| 32 | 29 | ESI+: 549.4 |
| 33 | 29 | ESI+: 572.3, 574.3 |
| 34 | 29 | ESI+: 556.4 |
| 35 | 29 | ESI+: 552.4 |
| 36 | 29 | ESI+: 596.4 |
| 37 | 29 | ESI+: 570.4 |
| 38 | 29 | ESI+: 571.4 |
| 39 | 29 | ESI+: 570.4 |
| 40 | 29 | ESI+: 545.4 |
| 41 | 29 | ESI+: 546.4 |
| 42 | 29 | ESI+: 541.4 |

TABLE 7-continued

| Ex | Syn | DAT |
|---|---|---|
| 43 | 29 | ESI+: 540.4 |
| 44 | 86 | ESI+: 559.4 |
| 45 | 29 | ESI+: 574.3<br>NMR DMSO-d6 (500 MHz): 1.54-1.89 (4H, m), 2.05-2.16 (1H, m), 2.34-2.48 (1H, m), 2.70-2.88 (2H, m), 2.95-3.10 (2H, m), 3.12-3.29 (2H, m), 6.93-7.06 (1H, m), 7.08-7.17 (1H, m), 7.19-7.28 (3H, m), 7.36-7.45 (1H, m), 8.17-8.77 (2H, m), 8.99 (1H, d), 9.42-9.48 (1H, m), 9.94-10.38 (2H, m) |
| 46 | 29 | ESI+: 587.2, 589.2 |
| 47 | 29 | ESI+: 585.4<br>NMR DMSO-d6 (500 MHz): 1.46 (1H, br s), 2.13-2.18 (3H, m), 2.22-2.57 (5H, m), 2.60-2.73 (2H, m), 2.80-2.93 (2H, m), 2.99-3.47 (3H, m), 7.00 (1H, d), 7.06-7.15 (1H, m), 7.19-7.27 (3H, m), 7.37-7.44 (1H, m), 8.13-8.69 (2H, m), 8.96-9.04 (1H, m), 9.39-9.48 (1H, m), 10.01-10.18 (2H, m) |
| 48 | 29 | ESI+: 543.3<br>NMR DMSO-d6 (500 MHz): 1.52-1.72 (4H, m), 1.76-1.91 (2H, m), 1.92-2.06 (2H, m), 2.15 (3H, s), 2.20-2.74 (7H, m), 2.76-2.90 (2H, m), 2.92-3.44 (4H, m), 7.23 (1H, d), 7.46-7.55 (1H, m), 8.23-8.70 (2H, m), 8.94-9.07 (1H, m), 9.38-9.48 (1H, m), 10.01-10.06 (1H, m), 10.11 (1H, s) |
| 49 | 29 | ESI+: 544.3 |
| 50 | 29 | ESI+: 557.3 |
| 51 | 29 | ESI+: 531.3 |
| 52 | 29 | ESI+: 571.3 |
| 53 | 29 | ESI+: 572.3 |
| 54 | 29 | ESI+: 571.3 |
| 55 | 29 | ESI+: 572.3 |
| 56 | 29 | ESI+: 553.3, 555.3 |
| 57 | 29 | ESI+: 554.3, 556.3 |
| 58 | 29 | ESI+: 574.3 |
| 59 | 29 | ESI+: 569.4 |
| 60 | 29 | ESI+: 570.4 |
| 61 | 29 | ESI+: 539.0 |
| 62 | 29 | ESI+: 552.0 |
| 63 | 29 | ESI+: 510.2 |
| 64 | 29 | ESI+: 614.1 |
| 65 | 29 | ESI+: 526.3 |
| 66 | 29 | ESI+: 540.4 |
| 67 | 29 | ESI+: 541.4 |
| 68 | 29 | ESI+: 527.4 |
| 69 | 29 | ESI+: 555.3 |
| 70 | 29 | ESI+: 541.3 |
| 71 | 29 | ESI+: 554.5 |
| 72 | 29 | ESI+: 539.3 |
| 73 | 29 | ESI+: 528.4 |
| 74 | 29 | ESI+: 527.2 |
| 75 | 29 | ESI+: 566.3 |
| 76 | 29 | ESI+: 580.3 |
| 77 | 29 | ESI+: 583.2 |
| 78 | 29 | ESI+: 597.4 |
| 79 | 29 | ESI+: 540.2 |
| 80 | 29 | ESI+: 584.3<br>NMR DMSO-d6 (400 MHz): 1.40-1.46 (1H, m), 2.09-2.71 (4H, m), 2.88-3.60 (7H, m), 7.00-7.27 (4H, m), 7.39-7.44 (1H, m), 8.11-8.74 (2H, m), 9.20-9.23 (1H, m), 9.51-9.56 (1H, m), 9.92 (1H, s), 10.24 (1H, s) |
| 81 | 29 | ESI+: 530.3 |
| 82 | 29 | ESI+: 529.5 |
| 83 | 29 | ESI+: 598.4 |
| 84 | 29 | ESI+: 583.4 |
| 85 | 29 | ESI+: 597.4 |
| 86 | 86 | ESI+: 551.3<br>NMR DMSO-d6 (500 MHz): 1.53 (1H, br s), 2.20 (3H, s), 2.36 (3H, s), 2.37-2.74 (3H, m), 2.77-3.06 (3H, m), 3.32-3.57 (2H, m), 3.63-3.76 (1H, m), 6.92-7.03 (1H, m), 7.06 (1H, d), 7.12-7.29 (3H, m), 7.33-7.46 (1H, m), 8.13-8.56 (2H, m), 8.96-9.07 (1H, m), 9.45 (1H, d), 10.07 (1H, s), 10.59 (1H, s) |
| 87 | 86 | ESI+: 601.4, 603.4 |
| 88 | 86 | ESI+: 531.4 |
| 89 | 86 | ESI+: 611.4 |
| 90 | 86 | ESI+: 535.4 |
| 91 | 29 | ESI+: 586.2, 588.2 |
| 92 | 86 | ESI+: 599.4 |
| 93 | 86 | ESI+: 568.3, 570.3 |
| 94 | 86 | ESI+: 567.3, 569.2 |
| 95 | 86 | ESI+: 601.4, 603.4 |
| 96 | 86 | ESI+: 603.3 |
| 97 | 86 | ESI+: 602.2, 604.2 |
| 98 | 86 | ESI+: 552.3 |
| 99 | 86 | ESI+: 545.3 |
| 100 | 86 | ESI+: 546.4 |
| 101 | 86 | ESI+: 585.4 |
| 102 | 86 | ESI+: 586.4 |
| 103 | 86 | ESI+: 558.0 |
| 104 | 86 | ESI+: 557.1 |
| 105 | 86 | ESI+: 568.2 |
| 106 | 86 | ESI+: 536.3 |
| 107 | 86 | ESI+: 521.4 |
| 108 | 86 | ESI+: 535.4 |
| 109 | 109 | ESI+: 542.5 |
| 110 | 109 | ESI+: 569.5 |
| 111 | 109 | ESI+: 593.5 |
| 112 | 112 | ESI+: 523.0 |
| 113 | 113 | ESI+: 569.3 |
| 114 | 113 | ESI+: 554.2 |
| 115 | 113 | ESI+: 594.3 |
| 116 | 113 | ESI+: 582.4 |
| 117 | 113 | ESI+: 568.2 |
| 118 | 113 | ESI+: 611.4 |
| 119 | 113 | ESI+: 558.4 |
| 120 | 113 | ESI+: 612.4 |
| 121 | 113 | ESI+: 557.3 |
| 122 | 122 | ESI+: 585.4<br>NMR DMSO-d6 (500 MHz): 2.22-2.54 (11H, m), 2.55-2.76 (3H, m), 2.82-2.98 (3H, m), 3.01-3.30 (2H, m), 6.95-7.04 (1H, m), 7.07-7.16 (1H, m), 7.19-7.28 (3H, m), 7.37-7.46 (1H, m), 8.09-8.66 (2H, m), 8.96-9.05 (1H, m), 9.39-9.50 (1H, m), 9.99-10.14 (2H, m)<br>2θ(°) = 8.4, 9.9, 10.5, 11.2, 11.4, 14.7, 16.3, 19.2, 22.2, 24.0 |
| 123 | 123 | ESI+: 585.4<br>NMR DMSO-d6 (500 MHz): 2.21-2.54 (11H, m), 2.56-2.77 (3H, m), 2.82-2.99 (3H, m), 3.01-3.28 (2H, m), 6.95-7.04 (1H, m), 7.06-7.17 (1H, m), 7.19-7.30 (3H, m), 7.35-7.46 (1H, m), 8.04-8.66 (2H, m), 8.96-9.05 (1H, m), 9.39-9.50 (1H, m), 9.99-10.18 (2H, m)<br>2θ(°) = 8.4, 9.9, 10.5, 11.2, 11.4, 14.7, 16.3, 19.2, 22.2, 24.0 |
| 124 | 123 | ESI+: 543.5<br>NMR DMSO-d6 (500 MHz): 1.47-1.75 (4H, m), 1.76-1.91 (2H, m), 1.91-2.08 (2H, m), 2.20-2.41 (11H, m), 2.53-2.80 (3H, m), 2.80-3.08 (6H, m), 7.24 (1H, br s), 7.47-7.58 (1H, m), 8.15-8.76 (2H, m), 8.94-9.14 (1H, m), 9.37-9.55 (1H, m), 9.95-10.23 (2H, m)<br>2θ(°) = 7.7, 8.1, 11.6, 12.8, 20.3, 20.7, 22.3 |
| 125 | 123 | ESI+: 551.4, 553.3<br>NMR DMSO-d6 (500 MHz): 2.32 (4H, s), 2.34-2.69 (8H, m), 2.73-2.83 (1H, m), 2.84-2.95 (2H, m), 2.95-3.03 (2H, m), 3.46-3.55 (1H, m), 3.62-3.74 (1H, m), 6.92-7.03 (1H, m), 7.07 (1H, d), 7.14-7.29 (3H, m), 7.35-7.45 (1H, m), 8.10-8.53 (2H, m), 8.97-9.04 (1H, m), 9.46 (1H, d), 9.95-10.10 (1H, m), 10.54 (1H, s)<br>2θ(°) = 7.0, 10.5, 12.1, 14.4, 14.6, 17.8, 19.3, 19.9, 20.2, 21.2 |
| 126 | 126 | ESI+: 574.4<br>NMR DMSO-d6 (500 MHz): 1.57-1.86 (2H, m), 2.05-2.21 (1H, m), 2.35 (4H, s), 2.38-2.47 (1H, m), 2.85-3.30 (6H, m), 6.92-7.07 (1H, m), 7.08-7.16 (1H, m), 7.18-7.29 (3H, m), 7.36-7.45 (1H, m), 8.16-8.77 (2H, m), 9.00 (1H, d), 9.41-9.50 (1H, m), 9.94-10.35 (2H, m)<br>2θ(°) = 9.4, 10.7, 12.3, 13.2, 14.0, 16.8, 20.7, 21.1, 23.0, 23.5 |

INDUSTRIAL APPLICABILITY

The compound or a salt thereof of the present invention is useful as a DGK ξ inhibitor, and can be used as an active ingredient of a pharmaceutical composition, for example a pharmaceutical composition for treatment of cancer related to activation of immune cells or cancer resistant to anti-PD-1 antibody/anti-PD-L1 antibody therapy.

The invention claimed is:

1. A compound of formula (I):

[Chemical Formula 1]

(I)

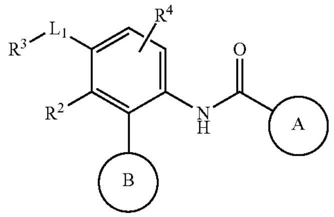

or a salt thereof, wherein

A is a group of formula (A-i), (A-ii), (A-iii), (A-iv) or (A-v):

[Chemical Formula 2]

(A-i)

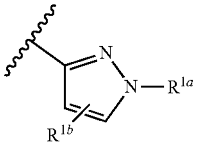

(A-ii)

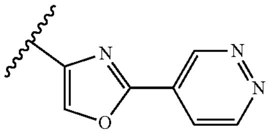

(A-iii)

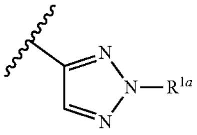

(A-iv)

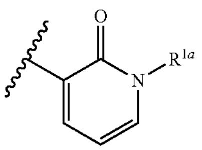

(A-v)

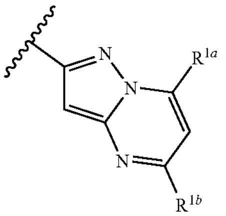

B is a group of formula (B-i), (B-ii), (B-iii) or (B-iv):

[Chemical Formula 3]

(B-i)

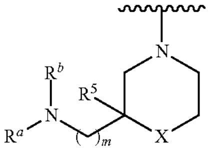

(B-ii)

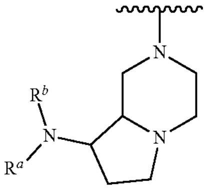

(B-iii)

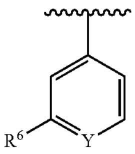

(B-iv)

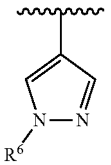

where B is a group of (B-i) when $R^{1a}$ is a halogeno-$C_{1-6}$ alkyl, $R^{1a}$ is pyridazinyl or a halogeno-$C_{1-6}$ alkyl, $R^{1b}$ is H or a $C_{1-6}$ alkyl, $R^2$ is a $C_{3-5}$ cycloalkyl, an —O—($C_{1-6}$ alkyl), a halogeno-$C_{1-6}$ alkyl, a halogen or a phenyl, $R^3$ is i) a phenyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulfonyl and a halogen, ii) a $C_{3-8}$ cycloalkyl optionally substituted with a group selected from the group consisting of a $C_{1-6}$ alkyl and a halogen, iii) a pyridyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulfonyl and a halogen, or iv) five- or six-membered partially unsaturated heterocyclic ring containing one to four hetero atoms selected from oxygen, sulfur and nitrogen, $R^4$ is H or F, $R^5$ is H or F, $R^6$ is -$L_2$-$(CH_2)_2NR^aR^b$ or piperidinyl, $L_1$ is a bond, O or NH, $L_2$ is a bond, O or $CH_2$, X is $CH_2$ or N-methyl, Y is CH or N, $R^a$ is H or methyl, $R^b$ is H, methyl, ethyl, cyclopropyl or —$(CH_2)_2O$—$CH_3$, and m is 1, 2 or 3.

2. The compound or a salt thereof according to claim 1, wherein $R^2$ is a halogeno-$C_{1-6}$ alkyl or a halogen, $R^3$ is i) a phenyl optionally substituted with a group selected from the group consisting of a $C_{1-6}$ alkyl, a halogeno-$C_{1-6}$ alkyl, a $C_{3-5}$ cycloalkyl, an —O—($C_{1-6}$ alkyl), an —O-(halogeno-$C_{1-6}$ alkyl), cyano, nitro, methanesulphonyl and a halogen, or ii) a $C_{3-8}$ cycloalkyl optionally substituted with a group selected from the group consisting of a $C_{1-6}$ alkyl and a halogen, and L1 is a bond or O.

3. The compound or a salt thereof according to claim 2, wherein B is a group of the following formula (B-i-a) or (B-ii):

[Chemical Formula 4]

(B-i-a)

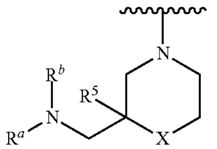

(B-ii)

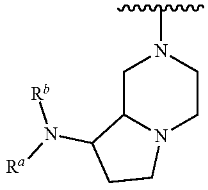

where B is a group of (B-i-a) when $R^{1a}$ is a halogeno-$C_{1-6}$ alkyl.

4. The compound or a salt thereof according to claim 3, wherein A is a group of the following formula (A-i) or (A-ii):

[Chemical Formula 5]

(A-i)

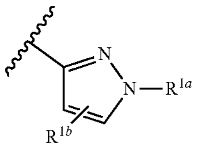

(A-ii)

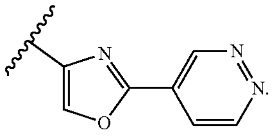

5. The compound or a salt thereof according to claim 4, wherein $R^3$ is a phenyl optionally substituted with a group selected from the group consisting of a $C_{1-6}$ alkyl and a halogen, or a $C_{3-5}$ cycloalkyl, and $R^b$ is H or methyl.

6. A pharmaceutical composition comprising the compound or a salt thereof according to claim 1, and one or more pharmaceutically acceptable excipients.

7. A method of treating cancer related to activation of immune cells or cancer resistant to anti-PD-1 antibody/anti-PD-L1 antibody therapy, the method comprising administering to a subject an effective amount of the pharmaceutical composition of claim 6.

8. A DGK ξ inhibitor comprising the compound or a salt thereof according to claim 1.

9. A method for treatment of cancer related to activation of immune cells or cancer resistant to anti-PD-1 antibody/anti-PD-L1 antibody therapy, the method comprising administering to a subject an effective amount of the compound or a salt thereof according to claim 1.

* * * * *